(12) United States Patent
Kaila et al.

(10) Patent No.: US 12,071,442 B2
(45) Date of Patent: Aug. 27, 2024

(54) SUBSTITUTED PYRROLO[3,4-C]PYRIDINES AS HPK1 ANTAGONISTS

(71) Applicant: Nimbus Saturn, Inc., Cambridge, MA (US)

(72) Inventors: Neelu Kaila, Lexington, MA (US); Ian Linney, Saffron Walden (GB); Stuart Ward, Saffron Walden (GB); Grant Wishart, Saffron Walden (GB); Benjamin Whittaker, Saffron Walden (GB); Alexandre Cote, West New York, NJ (US); Jeremy Robert Greenwood, Brooklyn, NY (US); Abba Leffler, Bronx, NY (US)

(73) Assignee: Nimbus Saturn, Inc., Boston, MA (US)

( * ) Notice: Subject to any disclaimer, the term of this patent is extended or adjusted under 35 U.S.C. 154(b) by 0 days.

(21) Appl. No.: 17/656,924

(22) Filed: Mar. 29, 2022

(65) Prior Publication Data

US 2022/0363695 A1   Nov. 17, 2022

Related U.S. Application Data

(60) Provisional application No. 63/182,313, filed on Apr. 30, 2021, provisional application No. 63/167,455, filed on Mar. 29, 2021.

(51) Int. Cl.
| | |
|---|---|
| *A61K 31/437* | (2006.01) |
| *C07D 471/04* | (2006.01) |
| *C07D 487/04* | (2006.01) |
| *C07D 519/00* | (2006.01) |

(52) U.S. Cl.
CPC .......... *C07D 519/00* (2013.01); *C07D 487/04* (2013.01)

(58) Field of Classification Search
CPC ..................... A61K 31/437; C07D 471/04
USPC .......................................... 514/300; 546/113
See application file for complete search history.

(56) References Cited

U.S. PATENT DOCUMENTS

| | | | |
|---|---|---|---|
| 2,475,569 | A | 7/1949 | Mowat |
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 7,081,449 | B2 | 7/2006 | Pietrzkowski et al. |
| 7,390,799 | B2 | 6/2008 | Bruncko et al. |
| 8,138,347 | B2 | 3/2012 | Knight et al. |
| 8,796,313 | B2 | 8/2014 | Dudash et al. |
| 8,906,682 | B2 | 12/2014 | June et al. |
| 11,021,481 | B2 | 6/2021 | Kaila et al. |
| 11,028,085 | B2 | 6/2021 | Kaila et al. |
| 11,034,694 | B2 | 6/2021 | Kaila et al. |
| 11,078,201 | B2 | 8/2021 | Kaila et al. |
| 2006/0287370 | A1 | 12/2006 | Curtin et al. |
| 2011/0245247 | A1 | 10/2011 | Braje et al. |
| 2016/0311772 | A1* | 10/2016 | Choi ................... C07D 209/48 |
| 2017/0226129 | A1 | 8/2017 | Yu et al. |
| 2018/0127396 | A1 | 5/2018 | Li et al. |
| 2018/0141951 | A1 | 5/2018 | Arikawa et al. |
| 2018/0179221 | A1 | 6/2018 | Sampson et al. |
| 2018/0282328 | A1 | 10/2018 | Chan et al. |
| 2019/0256520 | A1 | 8/2019 | Sokolsky et al. |
| 2020/0038378 | A1 | 2/2020 | Crew et al. |
| 2021/0078996 | A1 | 3/2021 | Kaila et al. |
| 2021/0078997 | A1 | 3/2021 | Kaila et al. |

FOREIGN PATENT DOCUMENTS

| | | |
|---|---|---|
| CA | 2988721 A1 | 6/2018 |
| EP | 1477472 B1 | 1/2009 |
| EP | 2108642 A1 | 10/2009 |
| WO | WO-2001042246 A2 | 6/2001 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |

(Continued)

OTHER PUBLICATIONS

Adams et al., "Big opportunities for small molecules in immuno-oncology," Cancer Therapy. 2015; 14: 603-622.
Berge et al., "Pharmaceutical salts," J. Pharmaceutical Sciences 1977; 66(1):1-19.
Di Bartolo et al. A novel pathway down-modulating T cell activation involves HPK-1-dependent recruitment of 14-3-3 proteins on SLP-76, J Exp Med. 2007; 204(3): 681-691.
Hu et al., "Human HPK1, a novel human hematopoietic progenitor kinase that activates the JNK/SAPK kinase cascade," Genes Dev. 1996; 10(18): 2251-64.

(Continued)

*Primary Examiner* — Douglas M Willis
(74) *Attorney, Agent, or Firm* — Dechert LLP; Andrea L. C. Reid; Todd Macklin

(57) ABSTRACT

The present invention provides compounds of formula I, compositions thereof, and methods of using the same for the inhibition of HPK1, and the treatment of HPK1-mediated disorders.

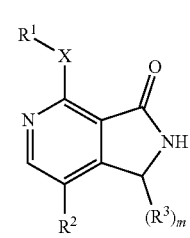

I

19 Claims, No Drawings

(56) References Cited

FOREIGN PATENT DOCUMENTS

| | | |
|---|---|---|
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |
| WO | WO-2006105021 A2 | 10/2006 |
| WO | WO-2006122806 A2 | 11/2006 |
| WO | WO-2007005874 A2 | 1/2007 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2020089026 A2 | 1/2008 |
| WO | WO-2008039218 A2 | 4/2008 |
| WO | WO-2008109943 A1 | 9/2008 |
| WO | WO-2008118802 A1 | 10/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009074812 A1 | 6/2009 |
| WO | WO-2009114512 A1 | 9/2009 |
| WO | WO-2009156652 A1 | 12/2009 |
| WO | WO-2010019570 A2 | 2/2010 |
| WO | WO-2010077634 A1 | 7/2010 |
| WO | 2010141406 A2 | 12/2010 |
| WO | WO-2011028683 A1 | 3/2011 |
| WO | WO-2011056652 A1 | 5/2011 |
| WO | WO-2011070024 A1 | 6/2011 |
| WO | WO-2011090760 A1 | 7/2011 |
| WO | WO-2011107553 A1 | 9/2011 |
| WO | WO-2011109400 A2 | 9/2011 |
| WO | WO-2011131407 A1 | 10/2011 |
| WO | WO-2011140249 A2 | 11/2011 |
| WO | WO-2012032433 A1 | 3/2012 |
| WO | WO-2012142237 A1 | 10/2012 |
| WO | WO-2012145493 A1 | 10/2012 |
| WO | WO-2013079174 A1 | 6/2013 |
| WO | WO-2013086397 A1 | 6/2013 |
| WO | WO-2013087699 A1 | 6/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014036357 A1 | 3/2014 |
| WO | WO-2014074660 A1 | 5/2014 |
| WO | WO-2014074661 A1 | 5/2014 |
| WO | WO-2015089143 A1 | 6/2015 |
| WO | WO-2015131080 A1 | 9/2015 |
| WO | WO-2016106106 A2 | 6/2016 |
| WO | WO-2021050964 A1 | 3/2021 |

OTHER PUBLICATIONS

Ikegami et al., "The expression of prostaglandin E receptors EP2 and EP4 and their different regulation by lipopolysaccharide in C3H/HeN peritoneal macrophages," J Immunol. 2001; 166(7): 4689-96.

Kiefer et al., "HPK1, a hematopoietic protein kinase activating the SAPK/JNK pathway," EMBO J. 1996; 15(24): 7013-25.

Lasserre et al., "Release of serine/threonine-phosphorylated adaptors from signaling microclusters down-regulates T cell activation," J Cell Biol. 2011; 195(5): 839-853.

Liou et al., "HPK1 is activated by lymphocyte antigen receptors and negatively regulates AP-1," Immunity. 2000; 12(4): 399-408.

Okazaki et al., "A rheostat for immune responses: the unique properties of PD-1 and their advantages for clinical application," Nat. Immunol. 2013; 14(12): 1212-1218.

PCT International Search Report from PCT/US2020/050524 dated Oct. 31, 2020.

PCT International Search Report from PCT/US2022/070627 dated Jun. 6, 2022.

PCT International Search Report from PCT/US2022/071403 dated Jun. 6, 2022.

PubChem-SID-369999312, Modify Date: May 28, 2018.

PubChem-SID-132639281, Modify Date: May 31, 2019.

Ramirez et al "Defining causative factors contributing in the activation of hedgehog signaling in diffuse large B-cell lymphoma" Leuk. Res. (2012), published online Jul. 17.

Ross et al., "Bispecific T cell engager (BITE®) antibody constructs can mediate bystander tumor cell killing," PLoS ONE. 2017; 12(8): e0183390.

Rostovtsev et al., "A stepwise huisgen cycloaddition process: copper(I)-catalyzed regioselective "ligation" of azides and terminal alkynes," Angew. Chem. Int. Ed., 2002, vol. 41, pp. 2596-2599.

Shui et al., "Hematopoietic progenitor kinase 1 negatively regulates T cell receptor signaling and T cell-mediated immune responses," Nat Immunol. 2007; 8(1): 84-91.

Sun et al., "Carbohydrate and protein immobilization onto solid surfaces by sequential Diels-Alder and azide-alkyne cycloadditions," Bioconjugate Chem., 2006, vol. 17, No. 1, pp. 52-57.

Toogood, "Small molecule immuno-oncology therapeutic agents," Bioorganic & Medicinal Chemistry Letters. 2018; 28(3): 319-329.

Wang et al., "Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction," J Biol Chem. 1997; 272(36): 22771-5.

Wang et al., "Down-regulation of B cell receptor signaling by hematopoietic progenitor kinase 1 (HPK1)-mediated phosphorylation and ubiquitination of activated B cell linker protein (BLNK)," J Biol Chem. 2012; 287(14): 11037-48.

Zhou et al., "Hematopoietic progenitor kinase 1 is a component of transforming growth factor beta-induced c-Jun N-terminal kinase signaling cascade," J Biol Chem. 1999; 274(19): 13133-8.

Zou et al., "PD-L1 (B7-H1) and PD-1 pathway blockade for cancer therapy: Mechanisms, response biomarkers, and combinations," Sci. Transl. Med. 2016; 8(328): 1-14.

Deguest et al., "One-Pot Synthesis of 2,3-Dihydro-pyrrolopyridinones Using in Situ Generated Formimines," Organic Letters. 2006; 8(25):5889-92.

PCT International Search Report from PCT/US2022/070970 dated Jul. 14, 2022.

Pubchem-CID-14005627, Modify Date: Feb. 9, 2007.

* cited by examiner

SUBSTITUTED PYRROLO[3,4-C]PYRIDINES AS HPK1 ANTAGONISTS

CROSS-REFERENCE TO RELATED APPLICATIONS

This application claims the benefit of priority to U.S. Provisional Appl. No. 63/182,313, filed Apr. 30, 2021 and U.S. Provisional Appl. No. 63/167,455, filed Mar. 29, 2021, the entirety of each of which is herein incorporated by reference.

TECHNICAL FIELD OF THE INVENTION

The present invention relates to compounds and methods useful for antagonizing hematopoietic progenitor kinase 1 (HPK1). The invention also provides pharmaceutically acceptable compositions comprising compounds of the present invention and methods of using said compositions in the treatment of various disorders.

BACKGROUND OF THE INVENTION

The hematopoietic progenitor kinase 1 (HPK1), otherwise known as mitogen activated protein kinase kinase kinase kinase 1 (MAP4K1), is a hematopoietic cell-restricted member of the Ste20 senne/threonine kinase super family. The MAP4Ks family includes MAP4K1/HPK1, MAP4K2/GCK, MAP4K3/GLK, MAP4K4/HGK, MAP4K5/KHS, and MAP4K6/MINK. HPK1 is a tissue-specific upstream activator of the MEKK/JNK/SAPK signaling pathway.

HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-PR) (Wang, W., et al., J Biol Chem, 1997. 272(36): p. 22771-5; Zhou, G., et al., J Biol Chem, 1999. 274(19): p. 13133-8), or Gs-coupled PGE2 receptors (EP2 and EP4) (Ikegami, R., et al., J Immunol, 2001. 166(7): p. 4689-96). As such, HPK1 regulates diverse functions of various immune cells. HPK1 is also an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) J Cell Biol 195(5):839-853). HPK1 can also become activated in response to prostaglandin E2, which is often secreted by tumors, contributing to the escape of tumor cells from the immune system.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48).

SUMMARY OF THE INVENTION

It has now been found that compounds of this invention, and pharmaceutically acceptable compositions thereof, are effective as antagonists of HPK1. In certain embodiments, the invention provides for compounds of the formulae presented herein.

Compounds of the present invention, and pharmaceutically acceptable compositions thereof, are useful for treating a variety of diseases, disorders or conditions, associated with regulation of signaling pathways implicating HPK1 kinases. Such diseases, disorders, or conditions include those described herein.

Compounds provided by this invention are also useful for the study of HPK1 enzymes in biological and pathological phenomena; the study of intracellular signal transduction pathways occurring in bodily tissues; and the comparative evaluation of new HPK1 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

In certain aspects, the present invention provides a compound of formula I:

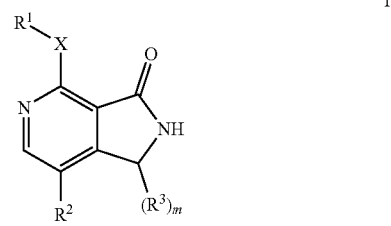

I or a pharmaceutically acceptable salt thereof, wherein each of X, $R^1$, $R^2$, $R^3$, and m, is as defined below and described in embodiments herein, both singly and in combination.

In some embodiments, the present invention provides a pharmaceutical composition comprising a compound of formula I and a pharmaceutically acceptable carrier, adjuvant, or diluent.

In some embodiments, the present invention provides a method of treating a HPK1-mediated disease, disorder, or condition comprising administering to a patient in need thereof, a compound of formula I, or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

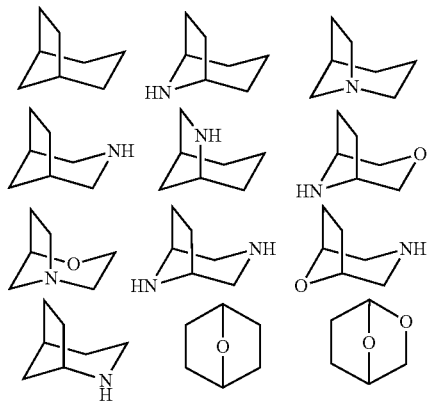

-continued

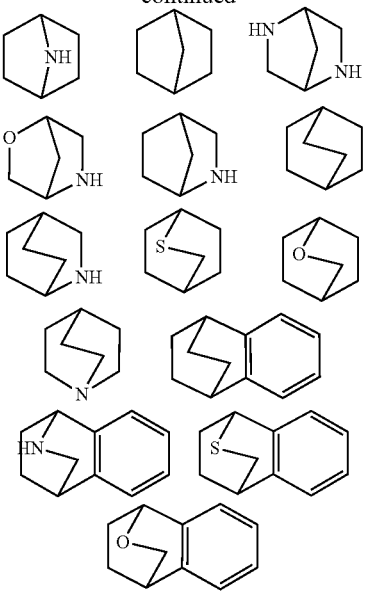

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$— pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —N(R°)C(NR°)N(R°)$_2$; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —(CH$_2$)$_{0-4}$P(O)$_2$R°; —(CH$_2$)$_{0-4}$P(O)R°$_2$; —(CH$_2$)$_{0-4}$OP(O)R°$_2$; —(CH$_2$)$_{0-4}$OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$)$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger{}_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger{}_2$, —C(S)NR$^\dagger{}_2$, —C(NH)NR$^\dagger{}_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet{}_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms. In certain embodiments, Ring B of a provided compound may be substituted with one or more deuterium atoms.

The structures as drawn represent relative configurations, unless labeled as absolute configurations. The invention contemplates individual enantiomers and racemic mixtures.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a HPK1 protein kinase activity between a sample comprising a compound of the present invention, or composition thereof, and a HPK1 protein kinase, and an equivalent sample comprising an HPK1 protein kinase, in the absence of said compound, or composition thereof.

3. Description of Exemplary Embodiments

As described above, in certain embodiments, the present invention provides a compound of formula I:

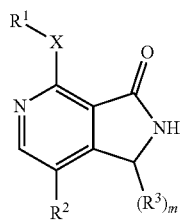

I or a pharmaceutically acceptable salt thereof, wherein:

X is a covalent bond, —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)S(O)$_2$—; or X is a C$_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;

R$^1$ is selected from C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and an 8-10 membered saturated or partially unsaturated bicyclic heterocyclic ring having 1-4 heteroatoms independently selected from nitrogen, oxygen, and sulfur; each of which is substituted with q instances of R$^C$; or R$^1$ is H;

R$^2$ is selected from C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; each of which is substituted with q instances of R$^C$; or R$^2$ is a 6-11 membered saturated, partially unsaturated, or unsaturated fused, bridged, or spiro bicyclic ring having 0-3 heteroatoms independently selected from nitrogen, oxygen, and sulfur; each of which is substituted with q instances of R$^C$; or R$^2$ is selected from —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, and —N(R)S(O)R;

each instance of R$^3$ is independently hydrogen or an optionally substituted C$_{1-6}$ aliphatic group;

each instance of R$^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$; or each instance of R$^C$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-11 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-3 heteroatoms independently selected from nitrogen, oxygen, and sulfur; each of which is substituted with r instances of R and s instances of R$^D$;

each instance of R$^D$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$;

each R is independently hydrogen, —CN, halogen, or an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur;

m is 0, 1, or 2;

each q is independently 0, 1, 2, 3, or 4;

each r is independently 0, 1, 2, 3, or 4; and each s is independently 0, 1, 2, 3, or 4.

As defined generally above, X is a covalent bond, —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)S(O)$_2$—; or X is a $C_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In certain embodiments, X is —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, —N(R)NR—, —N(R)S(O)$_2$NR—, or —N(R)S(O)$_2$—.

In some embodiments, X is a $C_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In certain embodiments, X is —NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, or —N(R)NR—.

In certain embodiments, X is —NR—. In certain embodiments, X is —NH—.

In some embodiments, X is selected from those depicted in Table 1, below.

As defined generally above, $R^1$ is selected from $C_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and an 8-10 membered saturated or partially unsaturated bicyclic heterocyclic ring having 1-4 heteroatoms independently selected from nitrogen, oxygen, and sulfur; each of which is substituted with q instances of $R_C$.

In some embodiments, $R^1$ is $C_{1-6}$ aliphatic which is substituted with q instances of $R^C$; phenyl which is substituted with q instances of $R^C$; a 3-7 membered saturated or partially unsaturated monocyclic carbocyclic ring, which is substituted with q instances of $R^C$; a 5-6 membered monocyclic heteroaryl ring having 1-4 heteroatoms independently selected from nitrogen, oxygen, and sulfur, which is substituted with q instances of $R^C$; a 3-7 membered saturated or partially unsaturated monocyclic heterocyclic ring having 1-2 heteroatoms independently selected from nitrogen, oxygen, and sulfur, which is substituted with q instances of $R^C$; or an 8-10 membered saturated or partially unsaturated bicyclic heterocyclic ring having 1-4 heteroatoms independently selected from nitrogen, oxygen, and sulfur; which is substituted with q instances of $R^C$.

In some embodiments, $R^1$ is phenyl or a 5-6 membered monocyclic heteroaryl ring having 1-4 heteroatoms independently selected from nitrogen, oxygen, and sulfur, each of which is substituted with q instances of $R^C$.

In certain embodiments, $R^1$ is phenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydropyranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of $R^C$.

In certain embodiments, $R^1$ is phenyl, furanyl, furazanyl, imidazolidinyl, imidazolinyl, imidazolyl, isothiazolyl, isoxazolyl, morpholinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, oxetanyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, tetrahydropyranyl, thiazolyl, thienyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of $R^C$.

In certain embodiments, R is furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, thiazolyl, thienyl, triazinyl, 1,2,3-triazolyl, 1,2,4-triazolyl, or 1,2,5-triazolyl, 1,3,4-triazolyl; each of which is substituted by q instances of $R^C$.

In certain embodiments, $R^1$ is phenyl, pyrazolyl, pyridinyl, pyrazinyl, or pyrimidinyl; each of which is substituted by q instances of $R^C$.

In certain embodiments, $R^1$ is pyrazolyl or pyridinyl; each of which is substituted by q instances of $R^C$.

In certain embodiments, $R^1$ is pyrazolyl or pyridinyl; each of which is substituted by q instances of $R^C$; wherein each $R^C$ is independently halogen, —CN, —OR, —S(O)$_2$R, —C(O)NR$_2$, or each instance of $R^C$ is independently an optionally substituted group selected from C$_{1-6}$ aliphatic; a 5-10 membered saturated or partially unsaturated bridged bicyclic ring having 0-3 heteroatoms independently selected from nitrogen, oxygen, and sulfur; a 6-12 membered saturated or partially unsaturated spirocyclic ring having 0-3 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or two $R^C$ groups together with the atoms to which each is attached, forms a bridged, fused, or spiro 5-6 membered aryl ring, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, phosphorous, silicon and sulfur; wherein each instance of $R^C$ is independently optionally substituted by R and $R^D$.

In certain embodiments, $R^1$ is

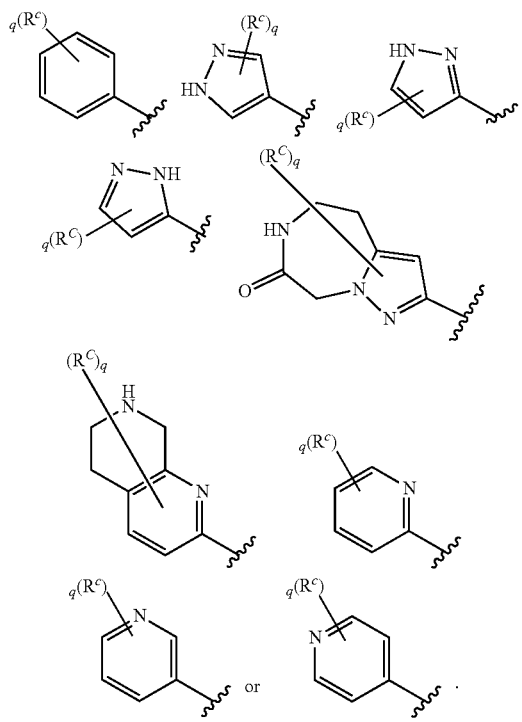

In certain embodiments, $R^1$ is

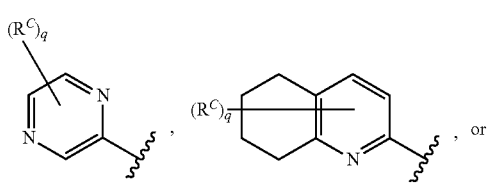

-continued

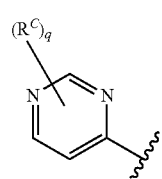

In certain embodiments, $R^1$ is

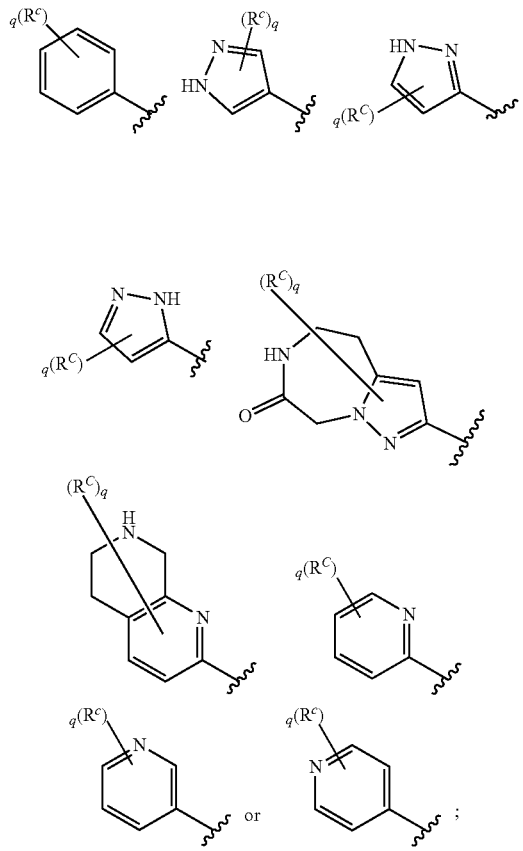

wherein each instance of $R^C$ is independently a 3-7 membered saturated or partially unsaturated monocyclic heterocyclic ring having 1-2 heteroatoms independently selected from nitrogen, oxygen, phosphorous, silicon and sulfur; or a 5-8 membered saturated or partially unsaturated bridged bicyclic ring having 0-3 heteroatoms independently selected from nitrogen, oxygen, and sulfur; each of which is substituted with r instances of R and s instances of $R^D$.

In certain embodiments, $R^1$ is

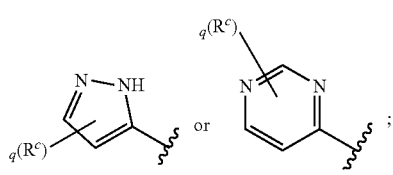

wherein each instance of $R^C$ is independently -Me, -Et, —CN, —F, —OMe, —S(O)$_2$Me,
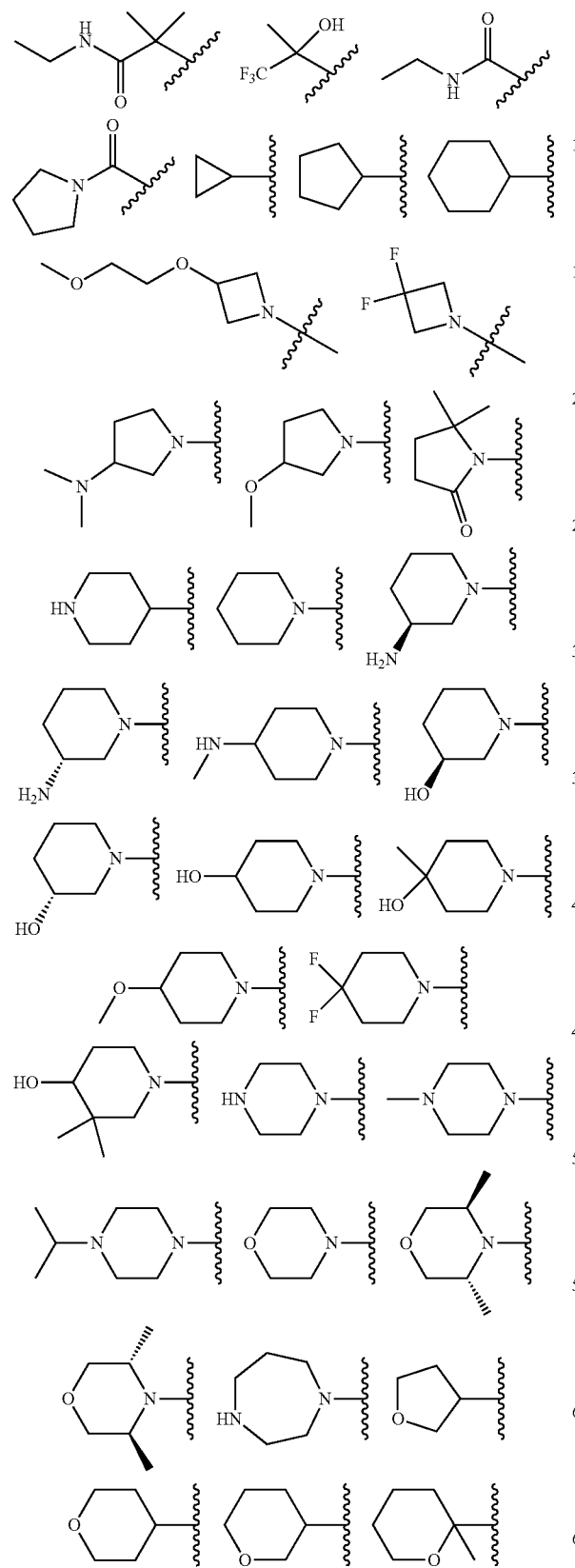
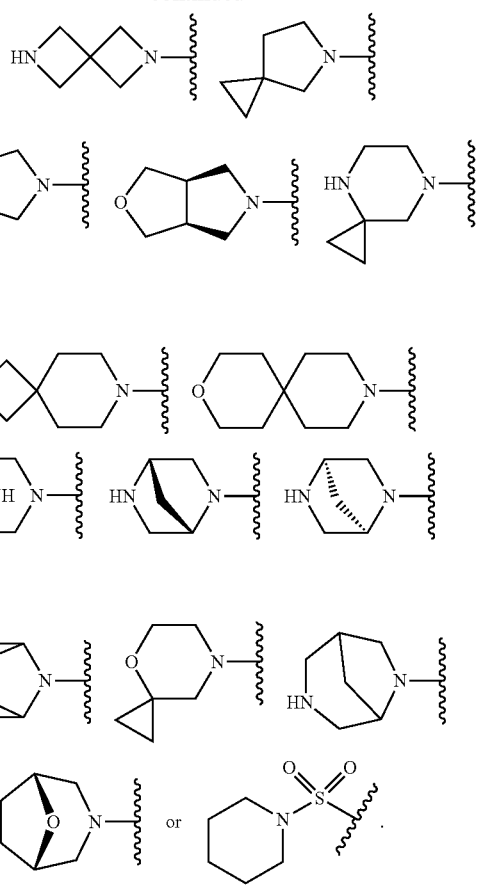
In certain embodiments, $R^1$ together with its $R^C$ substituents is
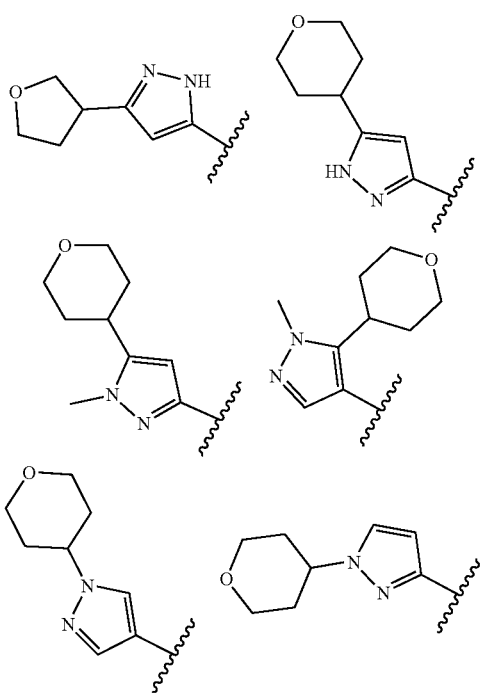

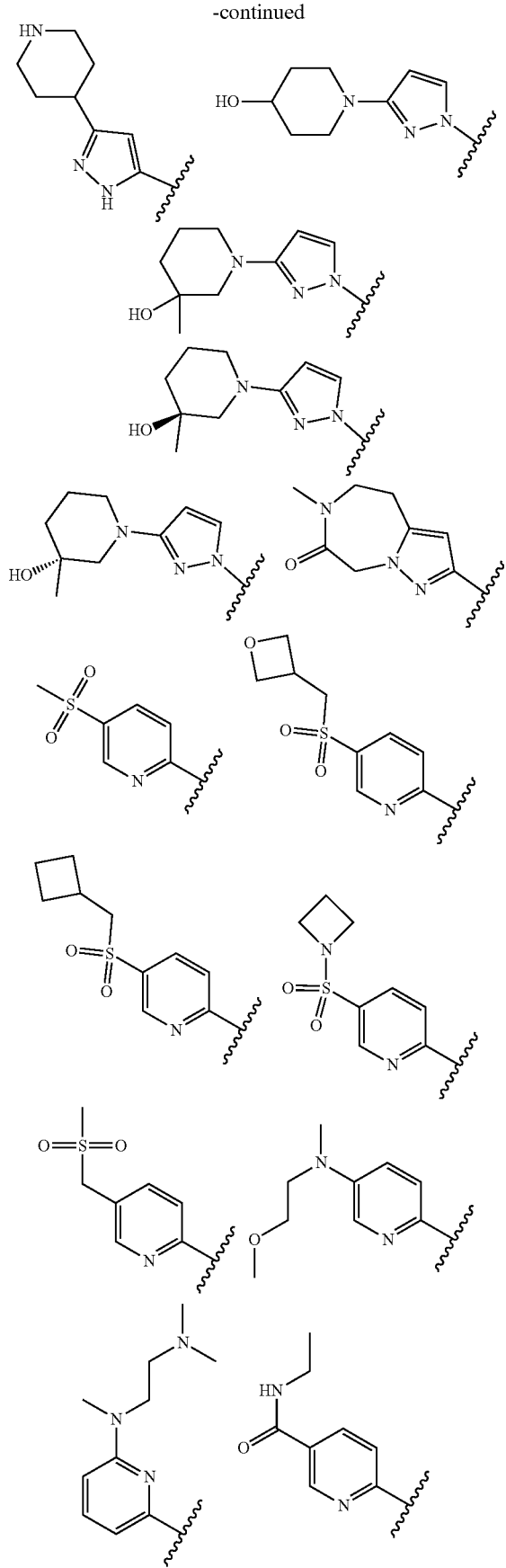
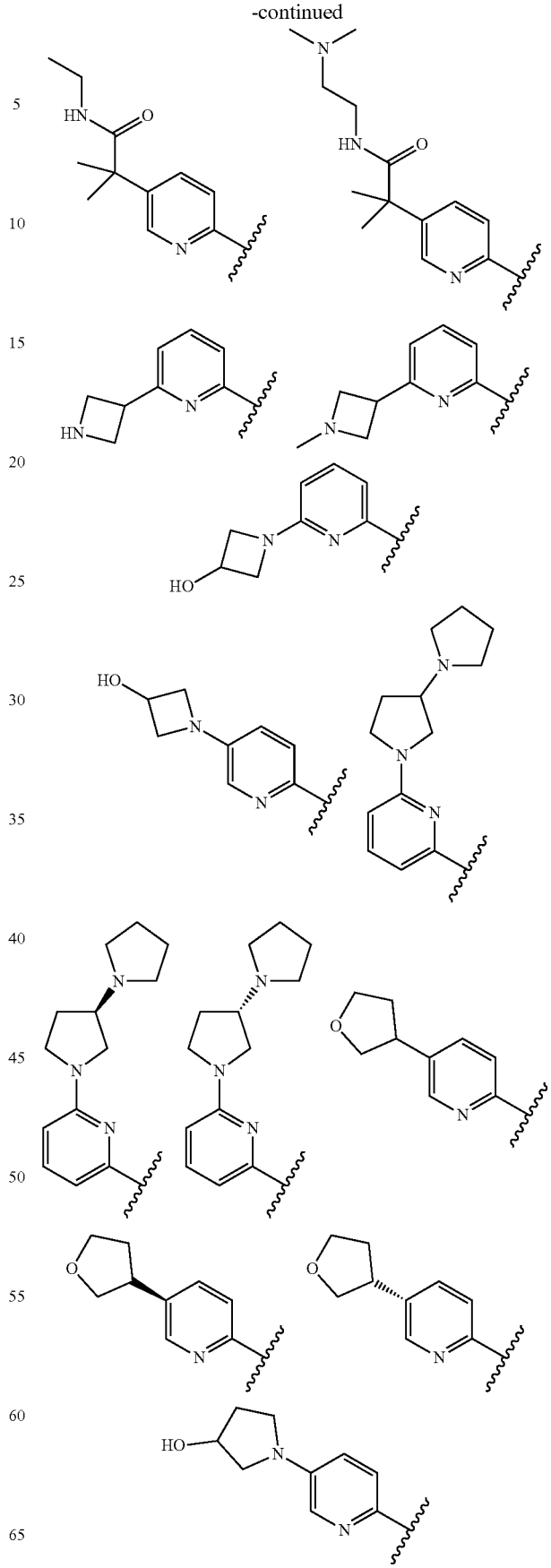

21
-continued
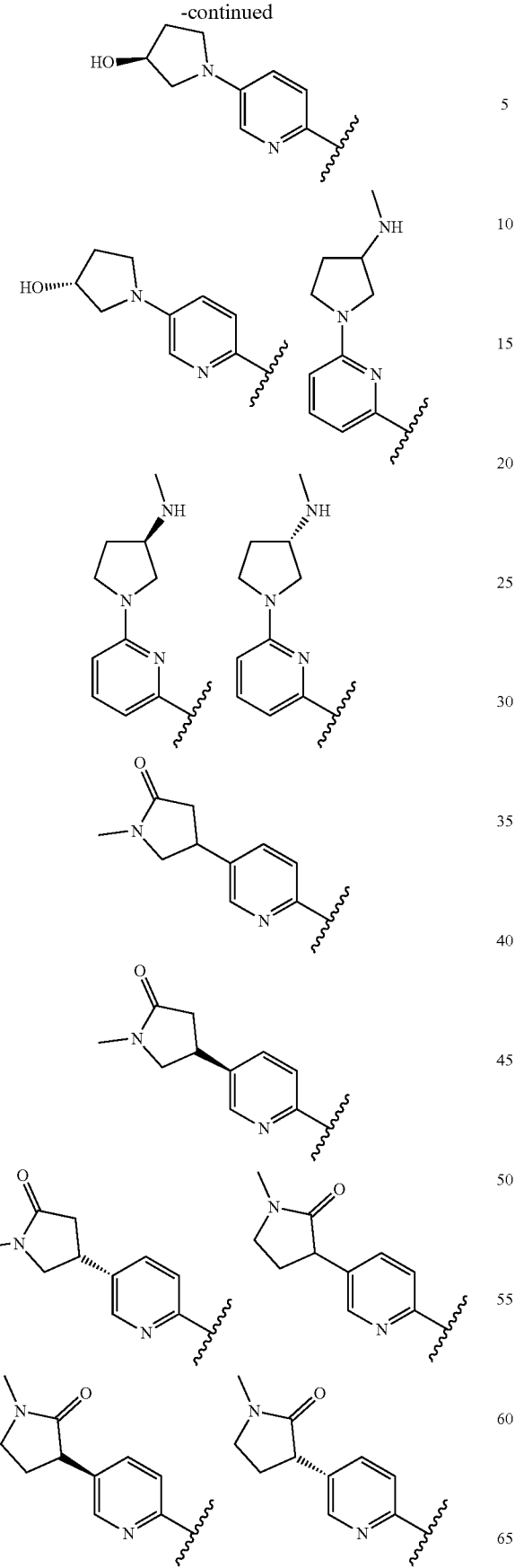
22
-continued
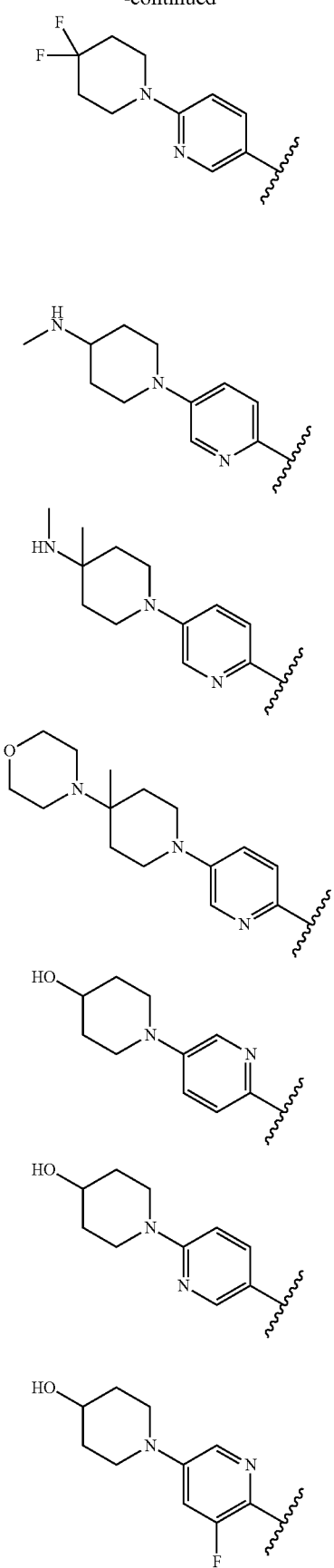

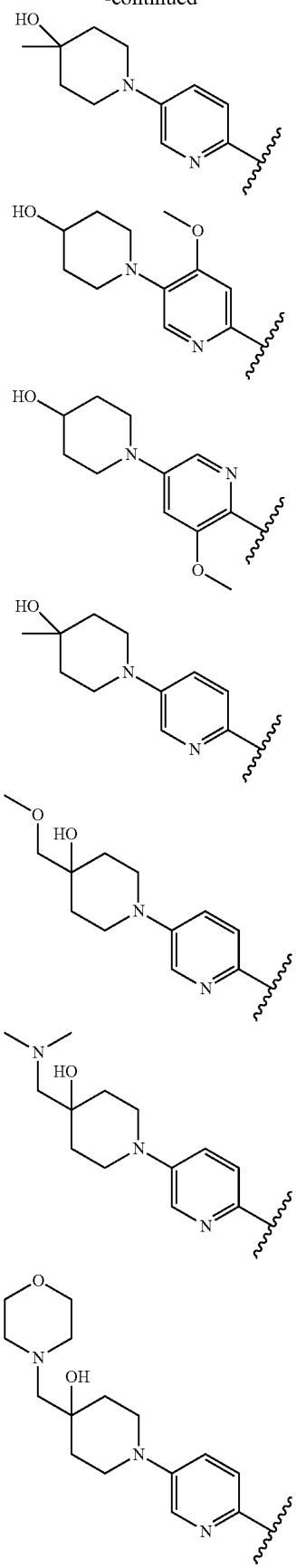
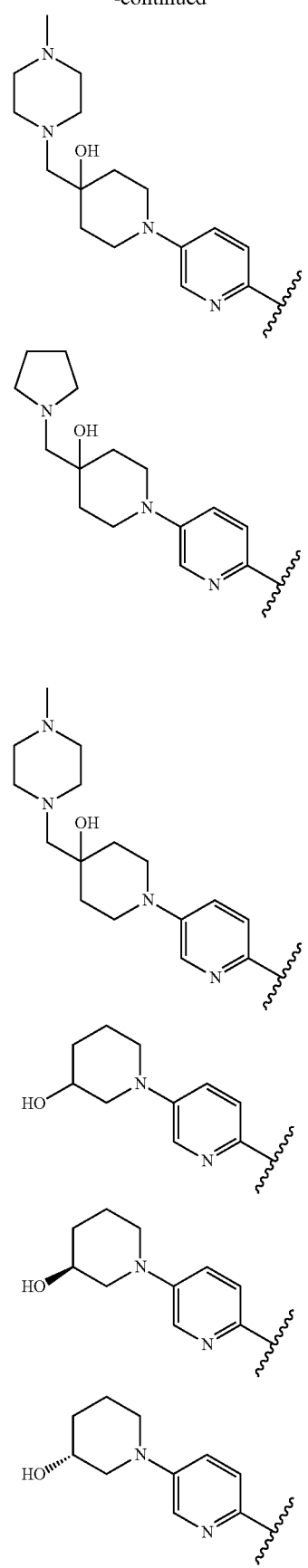

-continued
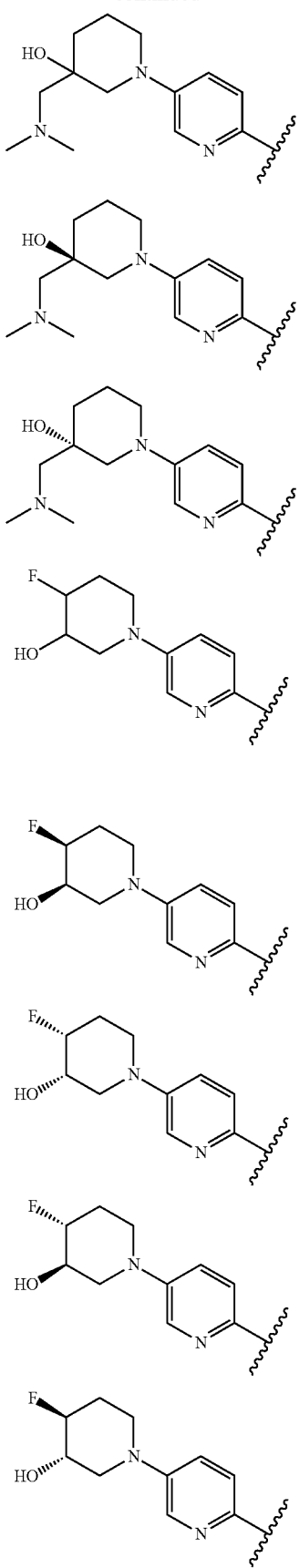
-continued
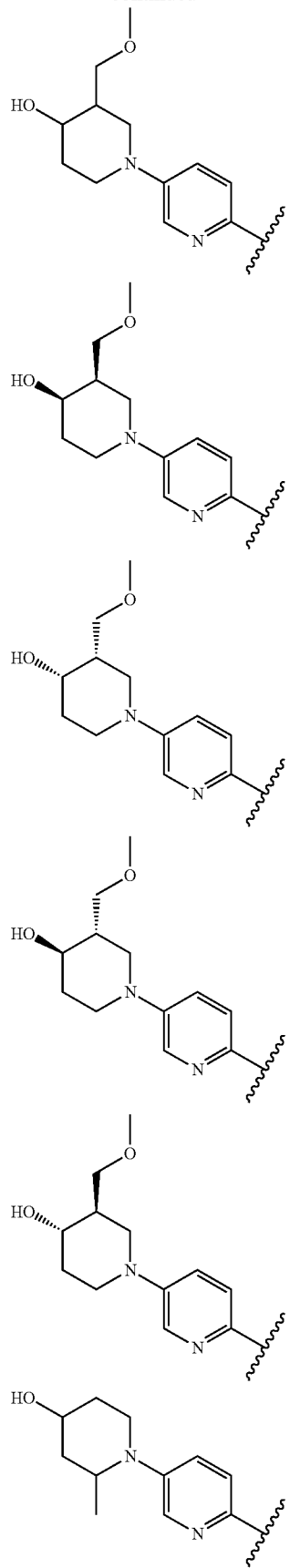

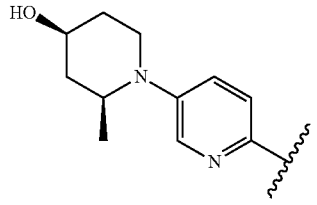
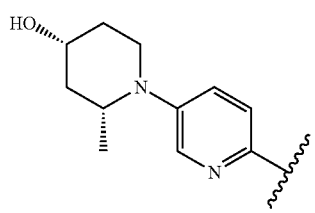
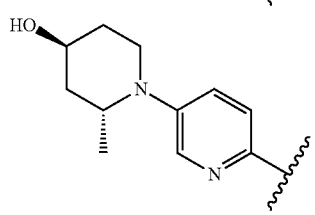
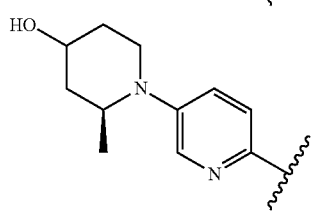
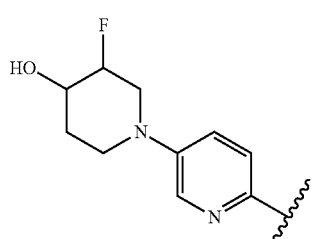
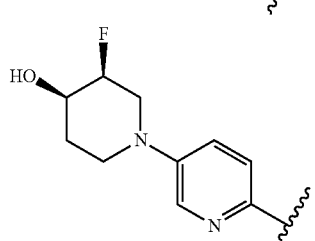
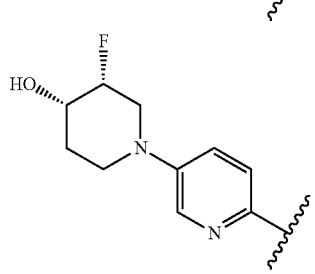
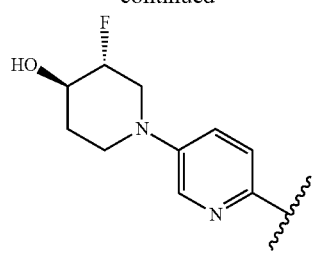
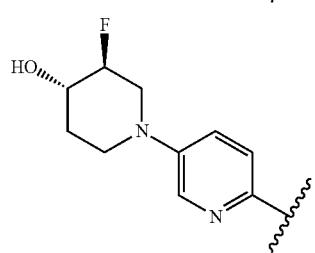
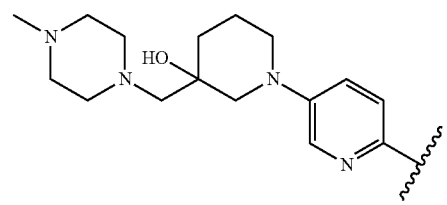
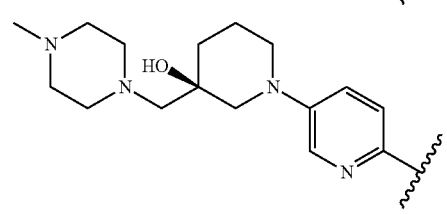
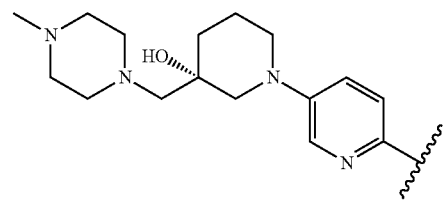
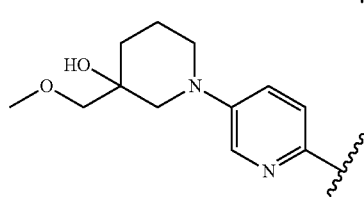
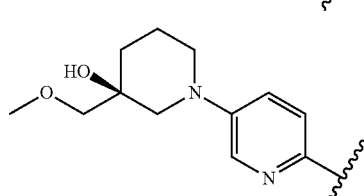
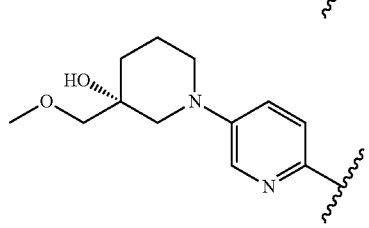

-continued
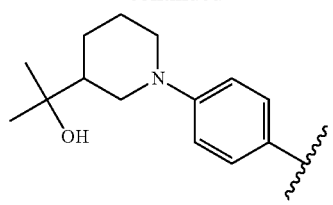
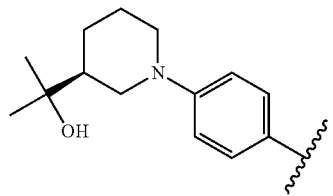
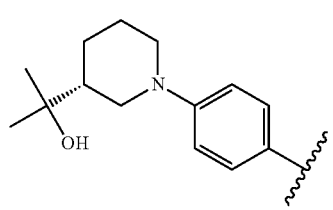
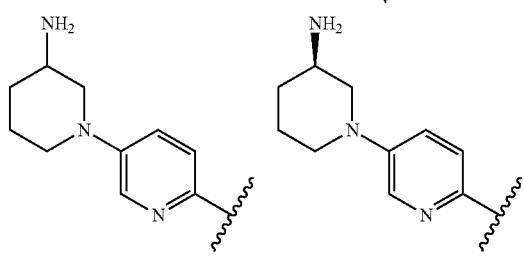
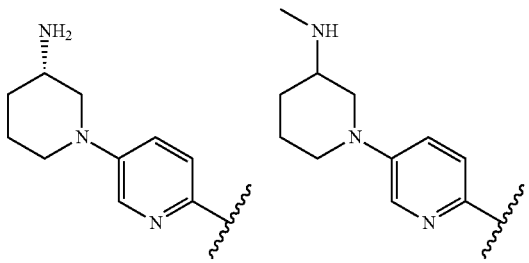
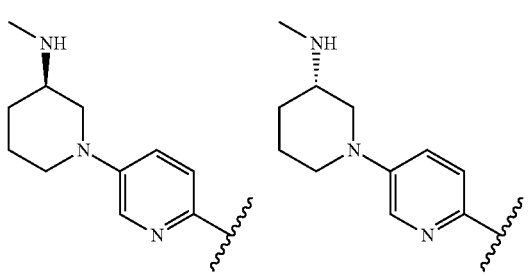
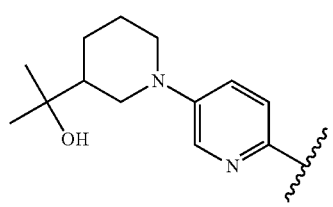
-continued
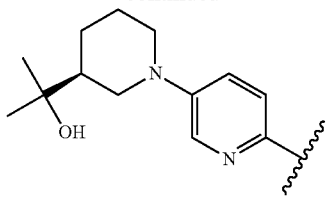
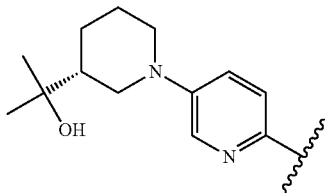
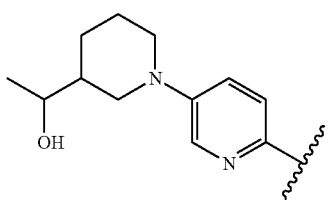
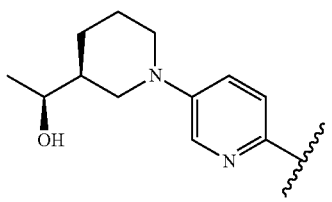
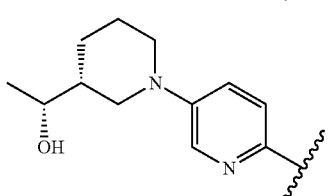
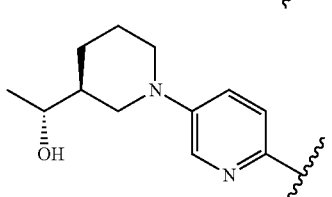
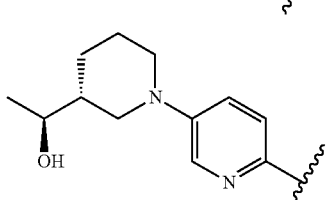
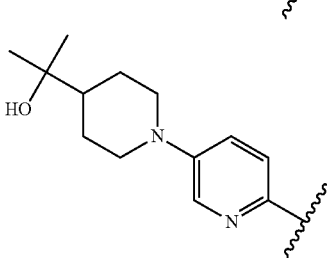

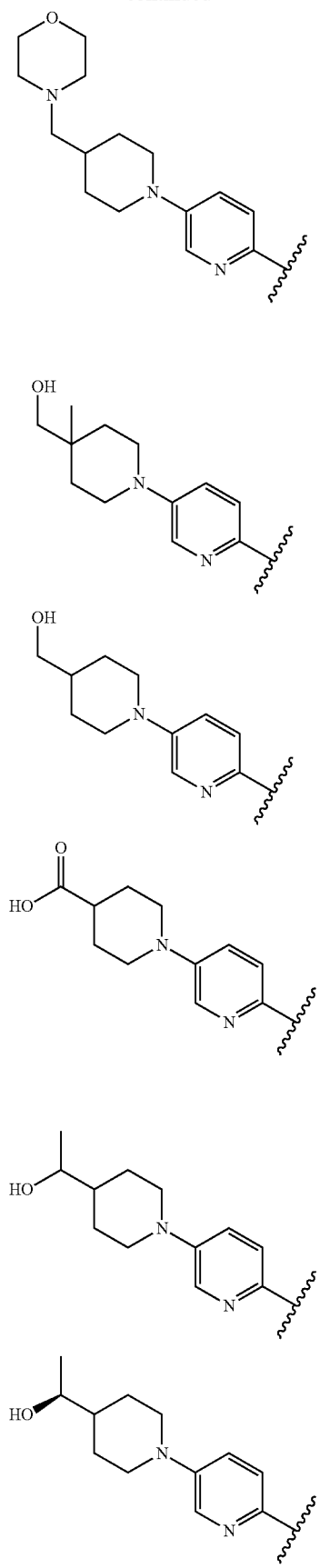
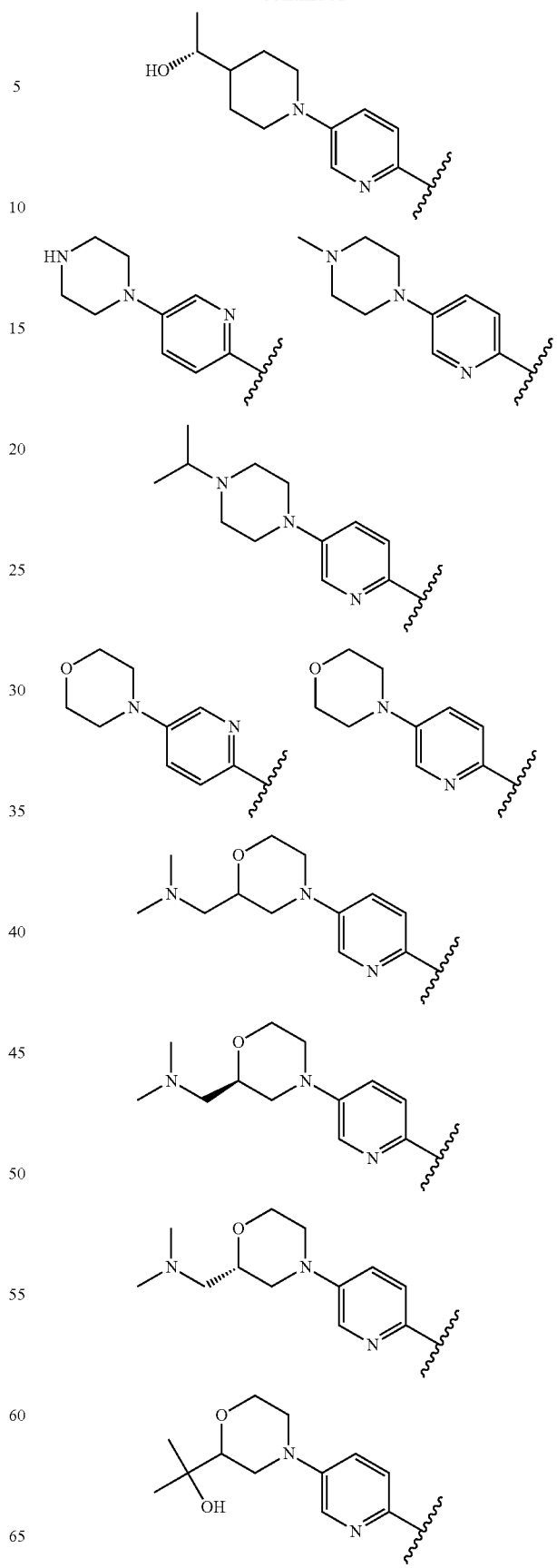

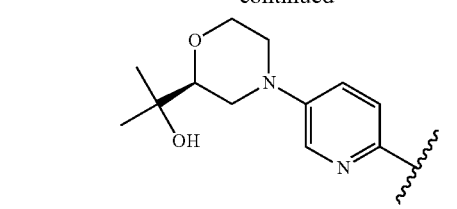
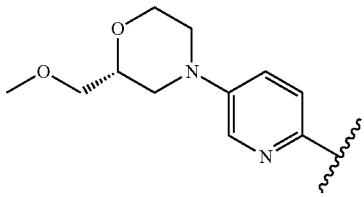
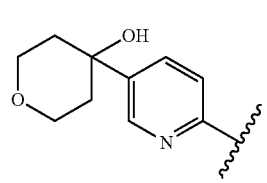 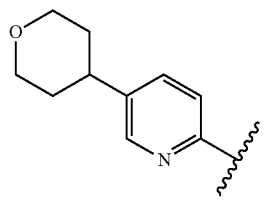
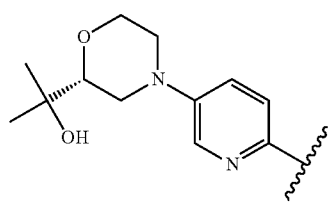
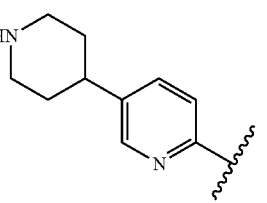 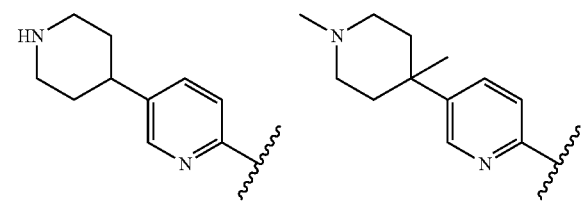
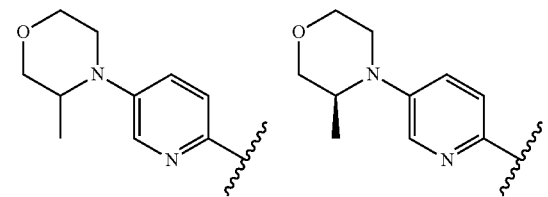
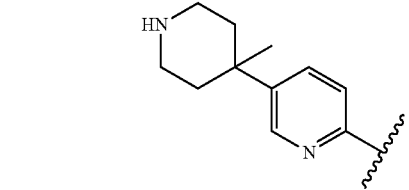
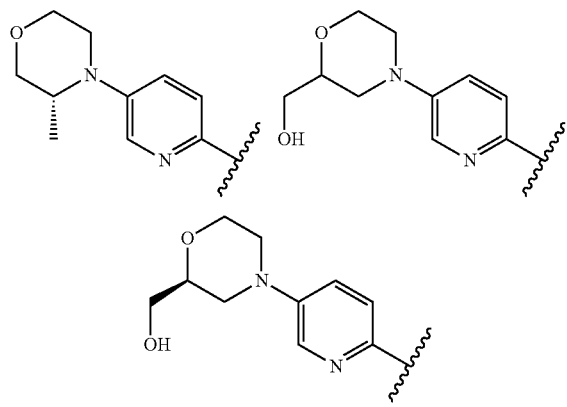
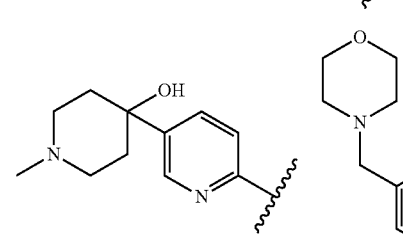
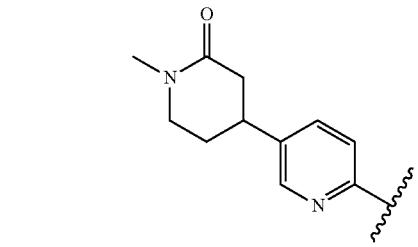
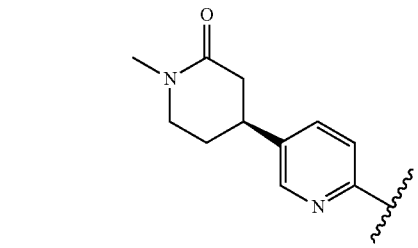

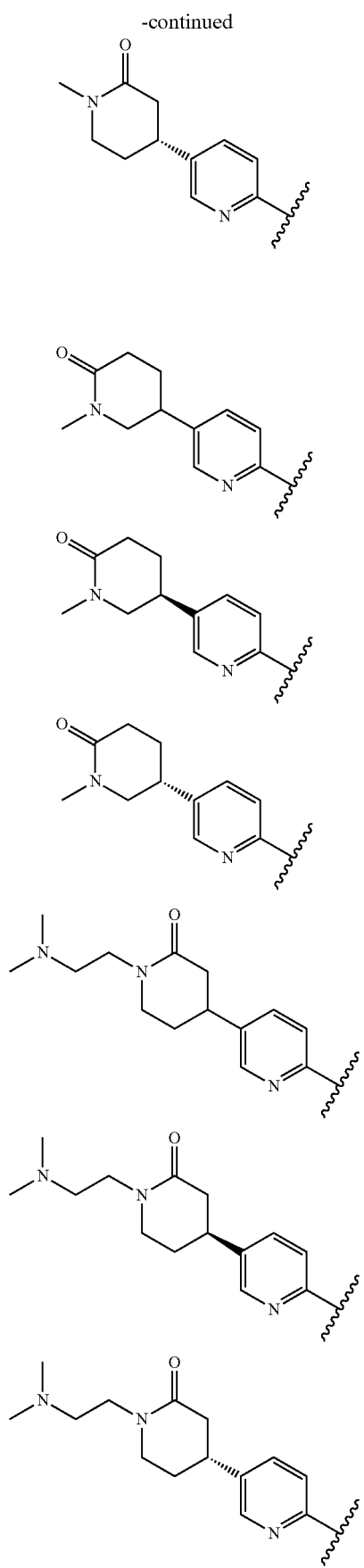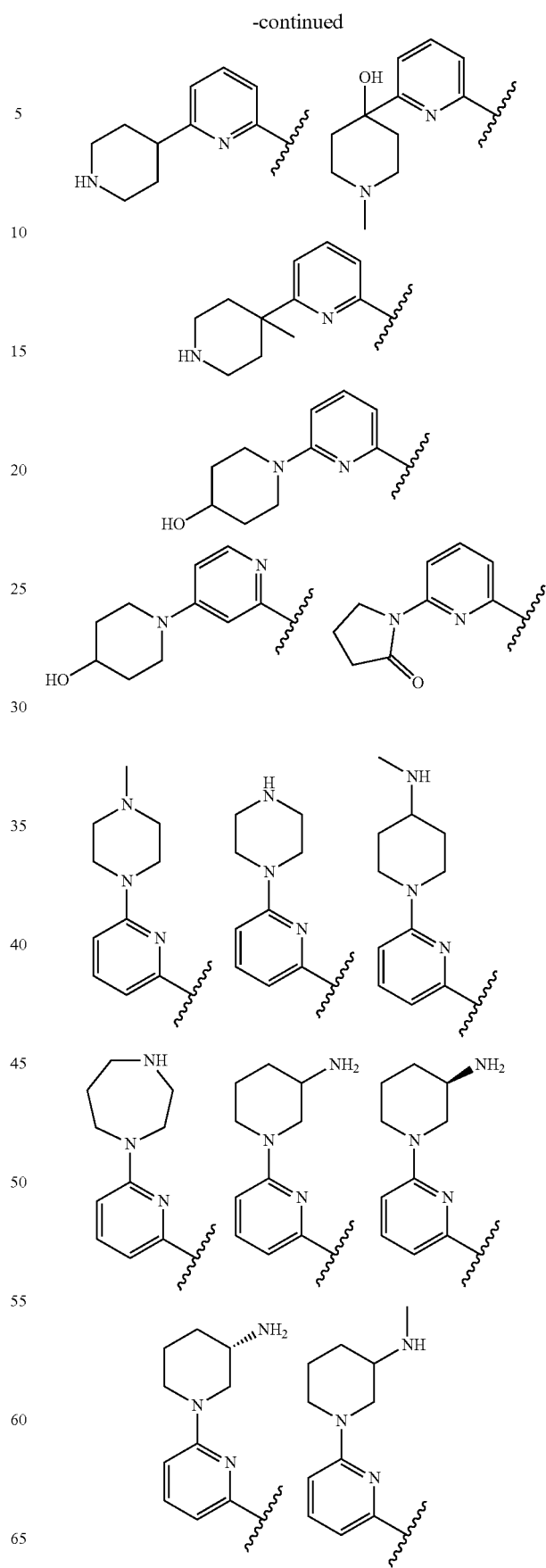

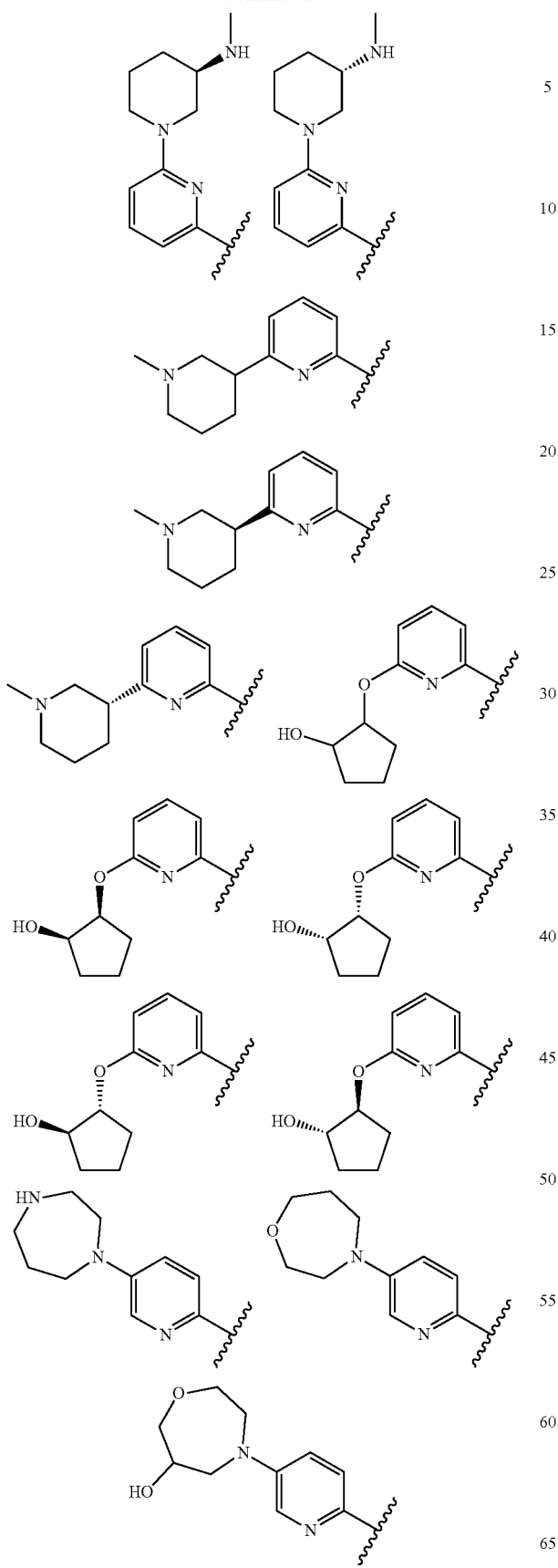
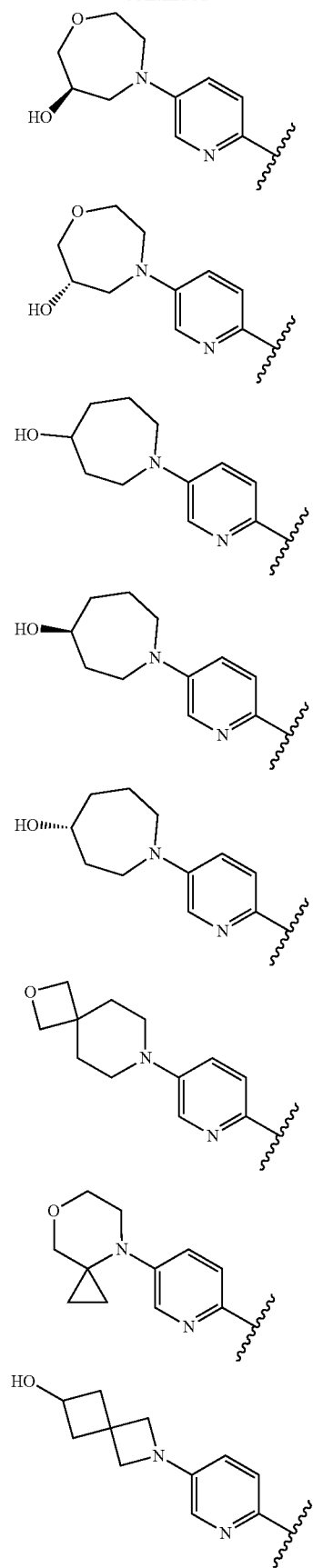

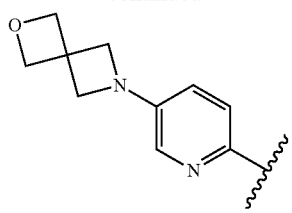
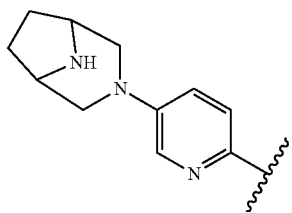
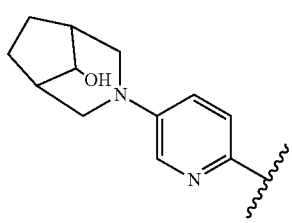
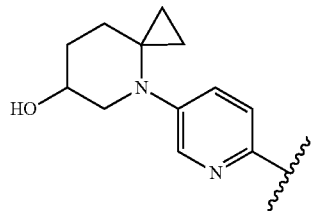
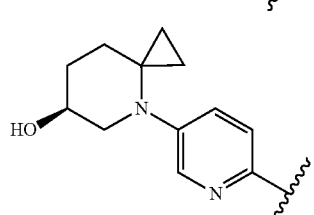
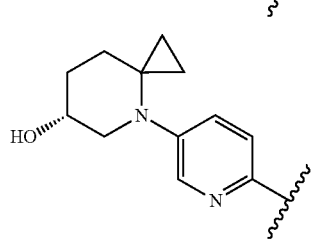
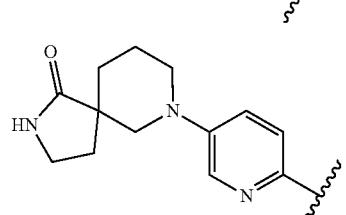
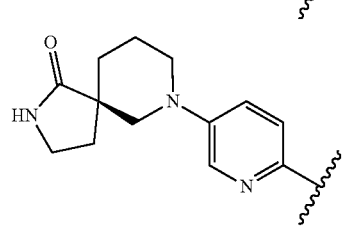
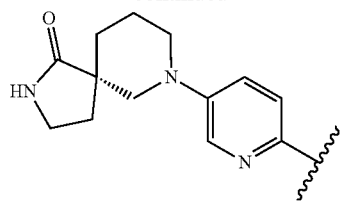
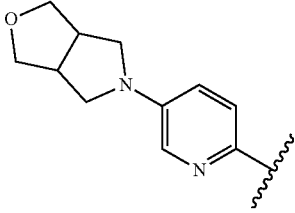
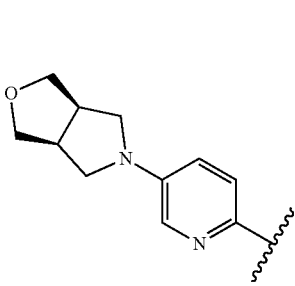
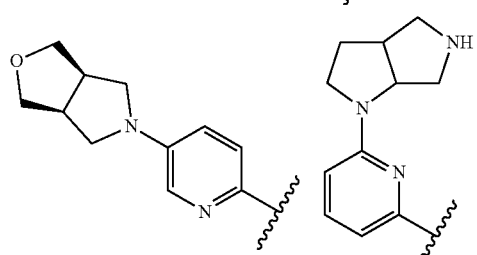
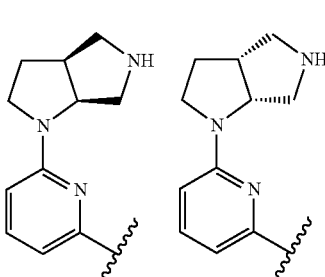
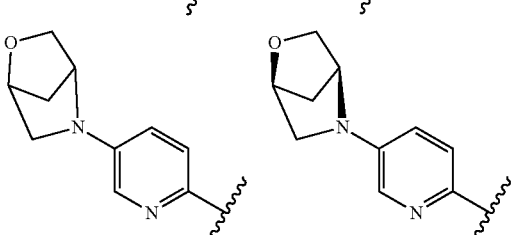
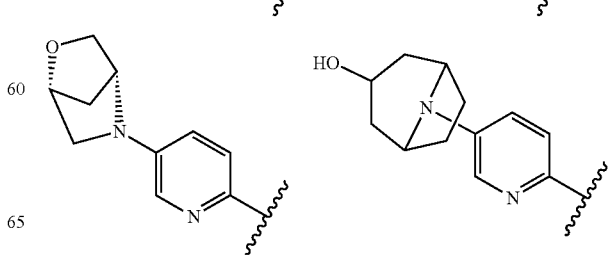

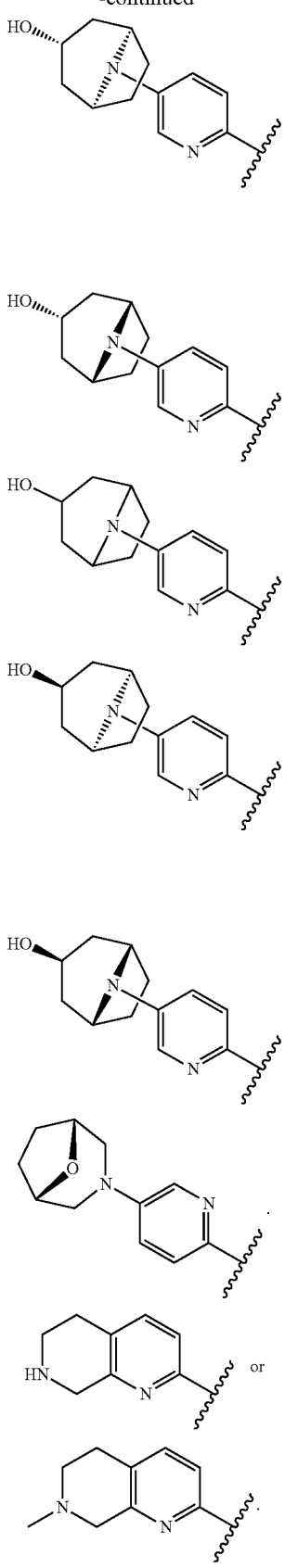
In certain embodiments, $R^1$ together with its $R^C$ substituents is
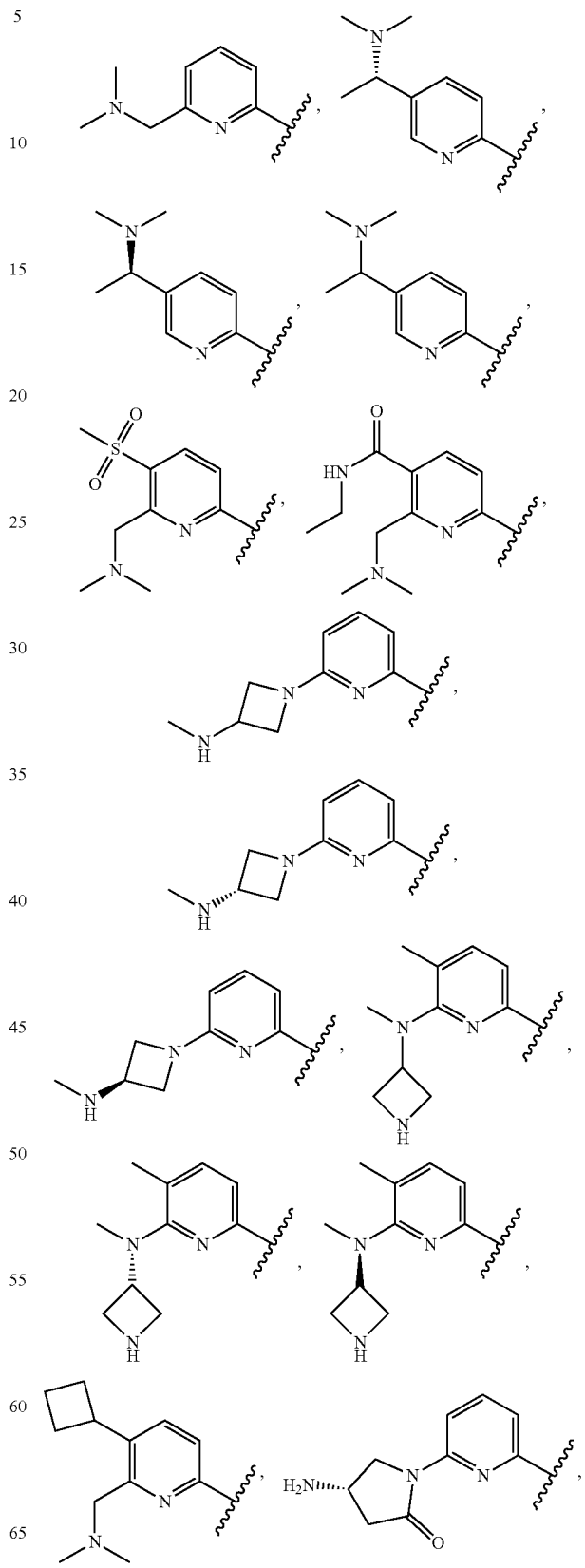

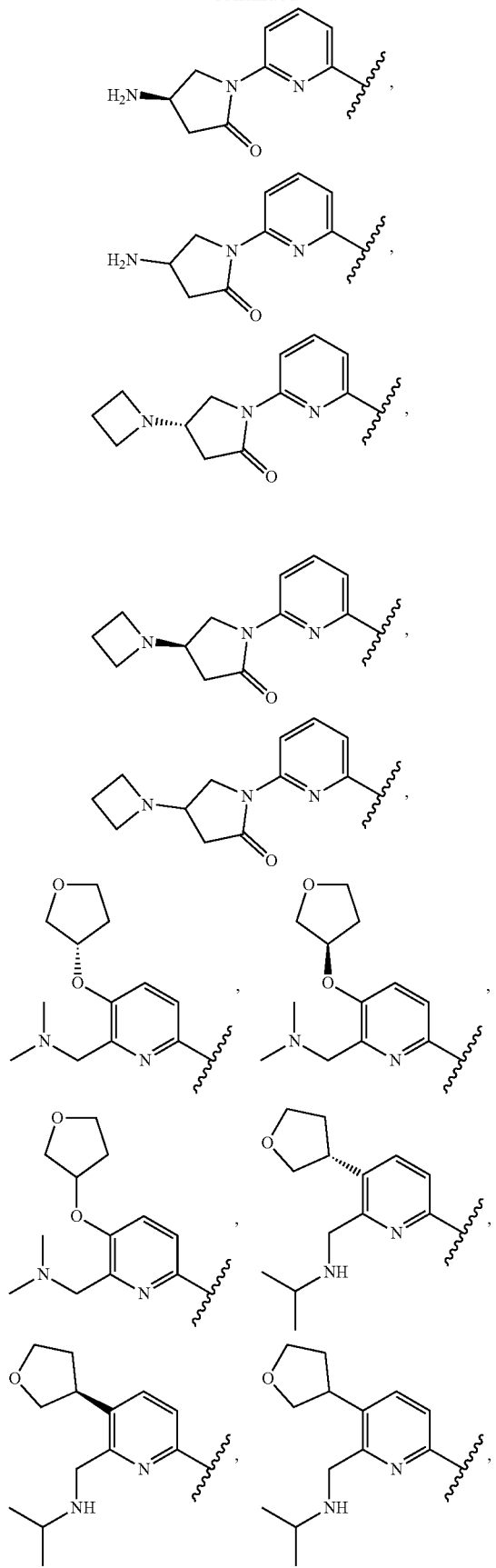
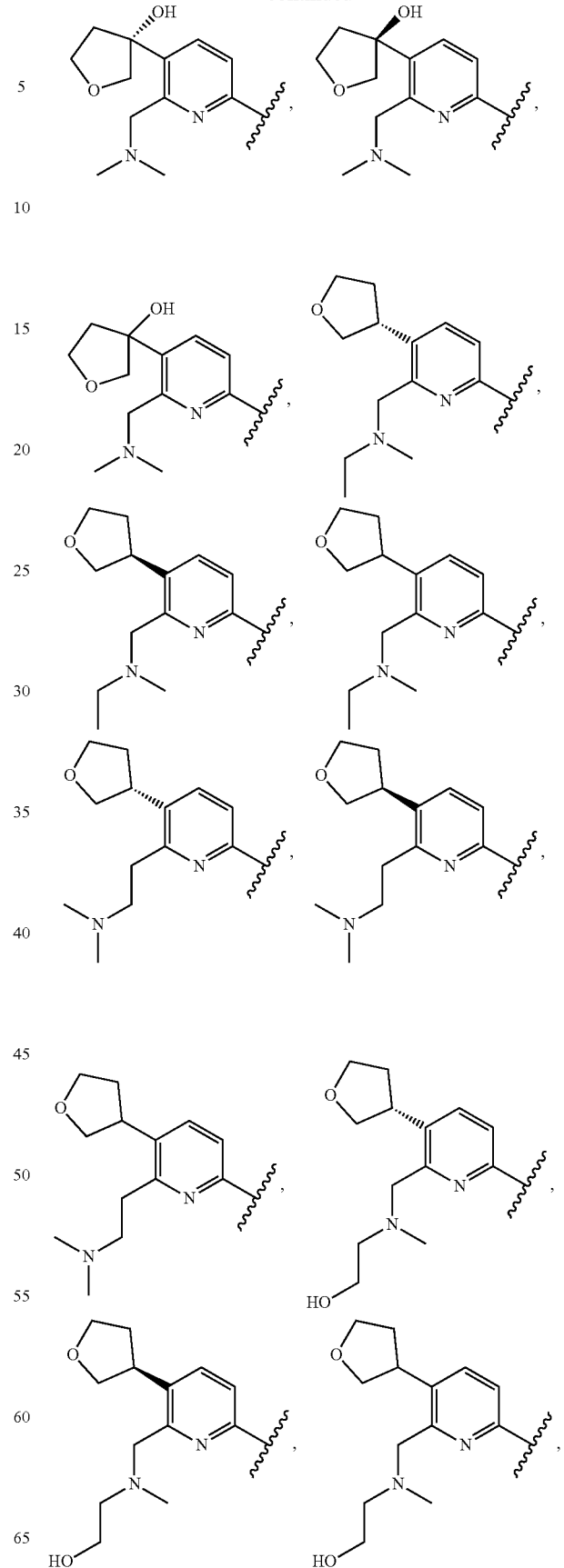

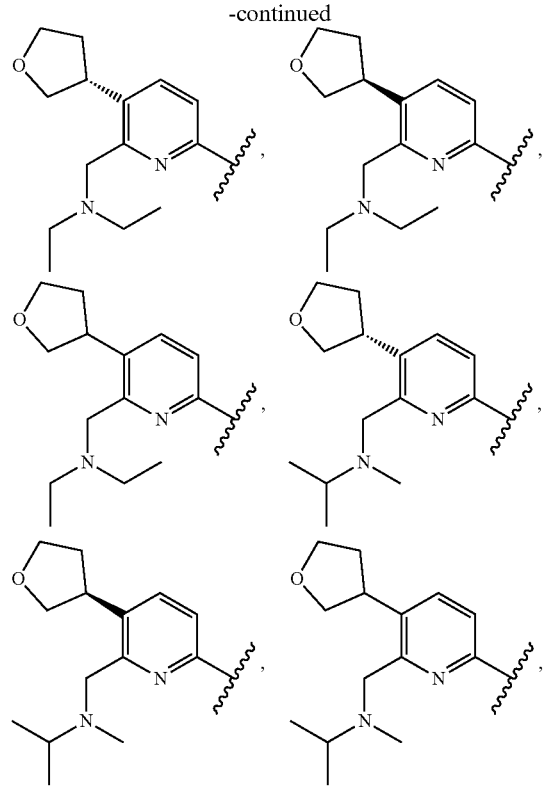
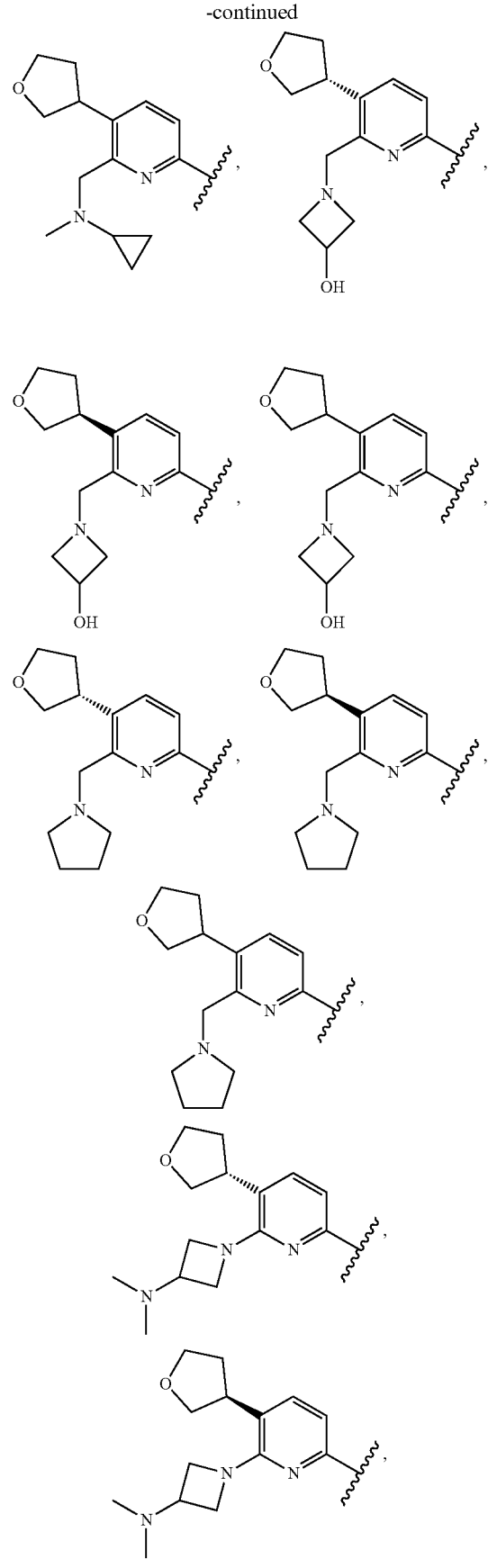

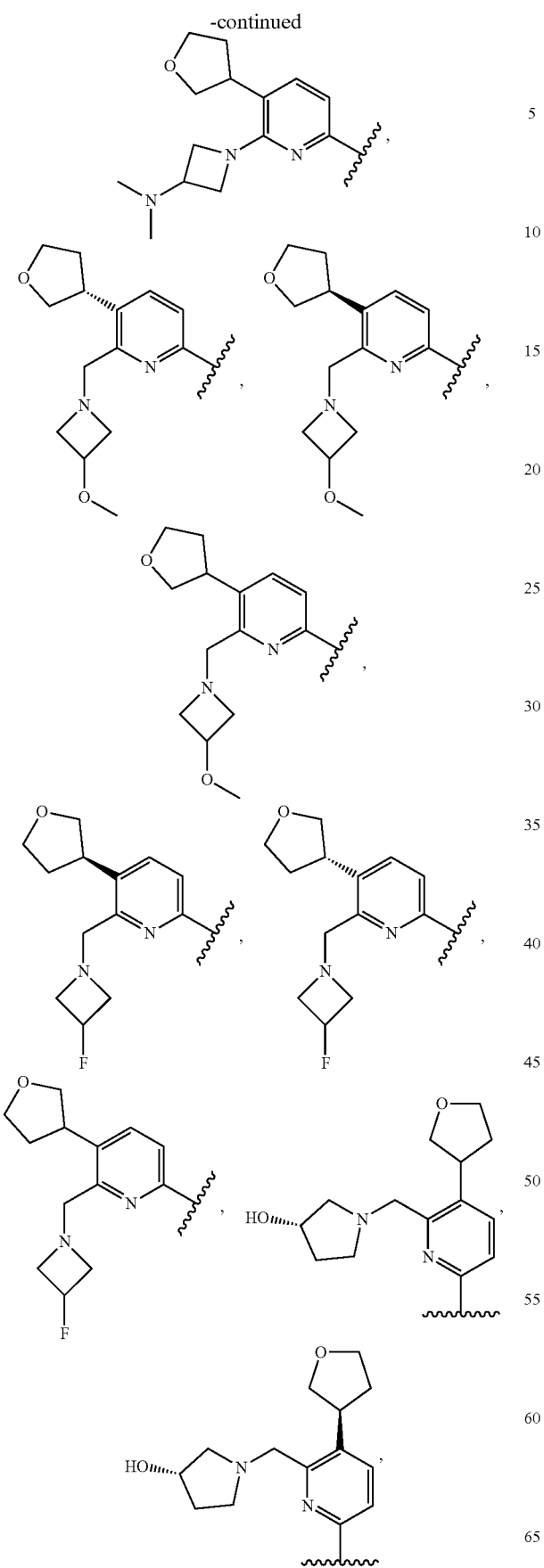
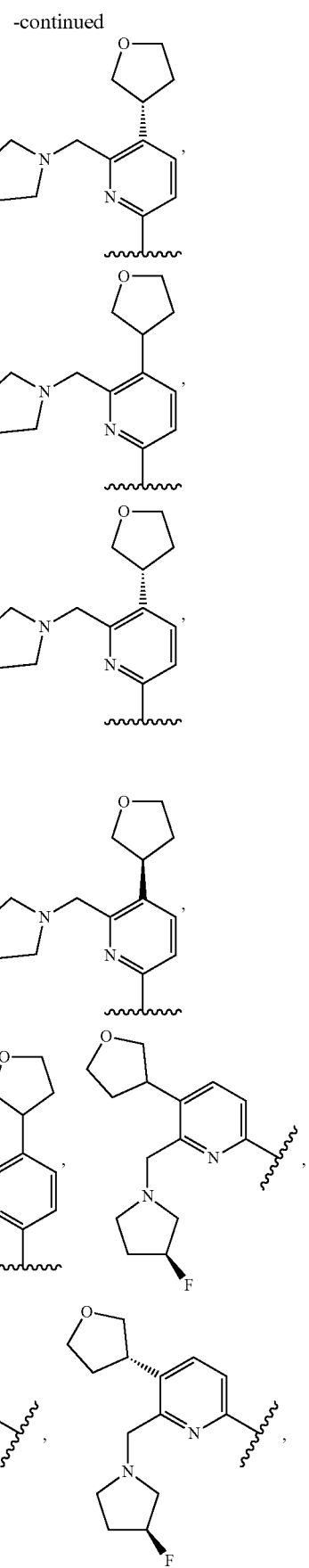

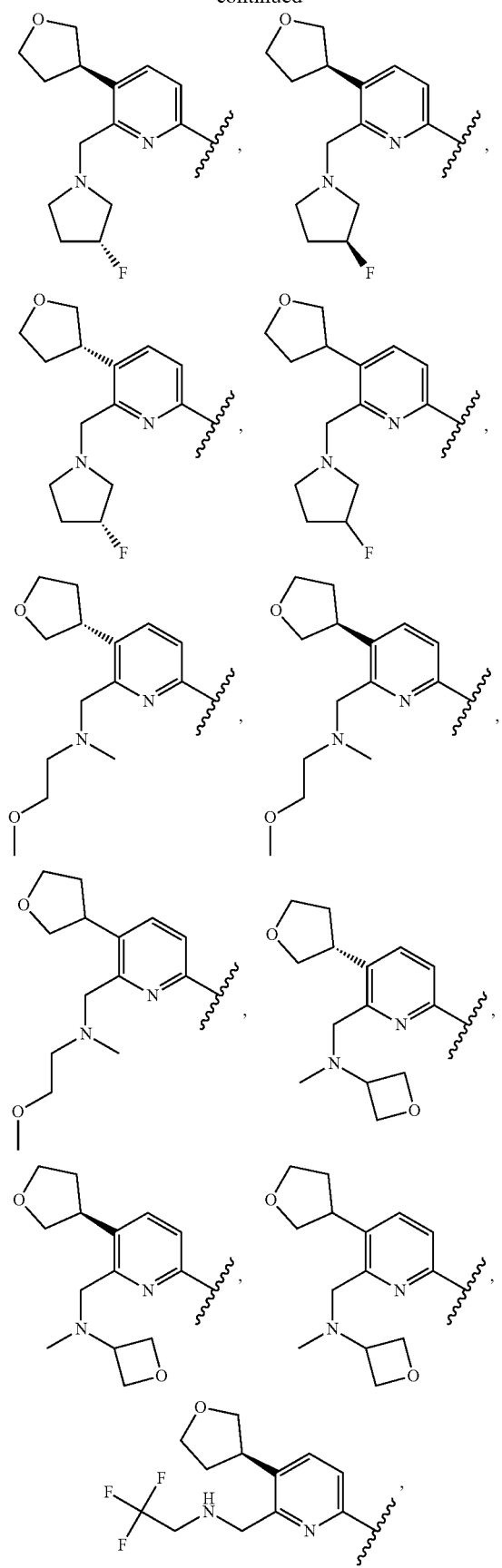
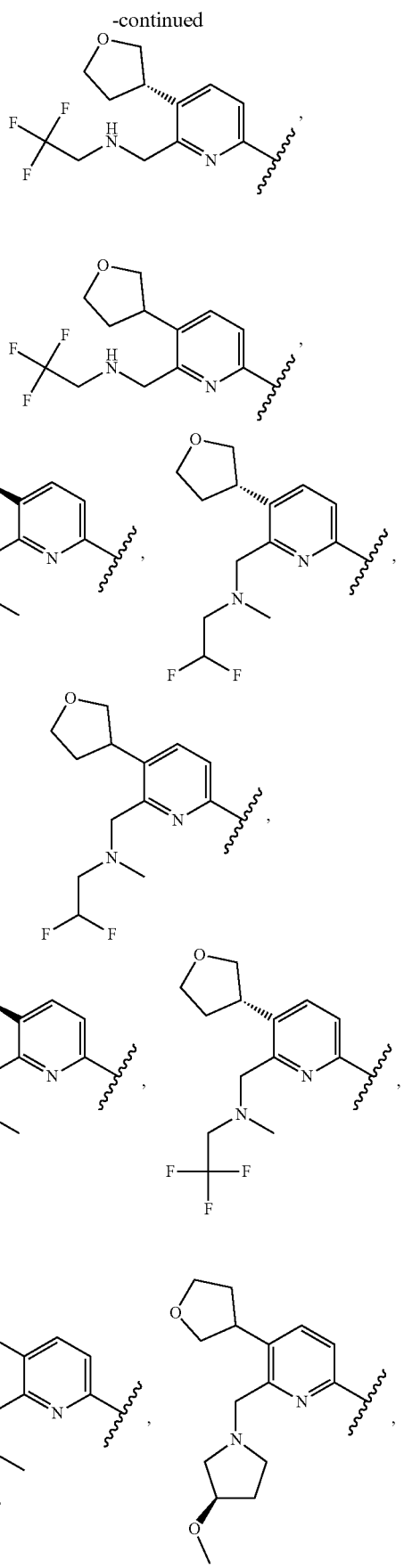

51
-continued
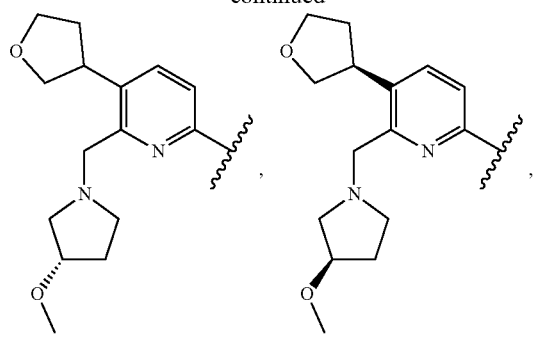
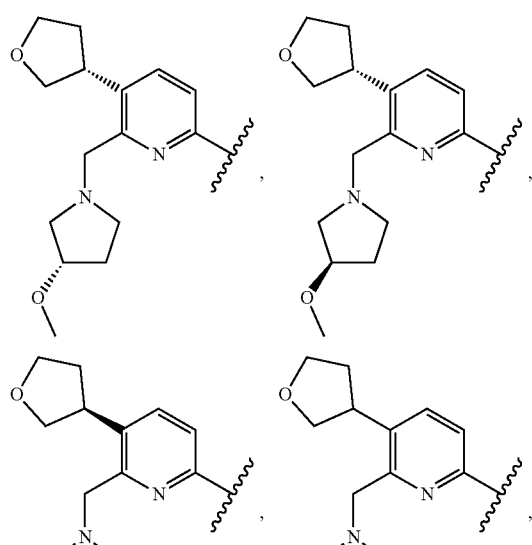
52
-continued
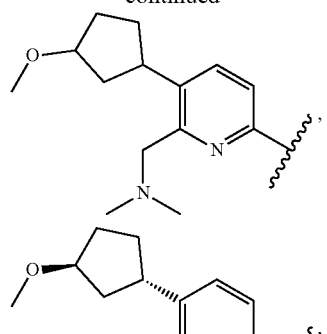
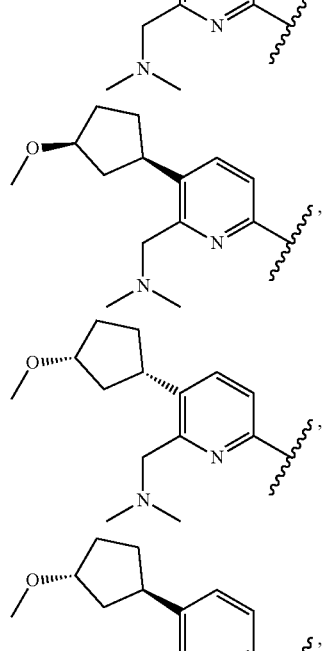
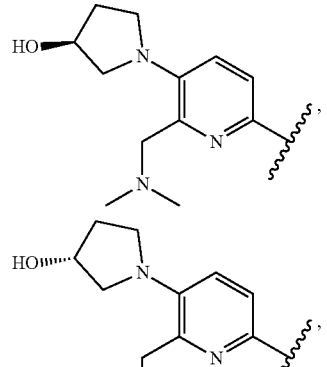
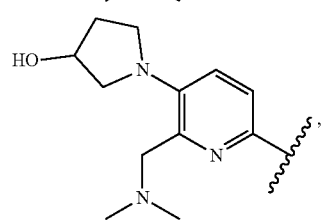

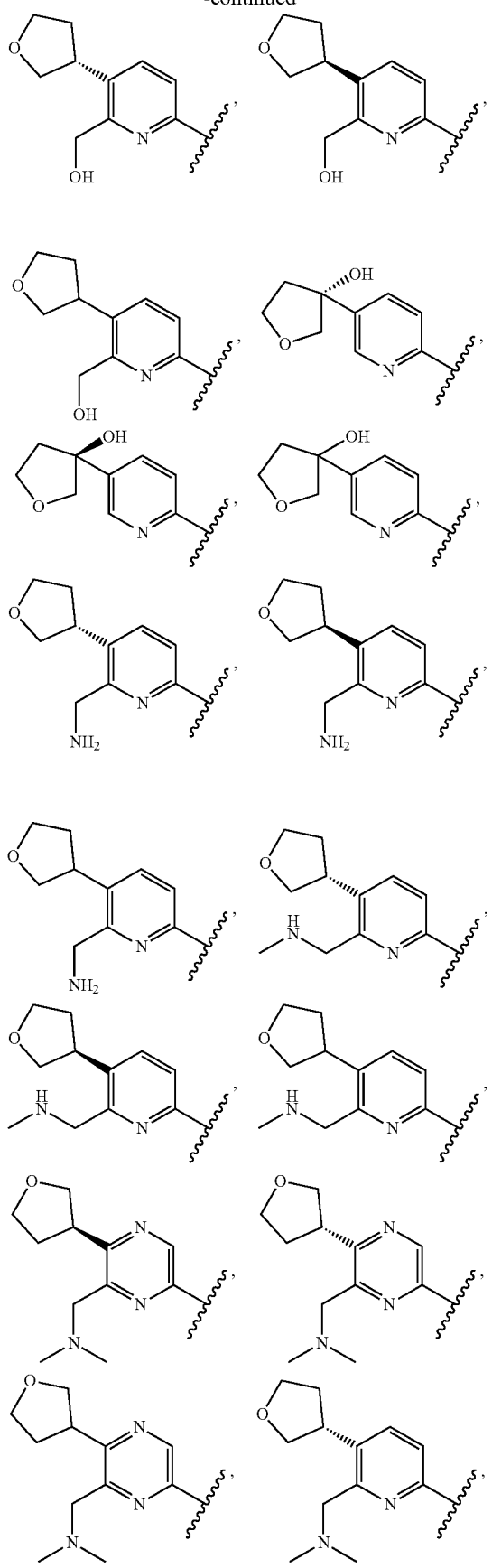
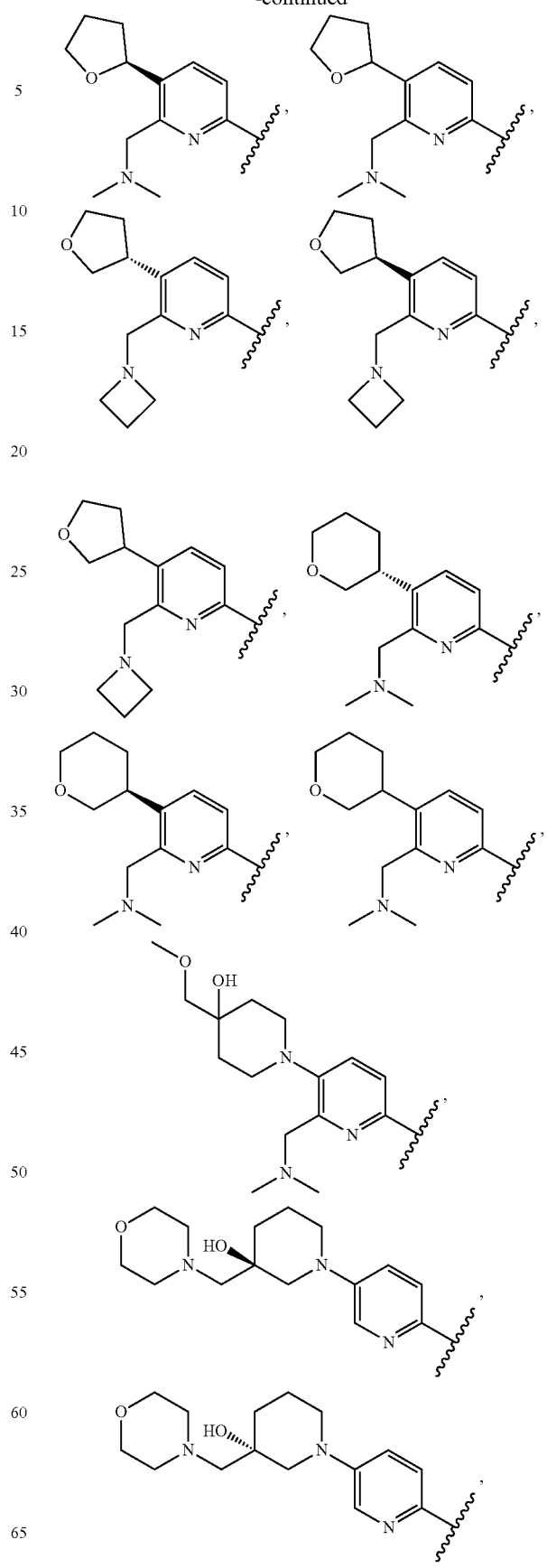

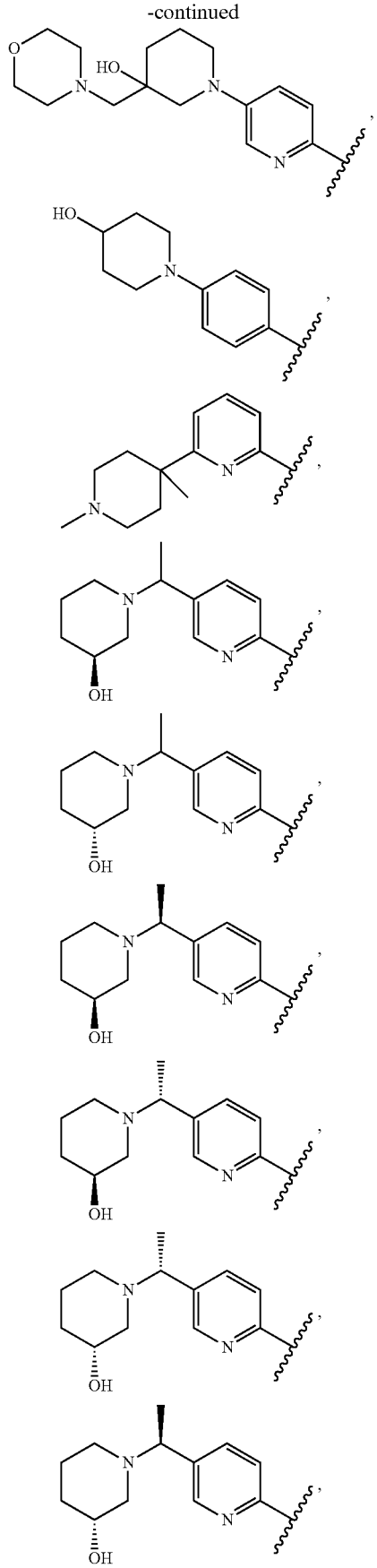
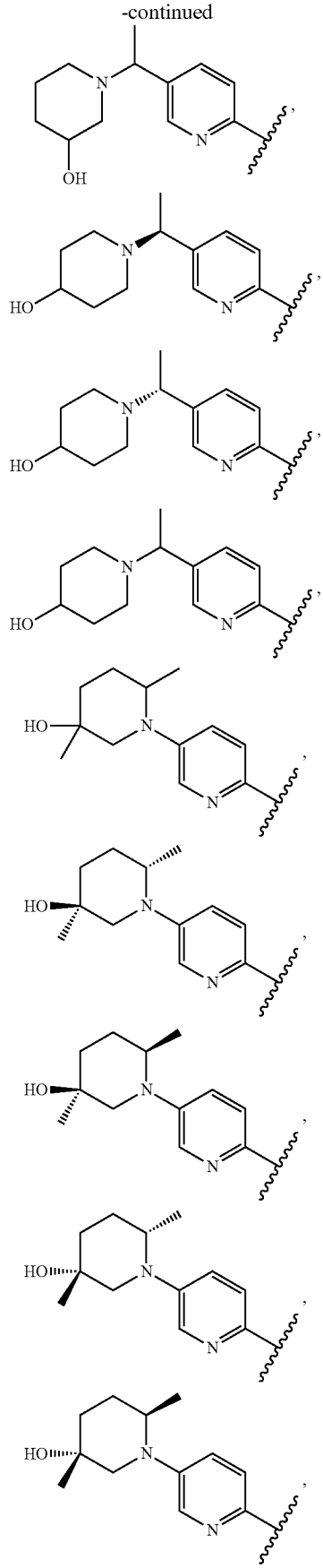

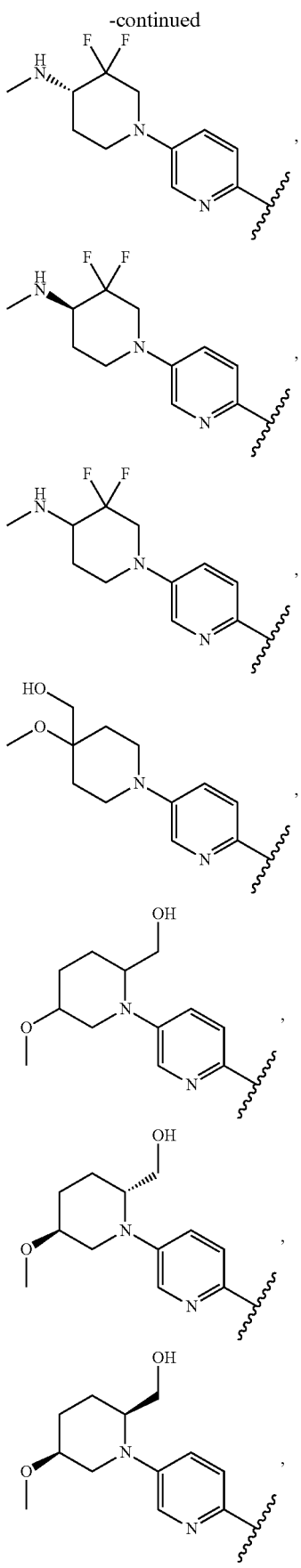
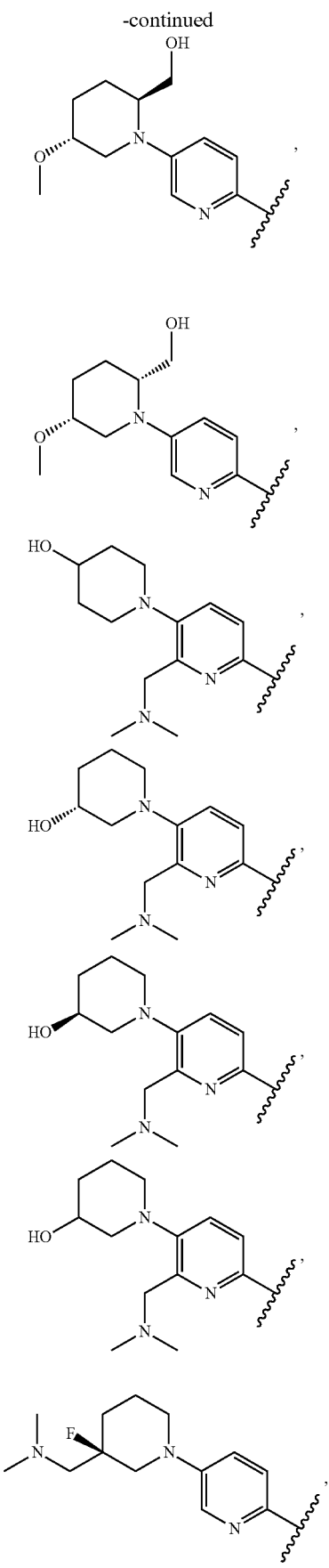

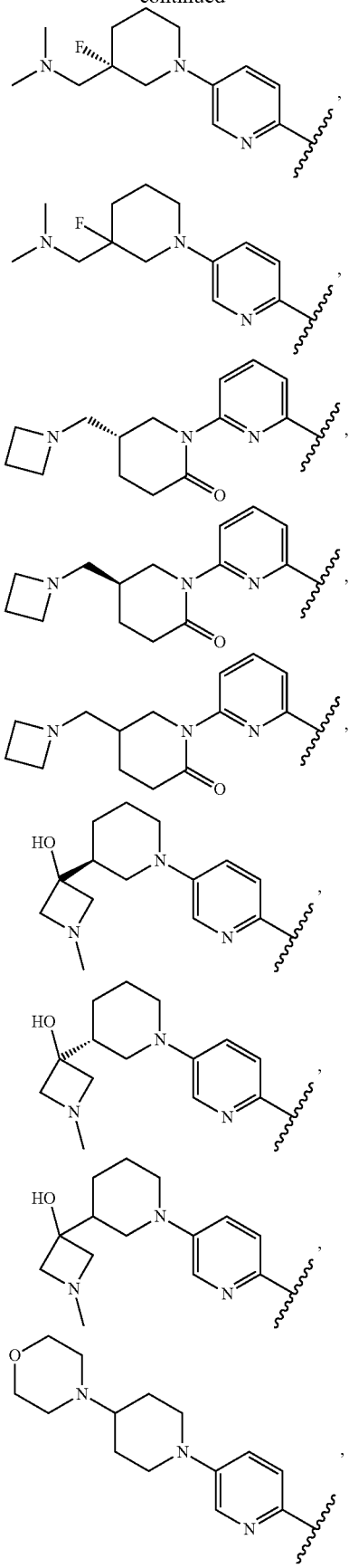
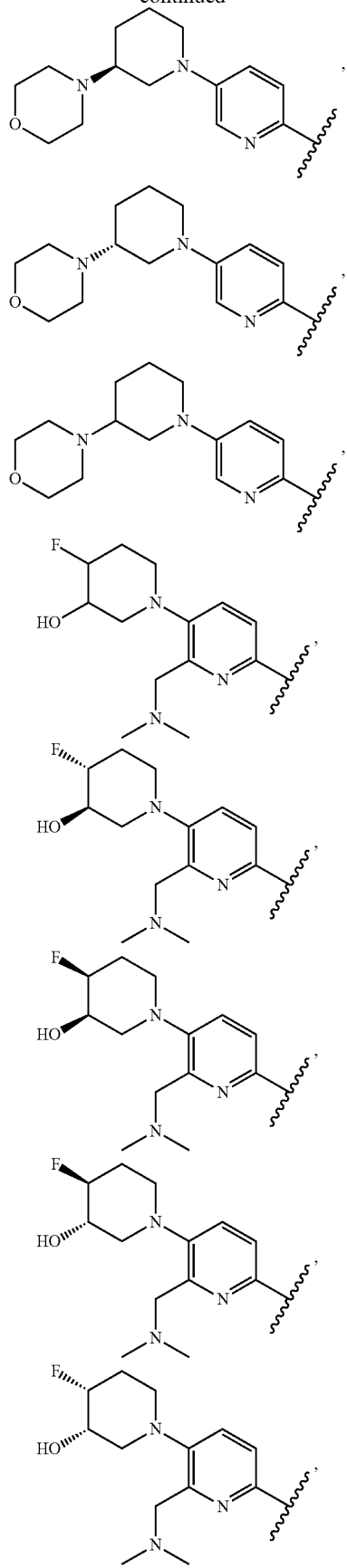

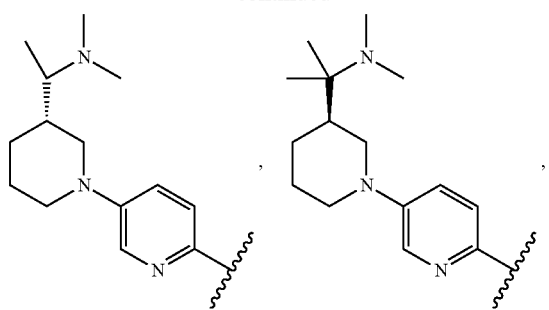
,
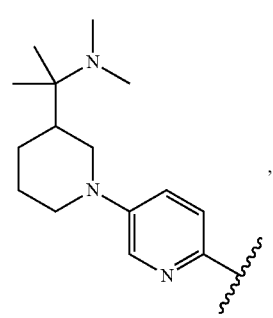
,
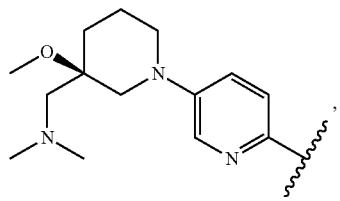
,
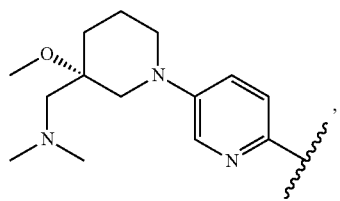
,
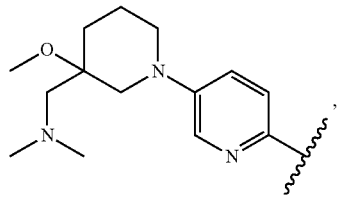
,
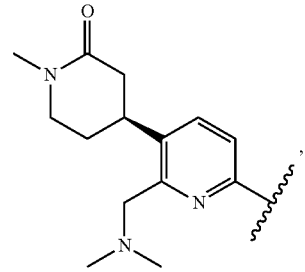
,
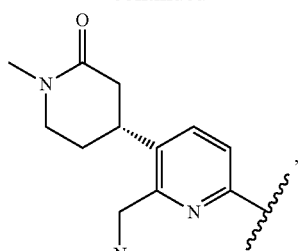
,
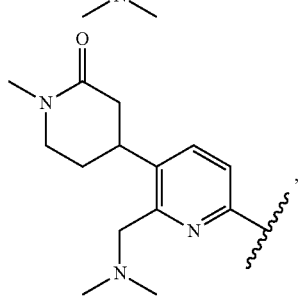
,
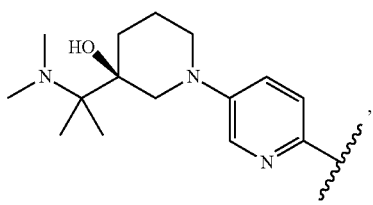
,
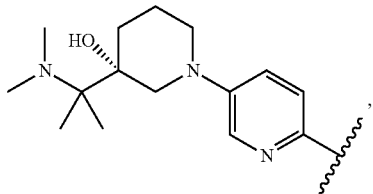
,
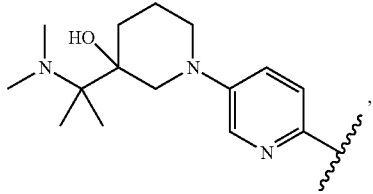
,
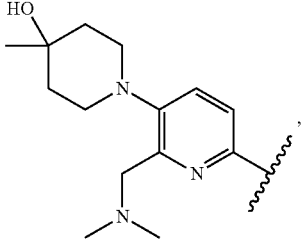
,
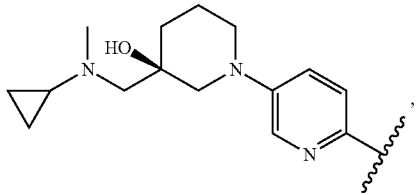
,

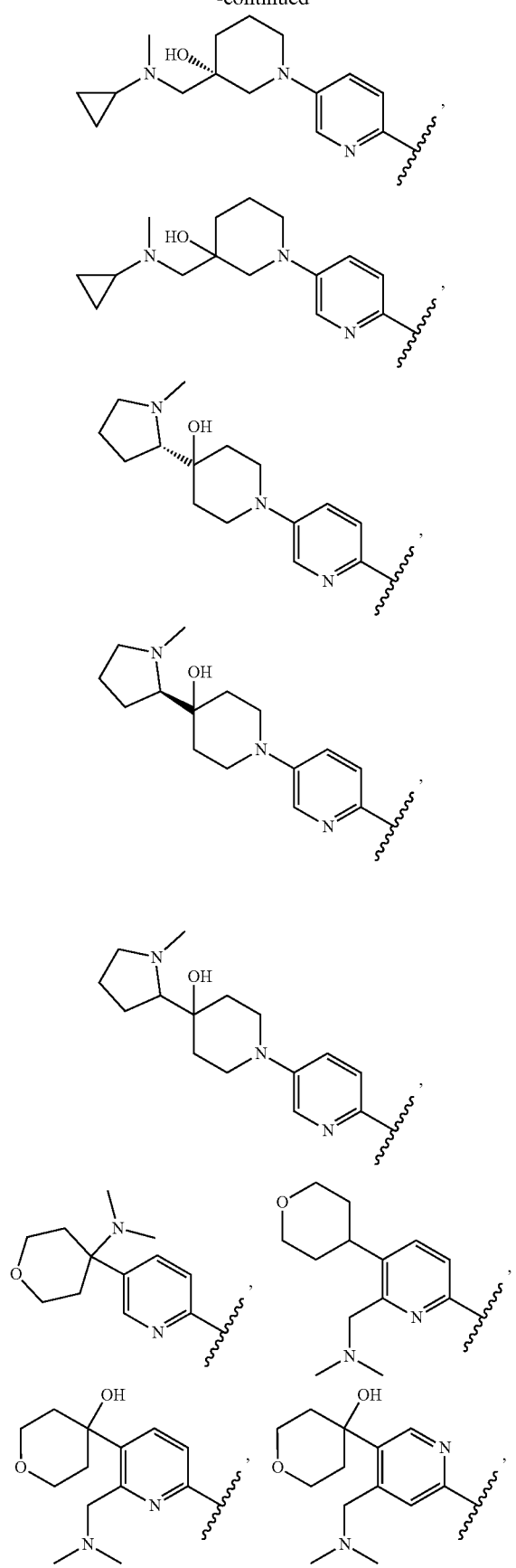
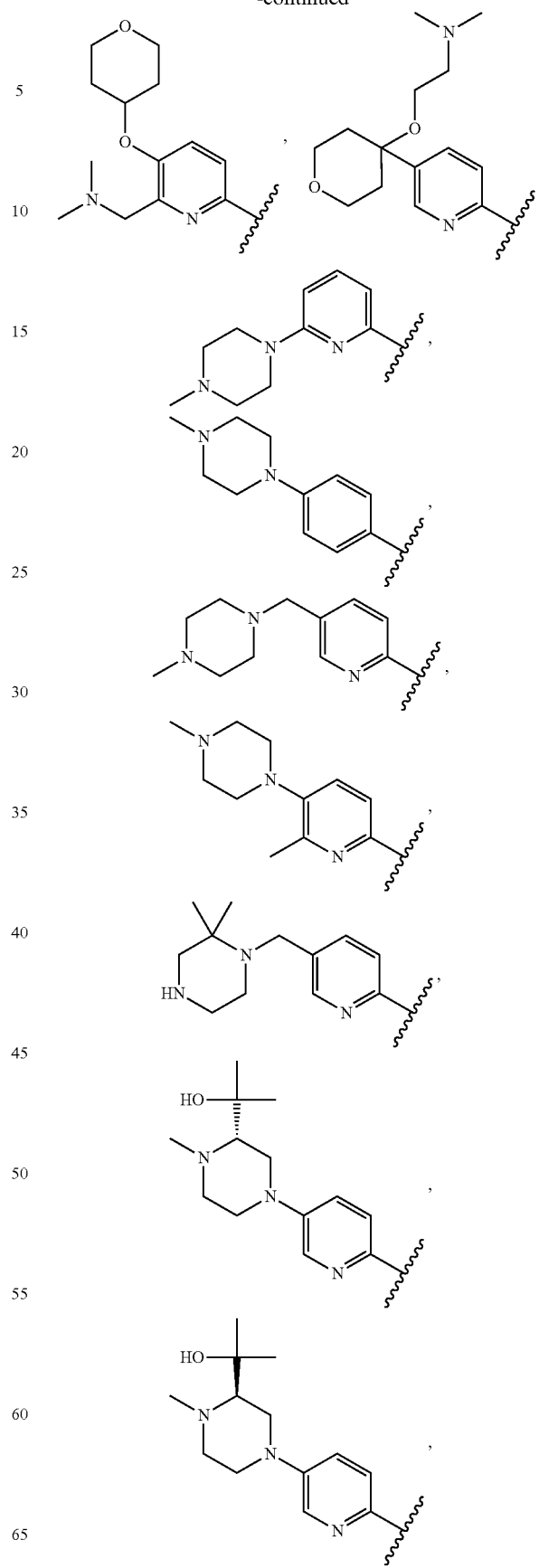

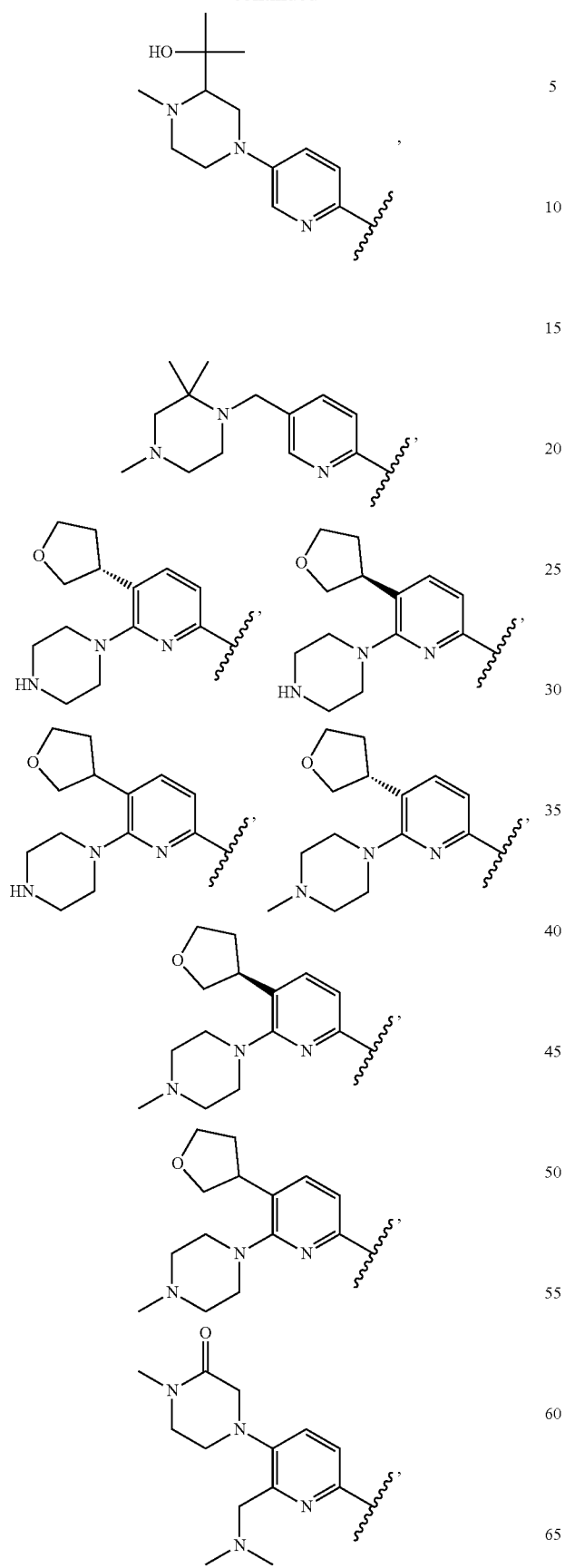
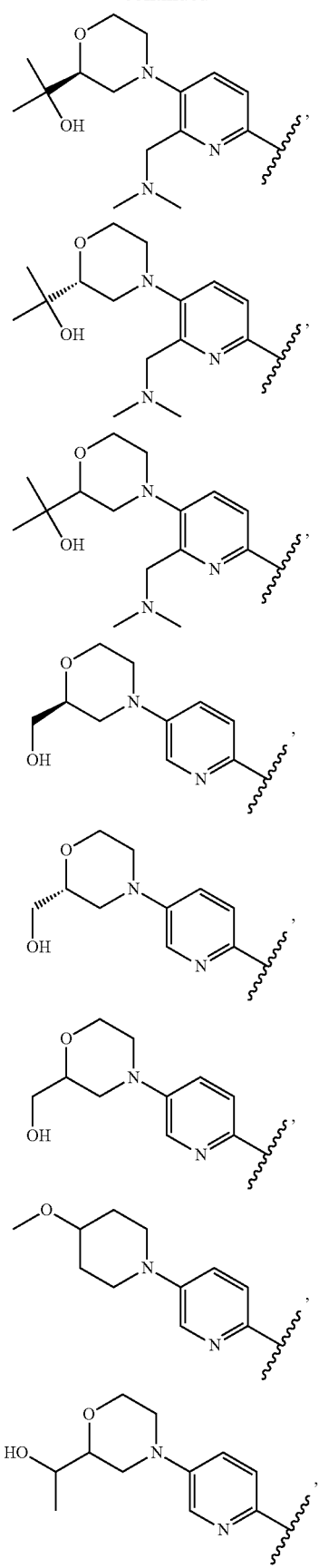

-continued
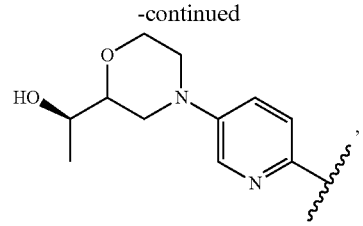,
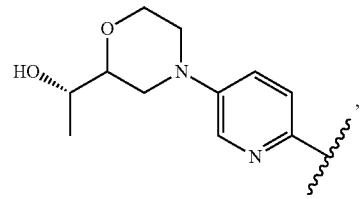,
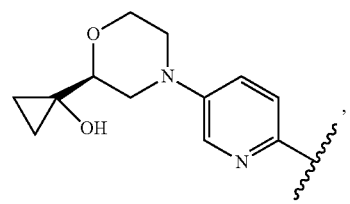,
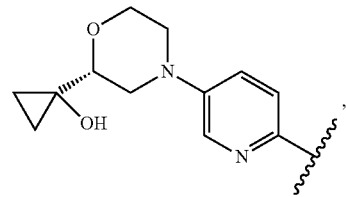,
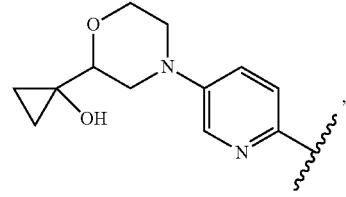,
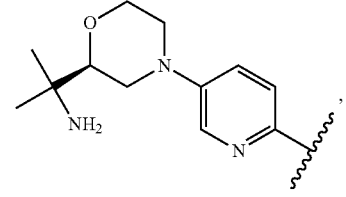,
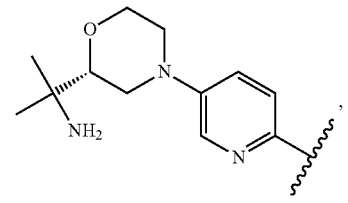,
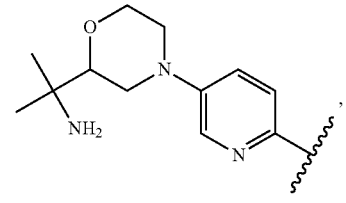,
-continued
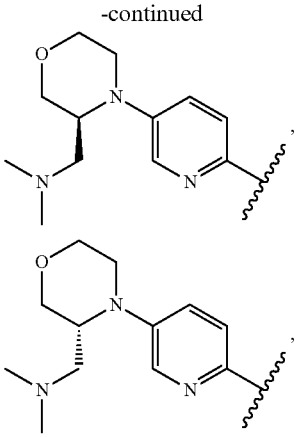,
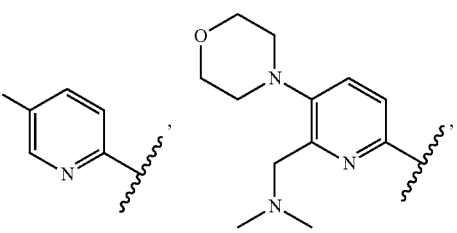,
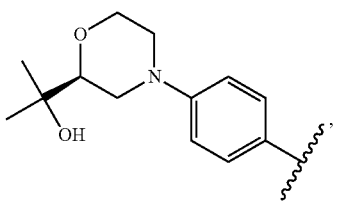,
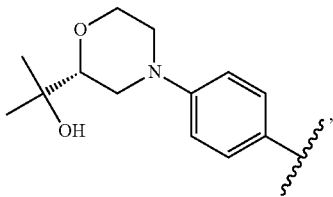,
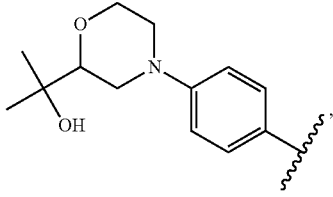,
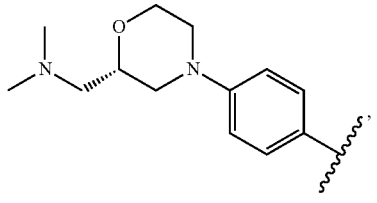,
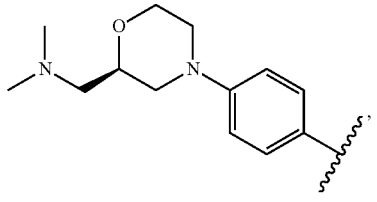,

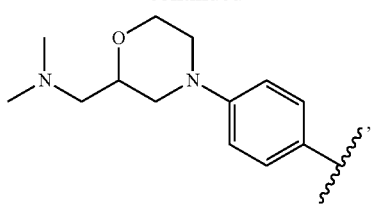
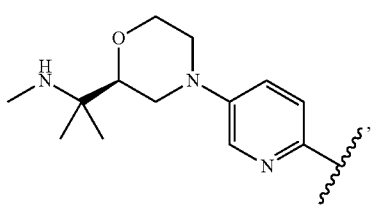
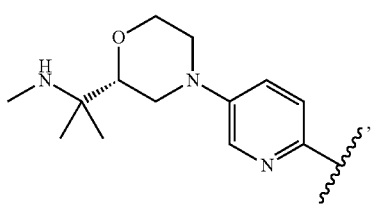
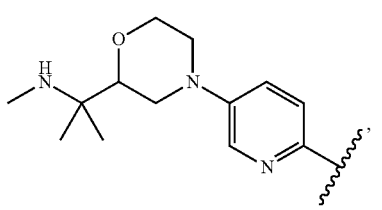

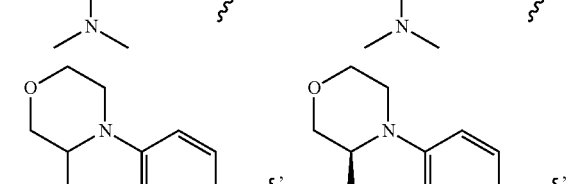
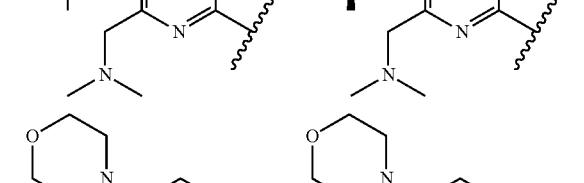
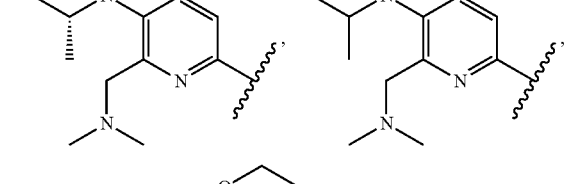
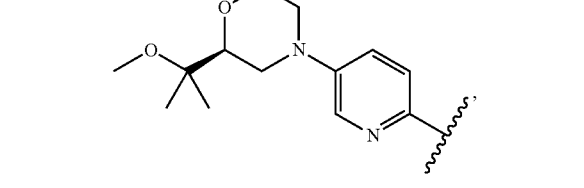
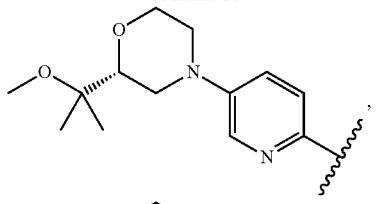
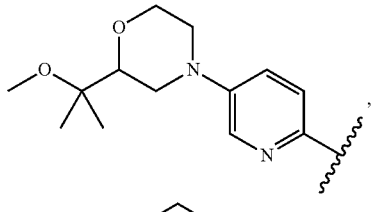
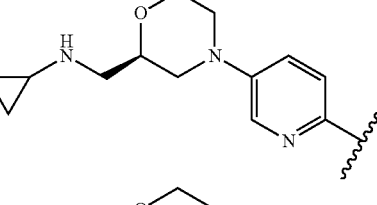
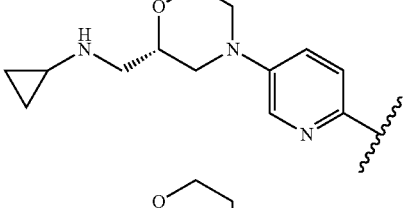
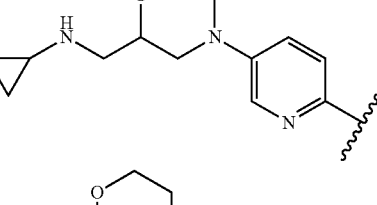
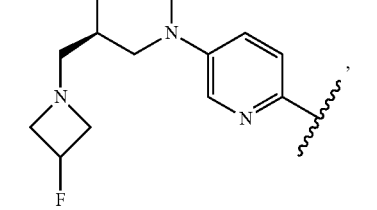
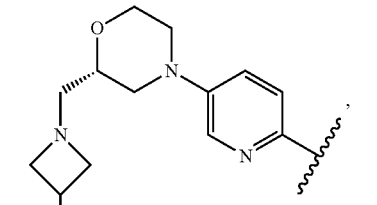
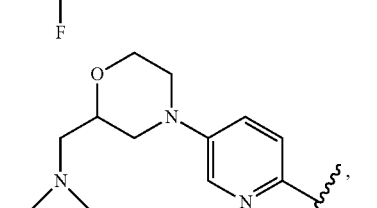

-continued
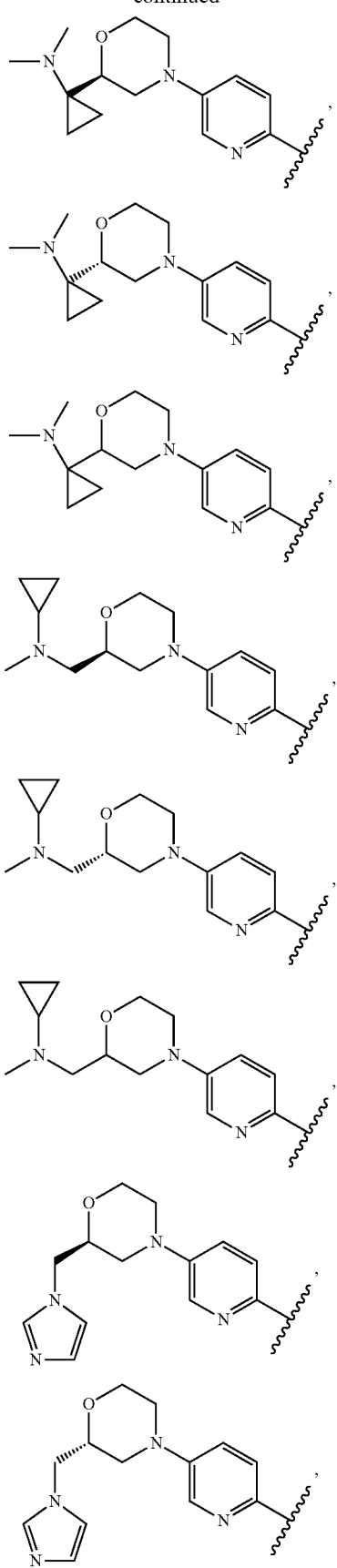
-continued
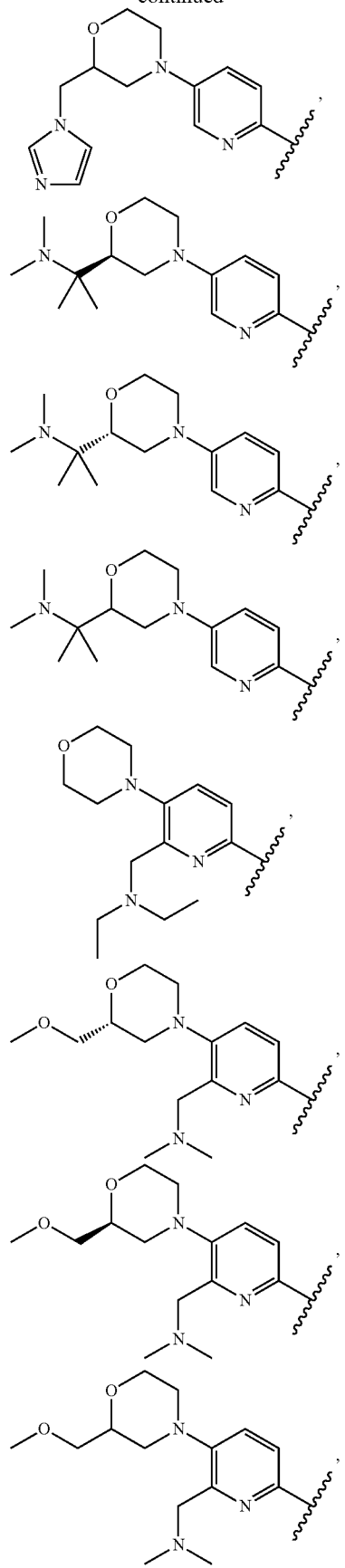

-continued

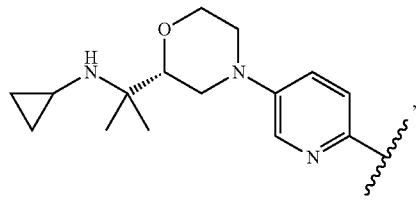
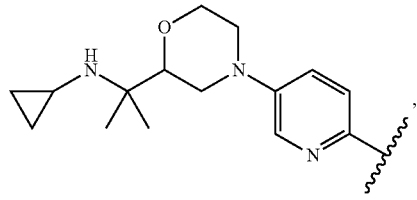
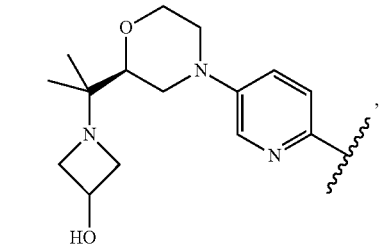
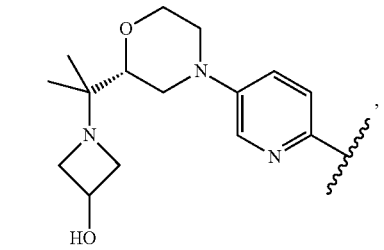
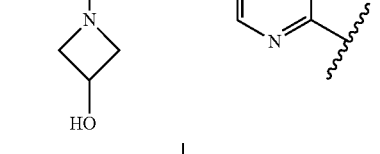
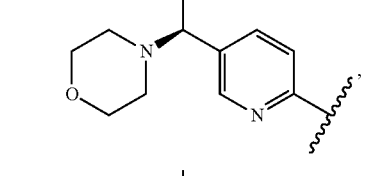
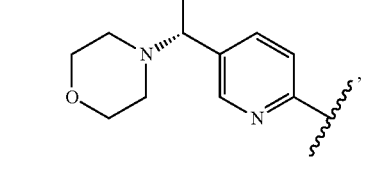
-continued
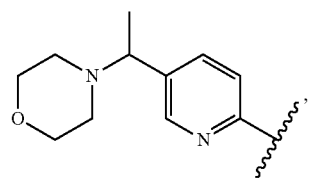
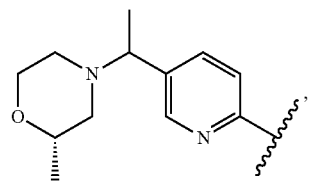
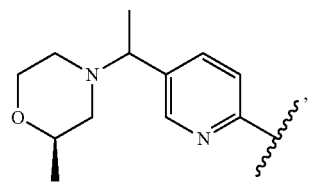
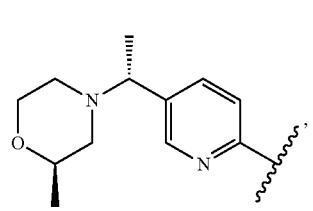
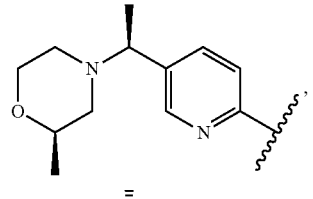
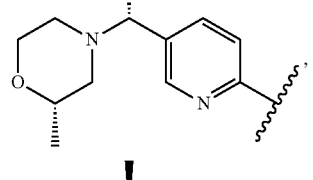
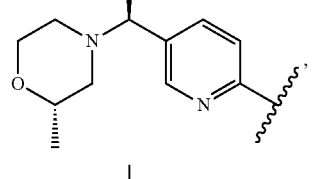
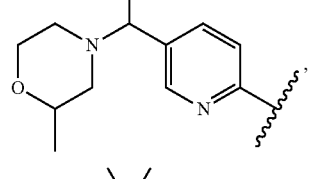
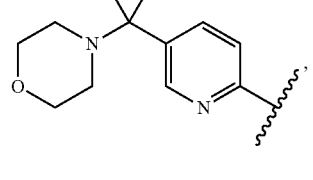

75
-continued
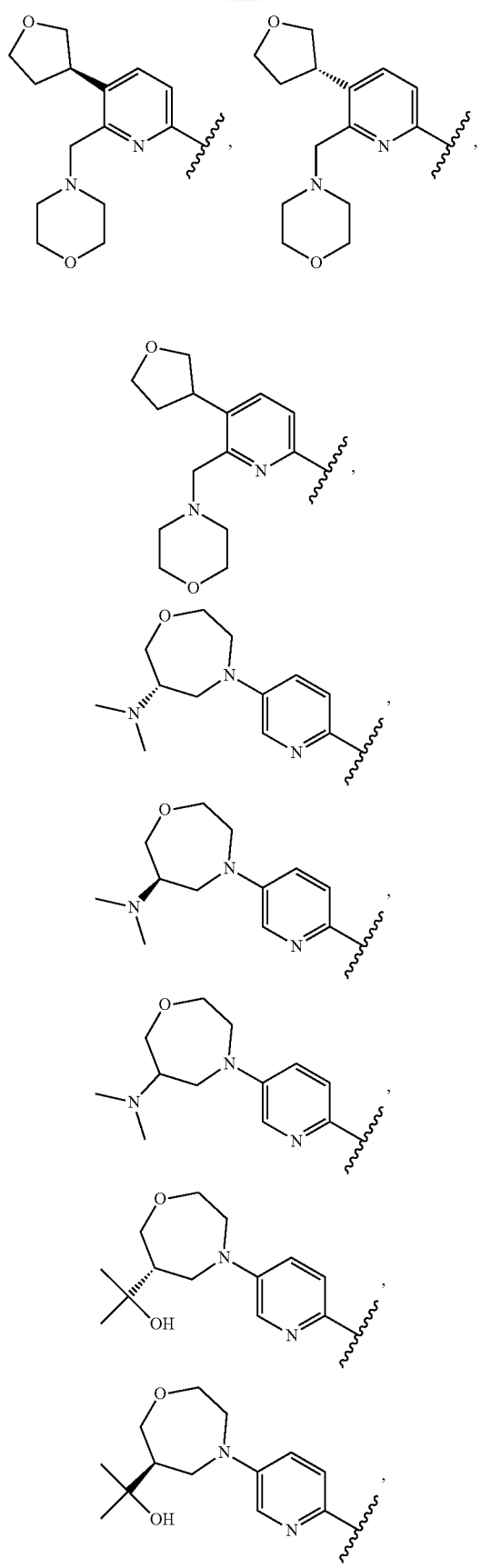
76
-continued
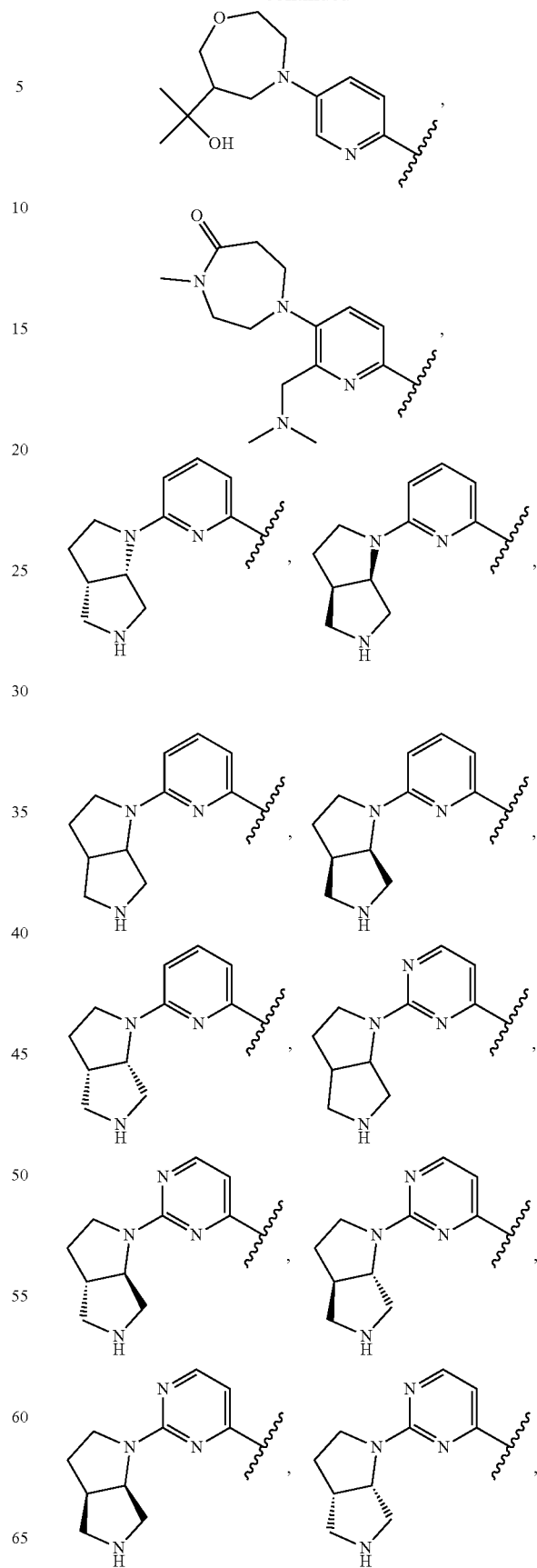

-continued
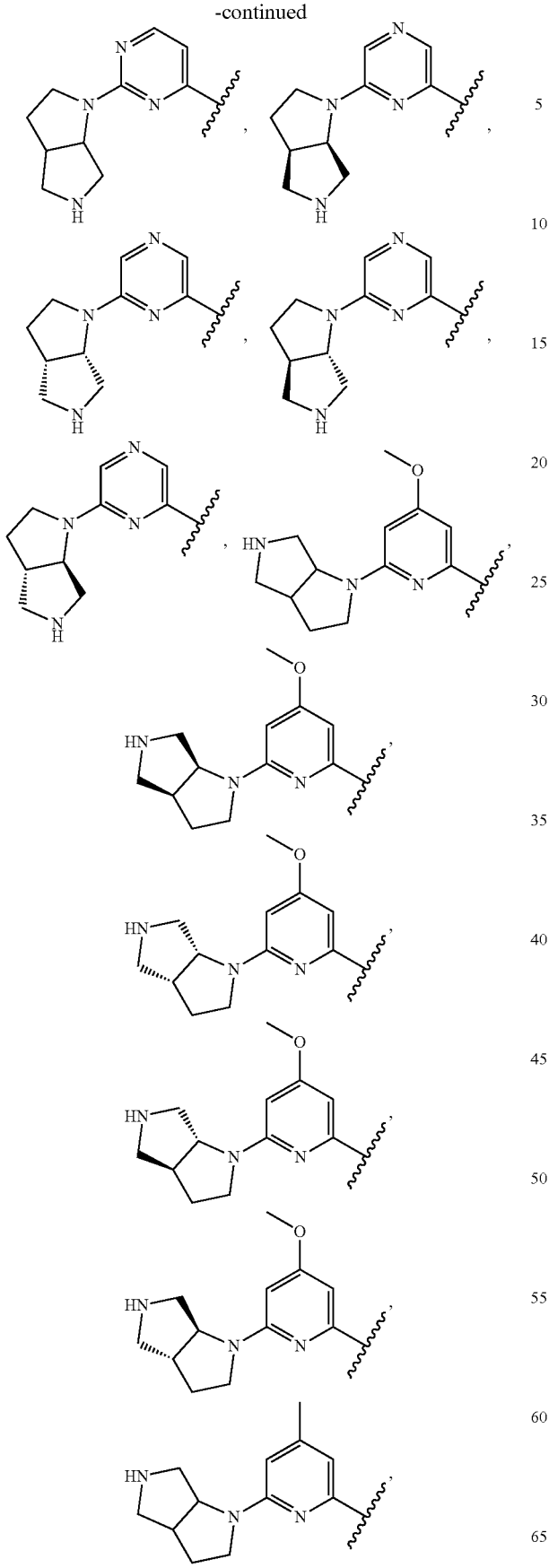
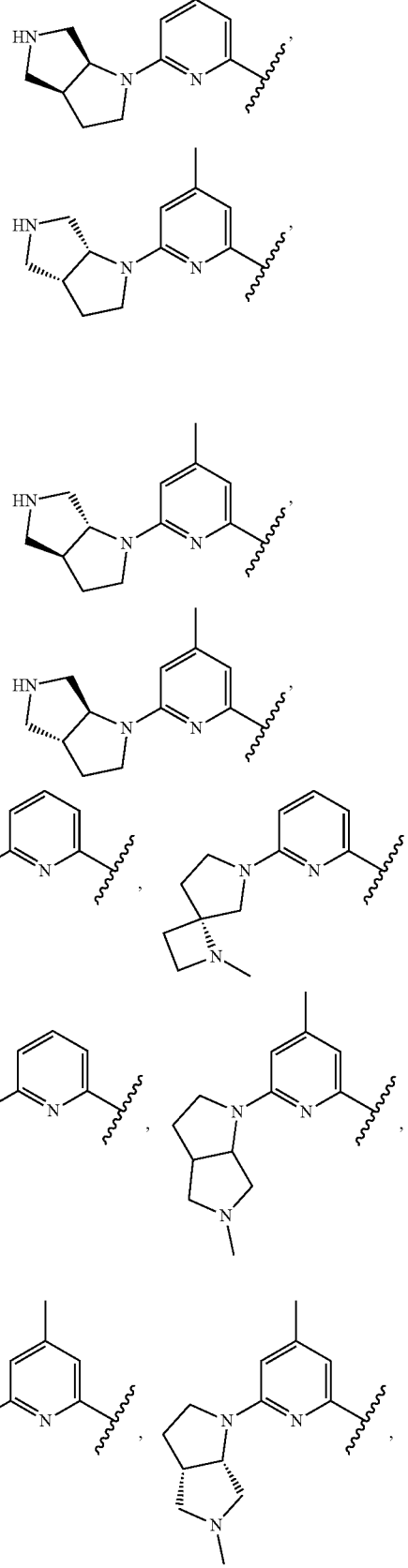

79
-continued
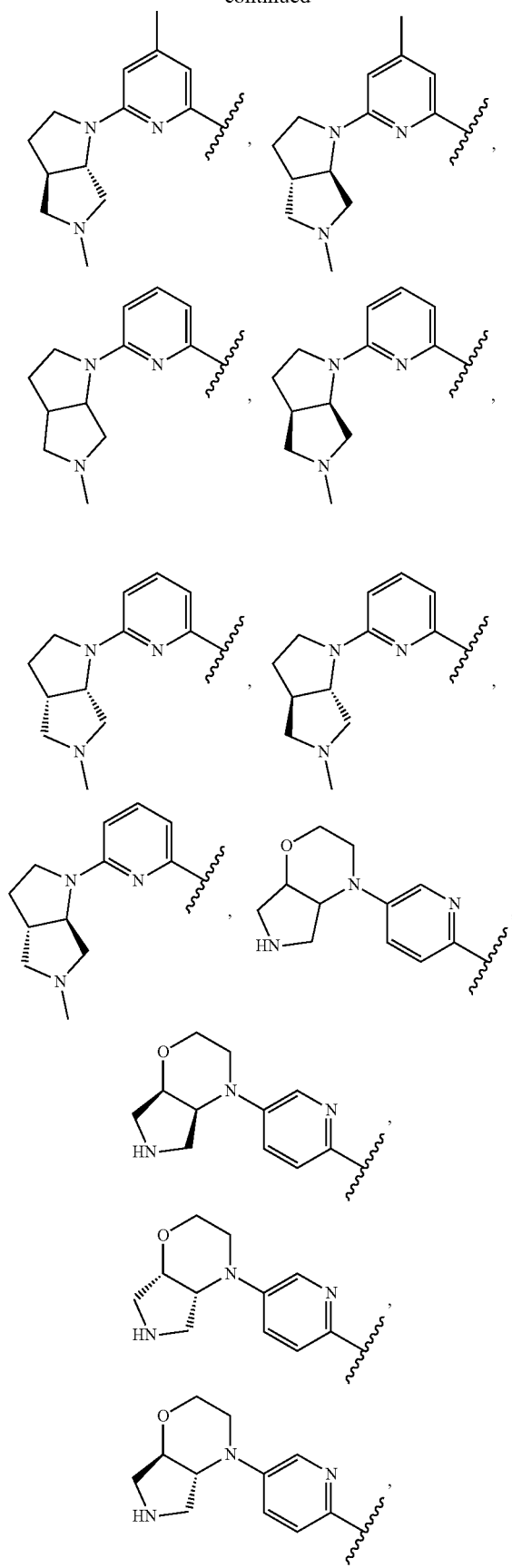
80
-continued
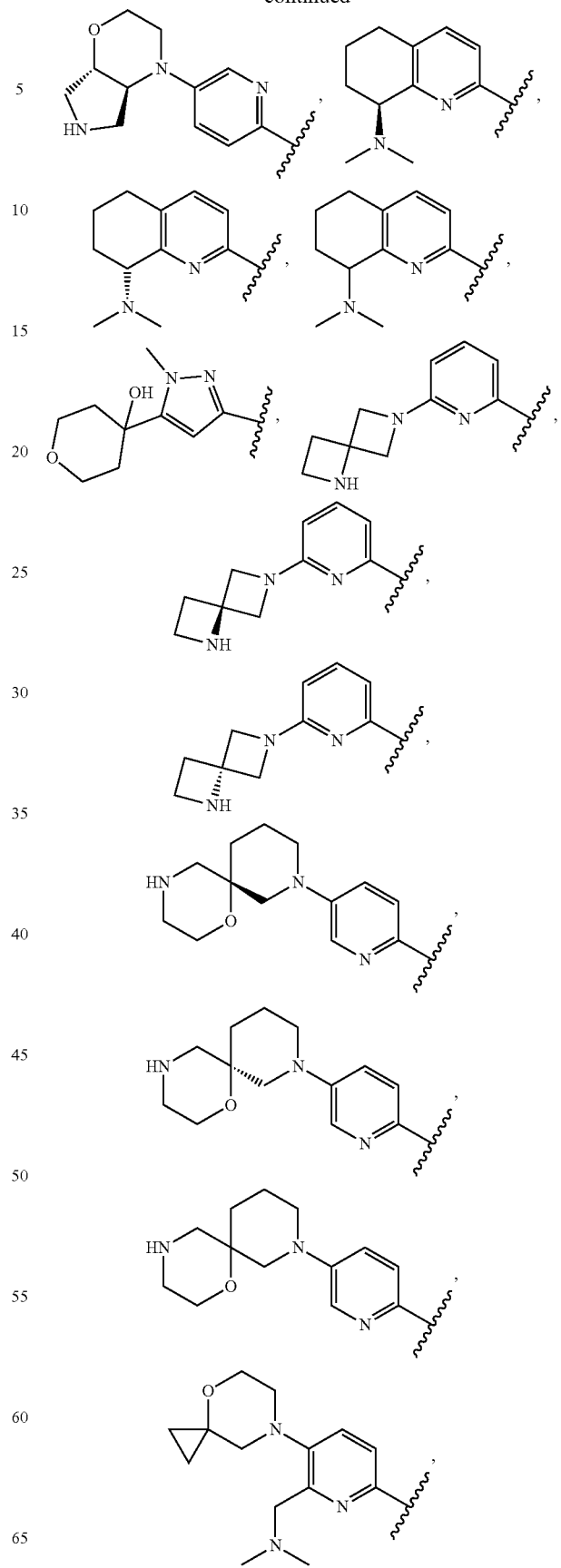

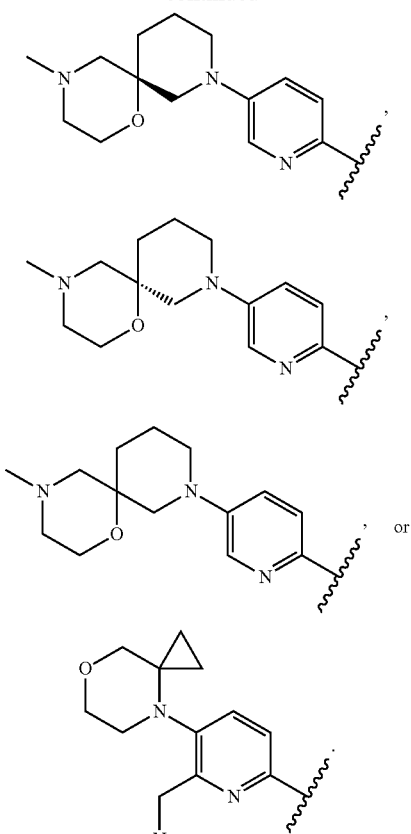
In certain embodiments, $R^1$ together with its $R^C$ substituents is
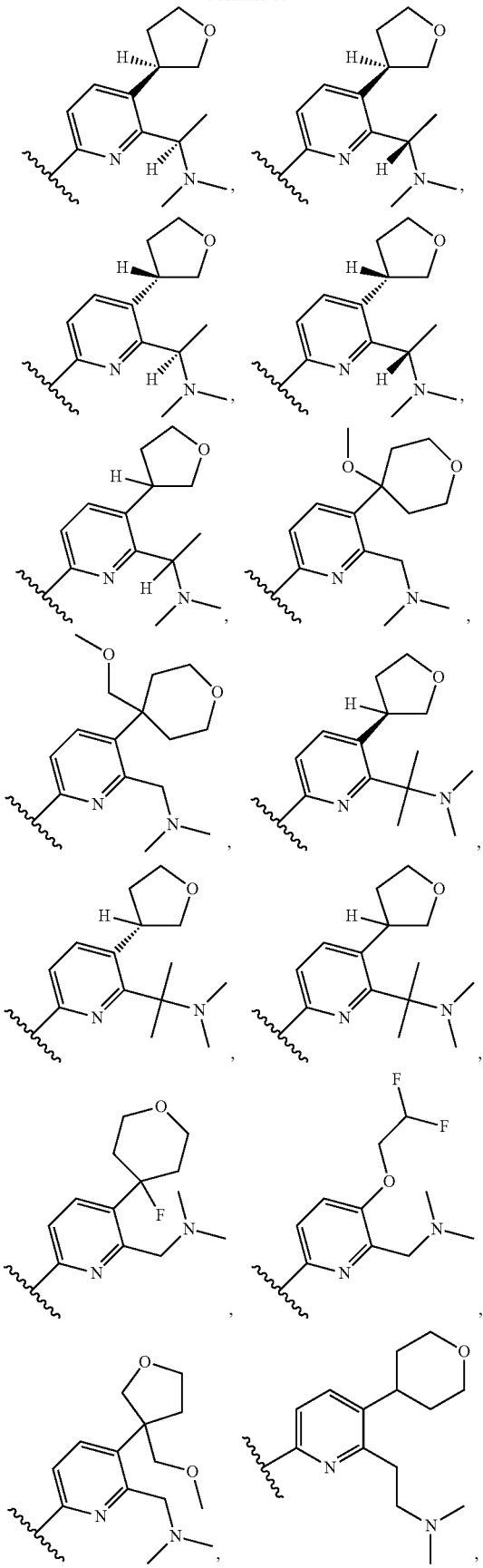

83
-continued
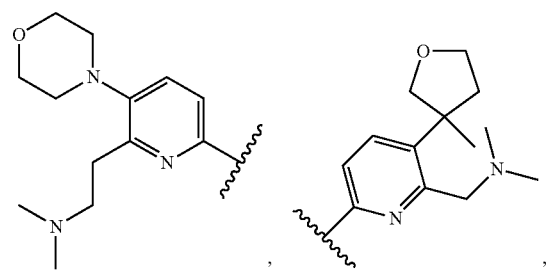
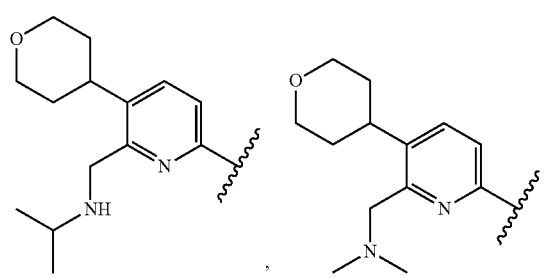
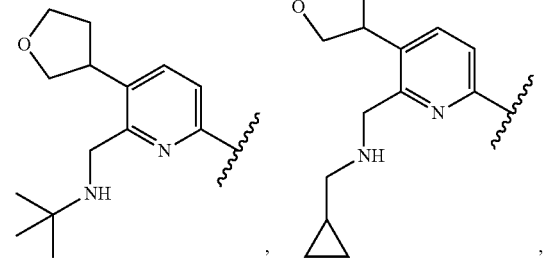
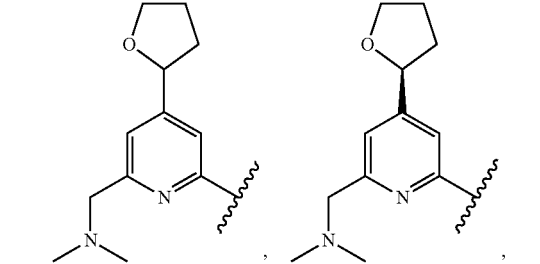
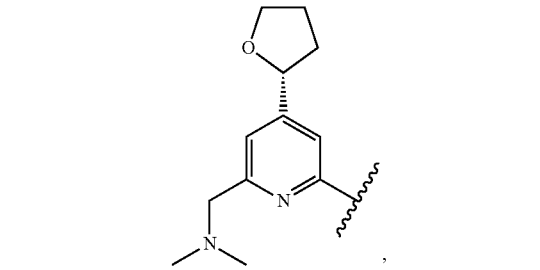
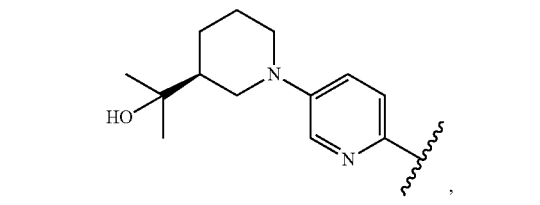
84
-continued
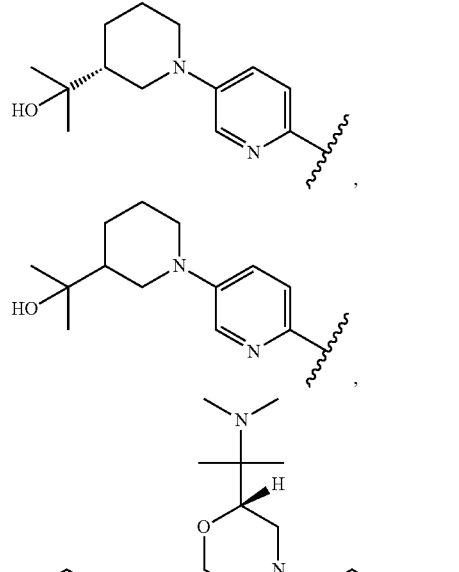
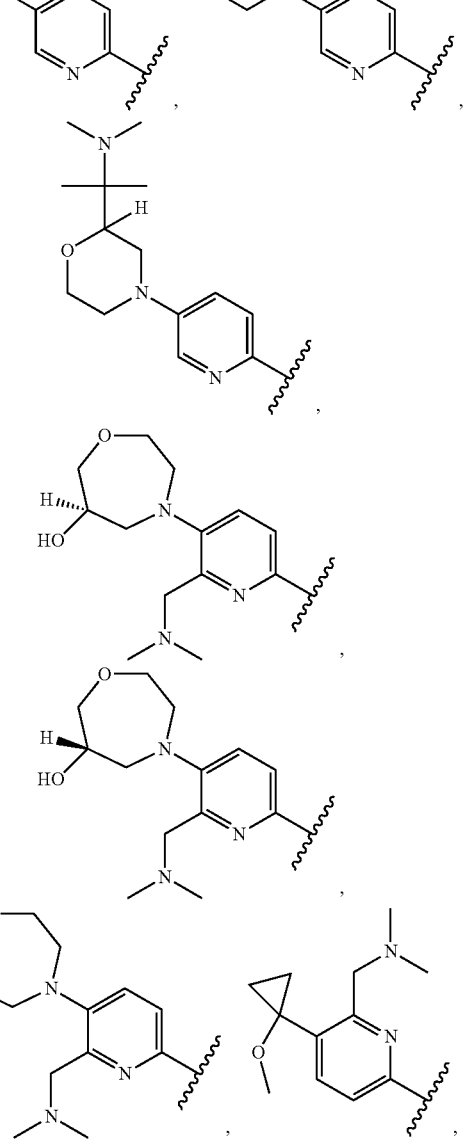

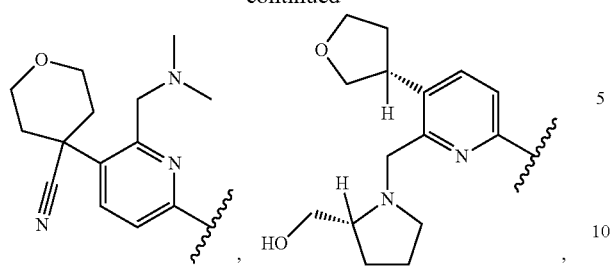
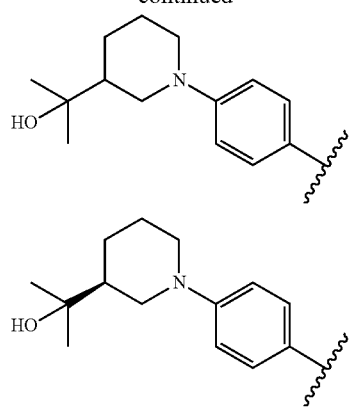
,
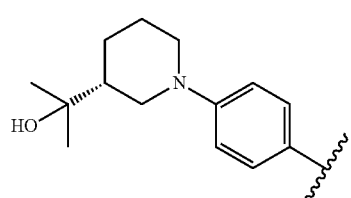
,
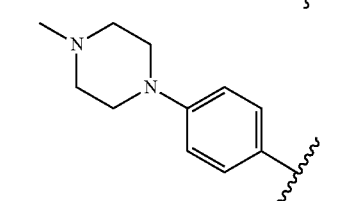
, or
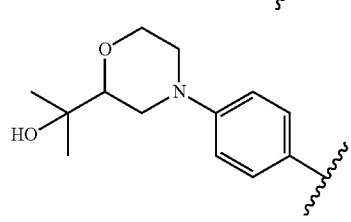
.
In some embodiments, R¹ is
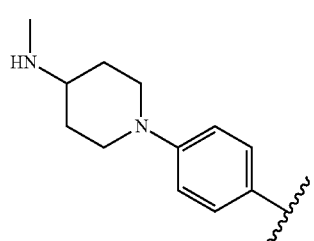
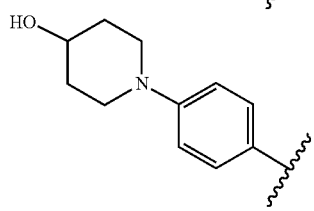
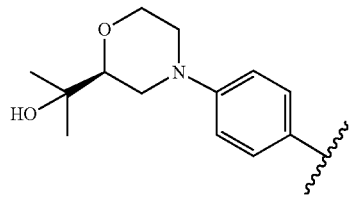
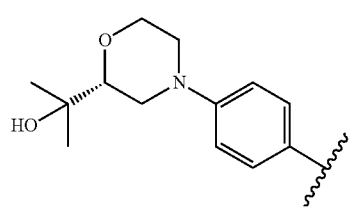
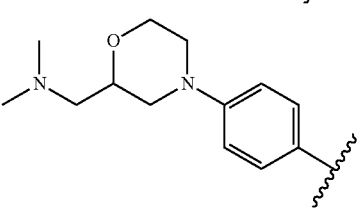

87

-continued

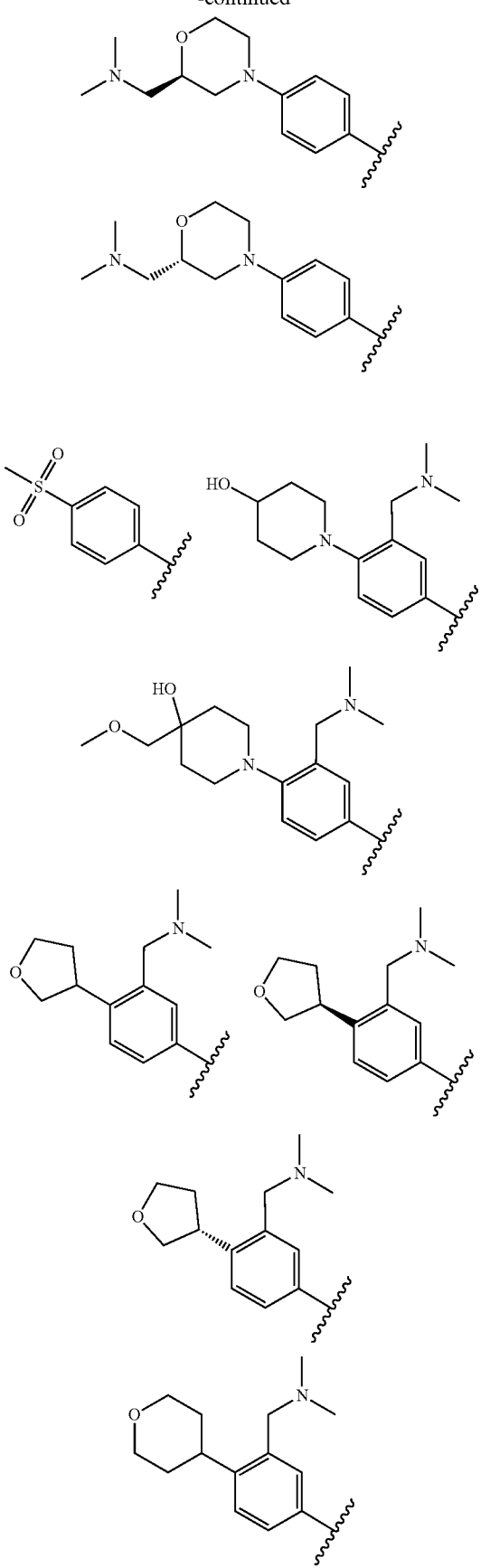

88

-continued

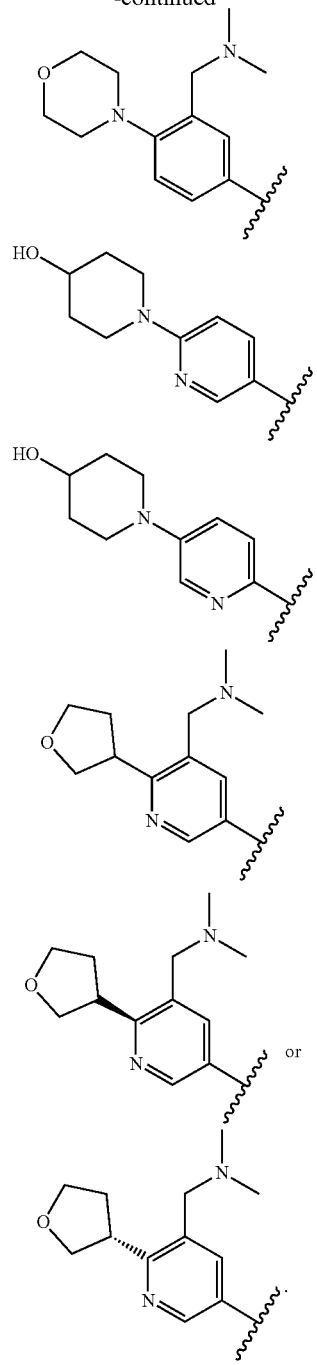

In some embodiments, $R^1$ is —H.

In some embodiments, $R^1$ is selected from those depicted in Table 1, below.

In some embodiments, $R^2$ is $C_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; and a 3-7 membered saturated or partially unsaturated monocyclic heterocyclic ring having 1-2 heteroatoms independently selected from nitrogen, oxygen, and sulfur; each of which is substituted with q instances of $R^C$; or $R^2$ is selected from —OR, —SR, —NR$_2$, —S(O)$_2$R, —S(O)$_2$NR$_2$, —S(O)R, —S(O)NR$_2$, —C(O)R, —C(O)OR, and —C(O)NR$_2$.

In certain embodiments, R² is methyl, ethyl, n-propyl, i-Pr, n-Bu, s-Bu, t-Bu, straight chain or branched pentyl, straight chain or branched hexyl, cyclopropyl, cyclobutyl, cyclopentyl, cyclohexyl, cycloheptyl, phenyl, furanyl, furazanyl, imidazolidinyl, imidazolinyl, imidazolyl, isothiazolyl, isoxazolyl, morpholinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, oxetanyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyridine-one, pyrimidinyl, pyrrolidinyl, pyrrolinyl, 2H-pyrrolyl, pyrrolyl, tetrahydropyranyl, 6H-1,2,5-thiadiazinyl, 1,2,3-thiadiazolyl, 1,2,4-thiadiazolyl, 1,2,5-thiadiazolyl, 1,3,4thiadiazolyl, thiazolyl, thienyl, thiophenyl, triazinyl, 1,2,3-triazolyl, 1,2,4-triazolyl, 1,2,5-triazolyl, 1,3,4-triazolyl, oxetanyl, or azetidinyl; each of which is substituted by q instances of $R^C$; or R² is selected from —OR, —SR, —NR₂, —S(O)₂R, —S(O)₂NR₂, —S(O)R, —S(O)NR₂, —C(O)R, —C(O)OR, and —C(O)NR₂.

In certain embodiments, R² is methyl, cyclopropyl, phenyl, imidazolyl, morpholinyl, oxazolyl, pyrazolyl, pyridazinyl, pyridinyl, pyridyl, pyridine-one, pyrimidinyl, pyrrolyl, or tetrahydropyranyl; each of which is substituted by q instances of $R^C$; or R² is selected from —S(O)₂R and —C(O)NR₂.

In certain embodiments, R² is

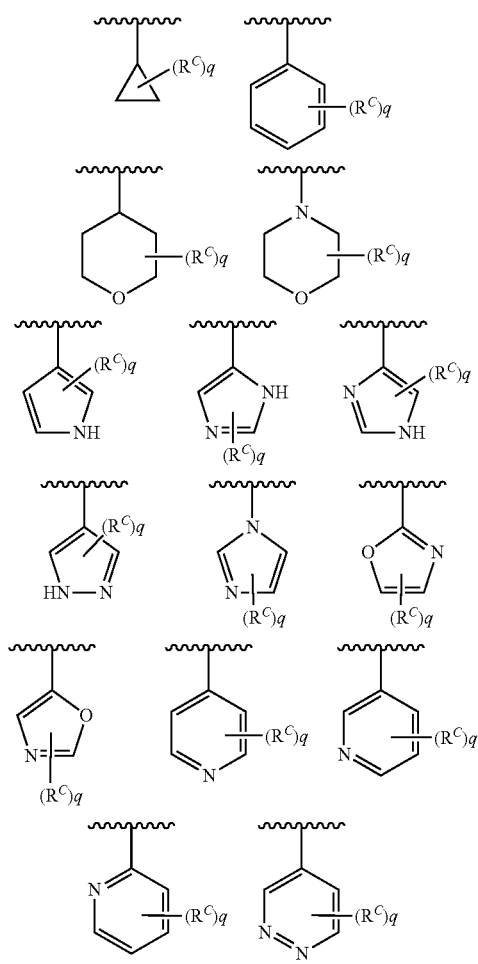

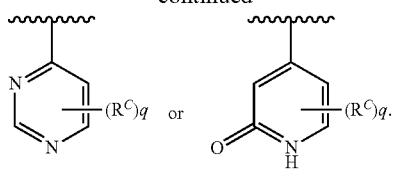

In certain embodiments, R² together with its $R^C$ substituents is

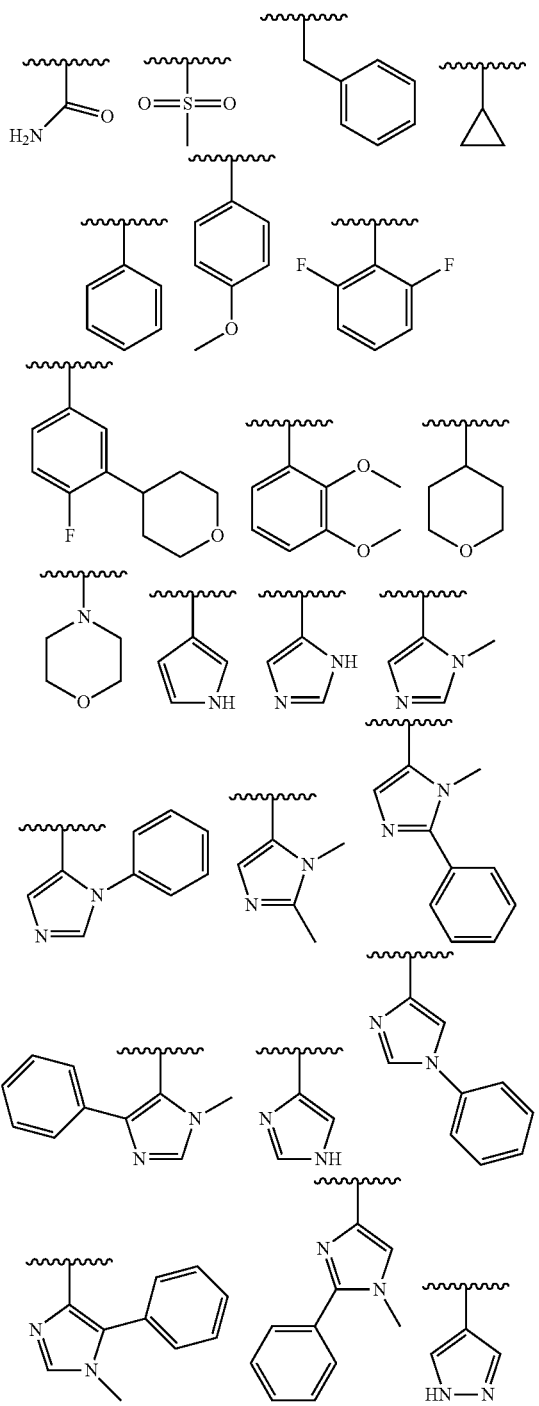

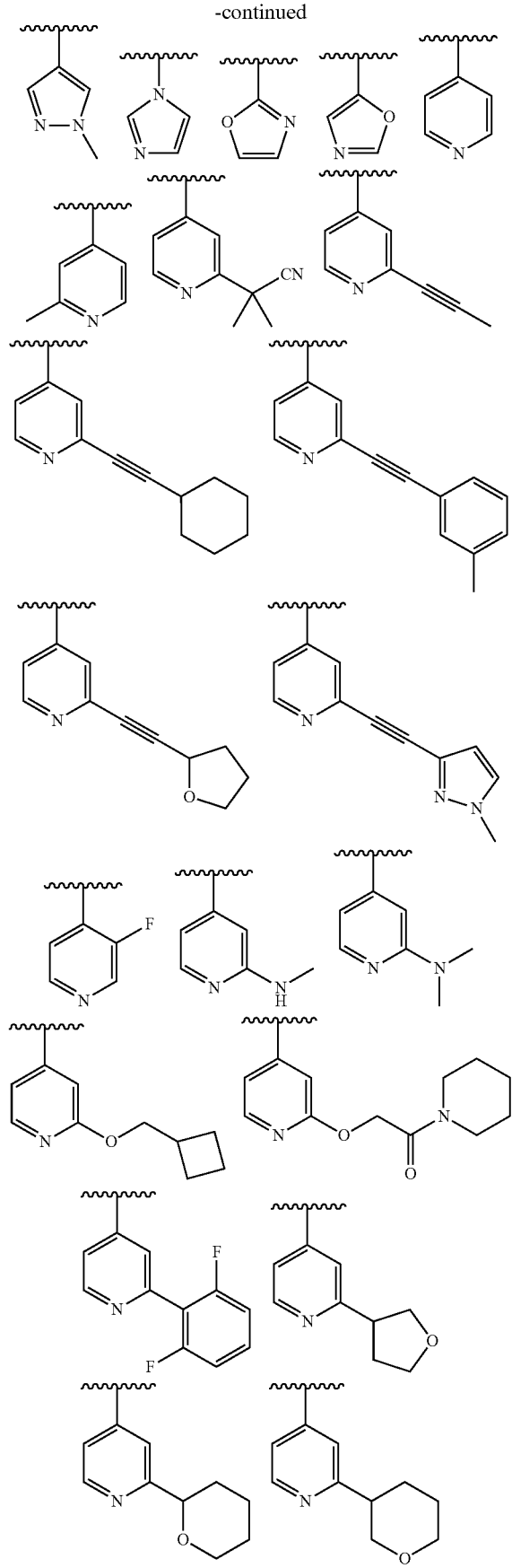
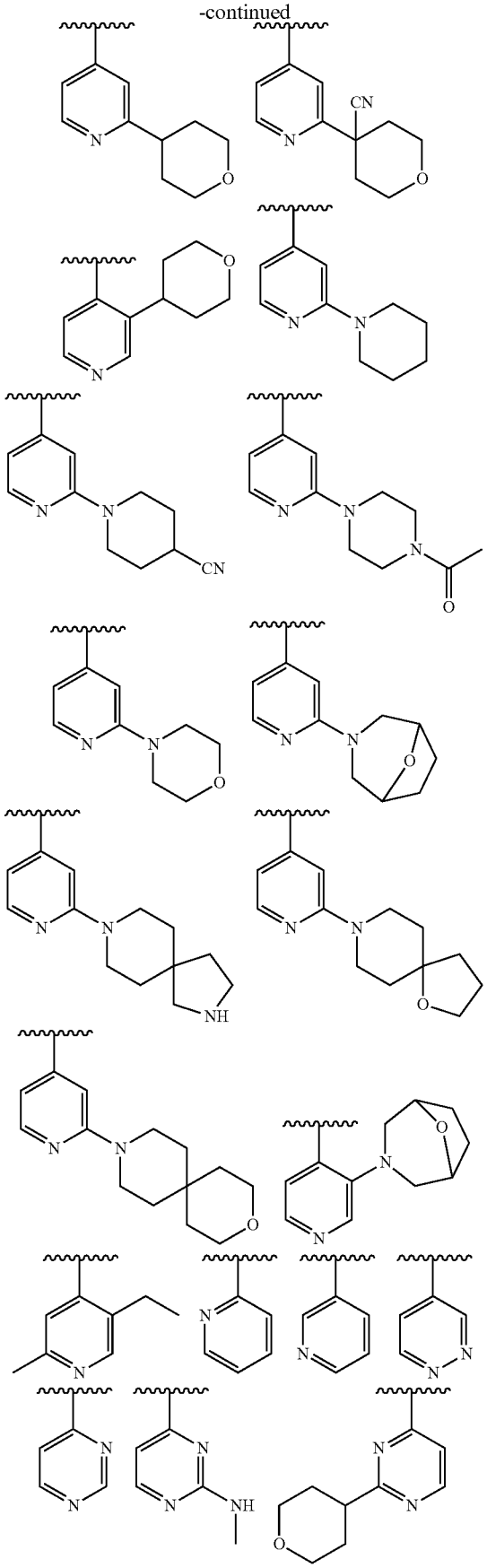

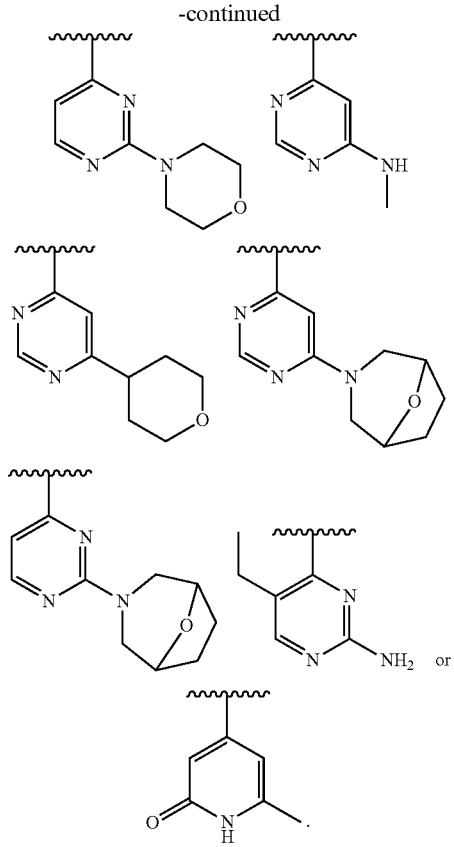
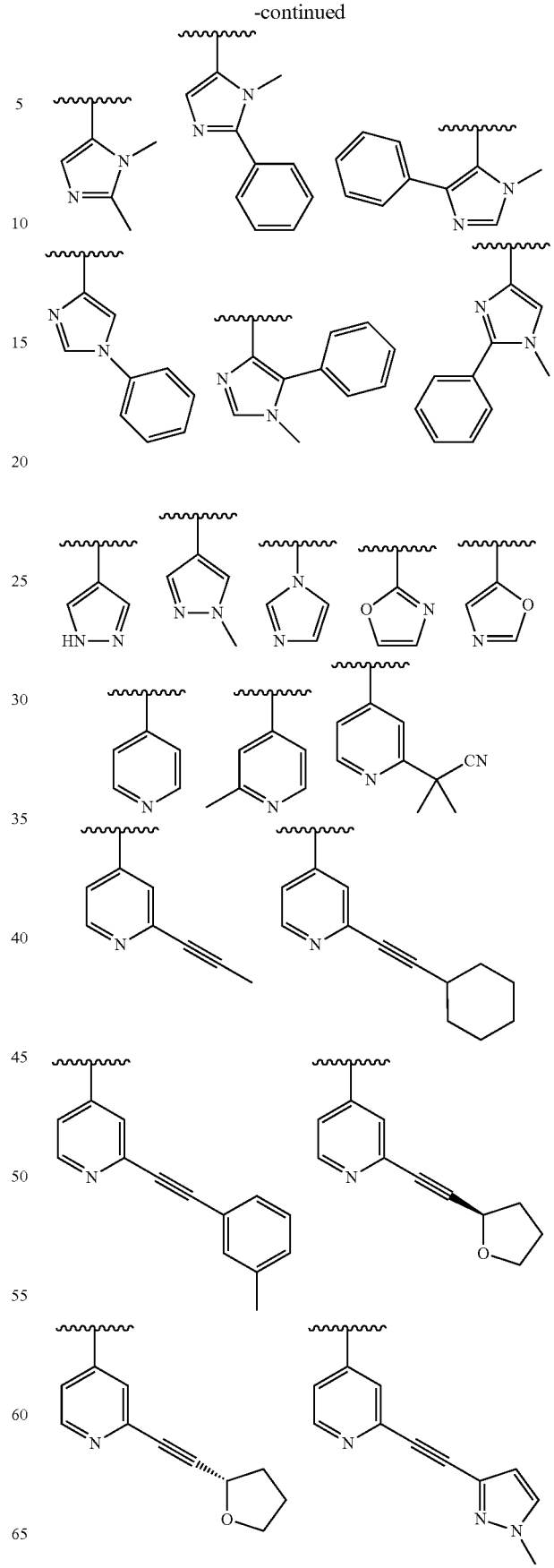
In certain embodiments, $R^2$ together with its $R^C$ substituents is
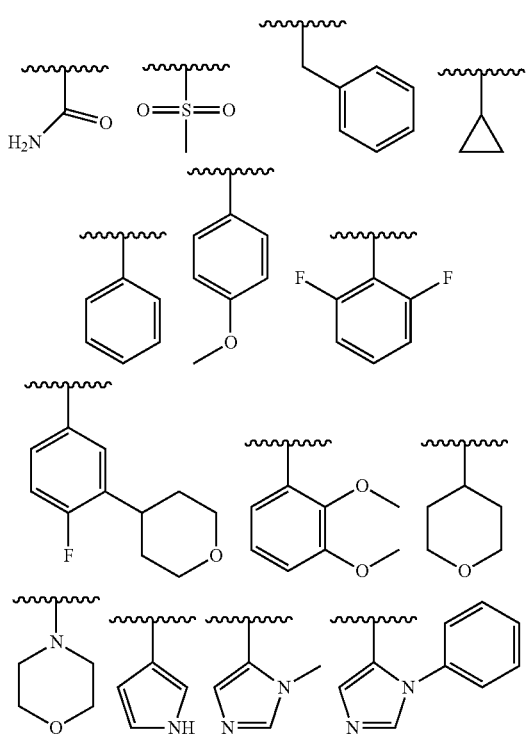

-continued
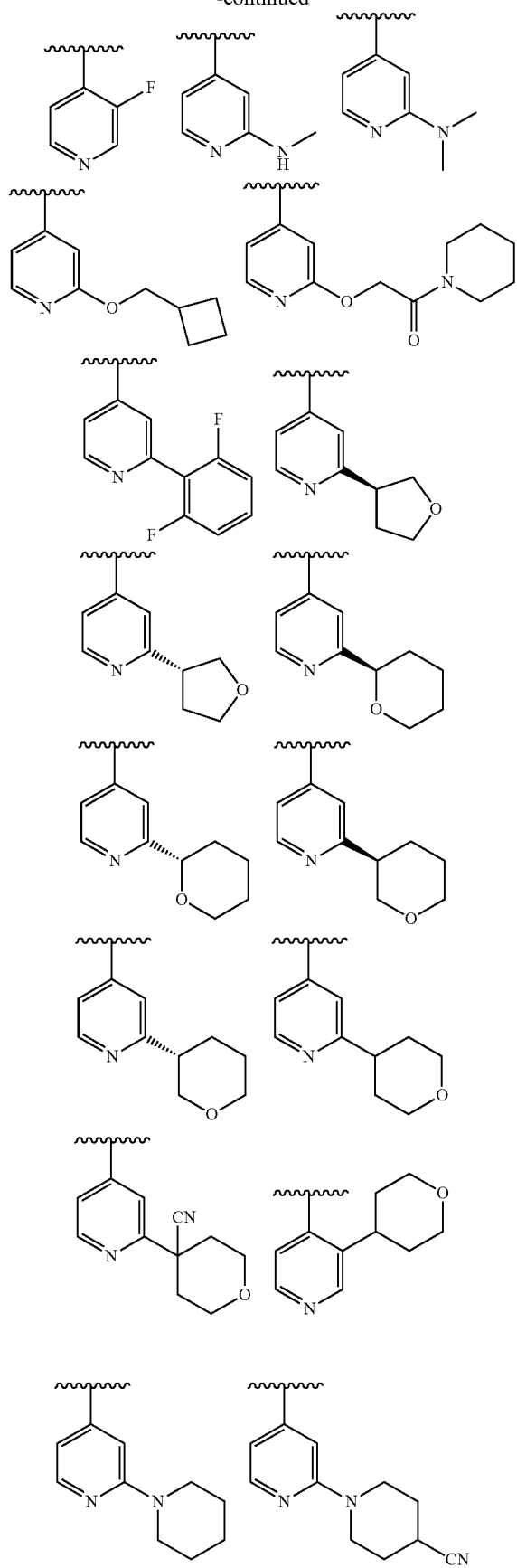
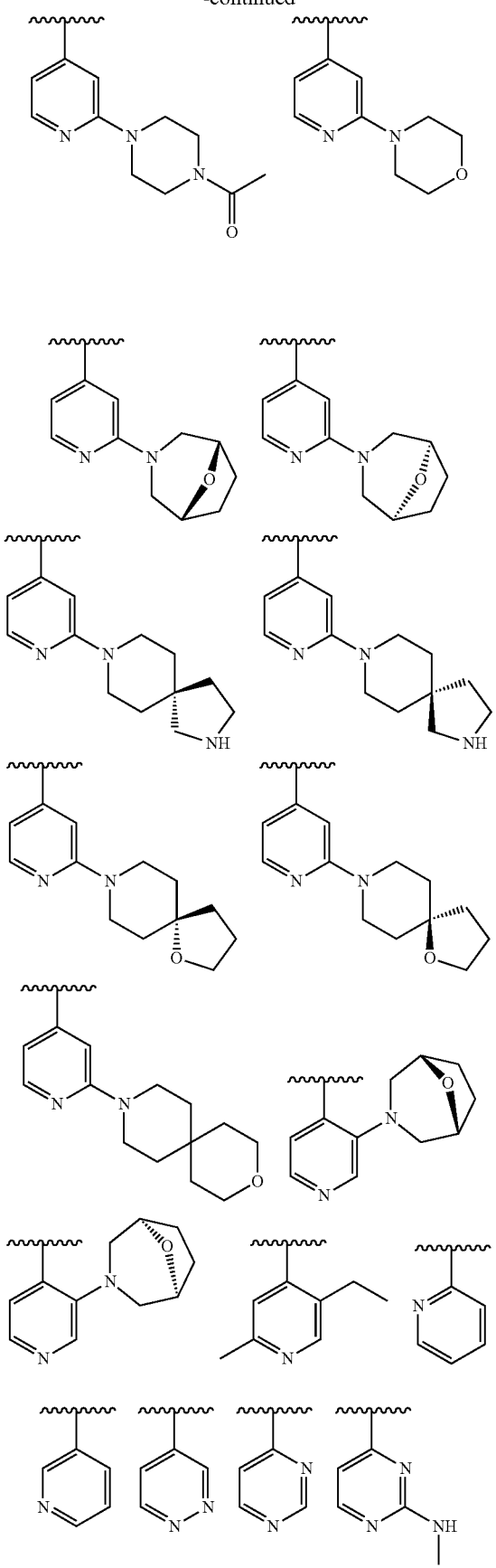

-continued

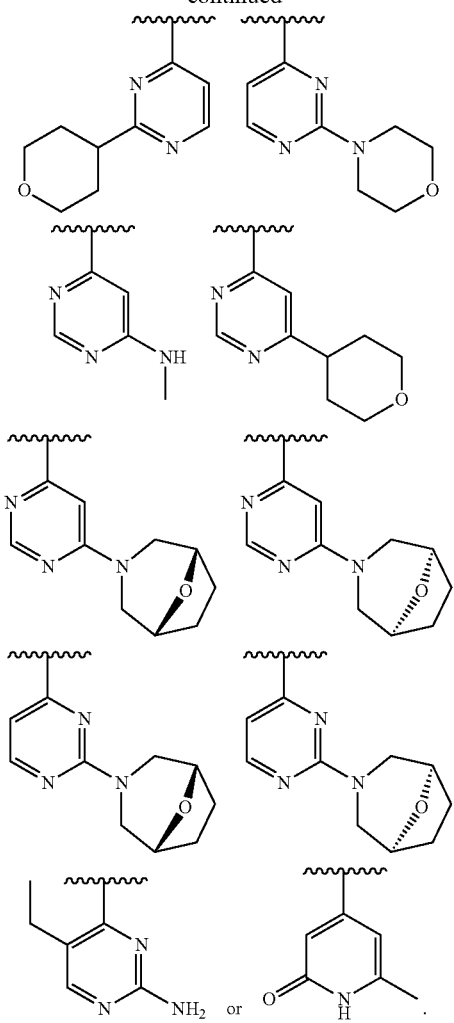

In some embodiments, $R^2$ is a 6-11 membered saturated, partially unsaturated, or unsaturated fused, bridged, or spiro bicyclic ring having 0-3 heteroatoms independently selected from nitrogen, oxygen, and sulfur; substituted with q instances of $R^C$.

In certain embodiments, $R^2$ is a 7-10-membered fused bicyclic ring having 1-3 nitrogen atoms; each of which is substituted by each of which is substituted by q instances of $R^C$.

In certain embodiments, $R^2$ is a 9-membered fused bicyclic ring having 1-3 nitrogen atoms; each of which is substituted by each of which is substituted by q instances of $R^C$; wherein each $R^C$ is independently halogen, —CN, —OR, —C(O)NR$_2$, —NR$_2$; or each instance of $R^C$ is independently an optionally substituted group selected from $C_{1-6}$ aliphatic; phenyl; a 3-7 membered saturated or partially unsaturated monocyclic heterocyclic ring having 1-2 heteroatoms independently selected from nitrogen, oxygen, phosphorous, silicon and sulfur; and a 6-11 membered saturated or partially unsaturated fused, bridged, or spiro bicyclic heterocyclic ring having 1-3 heteroatoms independently selected from nitrogen, oxygen, and sulfur; wherein each instance of $R^C$ is independently optionally substituted by r instances of R and s instances of $R^D$.

In certain embodiments, $R^2$ is

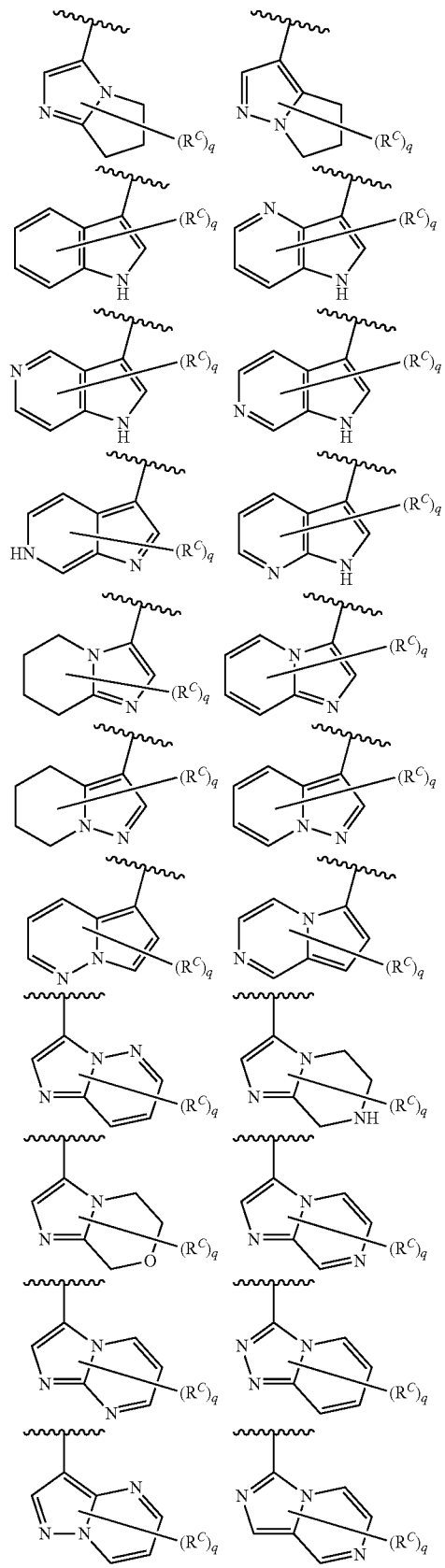

-continued
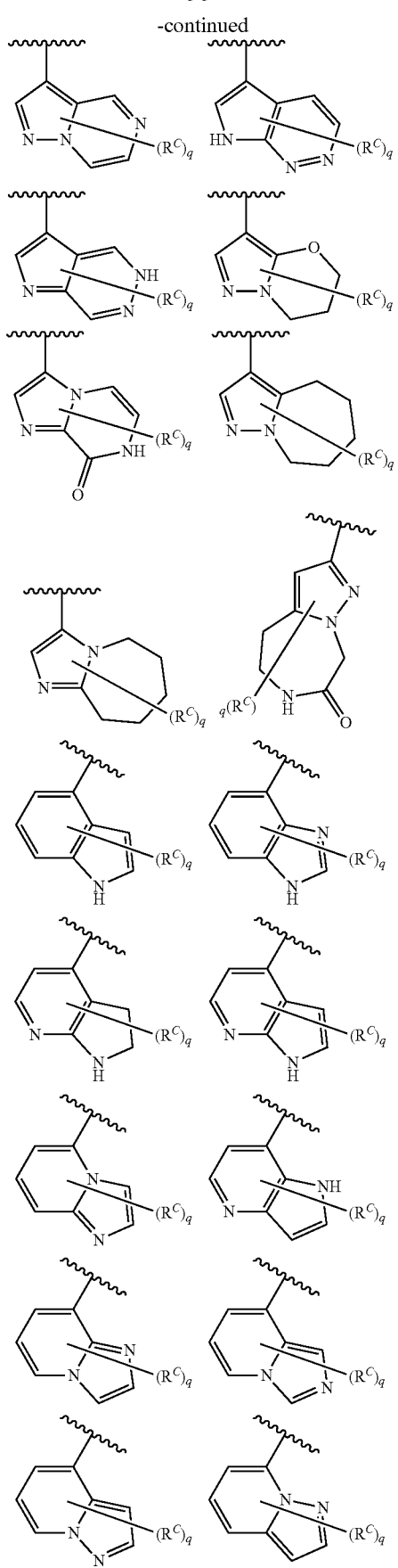
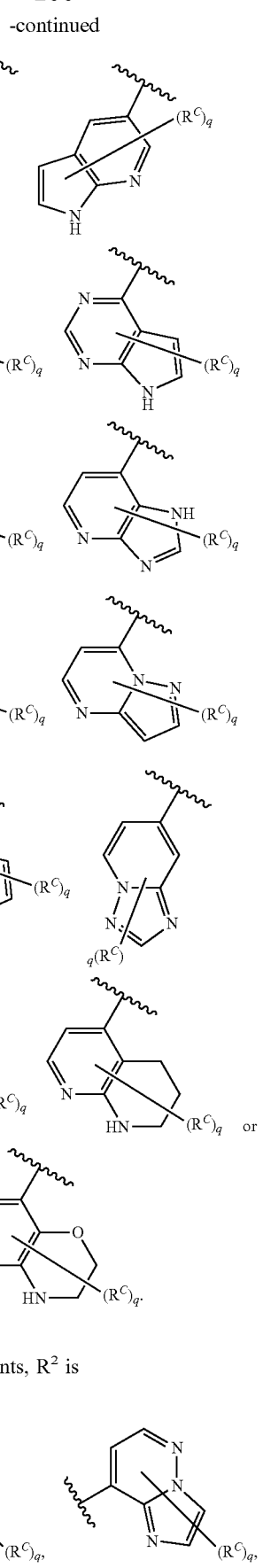
In certain embodiments, R² is
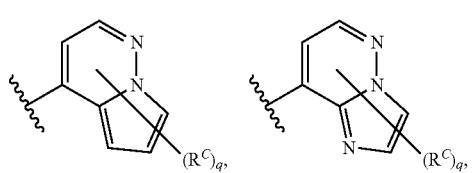

-continued
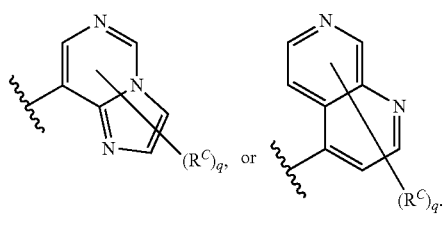
In certain embodiments, R²
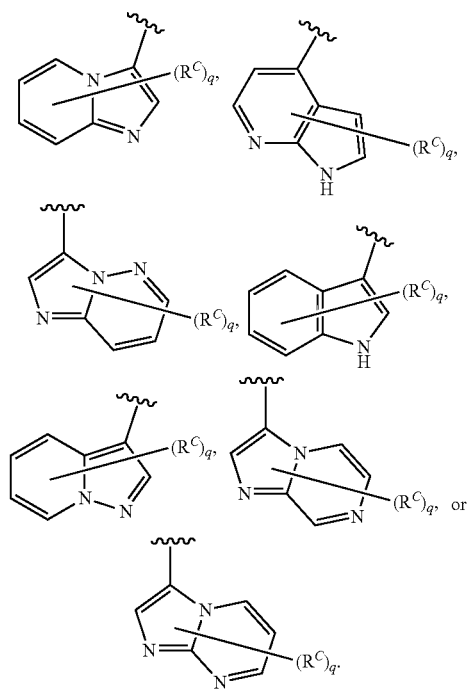
In certain embodiments, R² together with its $R^C$ substituents is
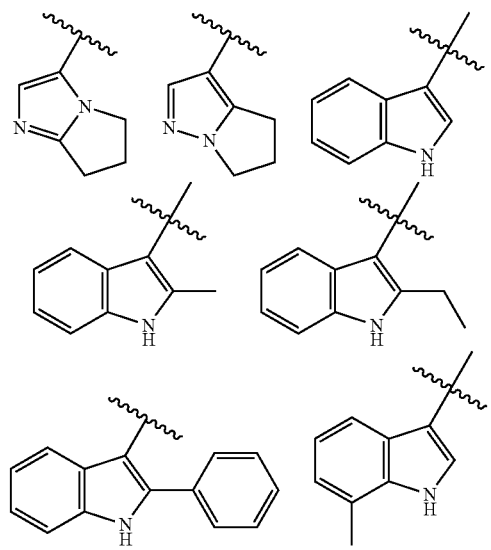
-continued
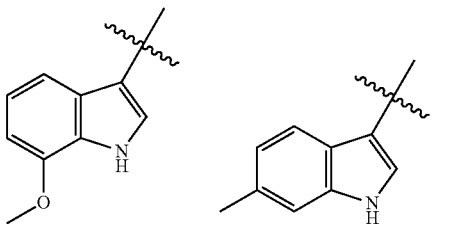
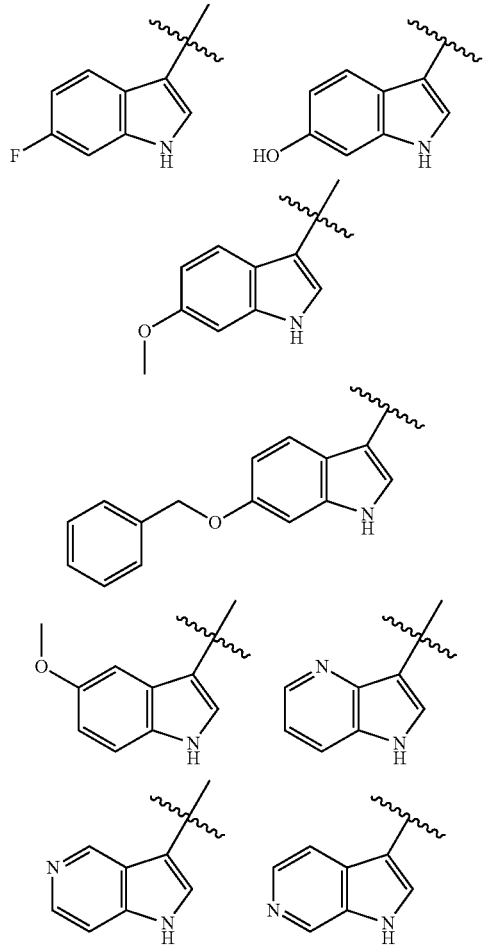
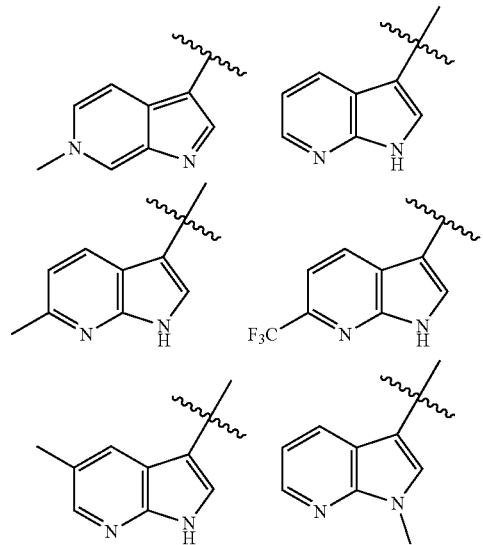

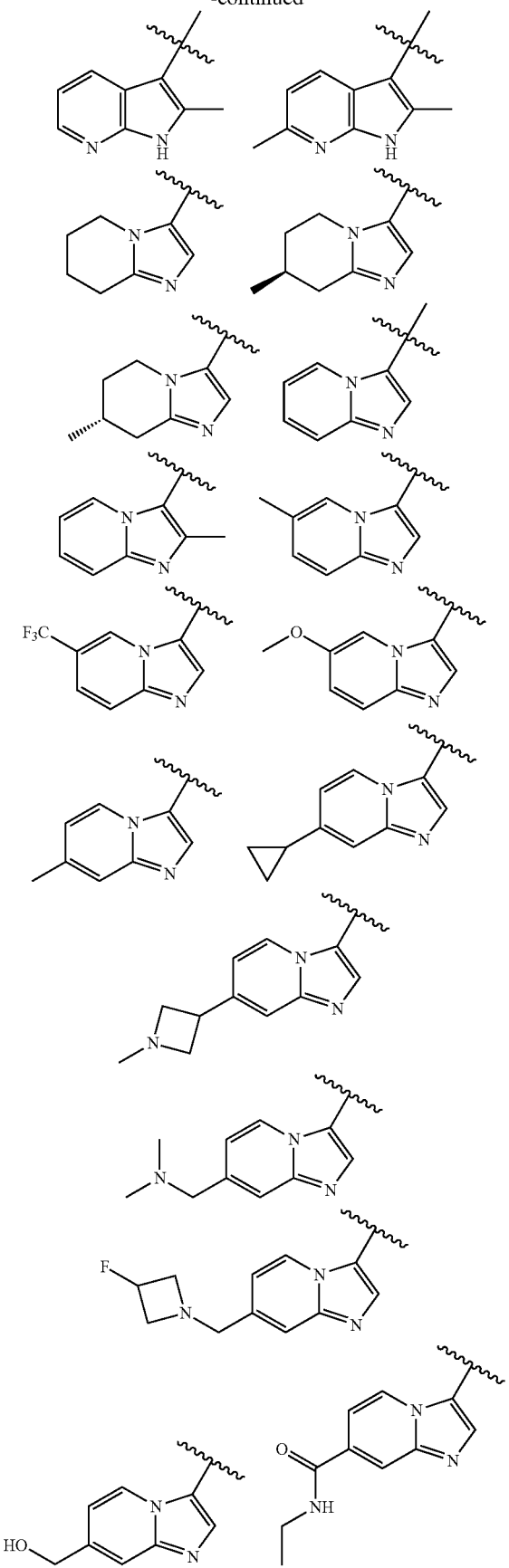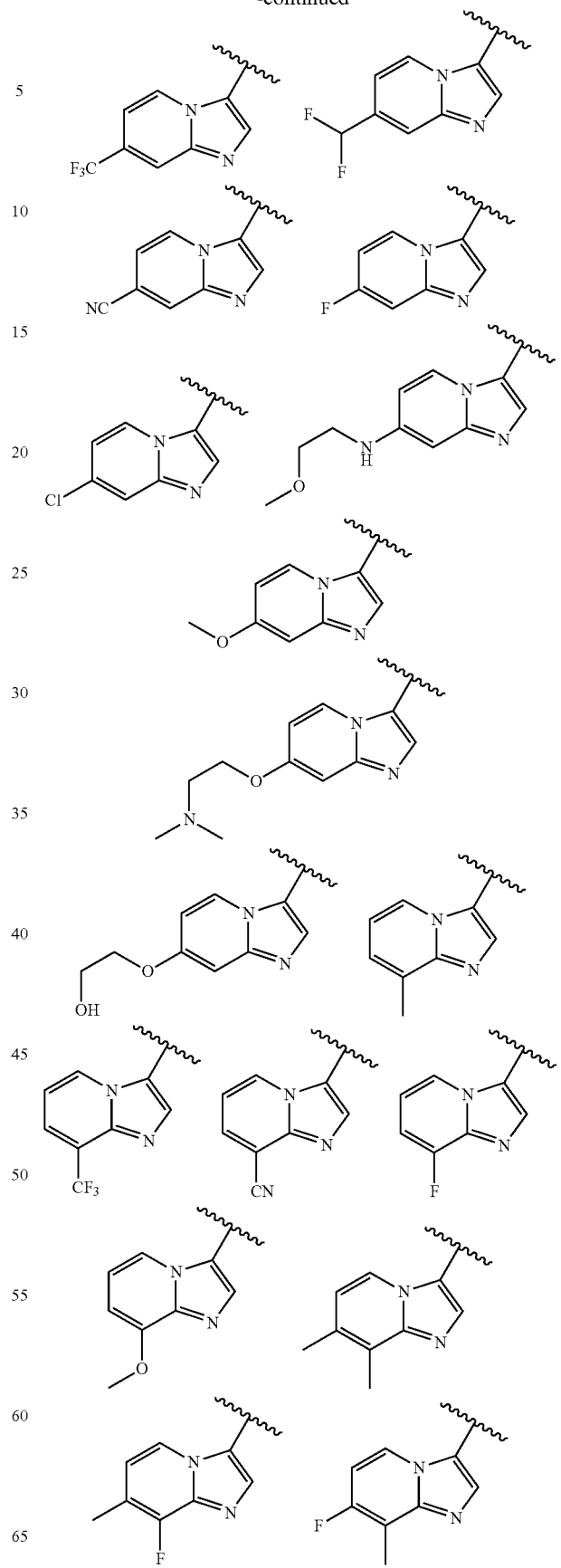

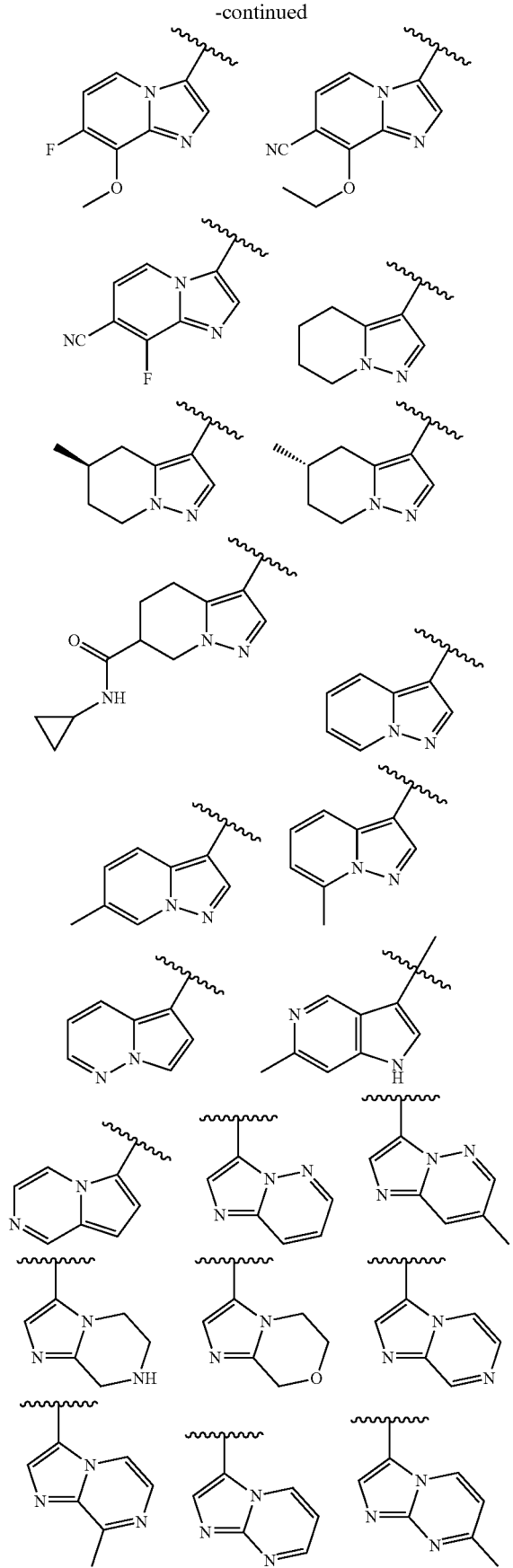
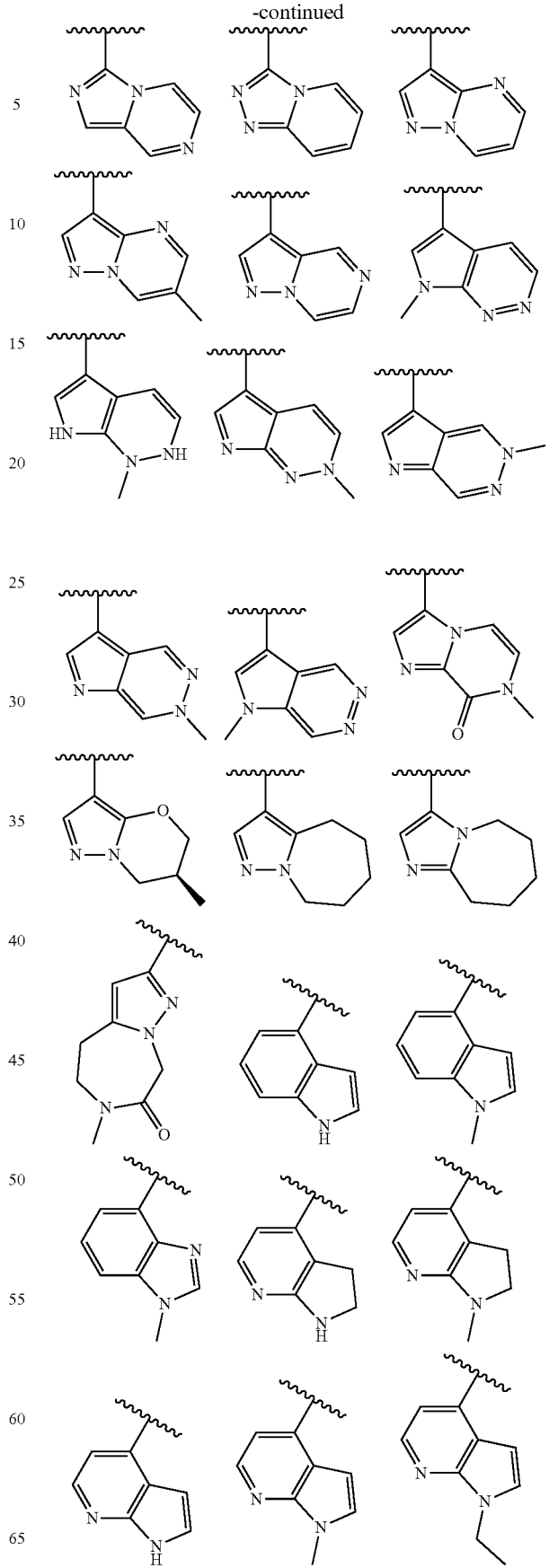

107
-continued
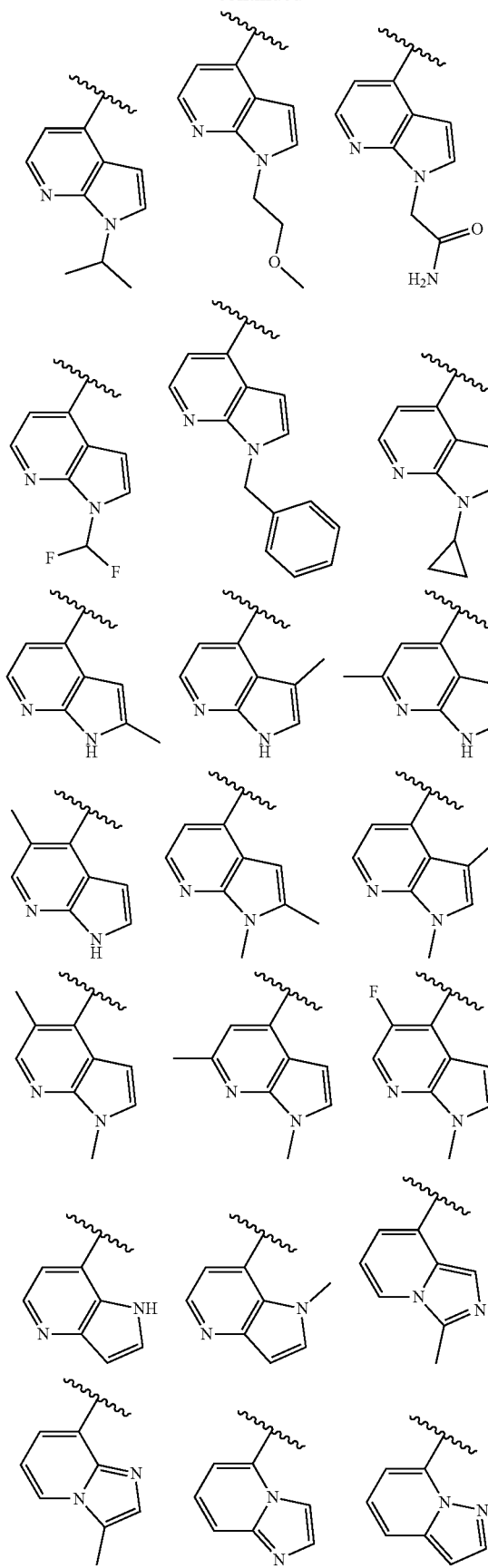
108
-continued
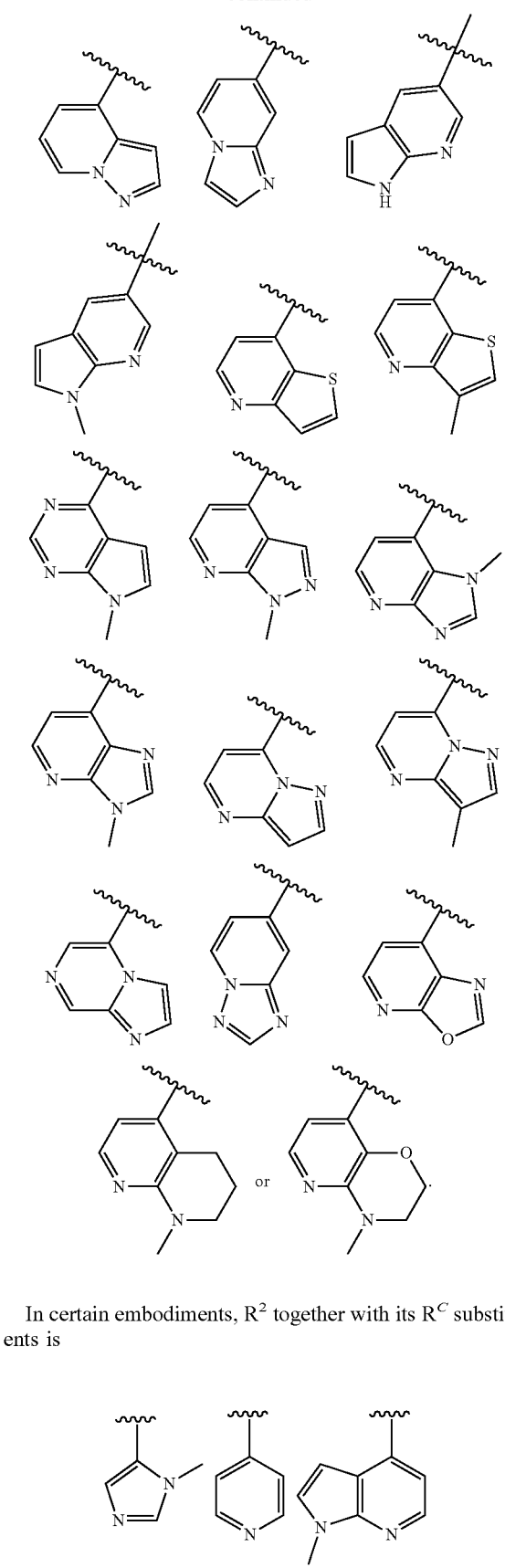
In certain embodiments, $R^2$ together with its $R^C$ substituents is
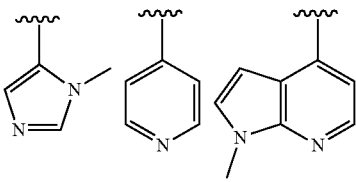

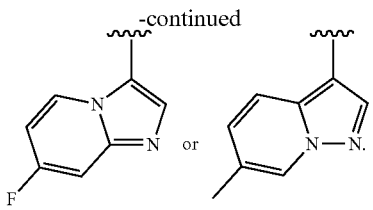

In some embodiments, $R^2$ is selected from those depicted in Table 1, below.

As defined generally above, each instance of $R^3$ is independently hydrogen or an optionally substituted $C_{1-6}$ aliphatic group.

In some embodiments, $R^3$ is hydrogen.

In some embodiments, R is an optionally substituted $C_{1-6}$ aliphatic group.

In some embodiments, $R^3$ is methyl. In some embodiments, $R^3$ is ⋏. In some embodiments, $R^3$ is ⋏.

In some embodiments, $R^3$ is selected from those depicted in Table 1, below.

As defined generally above, each instance of $R^C$ is independently oxo, halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N=$S(O)R_2$, —S(NR)(O)R, —N(R)S(O)R, —N(R)CN, —$P(O)(R)NR_2$, —P(O)(R)OR or —$P(O)R_2$; or each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of $R^D$.

In some embodiments, each instance of $R^C$ is independently oxo, halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N=$S(O)R_2$, —S(NR)(O)R, —N(R)S(O)R, —N(R)CN, —$P(O)(R)NR_2$, —P(O)(R)OR or —$P(O)R_2$; or each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^C$ is independently oxo, halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, —N(R)C(NR)$NR_2$, —N(R)$NR_2$, —N(R)$S(O)_2NR_2$, —N(R)$S(O)_2R$, —N=$S(O)R_2$, —S(NR)(O)R, —N(R)S(O)R, —N(R)CN, —$P(O)(R)NR_2$, —P(O)(R)OR or —$P(O)R_2$.

In some embodiments, each instance of $R^C$ is independently an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each $R^C$ is independently a 6-11 membered saturated or partially unsaturated spirocyclic ring having 0-3 heteroatoms independently selected from nitrogen, oxygen, and sulfur which is substituted with r instances of R and s instances of $R^D$.

In some embodiments, each $R^C$ is independently a 6-11 membered saturated or partially unsaturated bicyclic heterocyclic ring having 1-3 heteroatoms independently selected from nitrogen, oxygen, and sulfur which is substituted with r instances of R and s instances of $R^D$.

In some embodiments, each $R^C$ is independently methyl, oxo, fluoro or methoxy.

In some embodiments, each $R^C$ is independently

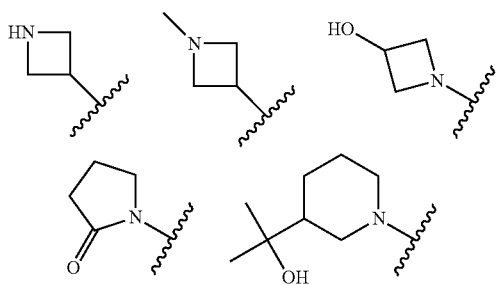

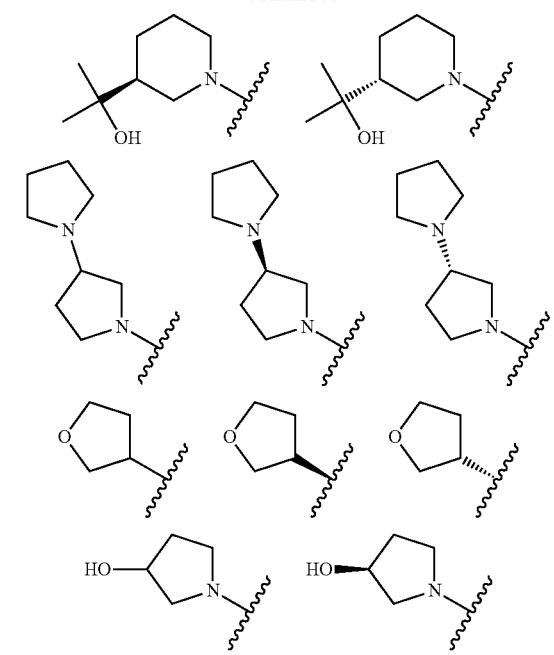
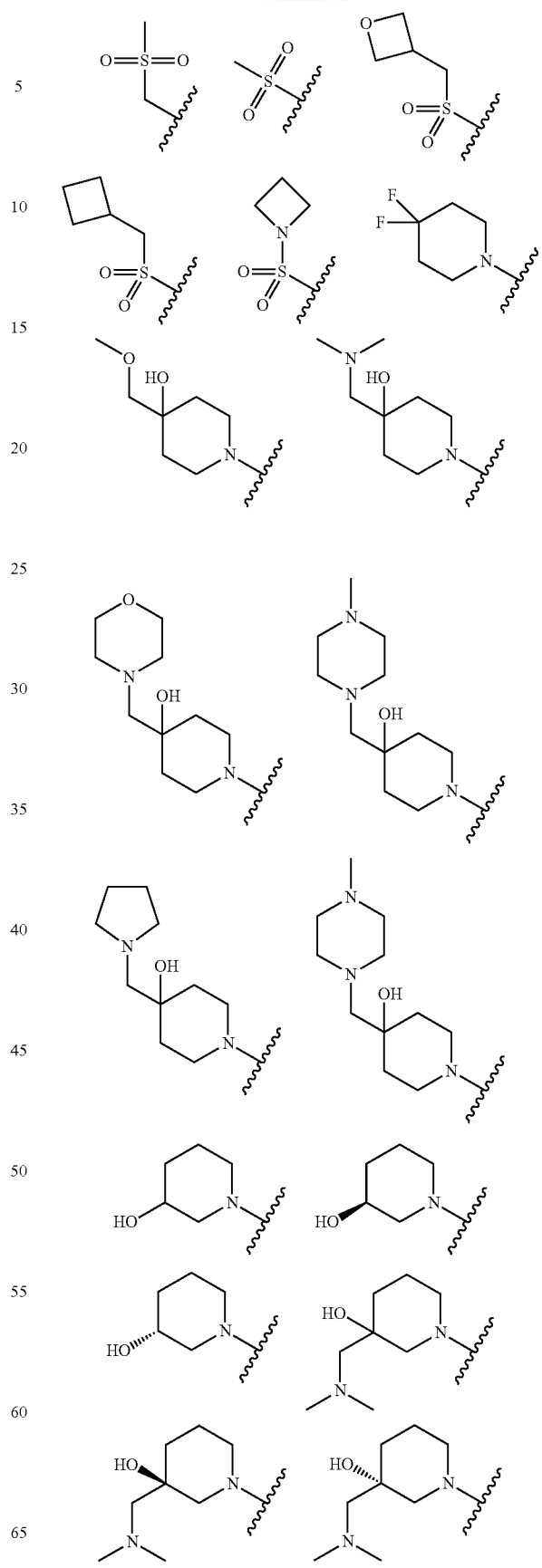

-continued
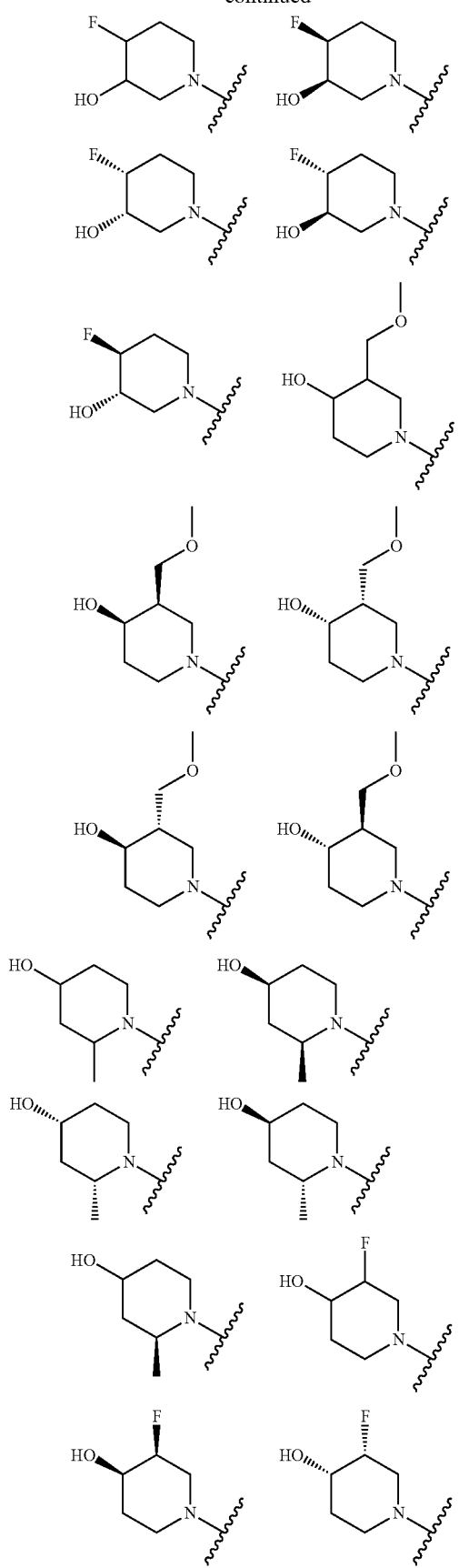
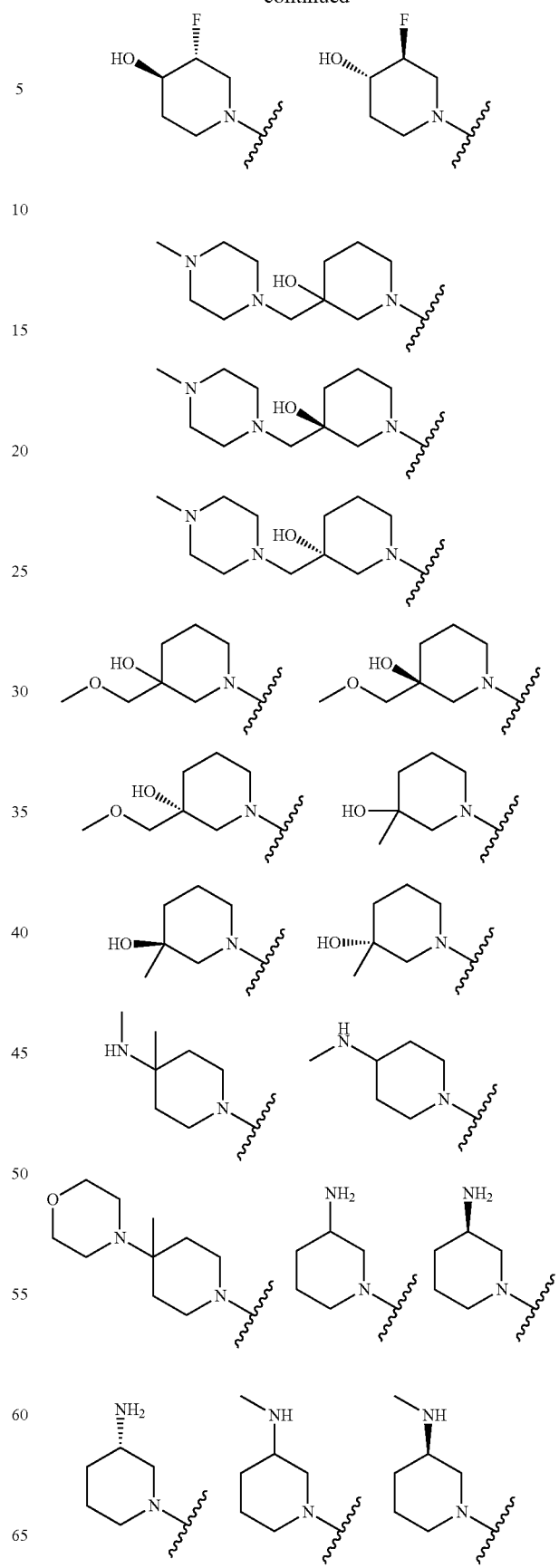

115
-continued
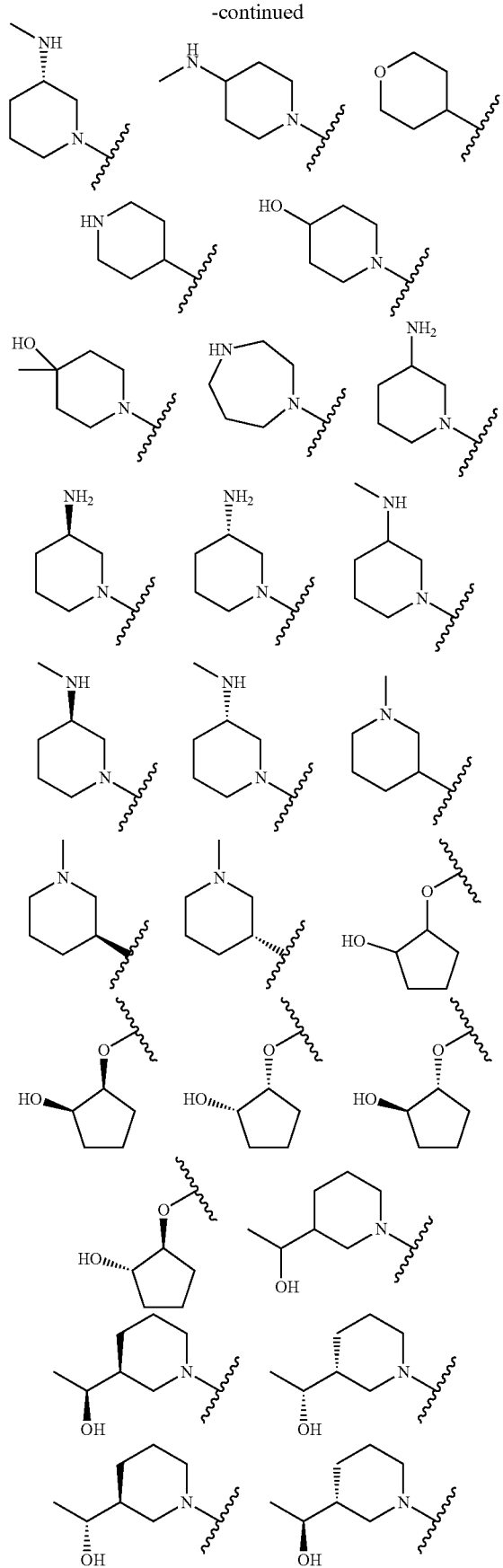
116
-continued
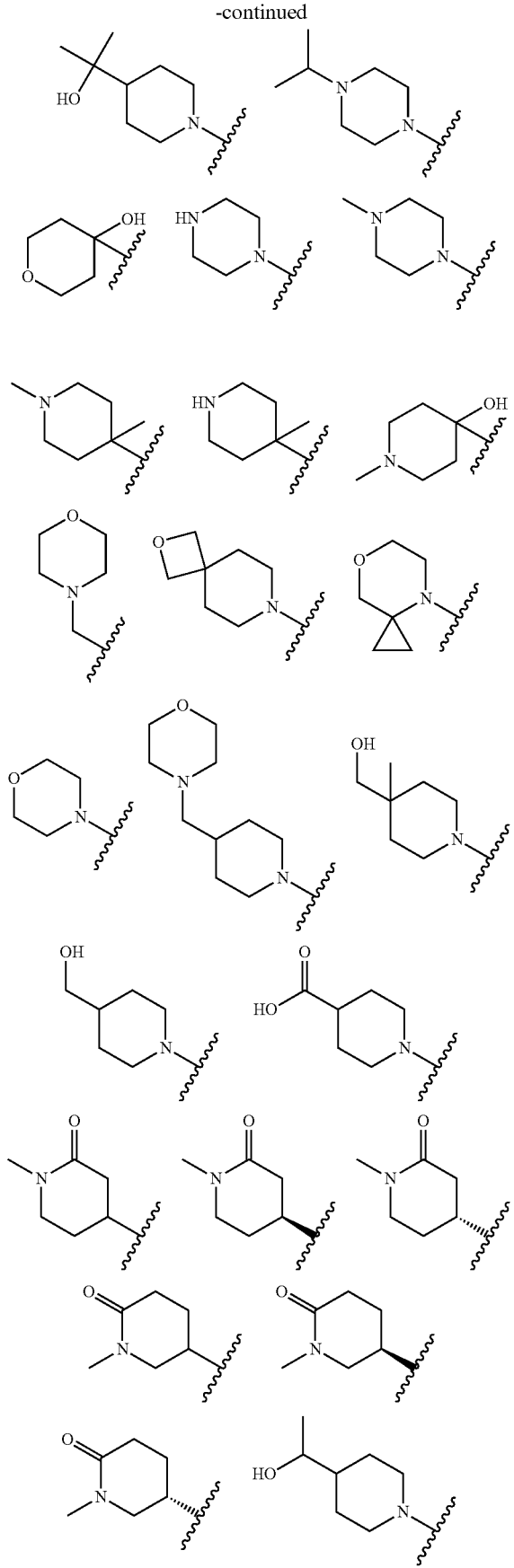

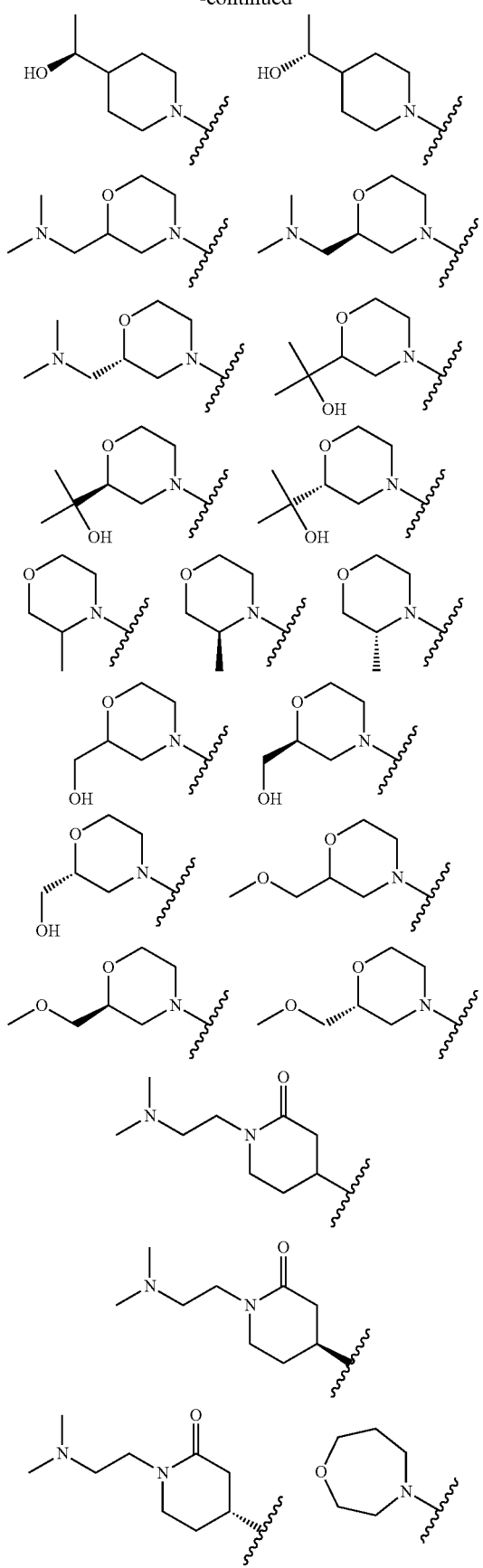
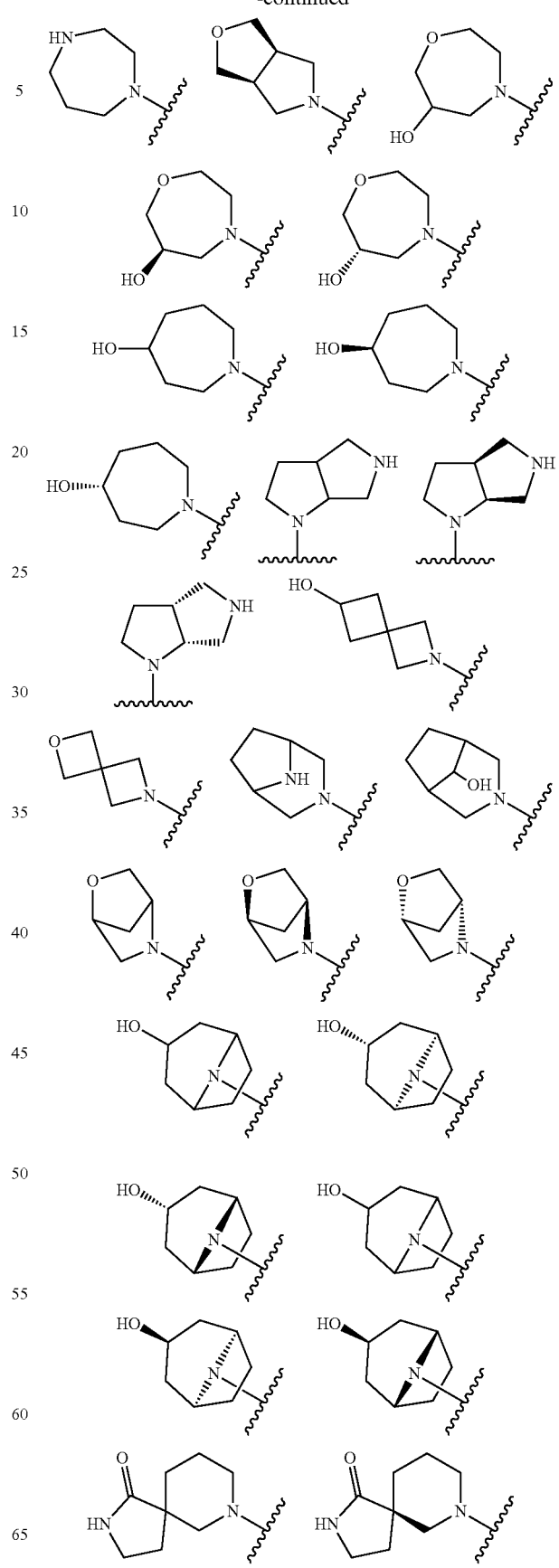

-continued
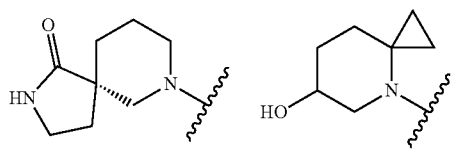
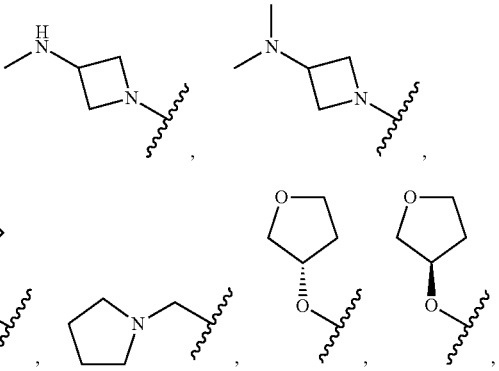
In some embodiments, each $R^C$ is independently —CHF$_2$ or chloro.
In some embodiments, each $R^C$ is independently
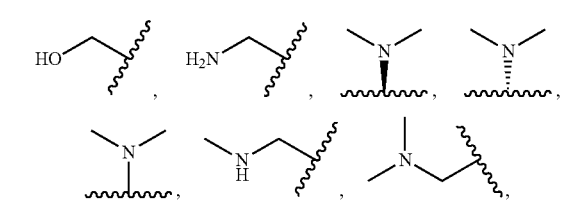
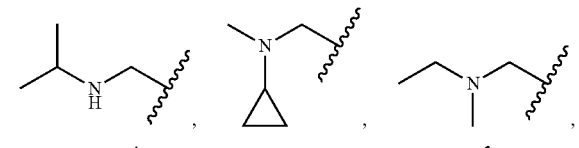
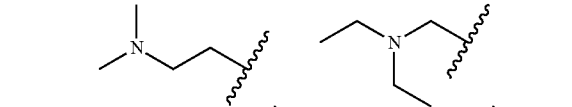
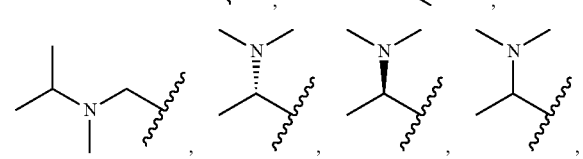
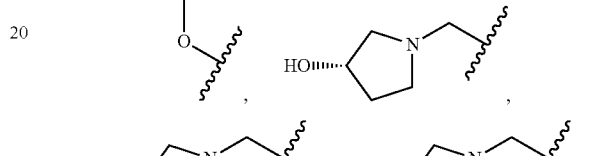
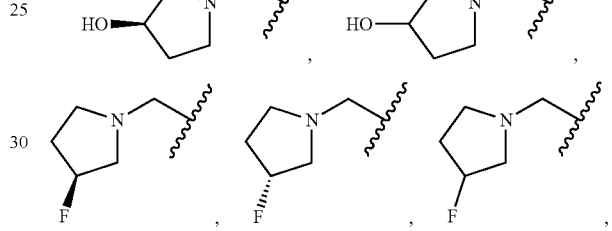
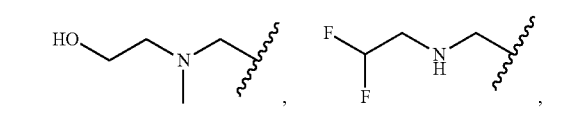
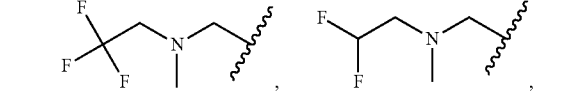
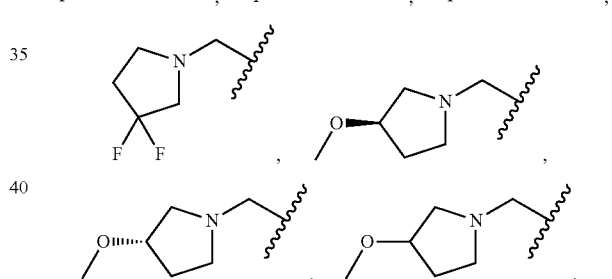
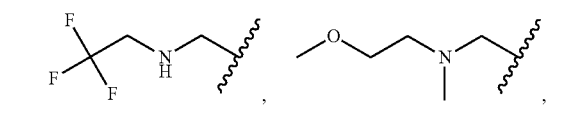
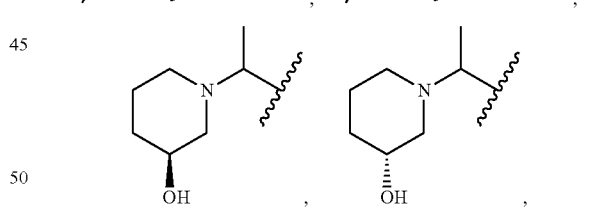
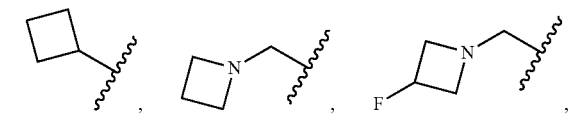
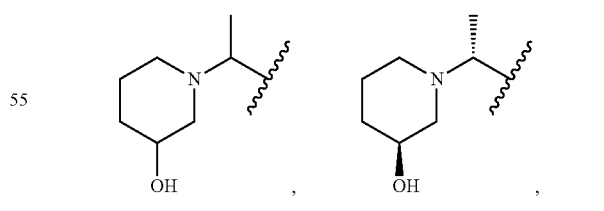
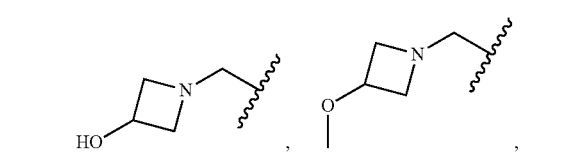
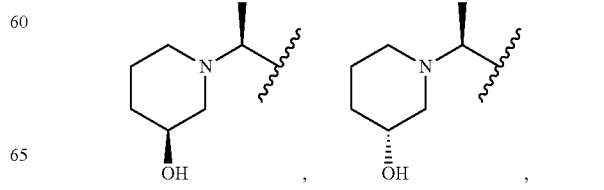

-continued
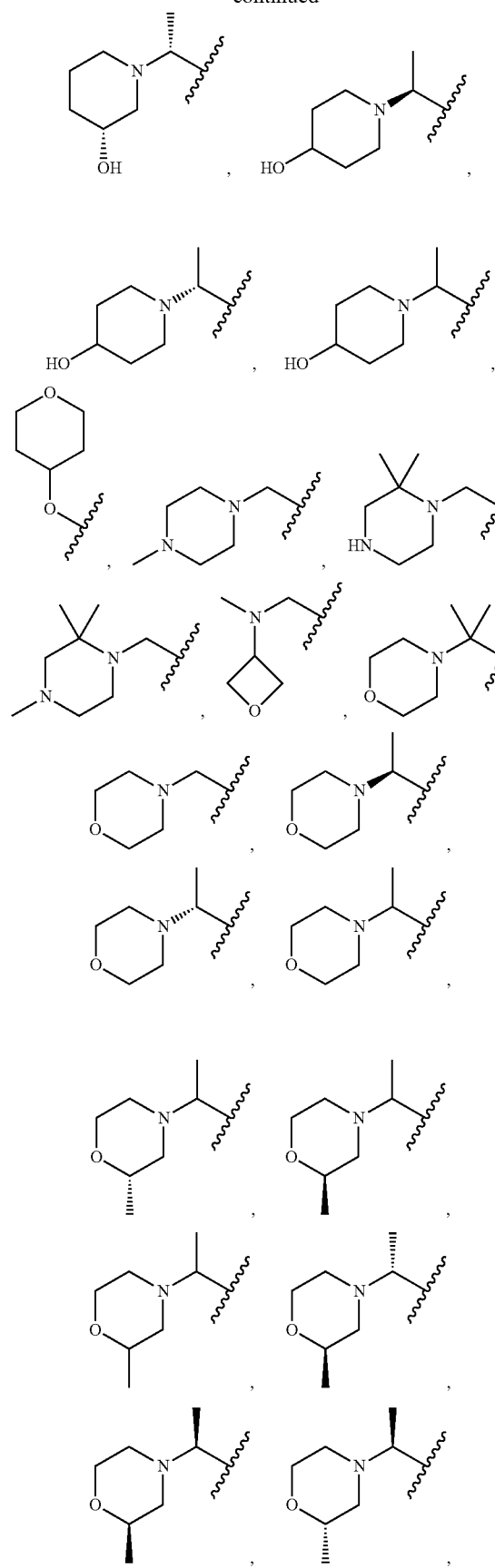
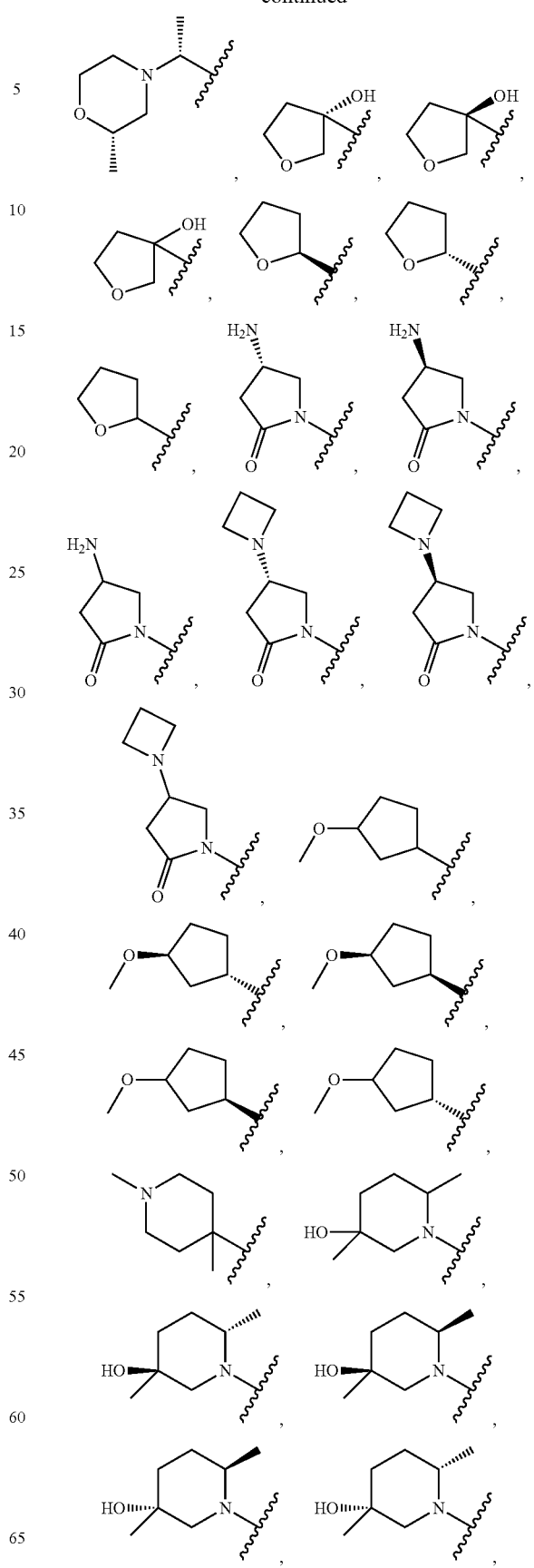

123
-continued

124
-continued

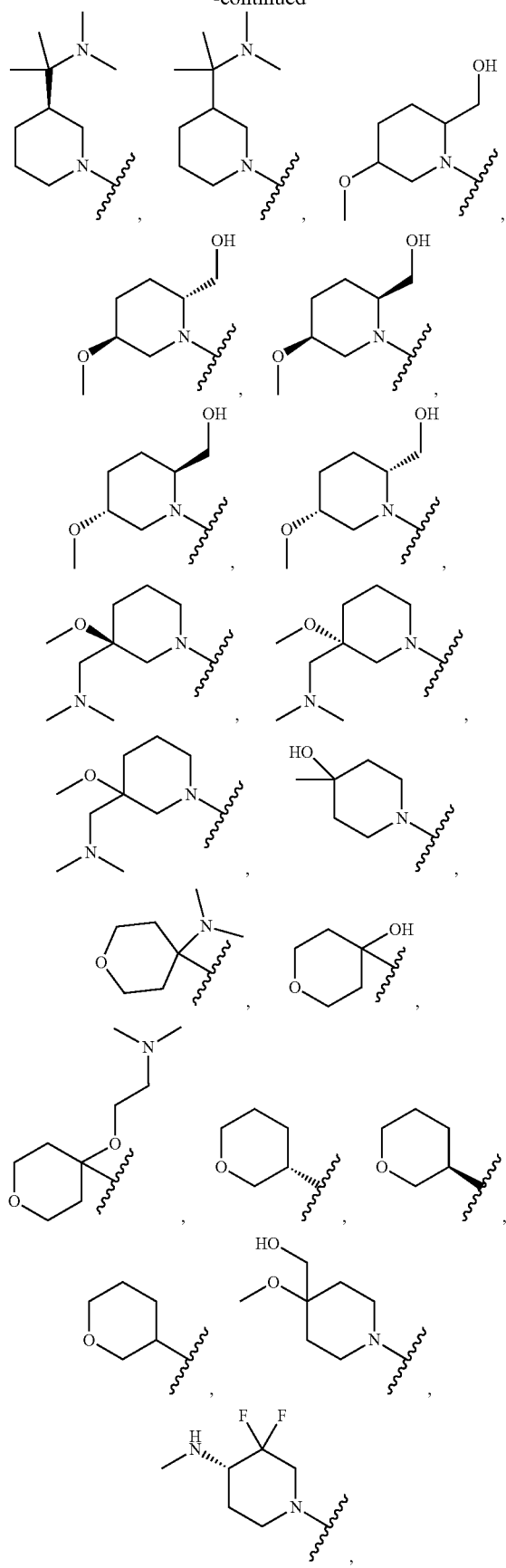
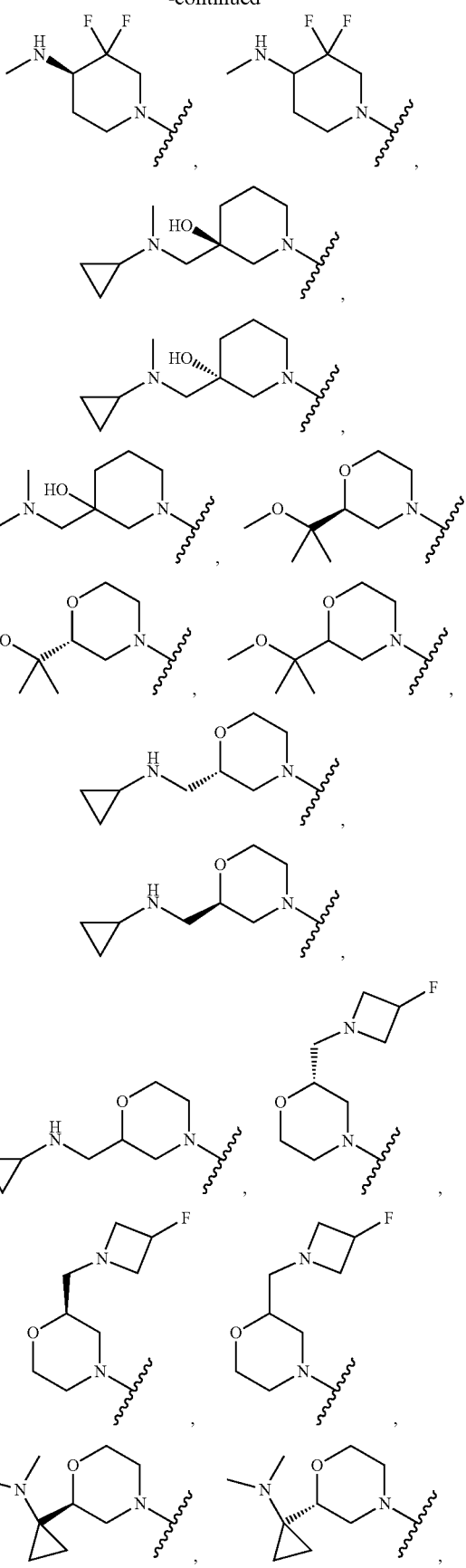

127
-continued
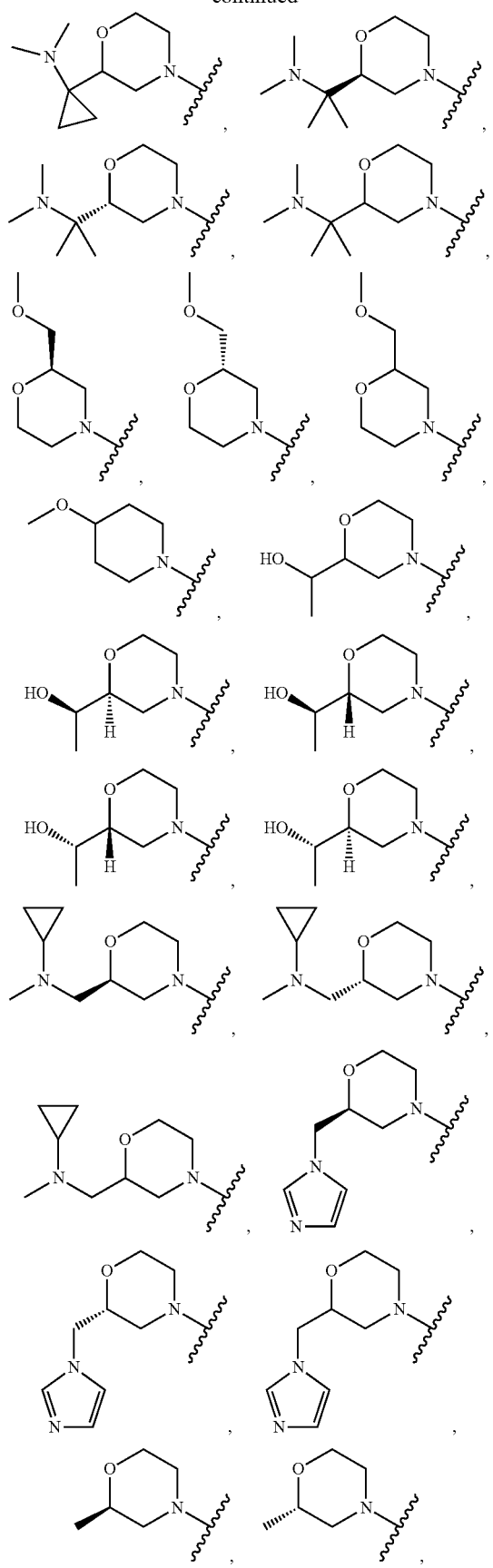
128
-continued
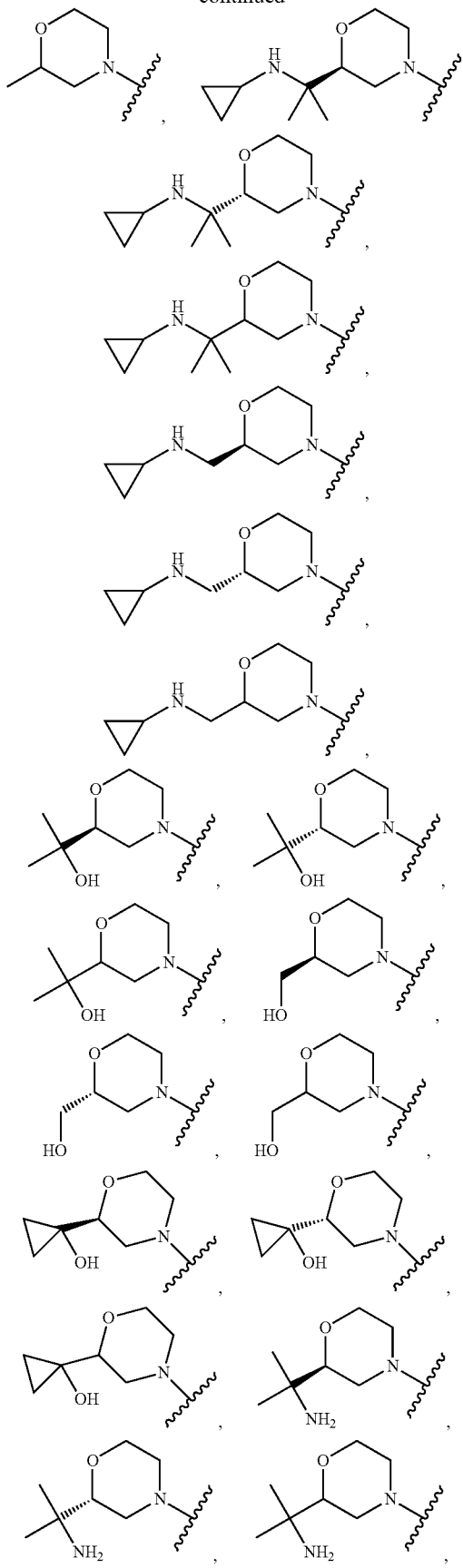

129
-continued
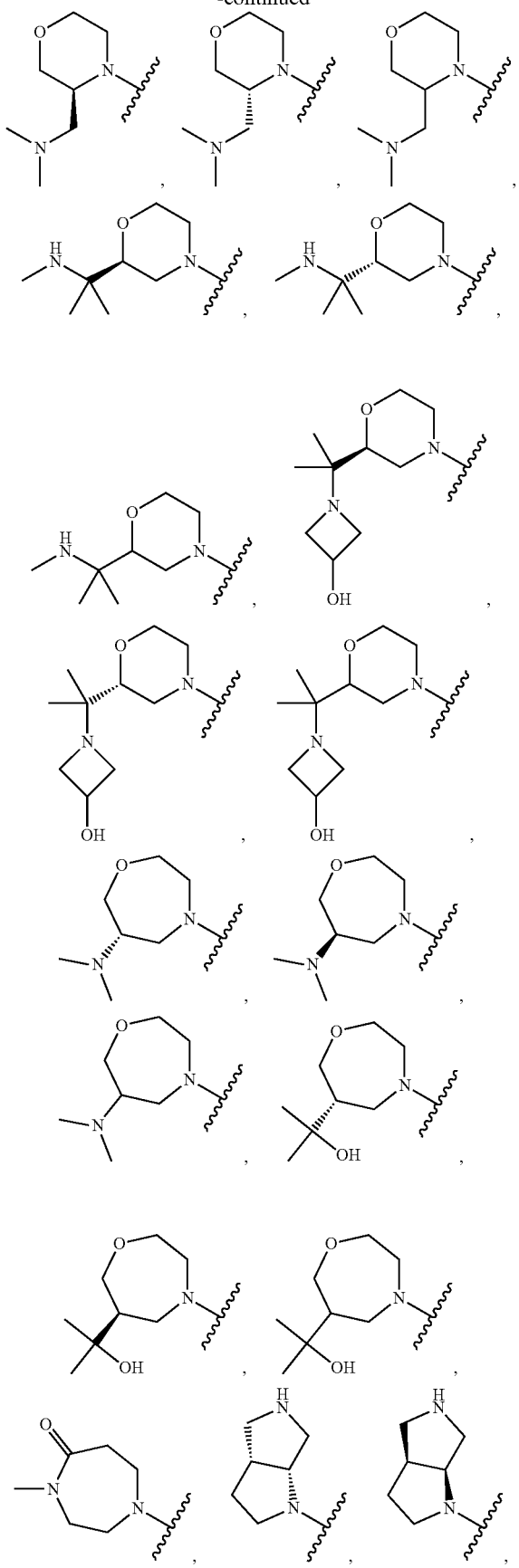
130
-continued
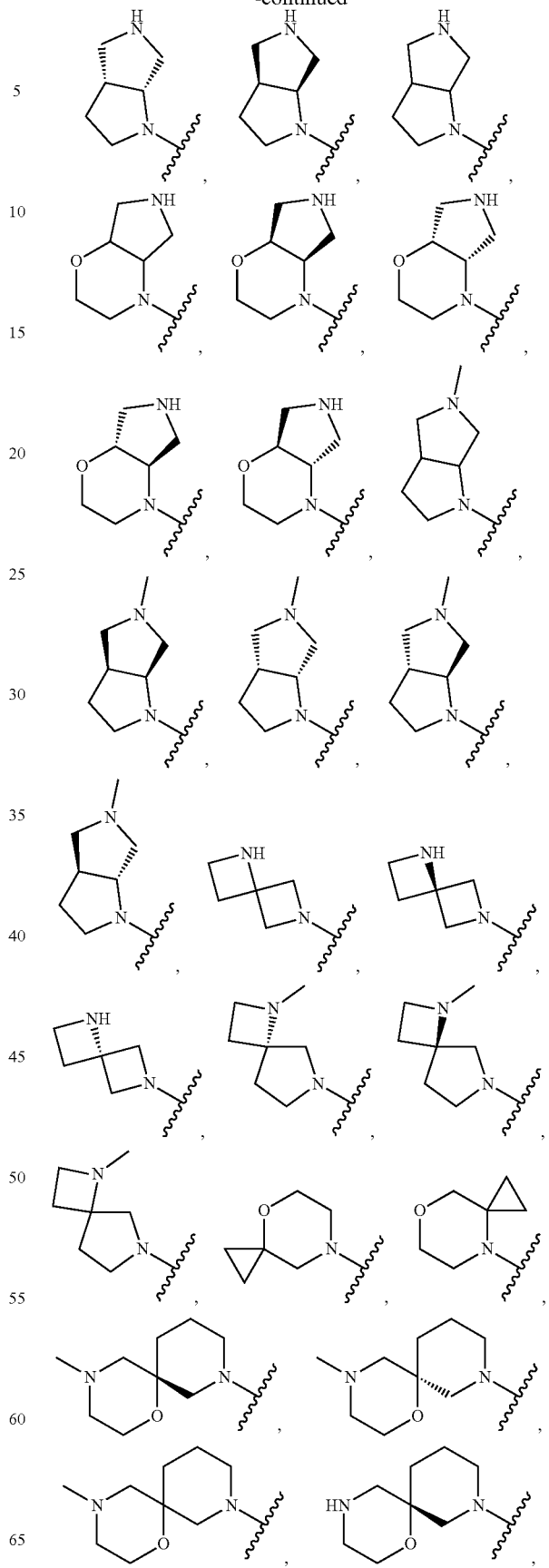

-continued
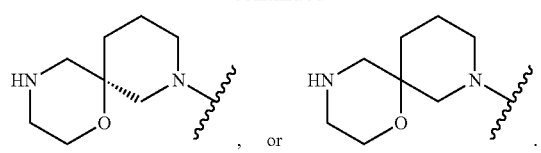
, or
In some embodiments, each $R^C$ is independently
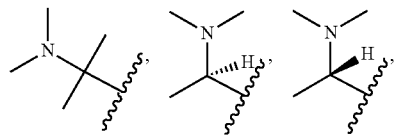
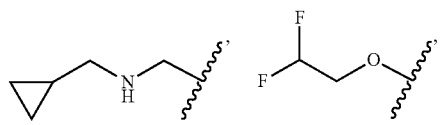
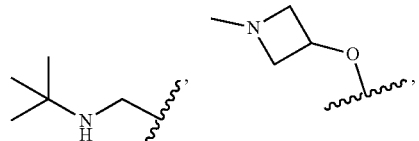
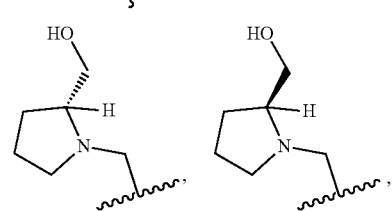
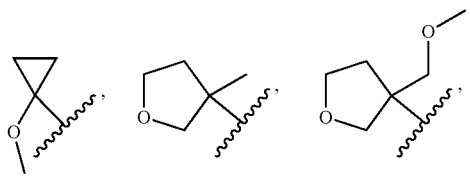
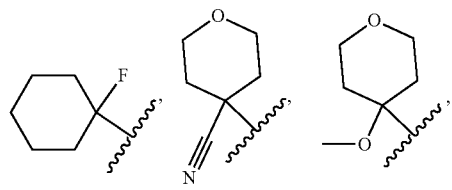
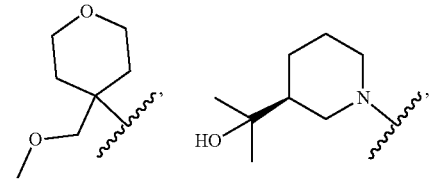
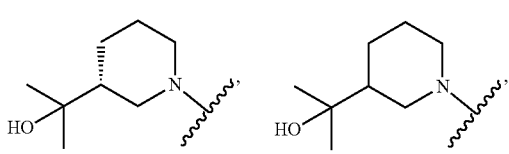
-continued
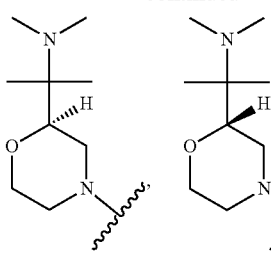
, or
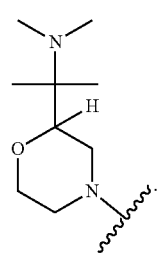
,  ,
In certain embodiments, each $R^C$ is independently -Me, -Et, —F, —OMe, —NH$_2$, —NHMe, —N(Me)$_2$,
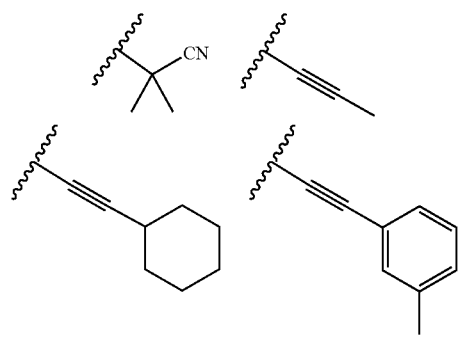
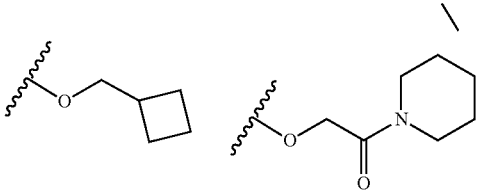
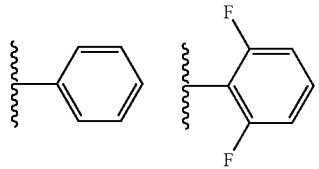

-continued

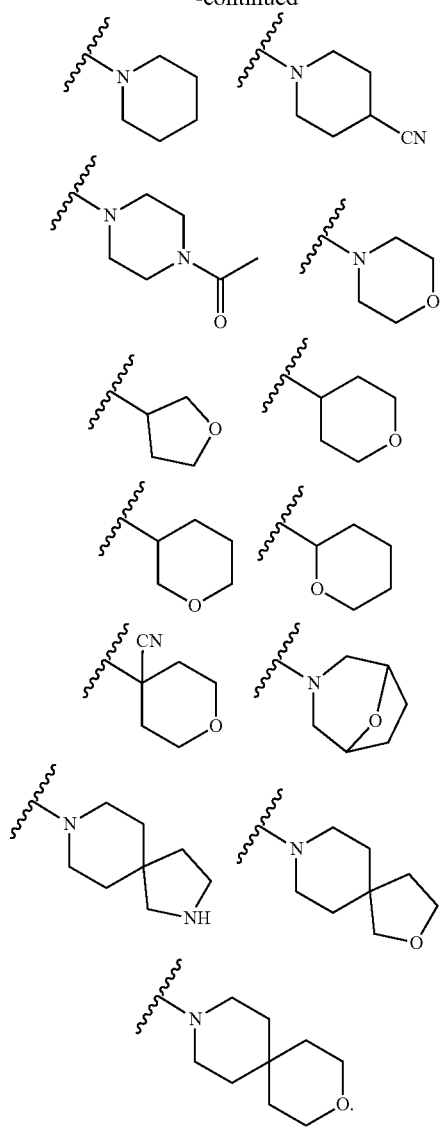

In some embodiments, each instance of $R^C$ is selected from those depicted in Table 1, below.

As defined generally above, each instance of $R^D$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, $R^D$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, $R^D$ is hydroxy, fluoro, or methoxy.

In some embodiments, $R^D$ is

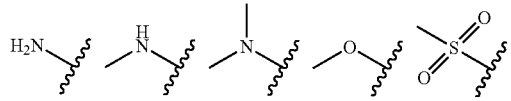

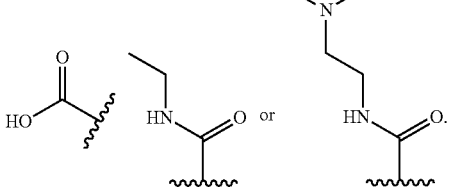

In some embodiments, $R^D$ is oxo.

In some embodiments, $R^D$ is

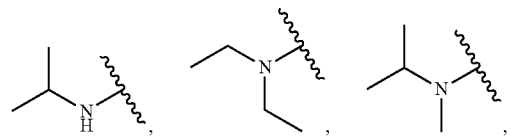

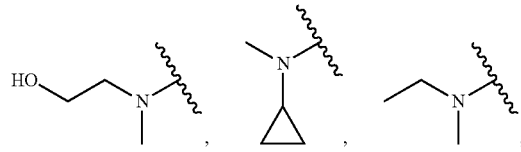

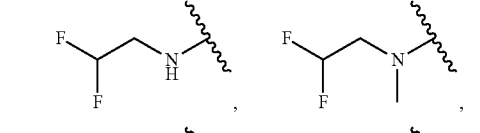

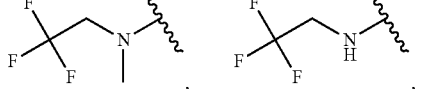

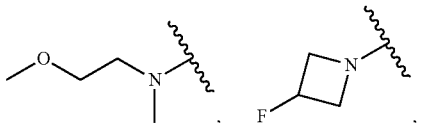

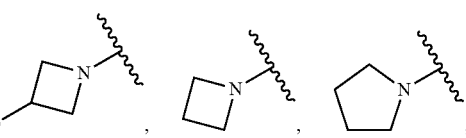

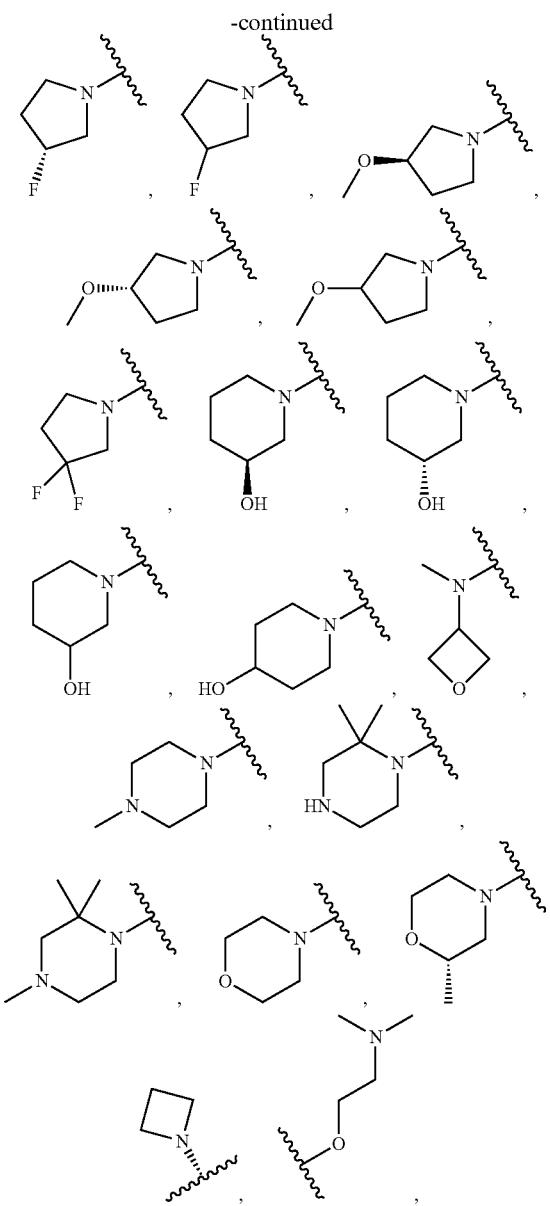

In some embodiments, $R^D$ is selected from those depicted in Table 1, below.

As defined generally above, each R is independently hydrogen, or an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur.

In some embodiments, R is methyl. In some embodiments, R is

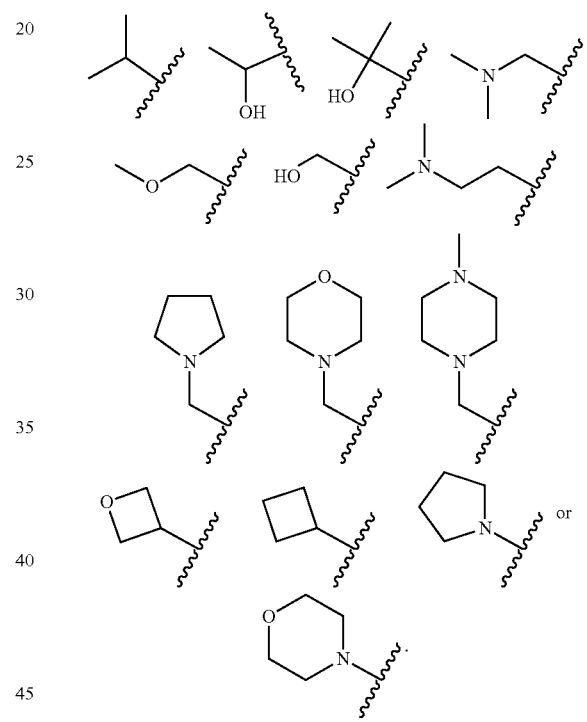

In some embodiments, R is ethyl.

In some embodiments, R is

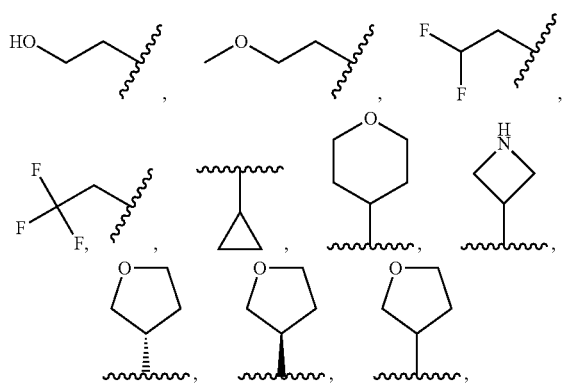

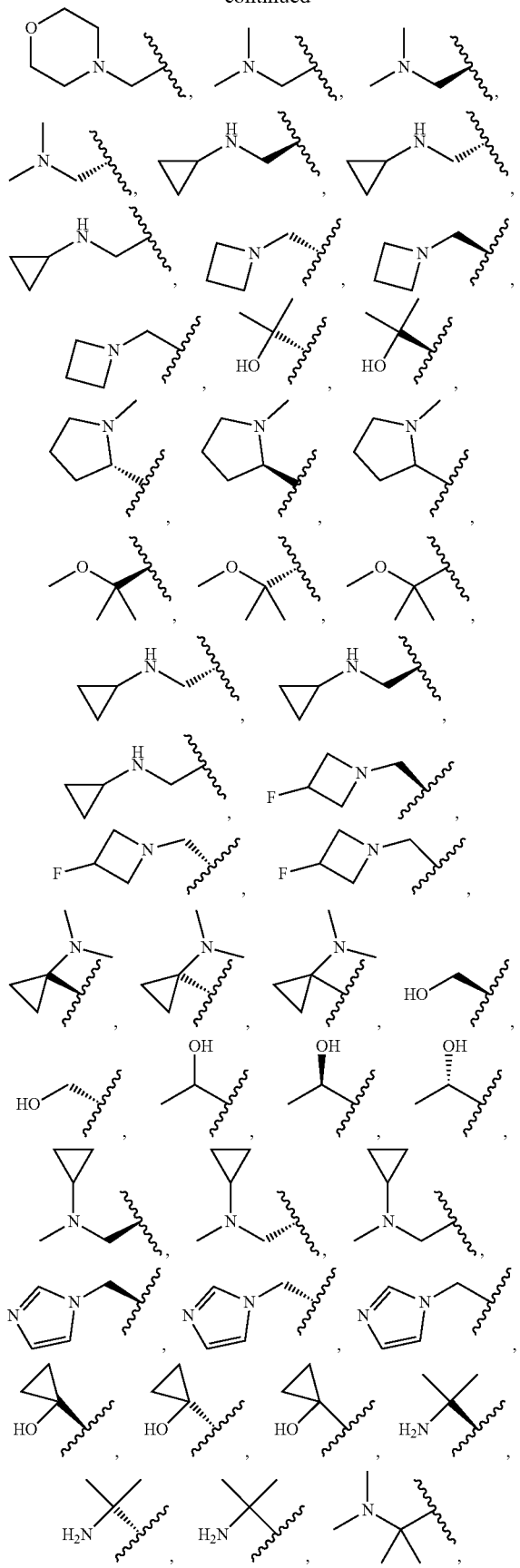

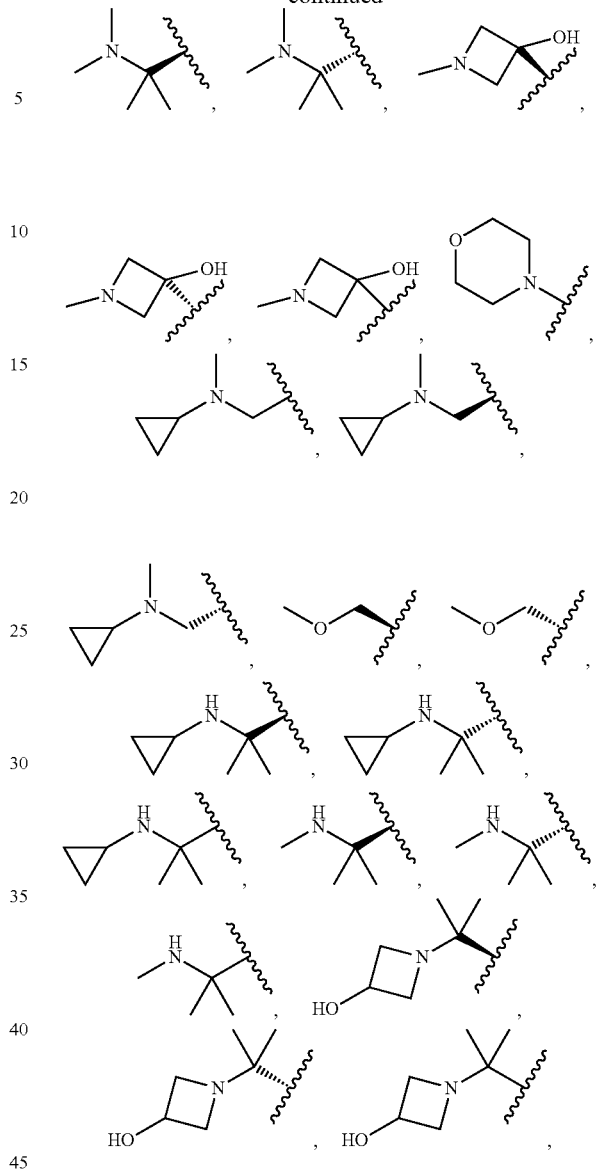

In some embodiments, R is selected from those depicted in Table 1, below.

As defined generally above, each hydrogen bound to carbon can be optionally and independently replaced by deuterium.

In some embodiments, a hydrogen bound to carbon is replaced by deuterium.

As defined generally above, m is 0, 1, or 2.

In some embodiments, m is 0. In some embodiments, m is 1. In some embodiments, m is 2.

In some embodiments, m is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is 1, 2, or 3. In some embodiments, q is 1 or 2.

In some embodiments, q is selected from those depicted in Table 1, below.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, r is 1 or 2. In some embodiments, r is 2 or 3. In some embodiments, r is 2, 3, or 4.

In some embodiments, r is selected from those depicted in Table 1, below.

As defined generally above, s is 0, 1, 2, 3, or 4. In some embodiments, s is 0. In some embodiments, s is 1, 2, 3, or 4. In some embodiments, s is 1. In some embodiments, s is 2. In some embodiments, s is 3. In some embodiments, s is 4.

In some embodiments, s is 1 or 2. In some embodiments, s is 2 or 3. In some embodiments, s is 2, 3, or 4.

In some embodiments, s is selected from those depicted in Table 1, below.

In some embodiments, the present invention provides a compound of formula II:

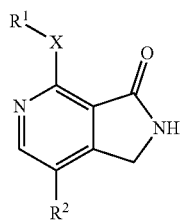

II or a pharmaceutically acceptable salt thereof, wherein each of X, $R^1$ and $R^2$, is as defined above and described in embodiments herein, both singly and in combination.

In some embodiments, the present invention provides a compound of formula III:

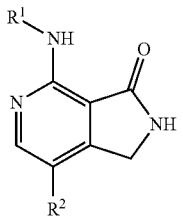

III or a pharmaceutically acceptable salt thereof, wherein each of $R^1$ and $R^2$, is as defined above and described in embodiments herein, both singly and in combination.

Exemplary compounds of the invention are set forth in Table 1, below.

TABLE 1

Selected Compounds

| I-# | Structure |
|---|---|
| I-1 | 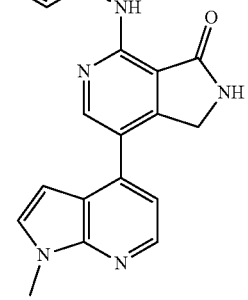 |
| I-2 | 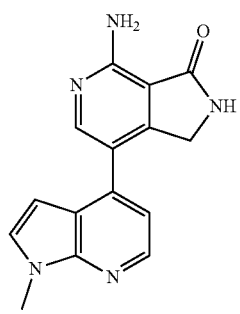 [SMILES: Cn1ccc2c(-c3cnc(N)c4c3CNC4=O)ccnc21] |
| I-3 | 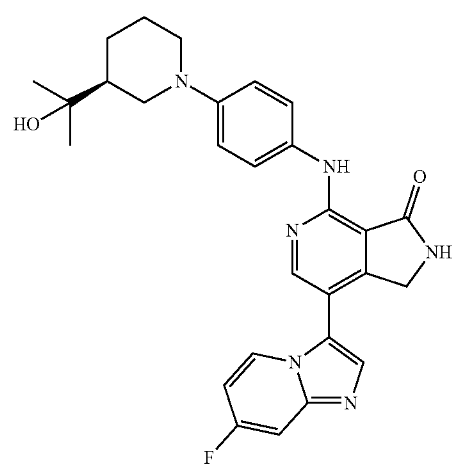 [SMILES: CC(C)(O)[C@H]1CCCN(c2ccc(Nc3ncc(-c4cnc5cc(F)ccn45)c4c3C(=O)NC4)cc2)C1] |

TABLE 1-continued
Selected Compounds
| I-# | Structure |
|---|---|
| I-4 | 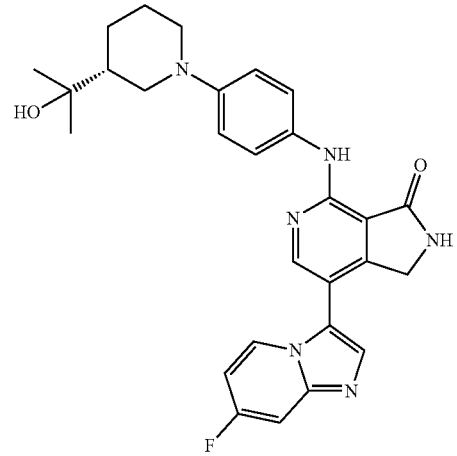 [SMILES: CC(C)(O)[C@@H]1CCCN(c2ccc(Nc3ncc(-c4cnc5cc(F)ccn45)c4c3C(=O)NC4)cc2)C1] |
| I-5 | 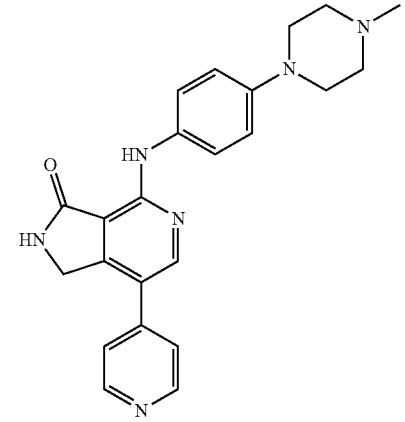 [SMILES: CN1CCN(c2ccc(Nc3ncc(-c4ccncc4)c4c3C(=O)NC4)cc2)CC1] |
| I-6 | 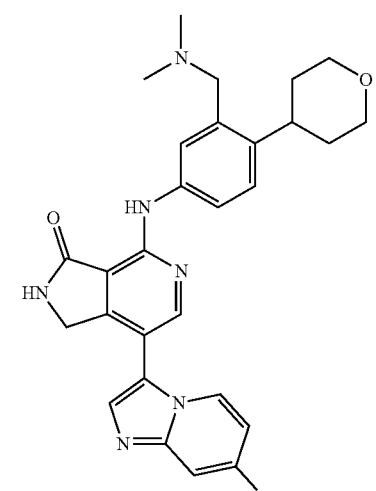 |
| I-7 | 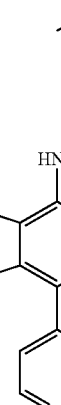 |
| I-8 | 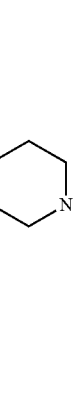 |
| I-9 | 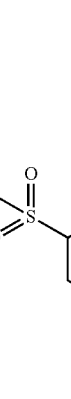 |

TABLE 1-continued
Selected Compounds
| I-# | Structure |
|---|---|
| I-10 | 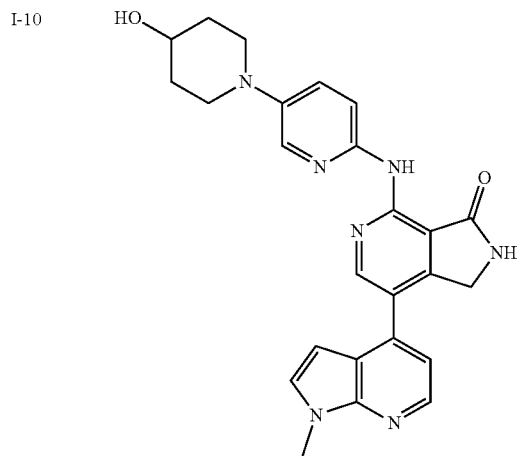 |
| I-11 | 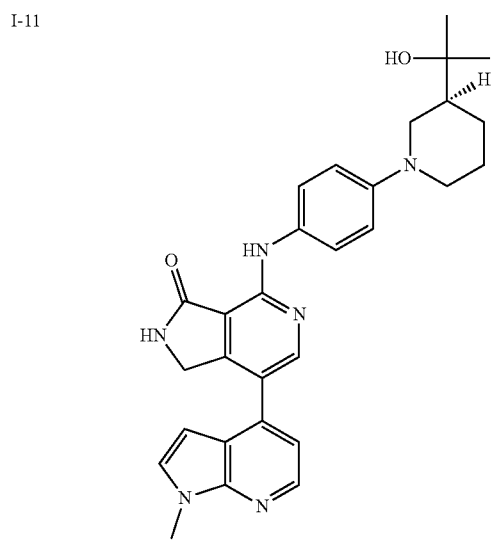 |
| I-12 | 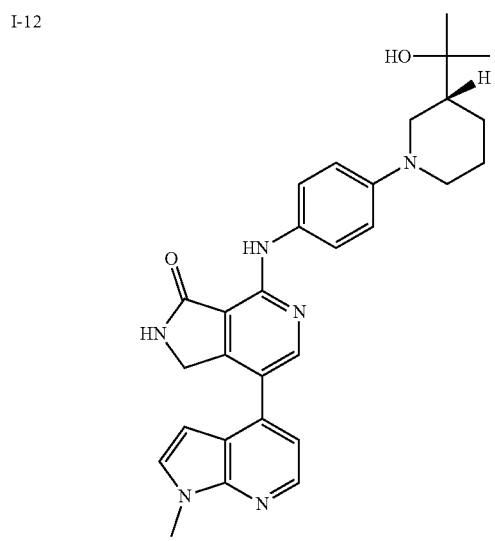 |
TABLE 1-continued
Selected Compounds
| I-# | Structure |
|---|---|
| I-13 | 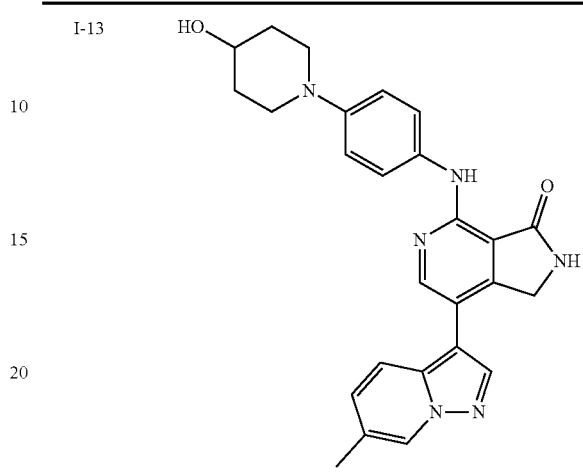 |
| I-14 | 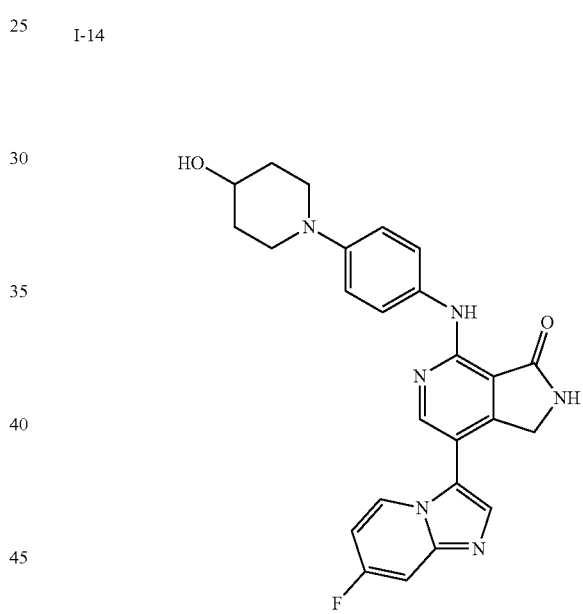 |
| I-15 | 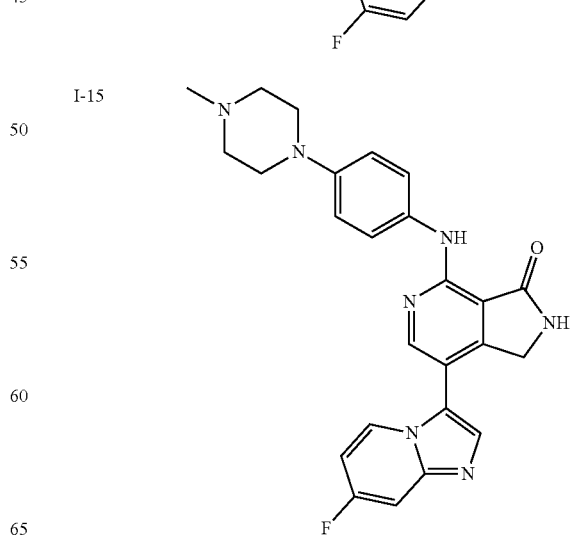 |

TABLE 1-continued

Selected Compounds

| I-# | Structure |
|---|---|
| I-16 | 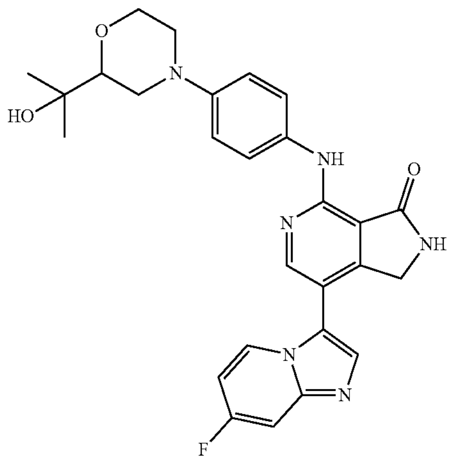 [SMILES: CC(C)(O)C1CN(c2ccc(Nc3ncc(-c4cnc5cc(F)ccn45)c4c3C(=O)NC4)cc2)CCO1] |
| I-17 | 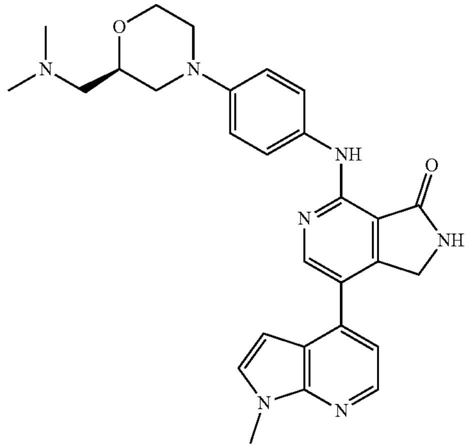 [SMILES: CN(C)C[C@@H]1CN(c2ccc(Nc3ncc(-c4ccnc5c4ccn5C)c4c3C(=O)NC4)cc2)CCO1] |
| I-18 | 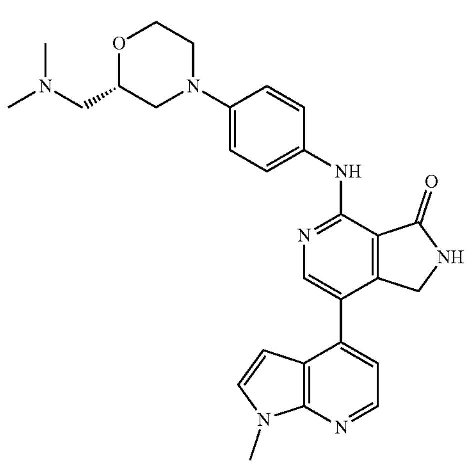 [SMILES: CN(C)C[C@H]1CN(c2ccc(Nc3ncc(-c4ccnc5c4ccn5C)c4c3C(=O)NC4)cc2)CCO1] |
| I-19 | |
| I-20 | |
| I-21 | |

TABLE 1-continued
Selected Compounds
| I-# | Structure |
|---|---|
| I-22 | 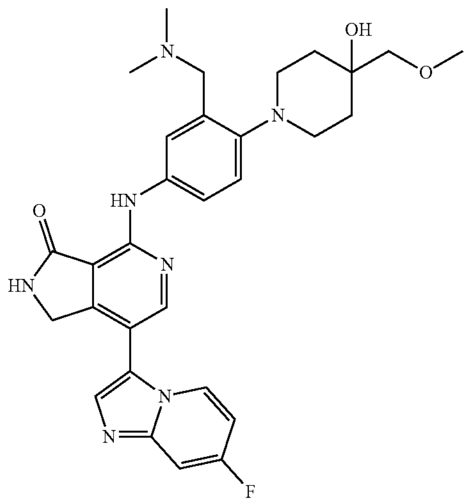 [SMILES: COCC1(O)CCN(c2ccc(Nc3ncc(-c4cnc5cc(F)ccn45)c4c3C(=O)NC4)cc2CN(C)C)CC1] |
| I-23 | 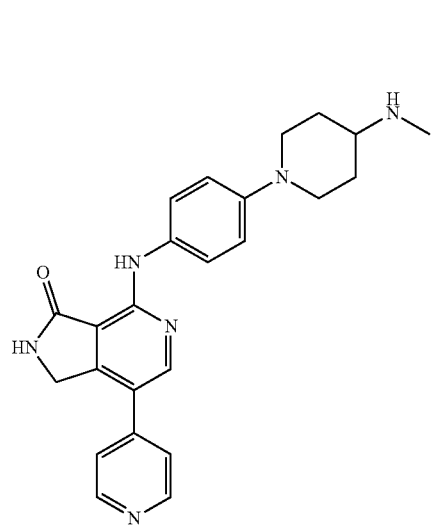 [SMILES: CNC1CCN(c2ccc(Nc3ncc(-c4ccncc4)c4c3C(=O)NC4)cc2)CC1] |
| I-24 | 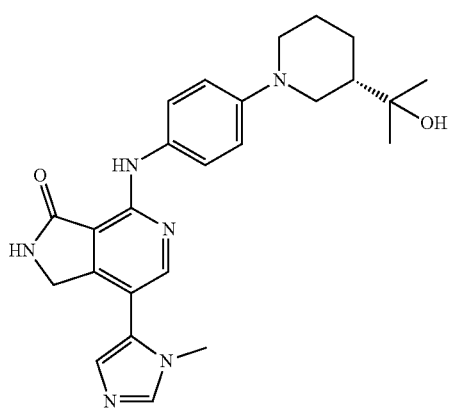 [SMILES: Cn1cncc1-c1cnc(Nc2ccc(N3CCC[C@H](C(C)(C)O)C3)cc2)c2c1CNC2=O] |
TABLE 1-continued
Selected Compounds
| I-# | Structure |
|---|---|
| I-25 | 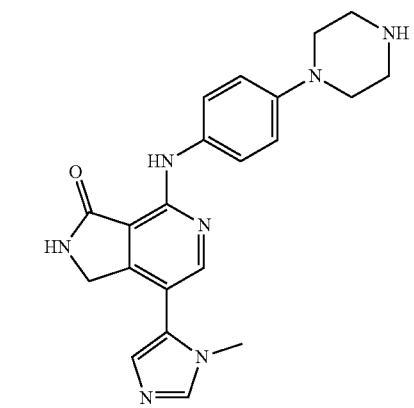 [SMILES: Cn1cncc1-c1cnc(Nc2ccc(N3CCNCC3)cc2)c2c1CNC2=O] |
| I-26 | 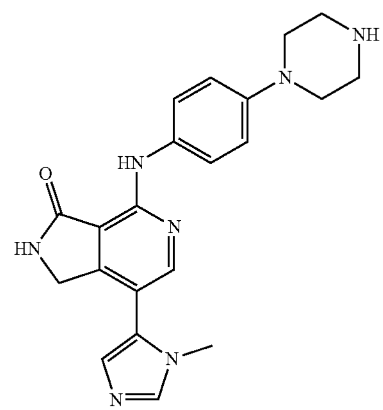 |
| I-27 | 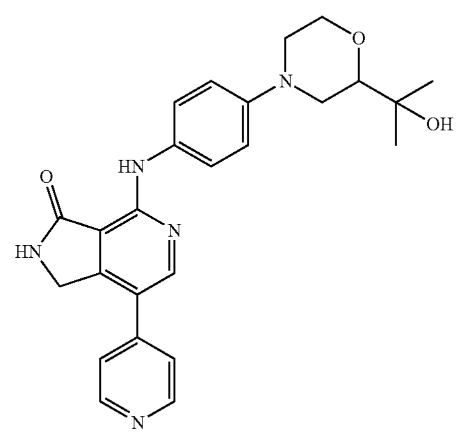 |

TABLE 1-continued

Selected Compounds

| I-# | Structure |
|---|---|
| I-28 | *[chemical structure: morpholine with 2-(2-hydroxypropan-2-yl) substituent, connected via phenyl-NH to a pyrrolopyridinone core bearing a pyridin-4-yl group]* |
| I-29 | *[chemical structure: dimethylaminomethyl-phenyl with (S)-tetrahydrofuran-3-yl substituent, connected via NH to a pyrrolopyridinone core bearing a 6-fluoroimidazo[1,2-a]pyridin-3-yl group]* |
| I-30 | *[chemical structure: dimethylaminomethyl-phenyl with (R)-tetrahydrofuran-3-yl substituent, connected via NH to a pyrrolopyridinone core bearing a 6-fluoroimidazo[1,2-a]pyridin-3-yl group]* |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In some embodiments, the invention also provides compounds of formula I described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of formula I described herein or pharmaceutical compositions described herein for use in a method for inhibiting HPK1 as described herein.

In some embodiments, the invention also provides compounds of formula I described herein or pharmaceutical compositions described herein for use in a method for enhancing an immune response in a subject in need thereof as described herein.

In some embodiments, the invention also provides compounds of formula I described herein or pharmaceutical compositions described herein for use in a method for treating a HPK1-dependent disorder as described herein.

In some embodiments, the invention also provides the use of a compound of formula I described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of formula I described herein or a pharmaceutical composition described herein for the manufacture of a medicament for inhibiting HPK1.

In some embodiments, the invention also provides the use of a compound of formula I described herein or a pharmaceutical composition described herein for the manufacture of a medicament for enhancing an immune response in a subject in need thereof.

In some embodiments, the invention also provides the use of a compound of formula I described herein or a pharmaceutical composition described herein for the manufacture of a medicament treating a HPK1-dependent disorder.

In some embodiments, the invention also provides the use of compounds of formula I described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of formula I described herein or pharmaceutical compositions described herein in a method for inhibiting HPK1 as described herein.

In some embodiments, the invention also provides the use of compounds of formula I described herein or pharmaceutical compositions described herein in a method for enhancing an immune response in a subject in need thereof as described herein.

In some embodiments, the invention also provides the use of compounds of formula I described herein or pharmaceutical compositions described herein in a method for treating a HPK1-dependent disorder as described herein.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit HPK1, or a mutant thereof, in a biological sample or in a patient. In certain embodiments, the amount of compound in compositions of this invention is such that is effective to measurably inhibit HPK1, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of HPK1, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The compounds and compositions described herein are generally useful for the inhibition of kinase activity of one or more enzymes. In some embodiments the kinase inhibited by the compounds and methods of the invention is HPK1.

The presently disclosed compounds find use in inhibiting the activity of the enzyme HPK1. HPK1 is a member of the germinal center kinase subfamily of Ste20-related serine/threonine kinases. HPK1 functions as a MAP4K by phosphorylating and activating MAP3K proteins, including MEKK1, MLK3 and TAK1, leading to the activation of the MAPK Jnk.

In one embodiment, the subject matter disclosed herein is directed to a method of inhibiting HPK1, the method comprising contacting HPK1 with an effective amount of a compound of the invention or a pharmaceutical composition described herein.

In certain embodiments, the subject matter disclosed herein is directed to a method for enhancing an immune response in a subject in need thereof, wherein the method comprises administering to the subject an effective amount of a compound of the invention or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+ CD8 T cells or enhanced levels of IL-2 or granzyme B production by T cells relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a compound of the invention.

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of the invention or a pharmaceutically acceptable salt, prodrug, metabolite, or derivative thereof. In some embodiments, the CD8 T cell priming is characterized by elevated CD44 expression and/or enhanced cytolytic activity in CD8 T cells. In some embodiments, the CD8 T cell activation is characterized by an elevated frequency of γ-IFN$^+$ CD8 T cells. In some embodiments, the CD8 T cell is an antigen-specific T-cell.

In some embodiments, the antigen presenting cells in the subject have enhanced maturation and activation relative to prior to the administration of the compound of the invention or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I or Ia or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) J Cell Biol 195(5):839-853).

In some embodiments, administration of a compound of the invention or a pharmaceutically acceptable salt, prodrug, metabolite, or derivative thereof to a subject results in an enhancement of T cell function.

Accordingly, the presently disclosed compounds of the invention or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, γ-IFN) and/or target cell killing.

The term "anergy" refers to the state of unresponsiveness to antigen stimulation resulting from incomplete or insufficient signals delivered through the T-cell receptor (e.g. increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Immunogenecity" refers to the ability of a particular substance to provoke an immune response. Tumors are immunogenic and enhancing tumor immunogenicity aids in the clearance of the tumor cells by the immune response.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., y-interferon, IL-2, IL-12, and TNFα), increased proliferation, increased antigen responsiveness (e.g., viral, pathogen, or tumor clearance) relative to such levels before the intervention, and increased effector granule production by CD8 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

The present disclosure provides methods of modulating (e.g., inhibiting) HPK1 activity, said method comprising administering to a patient a compound provided herein, or a pharmaceutically acceptable salt thereof.

In one aspect, provided herein is a method for treating of cancer in a subject in need thereof comprising administering to the subject an effective amount of a compound of the invention or a pharmaceutically acceptable salt, prodrug, metabolite, or derivative thereof.

In the methods described herein, a compound of the invention or a pharmaceutical composition thereof is administered to a subject that has cancer.

In certain embodiments, the subject matter disclosed herein is directed to a method for treating a HPK1-dependent disorder, the method comprising administering to a subject in need thereof an effective amount of a compound of the invention or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In some embodiments, the subject matter disclosed herein is directed to a method for treatment of chronic viral infections. In some embodiments, the subject matter disclosed herein is directed to the use of an HPK1 inhibitor as an adjuvant treatment for increasing the efficacy of vaccination.

In some embodiments, the invention provides a pharmaceutical composition comprising an effective amount of a compound of the invention, or a pharmaceutically acceptable salt, hydrate, solvate, or prodrug thereof, and a pharmaceutically acceptable carrier.

In certain aspects, the invention provides a method of treating cell proliferation disorders, including cancers, benign papillomatosis, gestational trophoblastic diseases, and benign neoplastic diseases, such as skin papilloma (warts) and genital papilloma.

In one aspect, the invention provides a method of treating a cell proliferation disorder in a subject, comprising administering a therapeutically effective amount of a compound of the invention, or a pharmaceutically acceptable salt, hydrate, solvate, or prodrug thereof, to the subject.

In certain embodiments, the cell proliferation disorder is cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In certain embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In a further embodiment, the cancer is selected from brain and spinal cancers. In particular embodiments, the cancer is selected from the group consisting of anaplastic astrocytomas, glioblastomas, astrocytomas, and estheosioneuroblastomas (olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (hepatocellular carcinoma). In particular embodiments, the cancer is bile duct cancer (cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, and chordoma.

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, and primary central nervous system lymphomas.

In specific embodiments, the cancer is selected from glandular cancers. In particular embodiments, the cancer is selected from the group consisting of adrenocortical cancer, pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, 0.01 µg/kg, 0.05 g/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Azanol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting HPK1, or a mutant thereof, activity in a biological sample comprising the step of contacting said biological sample with a compound of this invention, or a composition comprising said compound. In certain embodiments, the invention relates to a method of irreversibly inhibiting HPK1, or a mutant thereof, activity in a biological sample comprising the step of contacting said biological sample with a compound of this invention, or a composition comprising said compound.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of HPK1 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of HPK1, or a mutant thereof, in a patient comprising the step of administering to said patient a compound of the present invention, or a composition comprising said compound. According to certain embodiments, the invention relates to a method of reversibly or irreversibly inhibiting one or more of HPK1, or a mutant thereof, activity in a patient comprising the step of administering to said patient a compound of the present invention, or a composition comprising said compound. In other embodiments, the present invention provides a method for treating a disorder mediated by HPK1, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™ Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™) The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™ Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; 1sis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C$_{1-10}$33, EKB-569, GW-2016, ELI, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD 113, GPR56, VISTA, 2B4, CD48, GARP, PDIH, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137

(4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, New-Link Genetics Corporation); capmanitib (INC280, Novartis); GDC-0919 (Genentech/Roche); PF-06840003 (Pfizer); BMS.F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO®, Bristol-Myers Squibb, also known as ONO-4538, MDX1106 and BMS-936558), has shown potential to improve the overall survival inpatients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1 h68/GLV-1 h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFa-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the conten of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, $\gamma\delta$, and memory $CD8^+$ ($\alpha\beta$) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MED14736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca; and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirilumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MED10562 (Medimmune/AstraZeneca), an agonistic anti-OX40 antibody, in advanced solid tumors (NCT02318394 and NCT02705482); MED16469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

Method PB1—Preparation of 7-fluoro-3-iodoimidazo[1,2-a]pyridine (PB1)

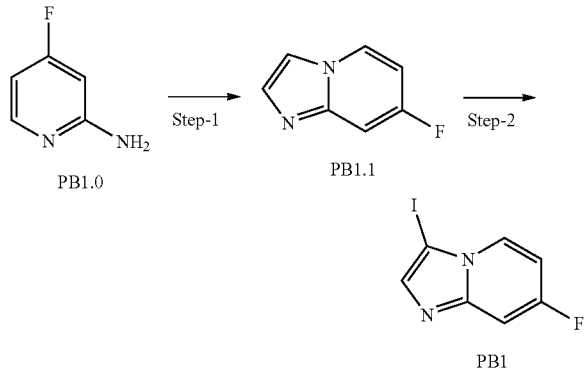

Step-1. 7-fluoroimidazo[1,2-a]pyridine (PB1.1)

To a solution of 4-fluoropyridin-2-amine (PB1.0) (50 g, 0.44 mol, 1.0 eq) in Ethanol (450 ml) was added Chloroacetaldehyde (50% in Water) (300 ml, 6V) and Sodium bicarbonate (74.9 g, 0.89 mol, 2.0 eq) then the reaction was stirred at 60° C. for 4 h. After completion of reaction, the reaction mixture was concentrated under vacuum. The Crude obtained was purified via column chromatography and the compound was eluted in 35% ethyl acetate in hexane to obtain PB1.1 (50 g, 82.35% yield) MS (ES): m/z 137.16 [M+H]+, 1H NMR (400 MHz, DMSO): δ 8.62 (t, 1H), 7.93 (s, 1H), 7.54 (s, 1H), 7.39 (d, 1H), 6.96 (t, 1H).

Step-2. 7-fluoro-3-iodoimidazo[1,2-a]pyridine (PB1)

To a solution 7-fluoroimidazo[1,2-a]pyridine (PB1.1) (28 g, 0.20 mol, 1.0 eq) in Chloroform (300 ml) was added N-iodosuccinimide (50.65 g, 0.22 mol, 1.1 eq) and stirred at room temperature for 3 h. After completion of reaction, the reaction mixture was quenched with a solution of sodium thiosulphate (1000 ml) and extracted with ethyl acetate (600 ml×3), dried over sodium sulphate and concentrated on vacuum. Crude was purified via column chromatography and the pure compound was eluted in 18% ethyl acetate in hexane to obtain PB1 (30 g, 56.6% yield) MS (ES): m/z 262.94 [M+H]+ 1H NMR (400 MHz, DMSO): δ 7.11 (m, 1H), 7.54 (d, 1H), 7.69 (s, 1H), 8.36-8.39 (t, 1H).

Method PB2—Preparation of 6-methyl-3-(4,4,5,5-tetramethyl-1,3,2-dioxaborolan-2-yl)pyrazolo[1,5-a]pyridine (PB2)

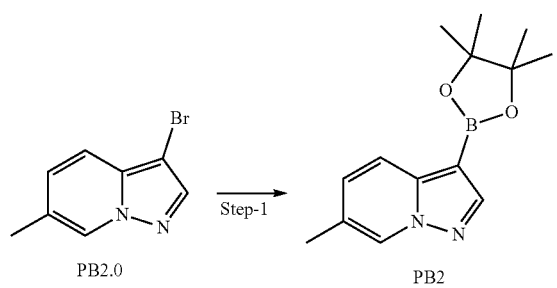

Step 1. 6-methyl-3-(4,4,5,5-tetramethyl-1,3,2-dioxaborolan-2-yl)pyrazolo[1,5-a]pyridine (PB2)

To a solution of 3-bromo-6-methylpyrazolo[1,5-a]pyridine (PB2.0) (0.88 g, 0.041 mol, 1.0 eq), Bis(pinacolato)diboron (3.17 g, 0.012.3 eq) and Tricyclohexylphosphine (116 mg, 0.00041 mol, 0.1 eq) in 1,4-dioxane (10 ml) was added potassium carbonate (1.7 g, 0.0121 mol, 3.0 eq) at room temperature. The reaction mixture was degassed via argon gas for 20 min. After 20 min, palladium(II)acetate (46 mg, 0.0002 mol, 0.05 eq) was added to the reaction mixture and stirred at 100° C. for 1 h. After completion of reaction, the reaction mixture was poured into water (70 ml) and the product was extracted with ethyl acetate (25 ml×3). The combined organic layer was washed with brine solution (20 ml), dried over sodium sulphate and concentrated under reduced pressure to obtain crude material. Crude was further purified via column chromatography and the compound was eluted in 15% ethyl acetate in hexane to obtain PB2 (500 mg, 46%). m/z 259.5 (M+H)+

Method PB3—Preparation of -methyl-4-(4,4,5,5-tetramethyl-1,3,2-dioxaborolan-2-yl)-1H-pyrrolo[2,3-b]pyridine (PB3)

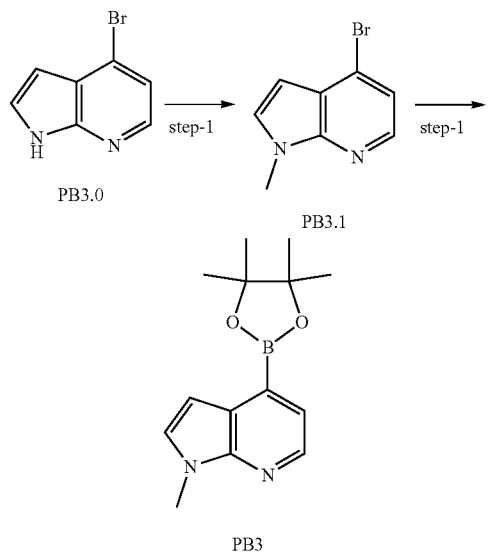

Step 1. 4-bromo-1-methyl-1H-pyrrolo[2,3-b]pyridine (PB3.1)

In a three neck flask, solution of DMF (100 ml) and 60% sodium hydride (8.12 g, 0.2030 mol, 2.0 eq) was stirred at 0° C. under Nitrogen atmosphere for 20 min. To the same reaction mixture was added a solution of 4-bromo-1H-pyrrolo[2,3-b]pyridine (PB3.0) (20.0 g, 0.0473 mol, 1.0 eq) in DMF (50 ml). The reaction mixture was stirred at the same temperature for 30 min. Methyl iodide (7.58 ml, 0.121 mol, 1.2 eq) was added to the reaction mixture and stirred at room temperature for 30 min. After completion of reaction, the reaction mixture was poured into ice-cold water and the product was extracted with ethyl acetate (300 ml×3). The organic layer was combined and dried over sodium sulphate and concentrated under reduced pressure to obtain crude PB3.1 (20 g, quantitative yield). MS (ES): m/z 211.50

[M+H]+ 1H NMR (400 MHz, DMSO): δ 8.15 (d, 1H), 7.67 (d, 1H), 7.38 (d, 1H), 6.45 (d, 1H), 3.90 (s, 3H).

Step 2. 1-methyl-4-(4,4,5,5-tetramethyl-1,3,2-dioxaborolan-2-yl)-1H-pyrrolo[2,3-b]pyridine (PB3)

To a solution of 4-bromo-1-methyl-1H-pyrrolo[2,3-b]pyridine (PB3.1) (10.0 g, 0.047 mol, 1.0 eq) and 4,4,4',4',5,5,5',5'-Octamethyl-2,2'-bi-(1,3,2-dioxaborolane) (11.99 g, 0.0473 mol, 1.0 eq) in 1,4-dioxane (100 ml) was added potassium acetate (13.09 g, 0.141 mol, 3.0 eq) at room temperature. The reaction mixture was degassed via argon gas for 20 min. After 20 min [1,1'-Bis(diphenylphosphino)ferrocene]dichloro palladium(II) dichloromethane complex (3.85 g, 3.85 mol, 0.1 eq) was added to the reaction mixture and stirred at 90° C. for 2.5 h. After completion of reaction, the reaction mixture was poured into water and the product was extracted with ethyl acetate (250 ml×3). The combined organic layer washed with brine solution (100 ml), dried over sodium sulphate and concentrated under reduced pressure to obtain crude material. Crude was further purified via column chromatography and the compound was eluted in 15% ethyl acetate in hexane to obtain PB3 (10.5 g, 82%). m/z 258.5 (M+H)+ 1H NMR (400 MHz, DMSO): δ 8.32 (d, 1H), 7.61 (d, 1H), 7.36 (d, 1H), 6.71 (d, 1H), 3.87 (s, 3H), 1.39 (m, 12H).

Method PA1—Preparation of 2-(1-(4-aminophenyl)piperidin-3-yl)propan-2-ol (PA1)

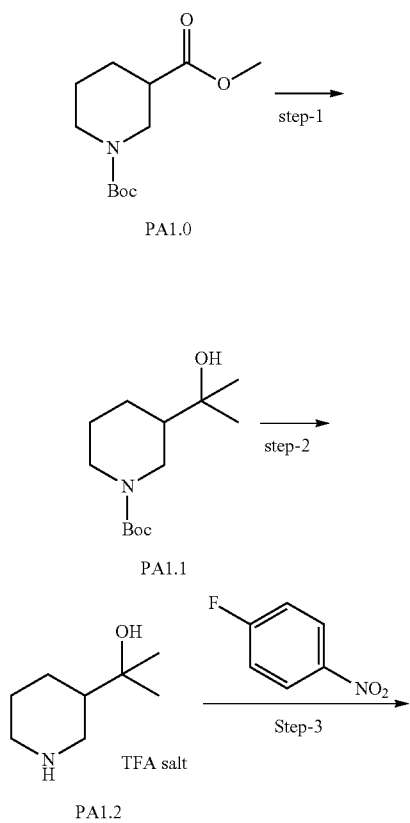

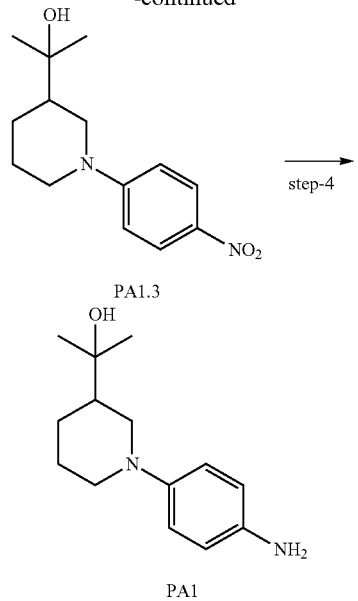

Step 1. tert-butyl 3-(2-hydroxypropan-2-yl) piperidine-1-carboxylate (PA1.1)

To a solution of 1-(tert-butyl) 3-methyl piperidine-1,3-dicarboxylate (PA1.0) (5.2 g, 21.2 mmol, 1.0 eq) in THF (30 ml) cooled at −78° C., was added 3.0M MeMgBr in THF (15.6 ml, 47.2 mmol, 2.2 eq) dropwise in reaction mixture and stirred at RT for 2 h. After completion, the reaction mixture was quenched in 1N HCl and extracted in EtOAc (3×100 ml). The combined organic layer was washed with brine (50 ml), then dried over Na2SO4, filtered, and concentrated under reduced pressure to afford PA1.1 (5.1 g, 58% yield) as a yellow oil. MS(ES): m/z 243.18 [M+H]+

Step 2. 2-(piperidin-3-yl) propan-2-ol (PA1.2)

To a solution of tert-butyl 3-(2-hydroxypropan-2-yl)piperidine-1-carboxylate (PA1.1) (7.8 g, 32.1 mmol, 1.0 eq) in DCM (80 ml), was added 4.0M HCl in Dioxane (24 ml, 3V) and the reaction mixture was stirred at RT for 1 h. After completion of reaction, the reaction mixture was quenched in saturated aqueous solution of NaHCO3 (100 ml) and extracted with ethyl acetate (3×100 ml). The organic extracts were combined and washed with brine (50 ml), then dried over Na2SO4, filtered, and concentrated under reduced pressure to afford PA1.2 (4.5 g, 98.2% yield) as a brown solid. MS(ES): m/z=143.23 [M+H]+

Step 3. 2-(1-(4-nitrophenyl) piperidin-3-yl) propan-2-ol (PA1.3)

To a solution of 2-(piperidin-3-yl) propan-2-ol (PA1.2) (4 g, 28 mmol, 1.0 eq) in DMSO (50 ml), were added 1-fluoro-4-nitrobenzene (6.62 g, 37 mmol, 1.3 eq) and N,N-Diisopropylethylamine (34 ml, 198 mmol, 7.0 eq). The reaction mixture was stirred at 100° C. temperature for 2 h. After completion, the reaction mixture was cooled at RT, diluted with cold water (80 ml), and extracted with EtOAc (3×70 ml). The organic layers were combined, dried over sodium sulphate and concentrated under reduced pressure to obtain residue which was triturated with Hexane (40 ml) to afford PA1.3 (6.65 g, 90.20% yield) as white solid. MS(ES): m/z=264.33 [M+H]+

Step 4. 2-(1-(4-aminophenyl) piperidin-3-yl) propan-2-ol (PA1)

To a suspension of 10% palladium on carbon (3 g) in methanol (60 ml), was added 2-(1-(4-nitrophenyl) piperidin-3-yl) propan-2-ol (PA1.3) (6.5 g, 0.024 mol, 1.0 eq). Hydrogen was purged continuously through reaction mixture at room temperature for 4 h. After completion of reaction, reaction mixture was filtered through Celite-bed and washed with methanol. Filtrate was concentrated under reduced pressure to obtain pure PA1 (5 g, quantitative). MS (ES): m/z 293.19[M+H]+

Method PA2—Preparation of 2-(4-(4-aminophenyl) morpholin-2-yl)propan-2-ol

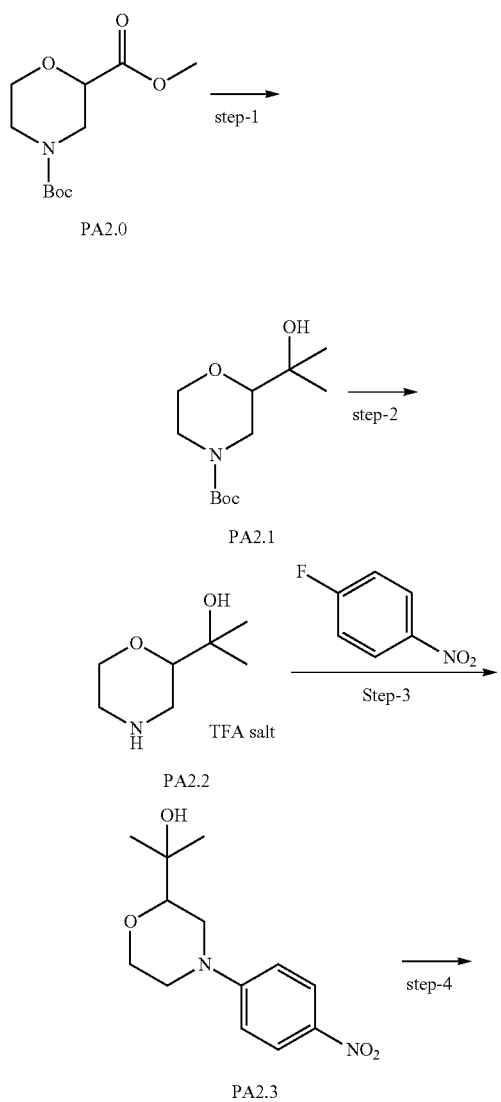

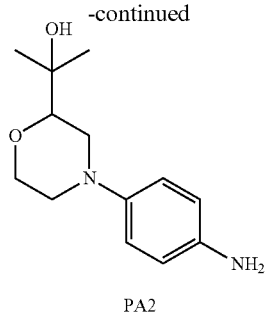

Step 1. tert-butyl 2-(2-hydroxypropan-2-yl)morpholine-4-carboxylate (PA2.1)

To a solution of 4-(tert-butyl) 2-methyl morpholine-2,4-dicarboxylate (PA2.0) (5.0 g, 20.38 mmol, 1.0 eq) in THF (30 ml), cooled at −78° C., was added a 3.0M solution of MeMgBr in THF (22.42 ml, 44.84 mmol, 2.2 eq) dropwise and stirred at RT for 2 h. After completion, the reaction quenched in 1N HCl and extracted in ethyl acetate (3×100 ml). The organic layer was combined and washed with brine (50 ml), then dried over Na2SO4, filtered, and concentrated under reduced pressure to afford PA2.1 (4.1 g, 81.9% yield) as a yellow oil. MS(ES): m/z 246.18 [M+H]+

Step 2. 2-(piperidin-3-yl) propan-2-ol (PA2.2)

To a solution of tert-butyl 2-(2-hydroxypropan-2-yl)morpholine-4-carboxylate (PA2.1) (4.1 g, 16.71 mmol, 1.0 eq) in DCM (80 ml), was added 4.0M HCl in Dioxane solution (24 ml, 3V), and the reaction mixture was stirred at RT for 1 h. After completion, the reaction mixture was quenched in NaHCO3 (100 ml) and extracted with ethyl acetate (3×100 ml). The organic extracts were combined, washed with brine (50 ml), dried over Na2SO4, filtered, and concentrated under reduced pressure to afford PA2.2 (1.75 g, 72.11% yield) as a brown solid, which was further used in next step without any further purification. MS(ES): m/z=146.4 [M+H]+

Step 3. 2-(1-(4-nitrophenyl) piperidin-3-yl) propan-2-ol (PA2.3)

To a solution of 2-(piperidin-3-yl) propan-2-ol (PA2.2) (3.5 g, 24.10 mmol, 1.0 eq) in DMSO (50 ml), was added 1-fluoro-4-nitrobenzene (4.42 g, 31.33 mmol, 1.3 eq) and N,N-Diisopropylethylamine (21.80 g, 168 mmol, 7.0 eq). The reaction mixture was stirred at 100° C. for 2 h. After completion, the reaction mixture was cooled at RT, diluted with cold water (80 ml), and extracted with ethyl acetate (3×70 ml). The organic layers were combined and concentrated under reduced pressure to obtain residue which was triturated with Hexane (40 ml) to afford PA2.3 (5.2 g, 81.01% yield) as white solid. MS(ES): m/z=267.3 [M+H]+

Step 4. 2-(1-(4-aminophenyl) piperidin-3-yl) propan-2-ol (PA2)

To a suspension of 10% palladium on carbon (3.0 g) in methanol (60 ml), was added 2-(1-(4-nitrophenyl) piperidin-3-yl) propan-2-ol (PA2.3) (5.0 g, 0.018 mol, 1.0 eq). Hydrogen was purged continuously through reaction mixture at room temperature for 4 h. After completion, the reaction mixture was filtered through Celite-bed and washed with methanol. The filtrate was concentrated under reduced pressure to obtain pure PA2. (5 g, quantitative). The crude residue was used further without any purification MS (ES): m/z 237.32[M+H]+

Method PA3—Preparation of 4-(2-((dimethylamino)methyl)morpholino)aniline (PA3)

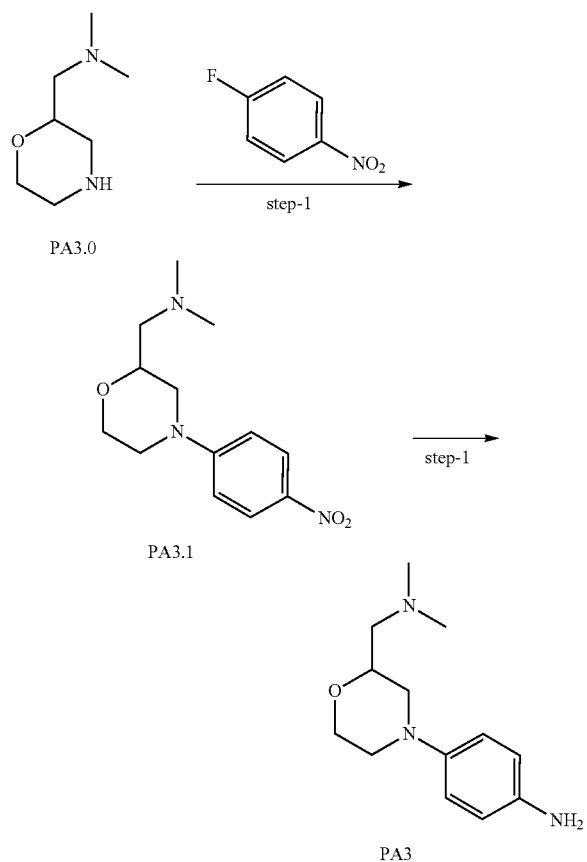

Step 1. N,N-dimethyl-1-(4-(4-nitrophenyl)morpholin-2-yl)methanamine (PA3.1)

To a solution of 1-fluoro-4-nitrobenzene (2 g, 14.1 mmol 1.0 eq) and N,N-dimethyl-1-(morpholin-2-yl)methanamine (PA3.0) (1.7 g, 17.02 mmol, 1.2 eq) in DMSO (20 ml), were added $K_2CO_3$ (5.8 g, 42.3 mmol 3.0 eq) and Tetrabutylammonium iodide (500 mg), and stirred at 120° C. for 2 h. After completion, the reaction mixture was diluted with water (100 ml), extracted with ethyl acetate (3×100 ml), the combined organic extracts were washed with brine (200 ml), then dried over $Na_2SO_4$, filtered, and concentrated under reduced pressure to obtain crude. The crude residue was purified by column chromatography and the pure product was eluted with 60% ethyl acetate in hexane to afford PA3.1 (1.8 g, 47% yield). MS(ES): m/z=266.3 [M+H]+

Step 2. 4-(2-((dimethylamino)methyl)morpholino)aniline (PA3.1)

To a suspension of 10% palladium on carbon (900 mg) in methanol (20 ml), was added N,N-dimethyl-1-(4-(4-nitrophenyl)morpholin-2-yl)methanamine (PA3.1) (1.8 g, 6.97 mmol, 1.0 eq). Hydrogen was purged continuously through reaction mixture at room temperature for 4 h. After completion of reaction, reaction mixture was filtered through Celite-bed and washed with methanol. Filtrate was concentrated under reduced pressure to obtain crude pure PA3. The crude residue was used further without any purification (1.4 g, 87% yield). MS (ES): m/z 236.4 [M+H]+

Method PA4—Preparation of 6-((dimethylamino)methyl)-5-(tetrahydro-2H-pyran-4-yl)pyridin-2-amine (PA4)

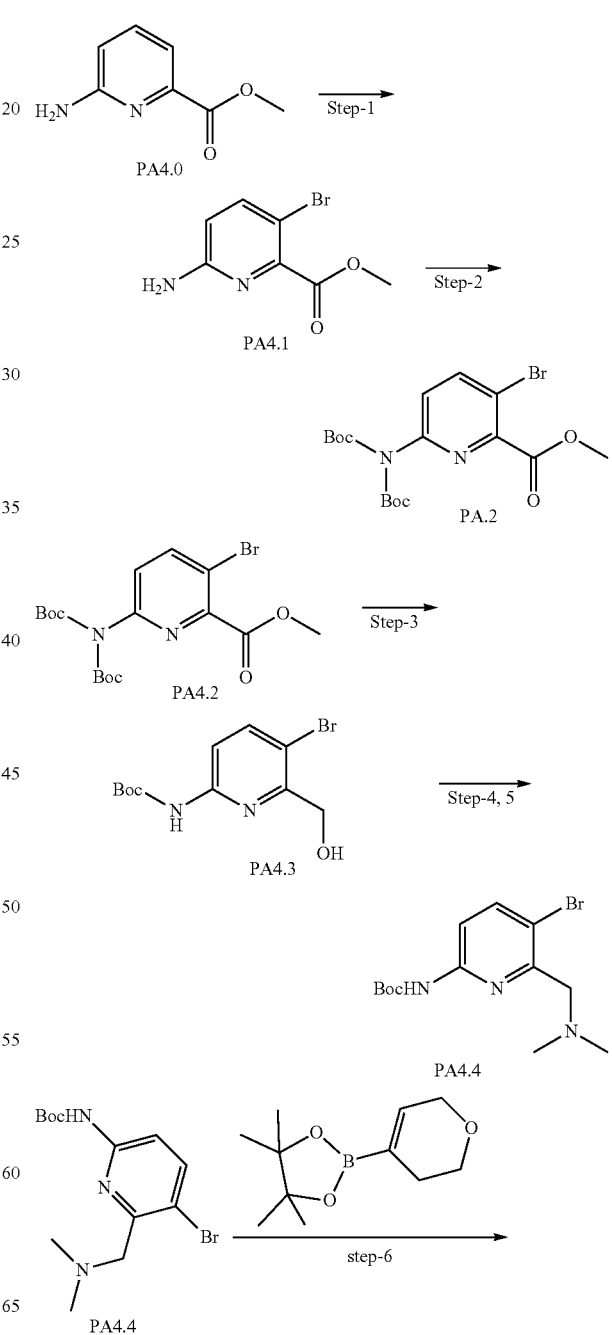

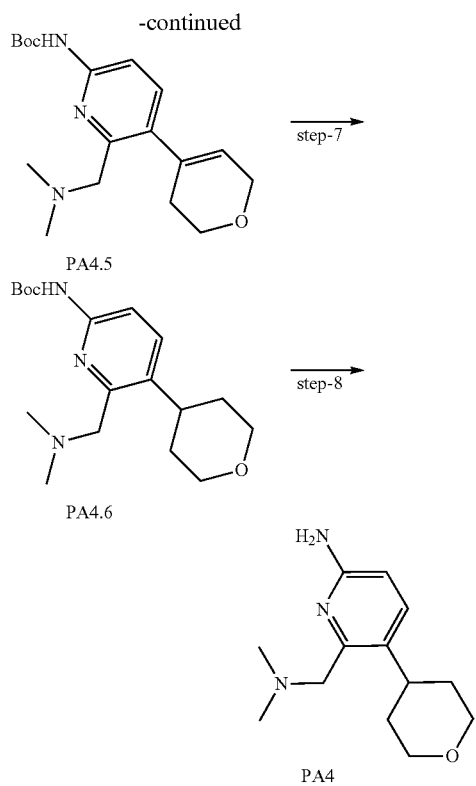

PA4.5

PA4.6

PA4

Step 1. methyl 6-amino-3-bromopicolinate (PA4.1)

To a solution of methyl 6-aminopicolinate (PA4.0) (500 g, 3289.4 mmol, 1.0 eq) in ACN (12.5 L) was added N-bromosuccinamide (644 g, 3618.4 mmol, 1.1 eq) portion-wise at room temperature over 30 min. The reaction mixture was stirred at room temperature for 30 min. After completion, the reaction mixture was quenched with 10% $Na_2S_2O_3$ solution in water (3.0 L) and the reaction mixture was evaporated to remove ACN. Residue was diluted with 10% $Na_2S_2O_3$ solution in water (20 L) and extracted with 50% ethyl acetate in Hexanes (10 L×5). Organic layer was combined and dried over sodium sulphate and concentrated under reduced pressure to obtain crude material. The crude material was triturated with 25% ethyl acetate in hexane (2×1 L) to obtain pure PA4.1. The product was combined with 3 other batches on the 500 gm+250 gm+250 g=Total 1.5 kg scale prepared by an identical method. (1300 g, 57.07% yield). MS (ES): m/z 231-233 [M+2]$^+$, $^1$H NMR (400 MHz, CDCL3): δ 7.66 (d, 1H), 6.53 (d, 1H), 4.68 (S, 2H), 3.98 (s, 3H). Note: other regio isomer (methyl 6-amino-5-bromopicolinate) was also formed and it was separated via silica purification and the product was eluted at 2% ethyl acetate in hexane. The required regio-isomer confirmed by $^1$H NMR and NOE analysis.

Step 2. methyl 3-bromo-6-(bis(tert-butoxycarbonyl)amino)picolinate (PA4.2)

To a solution of methyl 6-amino-3-bromopicolinate (PA4.1) (1100 g, 4782.6 mmol, 1.0 eq) in Tetrahydrofuran (20 L) were added Dimethyl amino pyridine (116.7 g, 956.5 mmol, 0.2 eq) and Boc anhydride (2502 g, 11478.2 mmol, 2.4 eq). The reaction mixture was stirred at 75° C. for 1.5 h. After completion of reaction, solvent was evaporated under reduced pressure and then obtained crude was diluted in brine solution (8 L) and extracted by ethyl acetate (2×10 L). Combined organic layers were dried over sodium sulphate and concentrated under reduced pressure to obtain crude which was purified by column chromatography. The pure product was eluted at 5% ethyl acetate in hexane. The material was yet again triturated with hexanes (4 L) to obtain pure PA4.2 (1700 g, 82.79% yield) as white solid. MS (ES): m/z 431-433 [M+2]$^+$. $^1$H NMR (400 MHz, DMSO): δ 8.32 (d, 1H), 7.61 (d, 1H), 3.90 (s, 3H), 1.40 (s, 18H).

Step 3. tert-butyl (5-bromo-6-(hydroxymethyl)pyridin-2-yl) carbamate (PA4.3)

A solution of methyl 3-bromo-6-(bis(tert-butoxycarbonyl)amino)picolinate (PA4.2) (50 g, 116.27 mmol, 1.0 eq) in ethanol (200 ml) was treated portion wise with sodium borohydride (26.3 g, 697.6 mmol, 6.0 eq) and stirred at 70° C. for 2 h. After completion of reaction, the ethanol was removed under reduced pressure and water (200 ml) was added dropwise to obtained crude. The crude was extracted with DCM (3×150 ml) and the combined organic layer was washed with brine (100 ml), dried over sodium sulphate, filtered and concentrated under reduced pressure to provide pure PA4.3 (27 g, 79% yield), as white solid. The crude was used in the next step without any further purification. MS(ES): m/z 395 [M+1]$^+$ $^1$H NMR (400 MHz, DMSO): δ 7.81 (d, 1H), 7.67 (d, 1H), 7.2 (d, 1H), 5.22 (d, 1H), 4.55 (t, 1H), 3.99 (s, 3H), 3.77 (m, 3H), 3.55 (m, 2H), 2.28 (d, 2H), 1.87 (d, 1H), 1.41 (s, 19H)

Step 4 & 5. tert-butyl (5-bromo-6-((dimethylamino)methyl)pyridin-2-yl)carbamate (PA4.4)

A solution of the tert-butyl (5-bromo-6-(hydroxymethyl) pyridin-2-yl) carbamate (PA4.3) (22.2 g, 73.2 mmol, 1.0 eq) and N—N diisopropyl ethylamine (33.3 g, 256.3 mmol, 3.5 eq) in DCM (200 ml) was cooled at 0° C., treated with methane sulfonyl chloride (12.5 g, 109.8 mmol, 1.5 eq), and stirred for 30 min. After the completion, the reaction was quenched with water (100 ml) and extracted with ethyl acetate (3×100 ml). The combined organic layer was washed with brine (100 ml), dried over sodium sulphate, filtered and concentrated under reduced pressure to obtain the crude. The crude was then dissolved in ACN (200 ml), to which were added Dimethyl amine (15 g, 183.0 mmol, 2.5 eq) and N,N-Diisopropylethylamine (33.3 g, 256.3 mmol, 3.5 eq). The reaction mixture was heated at 70° C. for 1 h. After the completion of reaction, the reaction mixture was quenched with water (100 ml) and extracted into ethyl acetate (3×50 ml). The combined organic layer was washed with brine (50 ml), dried over sodium sulphate, filtered and concentrated under reduced pressure to obtain the crude. The crude was further purified by silica gel chromatography and the pure product was eluted with 50% ethyl acetate in hexane, affording PA4.4 (17.0 g, 94.3% yield). MS(ES): m/z 330 [M+H]$^+$

Step 6. tert-butyl (5-(3,6-dihydro-2H-pyran-4-yl)-6-((dimethylamino) methyl) pyridin-2-yl)carbamate (PA4.5)

To a solution of tert-butyl (5-bromo-6-((dimethylamino) methyl)pyridin-2-yl)carbamate (PA4.4) (50 g, 151.5 mmol, 1.0 eq) in 1,4-Dioxane:water (400 ml:100 ml), were added 2-(3,6-dihydro-2H-pyran-4-yl)-4,4,5,5-tetramethyl-1,3,2-dioxaborolane (47.7 g, 227.2 mmol, 1.5 eq) and potassium phosphate tribasic (96.3 g, 454.5 mmol, 3.0 eq). The reaction mixture was degassed with N₂ for 15 min. To the same reaction mixture, chloro(2-dicyclohexylphosphino-2',4',6'-triisopropyl-1,1'-biphenyl)[2-(2'-amino-1,1'-biphenyl)]palladium(II) (11.9 g, 15.1 mmol, 0.1 eq) was added and the reaction mixture was stirred at 140° C. for 4 h. After completion, the reaction mixture was cooled to RT, diluted with water (1 L), and extracted with ethyl acetate (2×2 L). Combined organic extracts were washed with brine (1 L), dried over Na₂SO₄, filtered, and concentrated under reduced pressure to obtain crude material. Crude residue was further purified by column chromatography and the product was eluted at 2.1% methanol in DCM to obtain PA4.5 (40 g, 79% yield), MS(ES): m/z 334.2 [M+H]⁺

Step 7. tert-butyl (6-((dimethylamino)methyl)-5-(tetrahydro-2H-pyran-4-yl) pyridin-2-yl)carbamate (PA4.6)

To a suspension of palladium hydroxide (130 g) in methanol (600 ml) and THF (40 ml), was added tert-butyl (5-(3,6-dihydro-2H-pyran-4-yl)-6-((dimethylamino) methyl) pyridin-2-yl)carbamate (PA4.5) (130 g, 0.38 mol, 1.0 eq). Hydrogen gas was purged through reaction mixture for 4 h at room temperature. After completion, the reaction mixture was filtered through celite-bed and washed with methanol (500 ml×3). Filtrate was concentrated under reduced pressure to obtain pure PA4.6 (120 g, 91.75%). This was used in the next step without any further purification. MS (ES): m/z 336.2 [M+H]⁺

Step 8. 6-((dimethylamino)methyl)-5-(tetrahydro-2H-pyran-4-yl)pyridin-2-amine (PA4)

To a solution of tert-butyl (6-((dimethylamino)methyl)-5-(tetrahydro-2H-pyran-4-yl) pyridin-2-yl)carbamate (PA4.6) (120 g, 356.9 mmol, 1.0 eq) into DCM (1.2 L), was added Trifluoroacetic acid (360 ml) dropwise and reaction mixture was stirred at 55° C. for 2 h. After completion, the reaction mixture was basified using saturated Sodium hydroxide solution and extracted with 10% methanol in dichloromethane (4×10 L). Combined organic layer was concentrated under reduced pressure to obtain PA4 (66 g, 78.40% yield). This was used further without any purification. MS(ES): m/z 236.1 [M+H]⁺

Method PA5—Preparation of 1-(4-amino-2-((dimethylamino) methyl)phenyl)piperidin-4-ol (PA5)

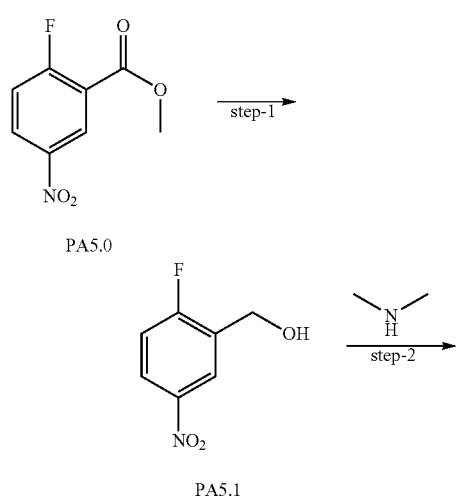

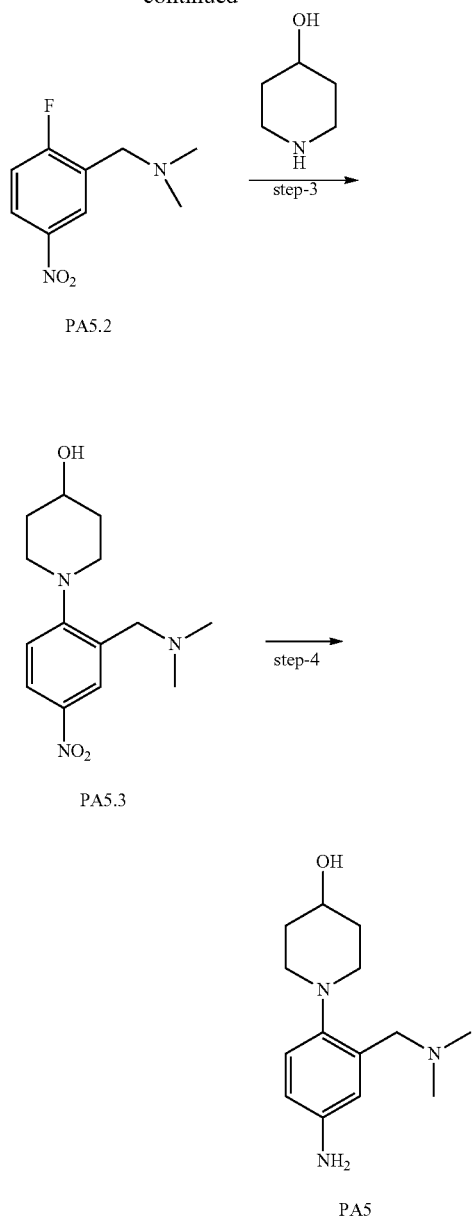

Step 1. (2-fluoro-5-nitrophenyl)methanol (PA5.1)

To a solution of methyl 2-fluoro-5-nitrobenzoate (PA5.0) (10 g, 46.38 mmol, 1.0 eq) in tetrahydrofuran (5 ml) and ethanol (5 ml) was added sodium borohydride (7.05 g, 185.5 mmol, 4.0 eq) portion wise for 20 min at 0° C., and stirred for 5 min. The reaction mixture was allowed to warm to RT, and then stirred for 15 min. After completion, the reaction mixture was poured into water (400 ml), and product was extracted with ethyl acetate (3×200 ml). The combined organic layer was washed with brine solution (100 ml), dried over sodium sulphate and concentrated under reduced pressure to obtain crude material. This was further purified by column chromatography and the compound was eluted in 8% ethyl acetate in hexane to obtain PA5.1 (5 g, 58.18% yield). MS(ES): m/z 173.3 [M+H]⁺

Step 2. 1-(2-fluoro-5-nitrophenyl)-N,N-dimethylmethanamine (PA5.2)

To a solution of (2-fluoro-5-nitrophenyl)methanol (PA5.1) (5 g, 26.73 mmol, 1.0 eq) in DCM (50 ml) was added N,N-Diisopropylethylamine (10.4 g, 80.2 mmol, 3.0 eq) at room temperature. The reaction was cooled to 0° C. and mesyl chloride (4.6 g, 40.10 mmol, 1.5 eq) was added, and the reaction mixture was stirred at 0° C. for 30 min. After completion, the reaction mixture was diluted with water (50 ml) and the crude was extracted with DCM (3×20 ml) and the combined organic extracts were washed with brine (20 ml), then dried over Na₂SO₄, filtered, and concentrated under reduced pressure. The crude residue was used for the next step without any further purification. To a mixture of the crude (7.5 g, 28.40 mmol, 1.0 eq), dimethyl amine hydrochloride (5.75 g, 71.02 mmol, 2.5 eq), and acetonitrile (50 ml), was added N,N-Diisopropylethylamine (14.7 g, 113.3 mmol, 4.0 eq). The reaction mixture was stirred at 100° C. for 1 h. After completion, the reaction mixture was quenched in to ice-cold water (100 ml), extracted with ethyl acetate (3×50 ml), and the combined organic layer was dried over sodium sulphate, and concentrated under reduced pressure to obtain crude material. The crude was further purified by column chromatography and the compound was eluted in 50% ethyl acetate in hexane to obtain sticky solid as PA5.2 (5 g, 86.36% yield). MS(ES): m/z 199.2 [M+H]⁺

Step 3. 1-(2-((dimethylamino)methyl)-4-nitrophenyl)piperidin-4-ol (PA5.3)

To a solution of 1-(2-fluoro-5-nitrophenyl)-N,N-dimethylmethanamine (PA5.2) (1 g, 4.67 mmol, 1.0 eq) in DMSO (8 ml) was added N,N-Diisopropylethylamine (2.4 g, 18.64 mmol, 4.0 eq) and 4-hydroxy piperidine hydrochloride (0.7 g, 5.6 mmol, 1.2 eq). Reaction mixture was stirred at 120° C. for 20 h. After completion, the reaction mixture was quenched in to ice-cold water (100 ml), extracted with ethyl acetate (3×50 ml), and the combined organic layer was dried over sodium sulphate and concentrated under reduced pressure to obtain crude material. This was further purified by column chromatography and the compound was eluted in 2.5% methanol in dichloromethane to obtain solid as PA5.3 (0.8 g, 56.76% yield). MS(ES): m/z 280.34 [M+H]⁺

Step 4. 1-(4-amino-2-((dimethylamino)methyl)phenyl)piperidin-4-ol (PA5)

To a solution of 1-(2-((dimethylamino)methyl)-4-nitrophenyl)piperidin-4-ol (PA5.3) (0.8 g, 0.28 mmol, 1.0 eq) in methanol (8 ml) and THF (8 ml) were added acetic acid (0.8 ml), ammonium formate (0.73 g, 11.45 mmol, 4.0 eq), and 20% wet palladium hydroxide on carbon (0.8 g). The reaction mixture was stirred under atmosphere of hydrogen gas for 2.5 h at room temperature. After completion, the reaction mixture was then filtered through Celite bad, and the filtrate was diluted by DCM (10 ml), washed with saturated sodium bicarbonate solution, dried over sodium sulphate, and concentrated under reduced pressure to obtain residue which was purified by column chromatography. The compound was eluted in 15% methanol in dichloromethane PA5 (0.5 g, 70.01%). MS(ES): m/z 250.3 [M+H]⁺

Method PA8—preparation of 4-(2-((dimethylamino)methyl)morpholino)aniline (PA8)

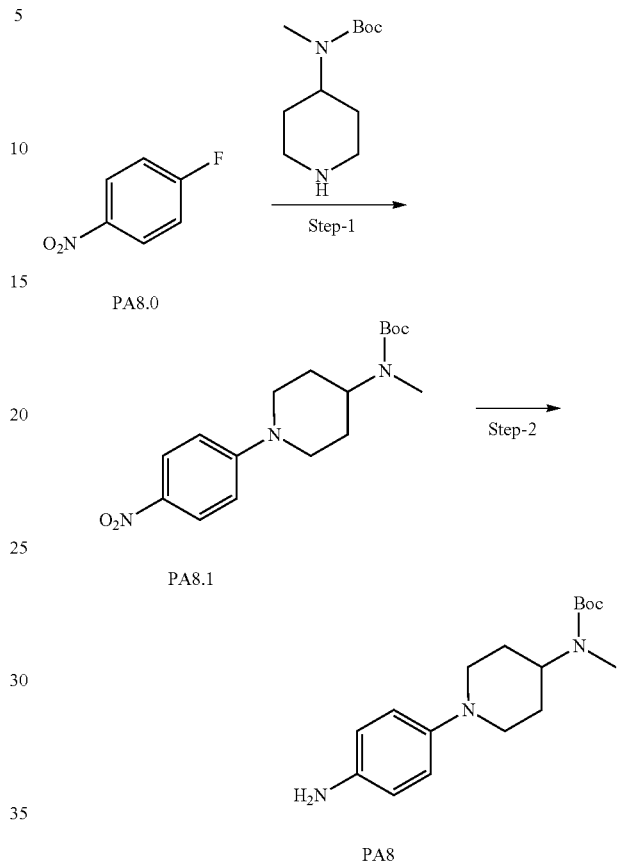

Step 1. tert-butyl methyl(1-(4-nitrophenyl)piperidin-4-yl)carbamate (PA8.1)

To a solution of 1-fluoro-4-nitrobenzene (PA8.0) (2 g, 14.1 mmol 1.0 eq) and tert-butyl methyl(piperidin-4-yl) carbamate (3.62 g, 17.02 mmol, 1.2 eq) in DMSO (20 ml), were added K₂CO₃ (5.8 g, 42.3 mmol 3.0 eq) and Tetra-n-butylammonium iodide (500 mg), and stirred at 120° C. for 2 h. After completion, reaction mixture was diluted with water (100 ml), extracted with ethyl acetate (3×100 ml), and the combined organic extracts were washed with brine (200 ml), then dried over Na₂SO₄, filtered, and concentrated under reduced pressure to obtain crude. The crude residue was purified by column chromatography and the pure product was eluted at 50% ethyl acetate in hexane to afford PA8.1 (1.8 g, 37.86% yield). MS(ES): m/z=336.4 [M+H]⁺

Step 2. tert-butyl (1-(4-aminophenyl)piperidin-4-yl)(methyl)carbamate (PA8)

To a suspension of 10% palladium on carbon (900 mg) in methanol (20 ml), was added tert-butyl methyl(1-(4-nitrophenyl)piperidin-4-yl)carbamate (PA8.1) (1.8 g, 5.36 mmol, 1.0 eq). Hydrogen was purged through reaction mixture at room temperature for 4 h. After completion, the reaction mixture was filtered through Celite-bed and washed with methanol (150 ml). Filtrate was concentrated under reduced pressure to obtain crude pure PA8. (1.4 g, 85.41% yield). MS (ES): m/z 306.42 [M+H]⁺

The following aniline intermediates in Table 2 were prepared according to any of Intermediate Methods PA1-PA9 as described above.

TABLE 2
| # | STRUCTURE | Method |
|---|---|---|
| PA6 | 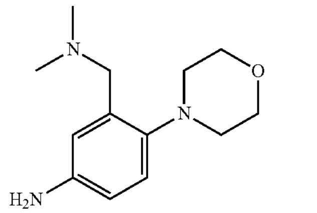 | 3-((dimethylamino)methyl)-4-morpholinoaniline (same as PA5) |
| PA7 | 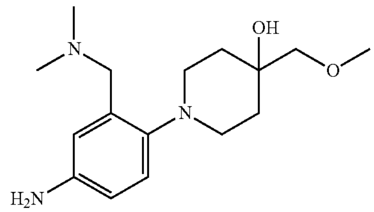 [SMILES: COCC1(O)CCN(c2ccc(N)cc2CN(C)C)CC1] | 1-(4-amino-2-((dimethylamino)methyl)phenyl)-4-(methoxymethyl)piperidin-4-ol (same as PA5) |
| PA9 | 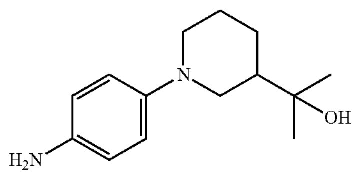 [SMILES: CC(C)(O)C1CCCN(c2ccc(N)cc2)C1] | 2-(1-(4-aminophenyl)piperidin-3-yl)propan-2-ol (same as PA8) |
| PA10 | 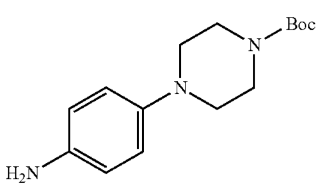 [SMILES: CC(C)(C)OC(=O)N1CCN(c2ccc(N)cc2)CC1] | tert-butyl 4-(4-aminophenyl)piperazine-1-carboxylate (same as PA8) |
Method PA11 Preparation of 3-((dimethylamino)methyl)-4-(tetrahydrofuran-3-yl)aniline (PA11)
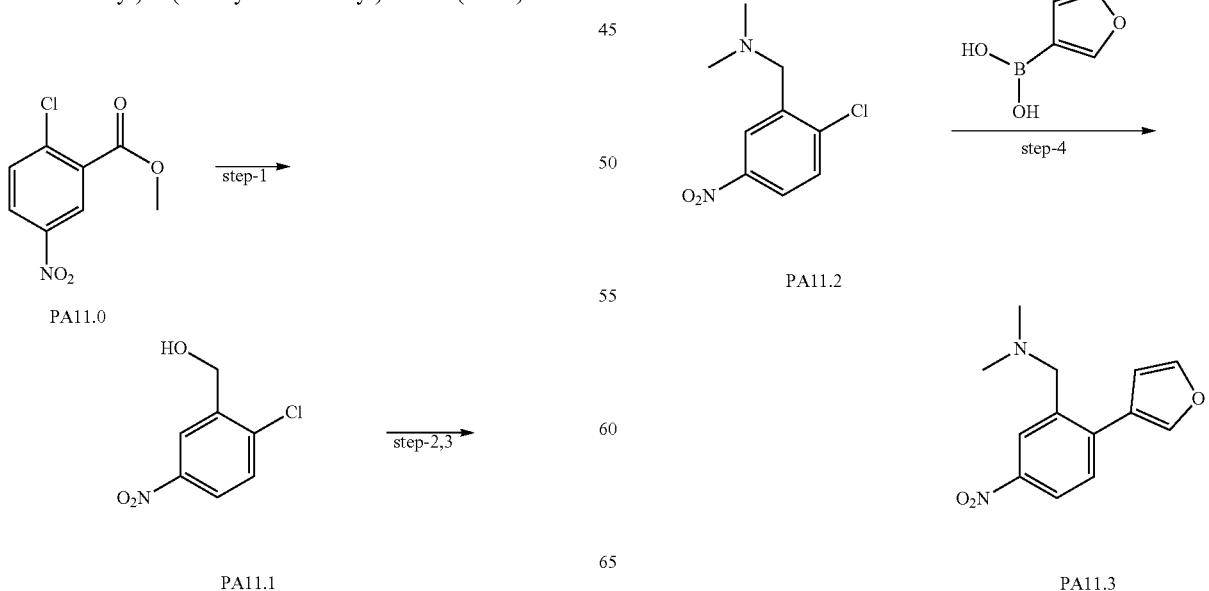
-continued

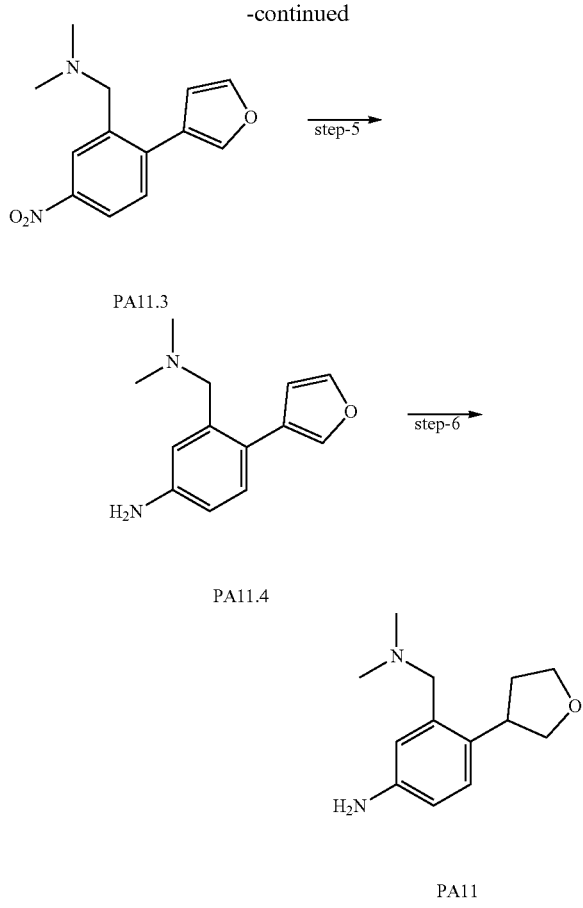

Step 1. (2-chloro-5-nitrophenyl)methanol (PA11.1)

To a solution of methyl 2-chloro-5-nitrobenzoate (PA11.0) (25.0 g, 116.27 mmol, 1.0 eq) in methanol (500 ml) was add portionwise Sodium borohydride (17.5 g, 465.08 mmol, 4.0 eq) at 0° C. The reaction mixture stirred at room temperature for 5-10 min. After completion, the reaction mixture was quench in water (700 ml) and the product was extracted with ethyl acetate (4×250 ml). Organic layer was combined, washed with brine solution (300 ml), dried over sodium sulphate and concentrated under reduced pressure to obtain crude material. This was further purified by column chromatography and the compound was eluted in 3-5% ethyl acetate in hexane to obtain (PA11.1) (13.0 g, 59.76%). MS(ES): m/z 188.01 [M+H]$^+$

Steps 2 and 3. 1-(2-chloro-5-nitrophenyl)-N,N-dimethylmethanamine (PA11.2)

To a solution of (2-chloro-5-nitrophenyl)methanol (PA11.1) (13.0 g, 69.51 mmol, 1.0 eq) in DCM (130 ml) was added dropwise N,N-Diisopropylethylamine (36.3 ml, 208.53 mmol, 3.0 eq) at 0° C. and stirred for 20 min, which was followed by drop wise addition of mesyl chloride (8.0 ml, 104.26 mmol, 1.5 eq) at 0° C. The reaction mixture was stirred at 0° C. for 20-25 min. After completion, the reaction mixture was quenched with water (400 ml) and extracted by DCM (3×180 ml). The combined organic layer was washed with brine (200 ml), a Na$_2$SO$_4$ solution, and concentrated under reduced pressure to provide a mesylated product. (18 g-crude, 97.76%). MS (ES): m/z 266.2 [M+1]$^+$. To a solution of mesylated above product (18.0 g, 67.92 mmol, 1.0 eq) in acetonitrile (180 ml) was added dropwise N,N-Diisopropylethylamine (35.5 ml, 203.77 mmol, 3.0 eq) followed by Dimethylamine hydrochloride (8.6 g, 101.88 mmol, 1.5 eq) at RT. The reaction mixture was stirred at 90° C. for 1 h. After completion, the reaction mixture was quenched in DM water (600 ml) and extracted by DCM (3×270 ml). The combined organic layer was washed with brine (300 ml), dried with Na$_2$SO$_4$ and concentrated under reduced pressure to obtain crude material. This was further purified by column chromatography and the compound was eluted in 50-60% ethyl acetate in hexane to obtain (PA11.2) (7.8 g, 53.63%). MS(ES): m/z 215.05 [M+H]$^+$

Step-4. 1-(2-(furan-3-yl)-5-nitrophenyl)-N,N-dimethylmethanamine (PA11.3)

A solution of 1-(2-chloro-5-nitrophenyl)-N,N-dimethylmethanamine (PA11.2) (7.8 g, 36.44 mmol, 1.0 eq), furan-3-ylboronic acid (6.1 g, 54.66 mmol, 1.5 eq), and potassium carbonate (15.0 g, 109.32 mmol, 3.0 eq), suspended in 1-4 dioxane:ethanol:water (23.4 ml:16 ml:8 ml), was degassed with flow of nitrogen for 15 min, then [1,1'-Bis(diphenylphosphino)ferrocene]dichloropalladium(II) (1.3 g, 1.82 mmol, 0.05 eq) was added and heated at 110° C. for 1 h. After completion, the reaction mixture was cooled to RT, diluted with water (300 ml), and extracted into ethyl acetate (3×120 ml). The combined organic layer was washed with brine (150 ml), dried with Na$_2$SO$_4$ and concentrated under reduced pressure to obtain crude material. This was further purified by column chromatography and the compound was eluted in 30-40% ethyl acetate in hexane to obtain (PA11.3) (5.1 g, 56.99%). MS(ES): m/z 247.2 [M+H]$^+$

Step-5. 3-((dimethylamino)methyl)-4-(furan-3-yl)aniline (PA11.4)

To a solution of 1-(2-(furan-3-yl)-5-nitrophenyl)-N,N-dimethylmethanamine (PA11.3) (5.1 g, 20.73 mmol, 1.0 eq) in methanol (75 ml) was added 20% Palladium on carbon (2.5 g). Hydrogen was purged through reaction mixture for 2 h at room temperature. After completion, the reaction mixture was filtered through a celite-bed and washed with methanol (50 ml×3). Filtrate was concentrated under reduced pressure to obtain crude material. This was further purified by trituration with n-pentane (20 ml×2) to obtain (PA11.4) (4.3 g, 96.00%). MS (ES): m/z 217.1 [M+H]$^+$

Step-6. 3-((dimethylamino)methyl)-4-(tetrahydrofuran-3-yl)aniline (PA11)

To a solution of 3-((dimethylamino)methyl)-4-(furan-3-yl)aniline (PA11.4) (4.3 g, 19.81 mmol, 1.0 eq) in methanol:THF (35 ml:9 ml) was added acetic acid (3.0 ml), followed by 20% palladium hydroxide on carbon (3.0 g) and ammonium formate (3.7 g, 59.43 mmol, 3.0 eq). Hydrogen was purged through the reaction mixture for 1 hr at room temperature. After completion, the reaction mixture was filtered through a celite-bed and washed with methanol (50 ml×2). Filtrate was concentrated under reduced pressure to obtain crude material. This was further purified by column chromatography and the compound was eluted in 3% methanol in dichloromethane to obtain (PA11) (0.2 g, 5.0%). MS (ES): m/z 221.1 [M+H]$^+$

Method PA12 Preparation of 5-((dimethylamino)methyl)-6-(tetrahydrofuran-3-yl)pyridin-3-amine (PA12)
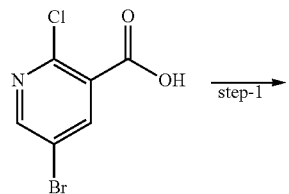
PA12.0
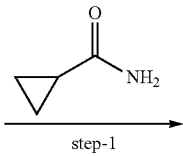
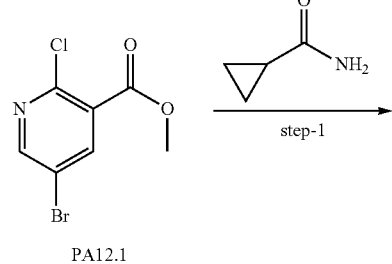
PA12.1
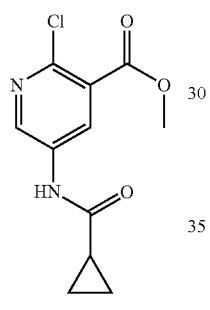
PA12.1
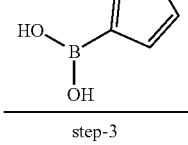
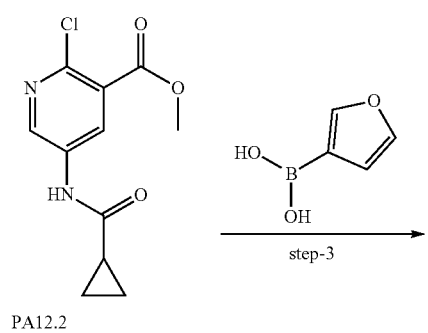
PA12.2
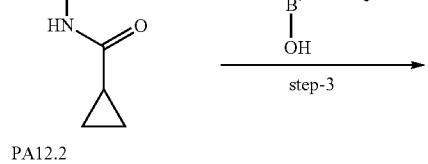
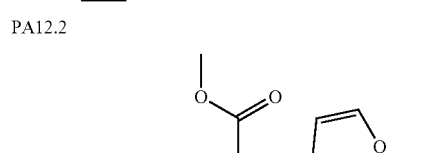
PA12.3
-continued
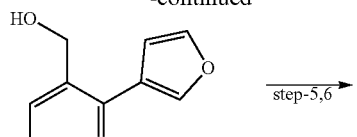
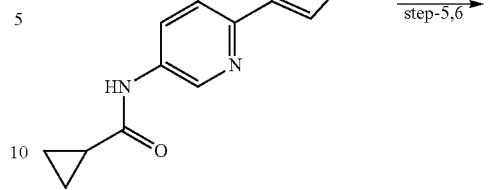
PA12.4
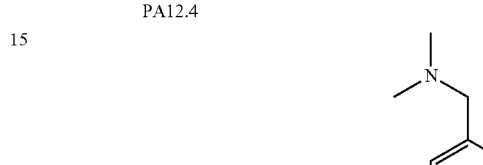
PA2.5
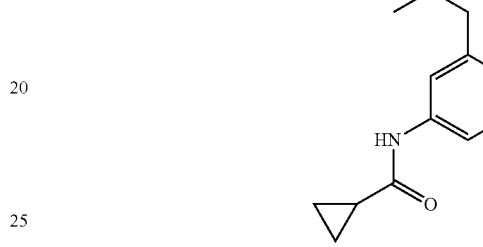
PA12.5
PA12.6
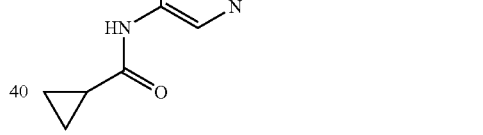
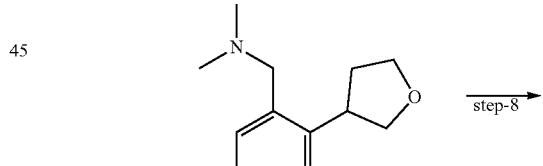
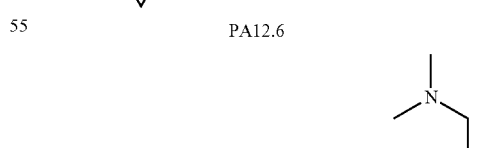
PA12.6

Step 1. methyl 5-bromo-2-chloronicotinate (PA12.1)

To a solution of 5-bromo-2-chloronicotinic acid (PA12.0) (25.0 g, 105.93 mmol, 1.0 eq) in methanol (250 ml) was added dropwise concentrated sulfuric acid (5 ml) at room temperature. The reaction mixture stirred at 60° C. for 16 h. After completion, the reaction mixture was transferred to water (400 ml) and product was extracted with DCM (3×150 ml). Organic layer was combined, washed with brine solution (250 ml), dried over sodium sulphate and concentrated under reduced pressure to obtain crude material. This was further purified by column chromatography and the compound was eluted in 10-12% ethyl acetate in hexane to obtain (PA12.1) (18.0 g, 67.97%). MS(ES): m/z 251.1 [M+H]$^+$

Step-2. methyl 2-chloro-5-(cyclopropanecarboxamido)nicotinate (PA12.2)

To a solution of methyl 5-bromo-2-chloronicotinate (PA12.1) (18.0 g, 72.00 mmol, 1.0 eq) and cyclopropanecarboxamide (7.34 g, 86.4 mmol, 1.2 eq), in 1,4-Dioxane (180 ml) was added cesium carbonate (46.8 g, 144 mmol, 2.0 eq). The reaction mixture was degassed for 10 min. under argon atmosphere, then tris(dibenzylideneacetone) dipalladium(O) (3.2 g, 3.6 mmol, 0.05 eq) and 4,5-Bis (diphenylphosphino)-9,9-dimethylxanthene (4.1 g, 7.2 mmol, 0.1 eq) were added and stirred at 100° C. for 1 h. After completion, the reaction mixture was cooled to RT, transferred into water (400 ml) and product was extracted with ethyl acetate (3×130 ml). Organic layer was combined, washed with brine solution (200 ml), dried over sodium sulphate and concentrated under reduced pressure to obtain crude material. This was further purified by column chromatography and the compound was eluted in 20% ethyl acetate in hexane to obtain (PA12.2) (12.4 g, 67.75%). MS(ES): m/z 255.2 [M+H]$^+$

Step-3. methyl 5-(cyclopropanecarboxamido)-2-(furan-3-yl)nicotinate (PA12.3)

To a solution of methyl 2-chloro-5-(cyclopropanecarboxamido)nicotinate (PA12.2) (12.4 g, 48.81 mmol, 1.0 eq) and furan-3-ylboronic acid (10.9 g, 97.62 mmol, 2.0 eq), in 1,4-Dioxane:water (100 ml:25 ml) was added potassium phosphate tribasic (31.0 g, 146.43 mmol, 3.0 eq). The reaction mixture was degassed for 15-20 min. under argon atmosphere, then Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride (3.8 g, 4.88 mmol, 0.1 eq) was added and reaction mixture was stirred at 120° C. for 1 h. After completion, the reaction mixture was cooled to RT, transferred into water (350 ml) and product was extracted with ethyl acetate (3×100 ml). Organic layer was combined, washed with brine solution (150 ml), dried over sodium sulphate and concentrated under reduced pressure to obtain crude material. This was further purified by column chromatography and the compound was eluted in 25% ethyl acetate in hexane to obtain (PA12.3) (11.1 g, 79.63%). MS(ES): m/z 287.1 [M+H]$^+$

Step-4. N-(6-(furan-3-yl)-5-(hydroxymethyl)pyridin-3-yl) cyclopropanecarboxamide (PA12.4)

To a solution of methyl 5-(cyclopropanecarboxamido)-2-(furan-3-yl)nicotinate (PA12.3) (11.1 g, 38.81 mmol, 1.0 eq) in ethanol (120 ml) was added portion wise sodium borohydride (8.8 g, 232.86 mmol, 6.0 eq) at RT. The reaction mixture was stirred at 60° C. for 6 h. After completion, the reaction mixture was transferred into brine solution (250 ml) and product was extracted with dichloromethane (3×80 ml). Organic layer was combined, dried over sodium sulphate and concentrated under reduced pressure to obtain crude material. This was further purified by column chromatography and the compound was eluted in 50% ethyl acetate in hexane to obtain (PA12.4) (8.5 g, 84.88%). MS(ES): m/z 259.1 [M+H]$^+$

Steps 5 and 6. N-(5-((dimethylamino)methyl)-6-(furan-3-yl)pyridin-3-yl)cyclopropanecarboxamide (PA12.5)

To a solution of N-(6-(furan-3-yl)-5-(hydroxymethyl) pyridin-3-yl) cyclopropanecarboxamide (PA12.4) (8.5 g, 32.94 mmol, 1.0 eq) in THF (85 ml) was added dropwise N,N-Diisopropylethylamine (17.2 ml, 98.82 mmol, 3.0 eq) at 0° C. and was stirred for 20 min. Methane sulfonyl chloride (3.8 ml, 49.41 mmol, 1.5 eq) was added dropwise at 0° C. and stirred at 0° C. for 45 min. After completion, the reaction mixture was quenched with DM water (180 ml) and product was extracted by ethyl acetate (3×50 ml). The combined organic layer was washed with brine (80 ml), passed through a Na$_2$SO$_4$, and concentrated under reduced pressure to provide a mesylated product. (10.0 g-crude, 90.34%). MS (ES): m/z 337.08 [M+H]$^+$. To a solution of Mesylated above product (10.0 g, 29.76 mmol, 1.0 eq) in Acetonitrile (100 ml) was added dropwise N,N-Diisopropylethylamine (23.5 ml, 133.92 mmol, 4.5 eq) followed by Dimethylamine hydrochloride (4.8 g, 59.52 mmol, 2.0 eq) at RT. The reaction mixture was stirred at 90° C. for 2 h. After completion, the reaction mixture was quenched in DM water (350 ml) and product was extracted by ethyl acetate (4×90 ml). The combined organic layer was washed with brine (200 ml), dried with Na$_2$SO$_4$ and concentrated under reduced pressure to obtain crude material. This was further purified by column chromatography and the compound was eluted in 2.5% methanol in dichloromethane to obtain (PA12.5) (5.5 g, 58.57%). MS(ES): m/z 286.1 [M+H]$^+$

Step-7. N-(5-((dimethylamino)methyl)-6-(tetrahydrofuran-3-yl)pyridin-3-yl)cyclopropanecarboxamide (PA12.6)

A solution of N-(5-((dimethylamino)methyl)-6-(furan-3-yl)pyridin-3-yl)cyclopropanecarboxamide (PA12.5) (5.5 g, 19.29 mmol, 1.0 eq) in methanol:THF (55 ml: 27.5 ml) was treated with ammonium formate (4.8 g, 77.16 mmol, 4.0 eq), acetic acid (2.7 ml, 0.5v), and 10% palladium hydroxide on carbon (5.5 g). The reaction mixture was stirred under pressure of H$_2$ gas at 20 psi for 16 h. After completion, the reaction mixture was filtered through a Celite bad, and washed with 10% methanol in dichloromethane (3×50 ml). Filtrate was concentrated under reduced pressure to obtain crude material. The crude product was purified by column chromatography and the compound was eluted in 2.5% methanol in dichloromethane to obtain (PA12.6) (3.5 g, 62.75%). MS(ES): m/z 290.2 [M+H]$^+$

Step 8. 5-((dimethylamino)methyl)-6-(tetrahydrofuran-3-yl)pyridin-3-amine (PA12)

To a solution of N-(5-((dimethylamino)methyl)-6-(tetrahydrofuran-3-yl)pyridin-3-yl)cyclopropanecarboxamide (PA12.6) (3.5 g, 12.11 mmol, 1.0 eq) in methanol:Water (28 ml:7 ml) was added sodium hydroxide (3.39 g, 84.77 mmol, 7.0 eq) at RT. The reaction mixture was stirred at 80° C. for 16 h. After completion, the reaction mixture was transferred into DM water (120 ml) and product was extracted in 10% methanol in dichloromethane (3×50 ml). Organic layer was combined, dried over sodium sulphate and concentrated under reduced pressure to obtain (PA12) (0.850 g, 31.76%). MS(ES): m/z 222.1 [M+H]$^+$ Example 1. Method AP Preparation of 4-((6-(4-hydroxypiperidin-1-yl)pyridin-3-yl)amino)-7-(1-methyl-1H-pyrrolo[2,3-b]pyridin-4-yl)-1,2-dihydro-3H-pyrrolo[3,4-c]pyridin-3-one (I-1)

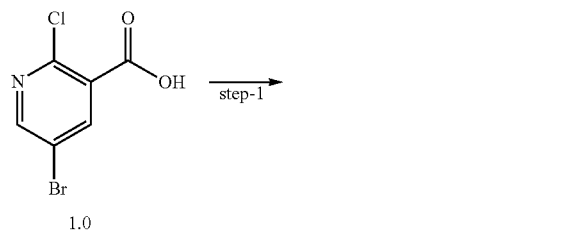

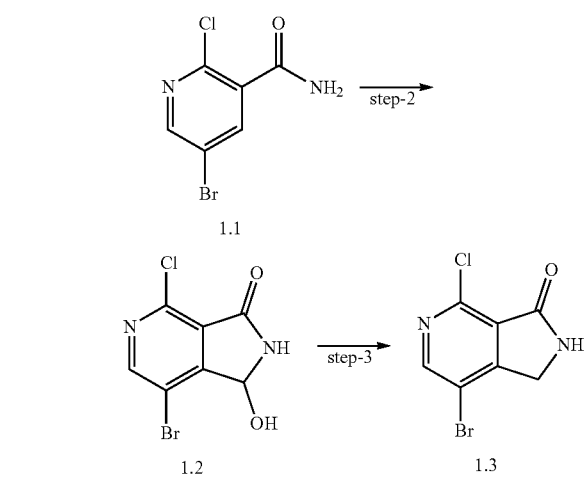

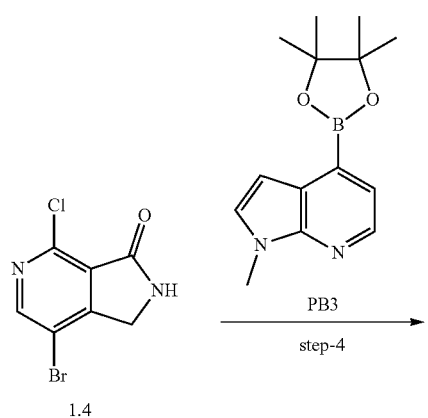

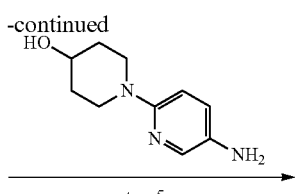

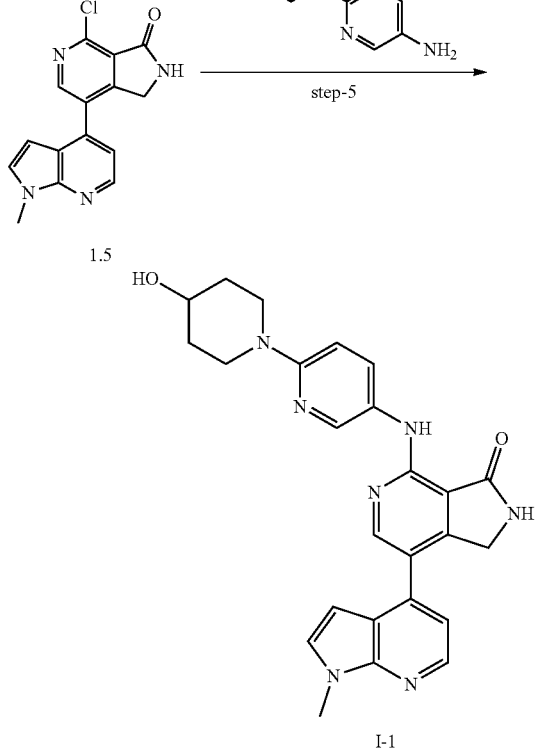

Step-1. 5-bromo-2-chloronicotinamide (1.1)

To a suspension of 5-bromo-2-chloronicotinic acid (1.0) (5.0 g, 21.18 mmol), DCM (125 ml), and Oxalyl chloride (3.20 g, 25.42 mmol), was added drop wise N,N-Dimethylformamide (0.15 g, 2.11 mmol) at RT. The reaction was stirred at room RT for 3 h then half volume of Dichloromethane was concentrated in vacuum. To the resulting residue was added a solution of 7M methanolic ammonia diluted in DCM at −78° C. The reaction mixture was allowed to stir for 18 h at RT. After completion, the reaction mixture was diluted with DCM (250 ml) and water (500 ml). The organic phase was separated and the aqueous phase was extracted with Dichloromethane (4×250 ml). The organic layers were combined and washed with brine (500 ml), then dried over Na$_2$SO$_4$, filtered, and concentrated under reduced pressure to afford the title compound (1.1) (3.6 g, 72.3% yield). The compound was taken forward to the next Step-without further purification. m/z=235.92 [M+H]$^+$.

Step-2. 7-bromo-4-chloro-1-hydroxy-1,2-dihydro-3H-pyrrolo[3,4-c]pyridin-3-one (1.2)

To a solution of 5-bromo-2-chloronicotinamide (1.1) (0.400 g, 1.70 mmol, 1.0 eq) in Tetrahydrofuran (24 ml) was added N,N-Dimethylformamide (0.372 g, 5.10 mmol, 3.0 eq). This reaction mixture was added drop wise into LOM Lithium bis(trimethylsilyl)amide in THF (4.21 ml, 4.21 mmol, 2.5 eq) at 0° C. The reaction mixture was allowed to stir for 3 h at 0° C. After completion, the solution was diluted with pre-cooled 2N HCl solution (7 ml), ethyl acetate (50 ml) and water (25 ml). The organic phase was collected and the aqueous phase was extracted with ethyl acetate (2×50 ml). The combined organic layers were washed with brine (30 ml), then dried over $Na_2SO_4$, filtered, and concentrated under reduced pressure. The crude compound was purified by column chromatography and pure product was eluted with 0-1.5% MeOH in DCM) to afford the title compound (1.2) (0.3 g, 67.3% yield). m/z=263.91 $[M+H]^+$.

Step-3. 7-bromo-4-chloro-1,2-dihydro-3H-pyrrolo[3,4-c]pyridin-3-one (1.3)

To a suspension of 7-bromo-4-chloro-1-hydroxy-1,2-dihydro-3H-pyrrolo[3,4-c]pyridin-3-one (1.2) (0.100 g, 0.380 mmol, 1.0 eq) in DCM (3 ml) was added Trifluoroacetic acid (1 ml) followed by Triethylsilane (1 ml) at RT. The reaction mixture was stirred at 40° C. for 16 h. After completion, the solution was diluted with water (12 ml) and basified with $NaHCO_3$ until pH 8-9. Precipitate formed and was collected by filtration. The crude compound was purified by column chromatography and product was eluted at 0-2% MeOH in DCM to afford the title compound (1.3) (0.02 g, 21.29% yield). m/z=247.92 $[M+H]^+$.

Step-4. 4-chloro-7-(1-methyl-1H-pyrrolo[2,3-b]pyridin-4-yl)-1,2-dihydro-3H-pyrrolo[3,4-c]pyridin-3-one (1.4)

To a solution of 7-bromo-4-chloro-1,2-dihydro-3H-pyrrolo[3,4-c]pyridin-3-one (1.3) (0.050 g, 0.144 mmol, 1.0 eq) in mixture of 1,4-dioxane (3 ml) and water (0.5 ml) were added 1-methyl-4-(4,4,5,5-tetramethyl-1,3,2-dioxaborolan-2-yl)-1H-pyrrolo[2,3-b]pyridine (PB3) (0.037 g, 0.144 mmol, 1.0 eq) and Sodium Carbonate (0.045 g, 0.43 mmol, 0.3 eq) at RT, then the entire mixture was degassed with Argon for 5 minutes. The catalyst complex (1,1'-Bis(diphenylphosphino)ferrocene)palladium(II) dichloride (0.011 g, 0.014 mmol, 0.1 eq) was added to the reaction mixture, degassed for 2 min at RT, and heated at 100° C. for 1 h. After completion, the reaction mixture was cooled to RT and then diluted with ethyl acetate (25 ml) and water (20 ml). The organic layer was collected and the aqueous phase was extracted with ethyl acetate (2×25 ml), and the combined organic extracts were washed with brine (20 ml), then dried over $Na_2SO_4$, filtered, and concentrated under reduced pressure. The crude residue was purified by column chromatography (0-2% gradient elution MeOH in DCM) to afford the title compound (1.4) (0.045 g, 74.56% yield). m/z=299.07 $[M+H]^+$.

Step-5. 4-((6-(4-hydroxypiperidin-1-yl)pyridin-3-yl)amino)-7-(1-methyl-1H-pyrrolo[2,3-b]pyridin-4-yl)-1,2-dihydro-3H-pyrrolo[3,4-c]pyridin-3-one I-1)

To a solution of 4-chloro-7-(1-methyl-1H-pyrrolo[2,3-b]pyridin-4-yl)-1,2-dihydro-3H-pyrrolo[3,4-c]pyridin-3-one (1.4) (0.300 g, 1.00 mmol, 1.0 eq) in N,N-Dimethylformamide (10 ml) were added 1-(5-aminopyridin-2-yl)piperidin-4-ol (0.212 g, 1.00 mmol, 1.0 eq) and Potassium Phosphate tribasic (0.640 g, 3.02 mmol, 3.0 eq) at RT, then the entire mixture was degassed with Argon for 10 minutes. The catalyst complex [(2-Di-cyclohexylphosphino-3,6-dimethoxy-2',4',6'-triisopropyl-1,1'-biphenyl)-2-(2'-amino-1,1'-biphenyl)]palladium(II) methanesulfonate (0.091 g, 0.10 mmol, 0.1 eq) was added to the reaction mixture and heated at 110° C. for 20 min. After completion, the reaction mixture was diluted with ethyl acetate (20 ml), washed with water (15 ml) and brine (15 ml), dried over $Na_2SO_4$, and concentrated in vacuum. The crude product was purified by preparative HPLC using column: SUNFIRE C18 (150*19) mm 5 u, mobile phase: 0.10% Trifluoroacetic acid (TFA) in water/acetonitrile as buffer, flow 13 ml/min, gradient 0-34 min and obtained fraction lyophilized to afford TFA salt of I-1. The salt was dissolved into methanol (3 ml) and neutralized with tetralkyl ammonium carbonate polymer-bound (basic resin) to isolate the free base of the title compound (I-1) (15 mg, 3.28%). m/z=456.21 $[M+H]^+$, $^1H$ NMR (400 MHz, DMSO): δ 8.94 (s, 1H), 8.85 (s, 1H), 8.45-8.43 (m, 2H), 8.32-8.30 (m, 1H), 7.98-7.96 (m, 1H), 7.59-7.58 (d, J=4 Hz, 1H), 7.25-7.24 (m, 1H), 6.88-6.86 (d, J=8.6 Hz, 1H), 6.52-6.51 (d, J=4 Hz, 1H), 4.69 (s, 1H), 4.52 (s, 2H), 3.98-3.97 (m, 2H), 3.95-3.81 (m, 3H), 3.67-3.65 (d, J=8 Hz, 1H), 3.06-2.99 (m, 2H), 1.79-1.77 (m, 2H), 1.41-1.33 (m, 2H).

Example 2. Method BP

Preparation of 1-methyl-1H-pyrrolo[2,3-b]pyridin-4-yl)-4-((6-(4-methylpiperazin-1-yl)pyridin-3-yl)amino)-1,2-dihydro-3H-pyrrolo[3,4-c]pyridin-3-one (I-2)

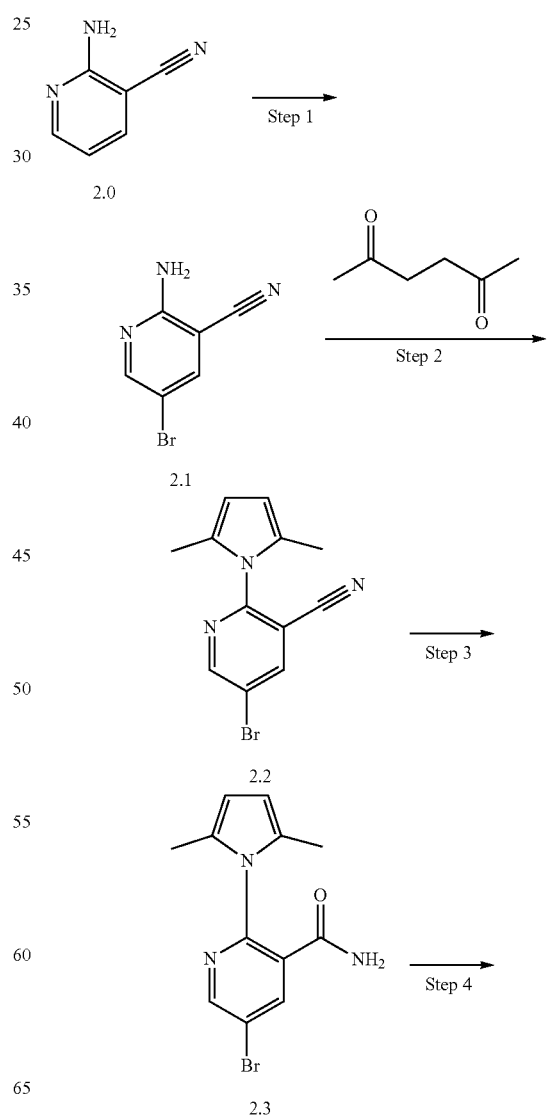

223

-continued

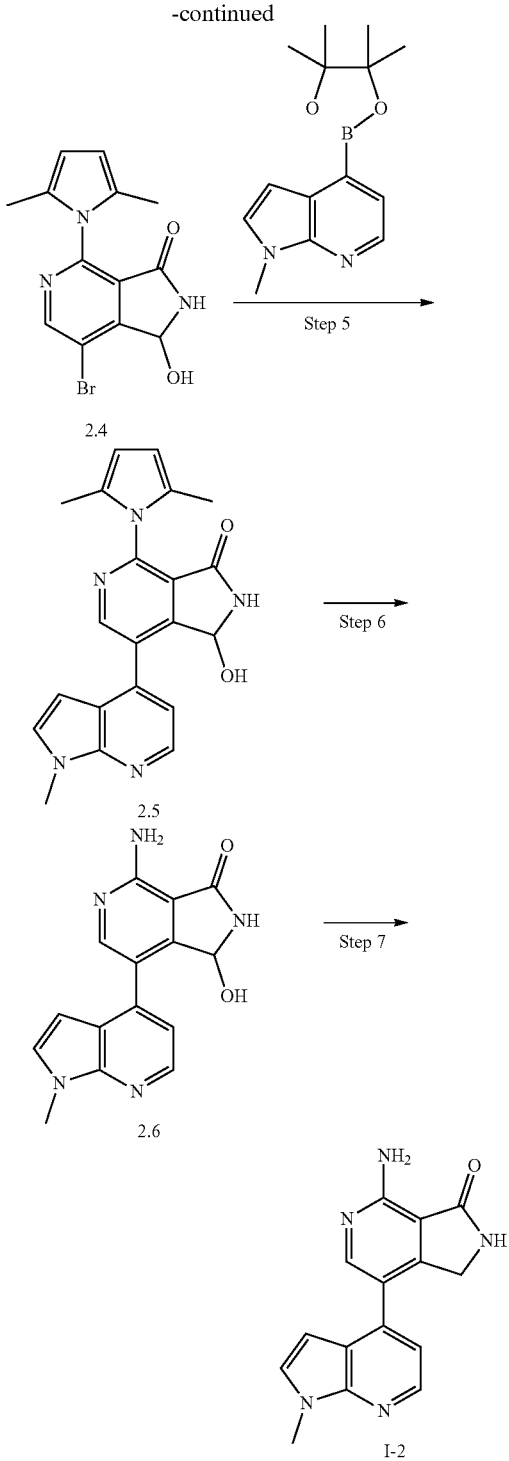

2.4

2.5

2.6

I-2

Step 1. 2-amino-5-bromonicotinonitrile (2.1)

To a solution of 2-aminonicotinonitrile (2.0) (25 g, 209.907 mmol) in AcOH (500 ml) was added Sodium carbonate (2.309 g, 230.89 mmol), and dilute $Br_2$ (37.0 g, 290.89 mmol.) in AcOH (500 ml) was added drop-wise to the reaction mixture at RT. The reaction mixture was stirred at RT for 3 h. After completion, the reaction mixture was poured onto ice-cold water (1000 ml) and the precipitate was collected by filtration. The solid was washed with water and dried under reduced pressure to afford (2.1) (35 g, 84.22%) as a white solid m/z=199.04 $[M+H]^+$ Step 2. 5-bromo-2-(2,5-dimethyl-1H-pyrrol-1-yl) nicotinonitrile (2.2)

To a solution of 2-amino-5-bromonicotinonitrile (2.1) (35 g, 176.749 mmol, 1.0 eq) in toluene (550 ml), were added hexane-2,5-dione (30.3 g, 265.125 mmol, 1.5 EQ) and p-Toluenesulfonic acid (1.01 g, 5.302 mmol, 0.2 eq) at RT. The reaction mixture was stirred at 140° C. for 16 h to remove water (14 ml) by Dean stark apparatus. After completion, the reaction mixture was cooled to RT, and toluene was removed under reduced pressure. The residue was diluted with ethyl acetate (500 ml) and water (800 ml). The organic phase was collected, and the aqueous phase was extracted with ethyl acetate (2×500 ml). The combined organic layers were washed with brine (500 ml), dried over $Na_2SO_4$, filtered, and concentrated under reduced pressure to afford the title compound (2.2) (45.00 g, 92.20% yield). The compound was taken forwards to the next step without purification. m/z=277.14 $[M+H]^+$, Step 3. 5-bromo-2-(2,5-dimethyl-1H-pyrrol-1-yl) nicotinamide (2.3)

To a solution 5-bromo-2-(2,5-dimethyl-1H-pyrrol-1-yl) nicotinonitrile (2.2) (45 g, 162.96 mmol, 1.0 eq) in DMSO (450 ml) was added potassium carbonate (67.5 g, 488.88 mmol, 3.0 eq) at RT. The reaction mixture was stirred at 60° C. for 40 min. $H_2O_2$ (92.4 ml, 814.804 mmol, 5.0 eq) was added dropwise to the reaction mixture at 60° C. and then the reaction mixture was cooled to RT and stirred for 3 h. After completion, the reaction mixture was diluted with ethyl acetate (500 ml) and washed with water (800 ml). The organic layer was collected separately and the aqueous phase was extracted with ethyl acetate (2×250 ml). The combined organic layers were washed with brine (300 ml), dried over $Na_2SO_4$, filtered, and concentrated under reduced pressure. The crude compound was purified by column chromatography (0-0.5% gradient elution MeOH in DCM) to afford the title compound (2.3) (40.0 g, 83.44%). m/z=295.15 $[M+H]^+$.

Step 4. 7-bromo-4-(2,5-dimethyl-1H-pyrrol-1-yl)-1-hydroxy-1,2-dihydro-3H-pyrrolo[3,4-c]pyridin-3-one (2.4)

To a solution of 5-bromo-2-(2,5-dimethyl-1H-pyrrol-1-yl)nicotinamide (2.3) (2 g, 6.779 mmol, 1.0 eq) in THF (100 ml) was added LOM Lithium bis(trimethylsilyl)amide in THF (27.1 ml, 27.1186 mmol, 4.0 eq) at −65° C. under nitrogen atmosphere. The reaction mixture was stirred at −65° C. for 1 h and then N,N-Dimethylformaamide was added (2.3 ml, 33.898 mmol, 5.0 eq) dropwise to the reaction mixture at −65° C. The reaction mixture was stirred at RT for 4 h. After completion, the solution was diluted with cold dilute 1N HCl solution (150 ml) and ethyl acetate (150 ml). The organic phase was collected separately, and the aqueous phase was extracted with ethyl acetate (2×100 ml). The combined organic layers were washed with brine (200 ml), dried over $Na_2SO_4$, filtered, and concentrated under reduced pressure. The crude compound was purified by column chromatography (0-75% gradient elution ethyl acetate in Hexanes) to afford the title compound (2.4) (0.33 g, 15.20%). m/z=323.16 [M+H]+.

Step 5. 4-(2,5-dimethyl-1H-pyrrol-1-yl)-1-hydroxy-7-(1-methyl-1H-pyrrolo[2,3-b]pyridin-4-yl)-1,2-dihydro-3H-pyrrolo[3,4-c]pyridin-3-one (2.5)

To a solution 7-bromo-4-(2,5-dimethyl-1H-pyrrol-1-yl)-1-hydroxy-1,2-dihydro-3H-pyrrolo[3,4-c]pyridin-3-one (2.4) (0.500 g, 1.552 mmol, 1.0 eq) into 1,4-dioxane (5 ml) were added 1-methyl-4-(4,4,5,5-tetramethyl-1,3,2-dioxaborolan-2-yl)-1H-pyrrolo[2,3-b]pyridine (0.48 g, 1.863 mmol, 1.2 eq), potassium carbonate (0.860 g, 6.211 mmol, 4.0 eq) and water (1 ml). The reaction mixture was degassed 15 min with argon; then Chloro(2-dicyclohexylphosphino-2',4',6'-triisopropyl-1,1'-biphenyl)[2-(2'-amino-1,1'-biphenyl)]palladium(II) (0.122 g, 0.155 mmol, 0.1 eq) was added. The reaction mixture was stirred in microwave at 110° C. temperature for 20 min. After completion, the reaction mixture was concentrated under reduced pressure to afford the title compound (2.5) (0.367 g, 63.33%). The compound was taken forward to the next step without purification. m/z=374.42 [M+H]+.

Step 6. 4-amino-1-hydroxy-7-(1-methyl-1H-pyrrolo[2,3-b]pyridin-4-yl)-1,2-dihydro-3H-pyrrolo[3,4-c]pyridin-3-one (2.6)

To a solution 4-(2,5-dimethyl-1H-pyrrol-1-yl)-1-hydroxy-7-(1-methyl-1H-pyrrolo[2,3-b]pyridin-4-yl)-1,2-dihydro-3H-pyrrolo[3,4-c]pyridin-3-one (2.5) (0.400 g, 1.07 mmol, 1.0 eq) in ethanol:water (40 ml:14 ml) were added triethylamine (0.6 ml, 4.28 mmol, 4.0 eq) and NH2OH.HCl (1.10 gm, 16.05 mmol, 15.0 eq) at RT. The reaction mixture was stirred at 80° C. for 16 h. After completion, the reaction mixture was diluted with ethyl acetate (50 ml) and water (25 ml). The organic phase was collected separately, and the aqueous phase was extracted with ethyl acetate (2×50 ml). The combined organic layers were washed with brine (30 ml), dried over Na2SO4, filtered, and concentrated under reduced pressure. The crude compound was purified by column chromatography (0-5% gradient elution MeOH in DCM) to afford the title compound (2.6) (0.270 g, 85.36%). m/z=296.30 [M+H]+.

Step 7. 4-amino-7-(1-methyl-1H-pyrrolo[2,3-b]pyridin-4-yl)-1,2-dihydro-3H-pyrrolo[3,4-c]pyridin-3-one (I-2)

To a solution 4-amino-1-hydroxy-7-(1-methyl-1H-pyrrolo[2,3-b]pyridin-4-yl)-1,2-dihydro-3H-pyrrolo[3,4-c]pyridin-3-one (2.6) (0.170 g, 0.57 mmol, 1.0 eq) in Trifluoroacetic acid (3 ml) was added triethylsilane (3 ml). The reaction mixture was heated at 80° C. for 16 h. After completion, the reaction mixture was distilled out and basified with saturated NaHCO3 for solid fallout which was collected by filtration. The crude solid product was purified by preparative HPLC using column: SUNFIRE C18 (250*19) mm 5 u, mobile phase: 0.1% Trifluoroacetic acid (TFA) in water/acetonitrile as buffer, flow 15 ml/min, gradient 0-38 min and obtained fraction lyophilized to afford TFA salt of I-2. The salt was dissolved into methanol (3 ml) and neutralized with tetralkyl ammonium carbonate polymer-bound (basic resin) to isolate the free base of to afford the title compound (I-2) (24 mg, 14.93%). m/z=280.30 [M+H]+, 1H NMR (400 MHz, DMSO): δ 8.54 (s, 1H), 8.350-8.297 (m, 2H), 7.59-7.58 (m, 1H), 7.22-7.21 (d, J=4.8 Hz, 1H), 6.88 (s, 2H), 6.49-6.48 (m, 1H), 4.45 (s, 2H), 3.87 (s, 3H).

Example 3. Method CP

Preparation of (R)—7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (I-3) and (S)-7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (I-4)

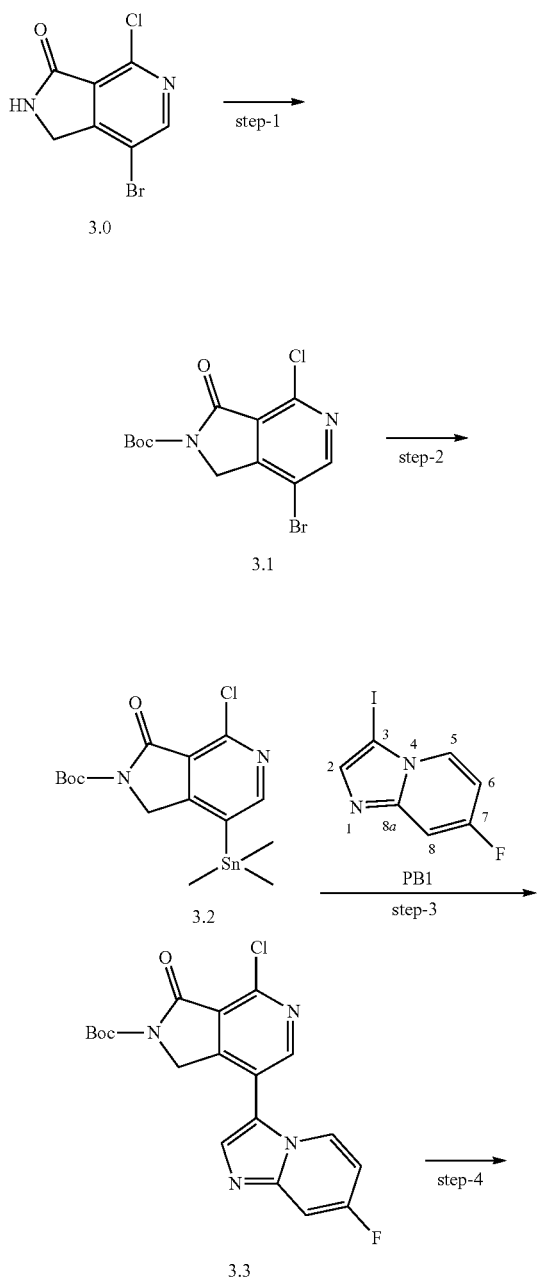

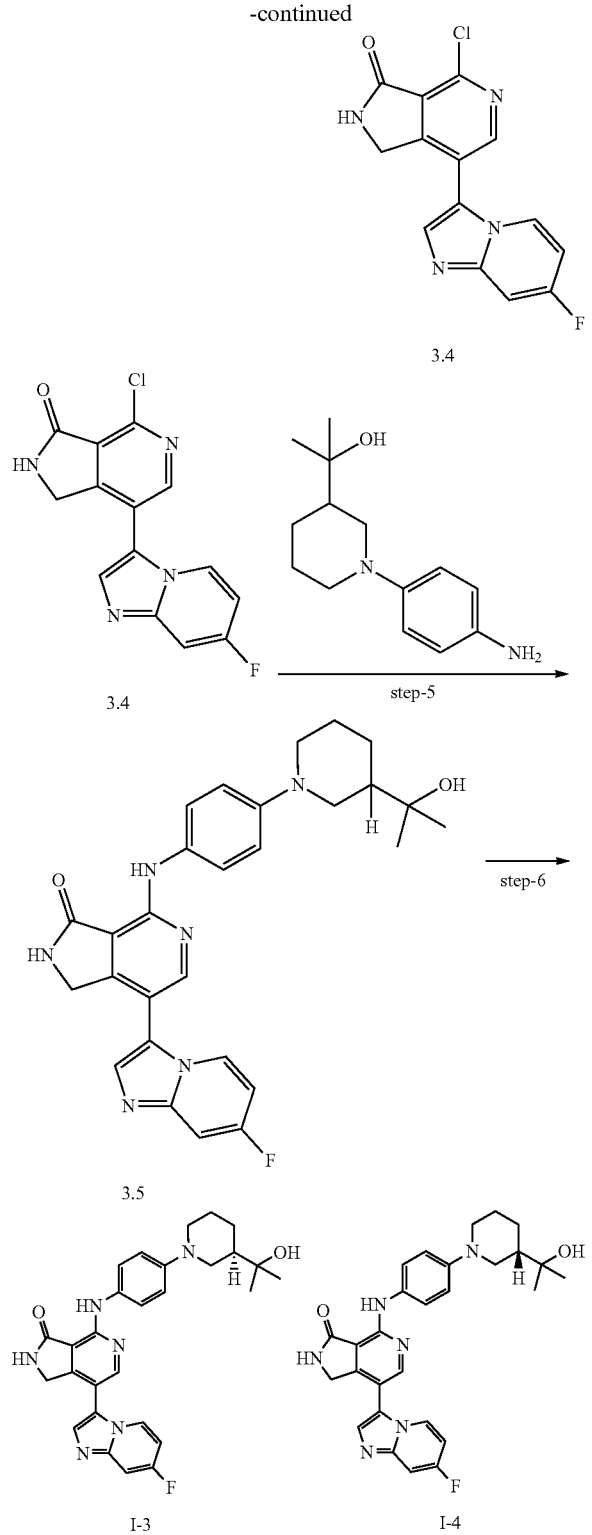

Step-1. tert-butyl 7-bromo-4-chloro-3-oxo-1,3-dihydro-2H-pyrrolo[3,4-c]pyridine-2-carboxylate (3.1)

To a solution of 7-bromo-4-chloro-1,2-dihydro-3H-pyrrolo[3,4-c]pyridin-3-one (3.0) (5 g, 20.24 mmol, 1.0 eq) in dioxane (250 ml) were added 4-Dimethylaminopyridine (0.24 g, 2.024 mmol, 0.1 eq) and Boc anhydride (5.0 g, 23.27 mmol, 1.15 eq). The reaction was stirred at RT for 1 h. After completion, the reaction mixture was diluted with water (300 ml) and extracted by ethyl acetate (250 ml×3). The combined organic layer was dried over sodium sulfate and concentrated under vacuum to afford crude. The crude residue was purified by column chromatography eluting with 5% ethyl acetate in hexane to afford 3.1 (5.5 g, 78.32% yield) as a white solid. MS(ES): m/z 347-349 [M+2]$^+$ Step-2. tert-butyl 4-chloro-3-oxo-7-(trimethylstannyl)-1,3-dihydro-2H-pyrrolo[3,4-c]pyridine-2-carboxylate (3.2)

To a solution of tert-butyl 7-bromo-4-chloro-3-oxo-1,3-dihydro-2H-pyrrolo[3,4-c]pyridine-2-carboxylate (3.1) (0.500 g, 1.44 mmol, 1.0 eq) in toluene (8 ml) was added hexamethylditin (0.712 g, 2.17 mmol, 1.5 eq). After degassing under N$_2$ for 15 min, Bis(triphenylphosphine)palladium (II) dichloride (0.051 g, 0.072 mmol, 0.05 eq) was added. The reaction was stirred at 115° C. for 2 h. After completion, the reaction mixture was cooled to RT and diluted with ethyl acetate (100 ml) and water (50 ml). The organic layer was collected separately, and the aqueous phase was yet again extracted with ethyl acetate (2×30 ml). The combined organic extracts were washed with brine (20 ml), dried over Na$_2$SO$_4$, filtered, and concentrated under reduced pressure. The residue was purified by column chromatography eluting with 9% ethyl acetate gradient in hexane to afford (3.2) (0.300 g, 48.3% yield). MS(ES): m/z=431.5 [M+2]+

Step-3. tert-butyl 4-chloro-7-(7-fluoroimidazo[1,2-a]pyridin-3-yl)-3-oxo-1,3-dihydro-2H-pyrrolo[3,4-c]pyridine-2-carboxylate (3.3)

To a solution of tert-butyl 4-chloro-3-oxo-7-(trimethylstannyl)-1,3-dihydro-2H-pyrrolo[3,4-c]pyridine-2-carboxylate (3.2) (0.500 g, 1.15 mmol, 1.0 eq) in DMF (8 ml) was added 7-fluoro-3-iodoimidazo[1,2-a]pyridine (PB1) (0.303 g, 1.15 mmol, 1.0 eq). After degassing with N$_2$ for 15 min, Tetrakis(triphenylphosphine)palladium(0) (0.066 g, 0.05 mmol, 0.05 eq) and CuI (0.022 g, 0.115 mmol, 0.1 eq) were added. The reaction mixture was stirred at 105° C. for 1.5 h. After completion, the reaction mixture was cooled at RT and diluted with ethyl acetate (20 ml) and water (15 ml). The organic layer was collected, and the aqueous phase was extracted with ethyl acetate (2×30 ml). The combined organic extracts were washed with brine (10 ml), dried over Na$_2$SO$_4$, filtered, and concentrated under reduced pressure. The residue was purified by column chromatography eluting with 50% ethyl acetate in hexane to afford title compound 3.3 (0.380 g, 81.4% yield), MS (ES): m/z 402.8[M+H]$^+$ Step-4. 4-chloro-7-(7-fluoroimidazo[1,2-a]pyridin-3-yl)-1,2-dihydro-3H-pyrrolo[3,4-c]pyridin-3-one (3.4)

To a solution of tert-butyl 4-chloro-7-(7-fluoroimidazo[1,2-a]pyridin-3-yl)-3-oxo-1,3-dihydro-2H-pyrrolo[3,4-c]pyridine-2-carboxylate (3.3) (0.920 g, 2.2 mmol, 1.0 eq) into DCM (15 ml) at 0° C. was added 4.0M HCl in dioxane (5 ml). The reaction mixture was stirred at RT for 1 h. After completion, the reaction mixture was neutralized using saturated sodium bicarbonate solution and extracted with DCM to afford 3.4 (0.600 g, 84.05%) MS (ES): m/z 302.6 (M+H).

Step-5. 7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (3.5)

To a solution of 4-chloro-7-(7-fluoroimidazo[1,2-a]pyridin-3-yl)-1,2-dihydro-3H-pyrrolo[3,4-c]pyridin-3-one (3.4) (0.100 g, 0.33 mmol, 1.0 eq) in DMF (3 ml) were added 2-(1-(4-aminophenyl)piperidin-3-yl)propan-2-ol (0.065 g, 0.33 mmol, 1.0 eq) and $K_3PO_4$ (0.210 g, 0.99 mmol, 3.0 eq). After degassing under $N_2$ for 15 min, [(2-Di-cyclohexylphosphino-3,6-dimethoxy-2',4',6'-triisopropyl-1,1'-biphenyl)-2-(2'-amino-1,1'-biphenyl)]palladium(II) methanesulfonate (0.030 g, 0.03 mmol, 0.1 eq) was added. Then, the reaction mixture was stirred at 80° C. for 1.5 h. After completion, the reaction mixture was cooled to RT and diluted with ethyl acetate (100 ml) and water (50 ml). The organic layer was collected, and the aqueous phase was extracted with ethyl acetate (2×30 ml). The combined organic extracts were washed with brine (20 ml), dried over $Na_2SO_4$, filtered, and concentrated under reduced pressure. The residue was purified by column chromatography to afford 3.5 (0.060 g, 36.2%), MS(ES): m/z 500.5[M+H]

Step-6. Separation of R)-7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (I-3) and (S)-7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (I-4)

Compound 3.5 (60 mg racemic) was separated on Shimadzu LC-20AP and UV detector. The column used was CHIRALPAK IB-N (250*21.0) mm, 5 micron, column flow was 20.0 ml/min. The mobile phase was (A) 0.1% DEA IN n-Hexane, (B) 0.1% DEA IN Propane-2-ol:methanol (50:50), to afford I-3 (25 mg) and I-4 (24 mg). The stereochemistry was arbitrarily assigned. I-3 MS(ES): m/z 500.5 [M+H] as a light brown colour. $^1$H NMR (400 MHz, DMSO-d6) δ 9.09 (s, 1H), 8.88 (s, 1H), 8.50 (dd, J=7.6, 5.7 Hz, 2H), 8.47 (s, 1H), 7.81 (s, 1H), 7.66 (d, J=9.0 Hz, 2H), 7.55 (dd, J=10.1, 2.6 Hz, 1H), 7.03-6.91 (m, 2H), 4.41 (s, 2H), 4.28 (s, 1H), 3.79 (d, J=12.1 Hz, 1H), 3.64 (d, J=12.3 Hz, 1H), 3.52 (s, 2H), 2.40 (t, J=11.7 Hz, 1H), 1.85 (d, J=12.5 Hz, 2H), 1.75 (d, J=13.1 Hz, 1H), 1.25 (s, 2H), 1.11 (d, J=11.0 Hz, 5H). I-4: MS(ES): m/z 500.5 [M+H] as a light brown colour. $^1$H NMR (400 MHz, DMSO-d6) δ 9.09 (s, 1H), 8.88 (s, 1H), 8.50 (dd, J=7.6, 5.7 Hz, 2H), 8.47 (s, 1H), 7.81 (s, 1H), 7.69-7.62 (m, 1H), 7.55 (dd, J=10.1, 2.7 Hz, 2H), 7.03-6.91 (m, 2H), 4.41 (s, 2H), 4.35 (s, 1H), 4.28 (s, 1H), 3.79 (d, J=11.8 Hz, 2H), 3.64 (d, J=12.2 Hz, 1H), 2.40 (t, J=11.6 Hz, 1H), 1.85 (d, J=12.6 Hz, 1H), 1.75 (d, J=13.1 Hz, 1H), 1.56 (s, 1H), 1.25 (s, 2H), 1.11 (d, J=11.0 Hz, 5H).

Example 4. Method DP

Preparation of 4-((6-(4-hydroxypiperidin-1-yl)pyridin-3-yl)amino)-7-(1-methyl-1H-pyrrolo[2,3-b]pyridin-4-yl)-1,2-dihydro-3H-pyrrolo[3,4-c]pyridin-3-one (I-5)

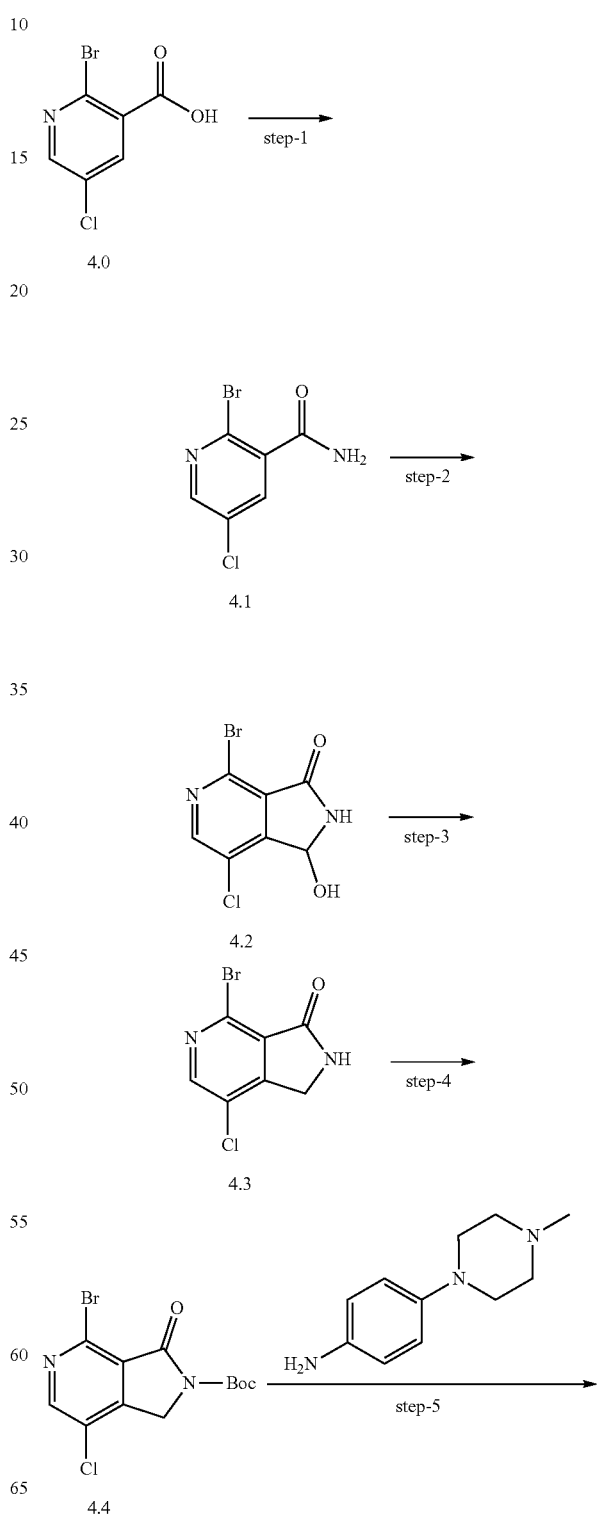

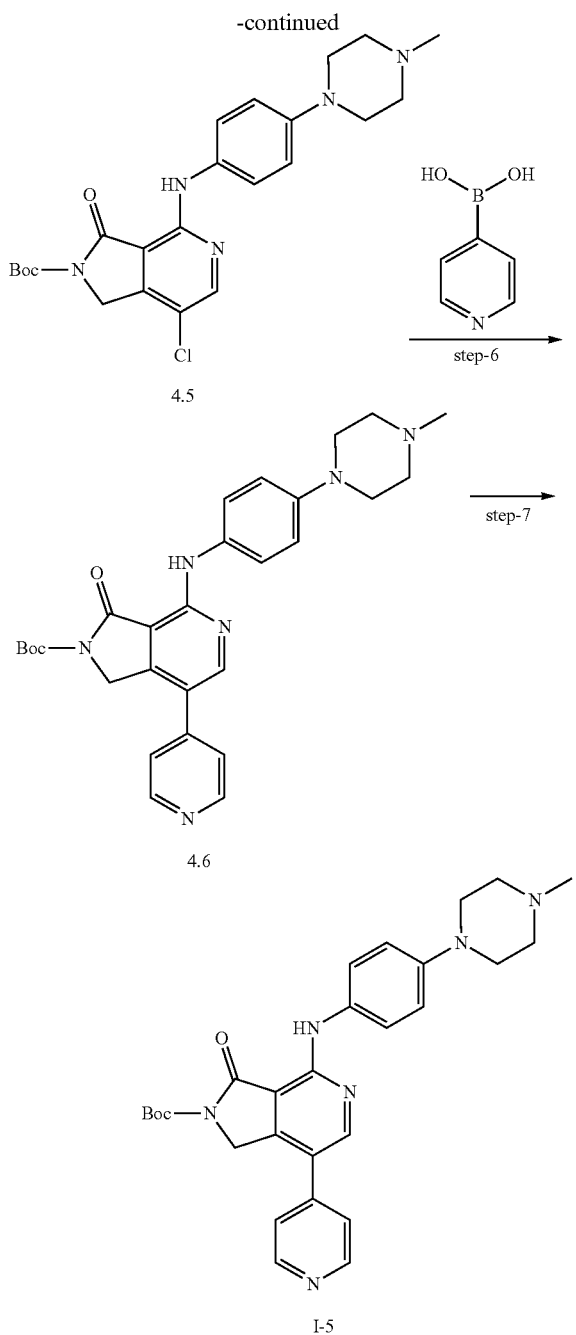

phase was extracted with DCM (4×250 ml). The combined organic layers were washed with brine (500 ml), then dried over $Na_2SO_4$, filtered, and concentrated under reduced pressure to afford the title compound (4.1) (3.6 g, 72.3% yield). The compound was taken forward to the next step without further purification. m/z=235.92 [M+H]⁺.

Step-2. 4-bromo-7-chloro-1-hydroxy-1,2-dihydro-3H-pyrrolo[3,4-c]pyridin-3-one (4.2)

To a solution of 2-bromo-5-chloronicotinamide (4.1) (0.400 g, 1.70 mmol, 1.0 eq) in THF (24 ml) was added N,N-Dimethylformamide (0.372 g, 5.10 mmol, 3.0 eq). This reaction mixture was added drop wise into LiHMDS (4.21 ml, 4.21 mmol, 2.5 eq) at 0° C. The reaction mixture was stirred for 3 h at 0° C. After completion, the solution was diluted with pre-cooled 2N HCl solution (7 ml), ethyl acetate (50 ml) and water (25 ml). The organic phase was collected and the aqueous phase was extracted with ethyl acetate (2×50 ml). The combined organic layers were washed with brine (30 ml), then dried over $Na_2SO_4$, filtered, and concentrated under reduced pressure. The crude compound was purified by column chromatography (0-1.5% gradient elution MeOH in DCM) to afford the title compound (4.2) (0.3 g, 67.3% yield). m/z=263.91 [M+H]⁺.

Step-3. 4-bromo-7-chloro-1,2-dihydro-3H-pyrrolo[3,4-c]pyridin-3-one (4.3)

To a suspension of 4-bromo-7-chloro-1-hydroxy-1,2-dihydro-3H-pyrrolo[3,4-c]pyridin-3-one (4.2) (0.100 g, 0.380 mmol) in dichloromethane (3 ml) was added Trifluoroaceticacid (1 ml) followed by Triethylsilane(1 ml) at RT. The reaction mixture was stirred at 40° C. for 16 h. After completion, the solution was diluted with and water (12 ml) and basified with $NaHCO_3$ until pH 8-9. Precipitate formed which was collected by filtration. The crude compound was purified by column chromatography (0-2% gradient elution MeOH in DCM) to afford the title compound (4.3) (0.02 g, 21.29% yield). m/z=247.92 [M+H]⁺.

Step-4. tert-butyl 4-bromo-7-chloro-3-oxo-1,3-dihydro-2H-pyrrolo[3,4-c]pyridine-2-carboxylate (4.4)

To a solution of 4-bromo-7-chloro-1,2-dihydro-3H-pyrrolo[3,4-c]pyridin-3-one (4.3) (5 g, 20.24 mmol, 1.0 eq) in Dioxane (250 ml) were added Dimethyl amino pyridine (0.24 g, 2.024 mmol, 0.1 eq) and Boc anhydride (5.0 g, 23.27 mmol, 1.15 eq). The reaction mixture was stirred at room temperature for 1 h. After completion, the solid precipitate that formed was dissolved in reaction mixture. Then the reaction was diluted by water and extracted by ethyl acetate. Combined organic layer dried over sodium sulphate and concentrated under vacuum to obtain crude which was purified by column chromatography 5% ethyl acetate in hexane to obtain 4.4 (5.5 g, 78.32% yield) as a white solid. MS(ES): m/z 347-349 [M+2]⁺

Step-5. tert-butyl 4-bromo-7-chloro-3-oxo-1,3-dihydro-2H-pyrrolo[3,4-c]pyridine-2-carboxylate (4.5)

To a solution of tert-butyl 4-bromo-7-chloro-3-oxo-1,3-dihydro-2H-pyrrolo[3,4-c]pyridine-2-carboxylate (4.4) (0.130 g, 0.373 mmol, 1.0 eq) in toluene (2 ml) were added Step-1. 2-bromo-5-chloronicotinamide (4.1)

To a suspension of 2-bromo-5-chloronicotinic acid (4.0) (5.0 g, 21.18 mmol, 1.0 eq) in Dichloromethane (125 mL), was added Oxalyl chloride (3.20 g, 25.42 mmol, 1.2 eq) followed by drop wise addition of N,N-Dimethylformamide (0.15 g, 2.11 mmol, 0.1 eq) at RT. The reaction was stirred at room RT for 3 h, then half volume of Dichloromethane was concentrated in vacuum. To the resulting residue was added solution of 7M methanolic ammonia (10 ml) diluted in DCM (30 ml) at −78° C. Then reaction mixture was allowed to stir for 18 h at RT. After the completion of reaction, the solution was diluted DCM (250 ml) and water (500 ml). The organic phase was collected and the aqueous 4-(4-methylpiperazin-1-yl)aniline (0.085 g, 0.448 mmol, 1.2 eq) and Potassium carbonate (0.154 g, 1.19 mmol, 3.0 eq) at RT. The mixture was degassed with Argon for 10 minutes, xanthphos (0.043 g, 0.074 mmol, 0.2 eq) and Pd$_2$dba$_3$ (0.034, 0.037 mmol, 0.1 eq) were added to the reaction mixture, and degassed for 5 min at RT, followed by heating at 110° C. for 30 min. After completion, the reaction mixture was diluted with water (30 ml) and extracted with ethyl acetate (20 ml×3). The organic layers were combined and washed with brine (25 ml), dried over Na$_2$SO$_4$, and concentrated in vacuum. The crude product was purified by column chromatography by 10% methanol in dichloromethane to afford (4.5) (0.115 g, 67.14% yield). m/z=458.5[M+ H]$^+$, Step-6. tert-butyl 4-((4-(4-methylpiperazin-1-yl) phenyl)amino)-3-oxo-7-(pyridin-4-yl)-1,3-dihydro-2H-pyrrolo[3,4-c]pyridine-2-carboxylate (4.6)

To a solution of tert-butyl 4-bromo-7-chloro-3-oxo-1,3-dihydro-2H-pyrrolo[3,4-c]pyridine-2-carboxylate (4.5) (0.115 g, 0.251 mmol, 1.0 eq) in 1,4-dioxane (1.5 ml) and water (0.5 ml), were added pyridin-4-ylboronic acid (0.037 g, 0.251 mmol, 1.0 eq) and potassium phosphate tribasic (0.159 g, 0.75 mmol, 3.0 eq) at room temperature. The mixture was degassed with Argon for 5 minutes. The catalyst complex Chloro(2-dicyclohexylphosphino-2',4',6'-triisopropyl-1,1'-biphenyl)[2-(2'-amino-1,1'-biphenyl)]palladium(II) (0.019 g, 0.025 mmol, 0.1 eq) was added to the reaction mixture and degassed for 2 min at RT, then heated at 100° C. for 25 min. After completion, the reaction mixture was cooled to RT and then diluted ethyl acetate (25 ml) and water (20 ml). The organic layer was collected separately and the aqueous phase was extracted with ethyl acetate (2×25 ml), and the combined organic extracts were washed with brine (20 ml), then dried over Na$_2$SO$_4$, filtered, and concentrated under reduced pressure. The crude residue was purified by column chromatography (0-2% gradient elution MeOH in DCM) to afford compound (4.6) (0.055 g, 43.75% yield). m/z=501.2 [M+H]$^+$.

Step-7. 4-((4-(4-methylpiperazin-1-yl)phenyl) amino)-7-(pyridin-4-yl)-1,2-dihydro-3H-pyrrolo[3,4-c]pyridin-3-one (I-5)

To a solution of tert-butyl 4-bromo-7-chloro-3-oxo-1,3-dihydro-2H-pyrrolo[3,4-c]pyridine-2-carboxylate (4.6) (0.055 g, 0.251 mmol, 1.0 eq) in dichloromethane (2 ml) was added 4M HCl in dioxane (1 ml, 0.5v) at RT. After completion, the reaction mixture was diluted by DCM (20 ml) and washed with saturated sodium bicarbonate solution (20 ml). Combined organic layer were dried over sodium sulphate and concentrated under vacuum to provide crude which was purified by column chromatography by 10% methanol in dichloromethane to afford (I-5) (0.018 g, 40.91% yield). m/z=401.3 [M+H]$^+$. 1H NMR (400 MHz, DMSO-d6) δ 9.222 (s, 1H), 8.960 (s, 1H), 8.644 (d, J=6.4, 2H), 8.567 (s, 1H), 7.668-7.654 (m, 4H), 6.965 (d, J=9.2 Hz, 2H), 4.720 (s, 2H), 3.335 (s, 1H), 3.189-3.097 (m, 4H), 2.538-2.506 (m, 3H), 2.241 (s, 3H).

Example 5. Method EP

Preparation of 4-((3-((dimethylamino)methyl)-4-(tetrahydro-2H-pyran-4-yl)phenyl)amino)-7-(7-fluoroimidazo[1,2-a]pyridin-3-yl)-1,2-dihydro-3H-pyrrolo[3,4-c]pyridin-3-one (I-6)

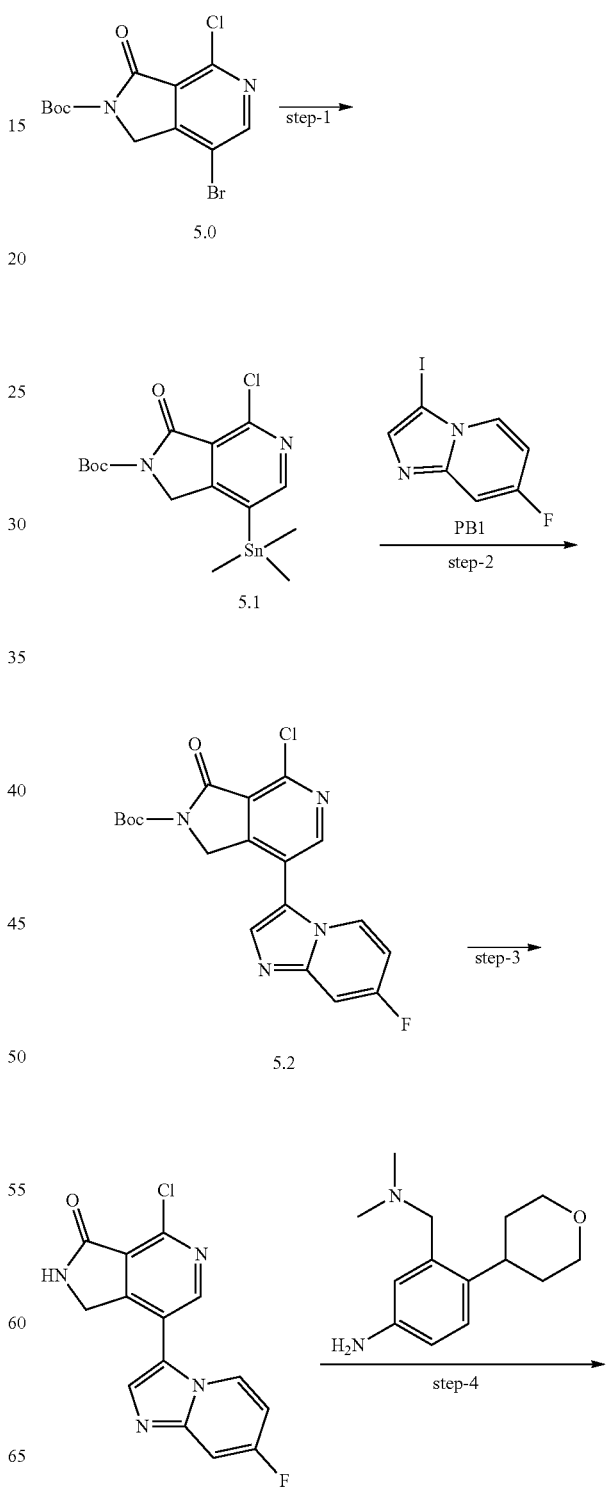

-continued

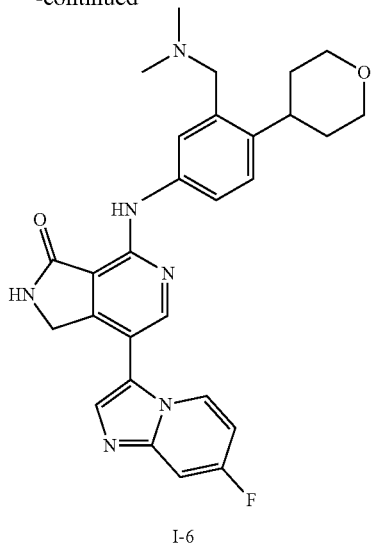

I-6

Step-1. tert-butyl 4-chloro-3-oxo-7-(trimethylstannyl)-1,3-dihydro-2H-pyrrolo[3,4-c]pyridine-2-carboxylate (5.1)

To a solution of tert-butyl 7-bromo-4-chloro-3-oxo-1,3-dihydro-2H-pyrrolo[3,4-c]pyridine-2-carboxylate (5.0) (0.500 g, 1.44 mmol, 1.0 eq) in toluene (8 ml) was added hexamethylditin (0.712 g, 2.17 mmol, 1.5 eq). After degassing under $N_2$ for 15 min, Bis(triphenylphosphine)palladium chloride (0.051 g, 0.072 mmol, 0.05 eq) was added. The reaction mixture was stirred at 115° C. for 2 h. After completion, the reaction mixture was cooled to RT and diluted with ethyl acetate (100 ml) and water (50 ml). The organic layer was collected, and the aqueous phase was extracted with ethyl acetate (2×30 ml). The combined organic extracts were washed with brine (20 ml), dried over $Na_2SO_4$, filtered, and concentrated under reduced pressure. The residue was purified by column chromatography eluting with 9% ethyl acetate gradient in hexane to afford (5.1) (0.300 g, 48.3% yield). MS(ES): m/z=431.5-433.1 [M+2]+

Step-2. tert-butyl 4-chloro-7-(7-fluoroimidazo[1,2-a]pyridin-3-yl)-3-oxo-1,3-dihydro-2H-pyrrolo[3,4-c]pyridine-2-carboxylate (5.2)

To a solution of tert-butyl 4-chloro-3-oxo-7-(trimethylstannyl)-1,3-dihydro-2H-pyrrolo[3,4-c]pyridine-2-carboxylate (5.1) (0.500 g, 1.15 mmol, 1.0 eq) in DMF (8 ml) was added 7-fluoro-3-iodoimidazo[1,2-a]pyridine (PB1) (0.303 g, 1.15 mmol, 1.0 eq). After degassing with $N_2$ for 15 min, Tetrakis(triphenylphosphine)palladium(0) (0.066 g, 0.05 mmol, 0.05 eq) and CuI (0.022 g, 0.115 mmol, 0.1 eq) were added. After stirring at 105° C. for 1.5 h, the reaction mixture was cooled to RT and diluted with ethyl acetate (20 ml) and water (15 ml). The organic layer was collected, and the aqueous phase was extracted with ethyl acetate (2×30 ml). The combined organic extracts were washed with brine (10 ml), dried over $Na_2SO_4$, filtered, and concentrated under reduced pressure. The residue was purified by column chromatography eluting with 50% ethyl acetate gradient in hexane to afford title compound 5.2 (0.380 g, 81.4%), MS (ES): m/z 403.8[M+H]+

Step-3. 4-chloro-7-(7-fluoroimidazo[1,2-a]pyridin-3-yl)-1,2-dihydro-3H-pyrrolo[3,4-c]pyridin-3-one (5.3)

To a solution of 5.2 (0.920 g, 2.2 mmol, 1.0 eq) into DCM (15 ml) at 0° C. was added 4.0M HCl in dioxane (5 ml). After stirring at RT for 1 h, the reaction mixture was neutralized using saturated sodium bicarbonate solution and extracted with DCM (40 ml×3). The organic layers were combined, dried over sodium sulphate and concentrated under reduced pressure to afford 5.3 (0.600 g, 84.05% yield). The obtained crude was used in the next step without any further purification. MS (ES): m/z 303.6 (M+H).

Step-4. 4-((3-((dimethylamino)methyl)-4-(tetrahydro-2H-pyran-4-yl)phenyl)amino)-7-(7-fluoroimidazo[1,2-a]pyridin-3-yl)-1,2-dihydro-3H-pyrrolo[3,4-c]pyridin-3-one (I-6)

To a solution of 4-chloro-7-(7-fluoroimidazo[1,2-a]pyridin-3-yl)-1,2-dihydro-3H-pyrrolo[3,4-c]pyridin-3-one (5.3) (0.140 g, 0.46 mmol, 1.0 eq) in DMSO (3 ml) were added 3-((dimethylamino)methyl)-4-(tetrahydro-2H-pyran-4-yl)aniline (0.108 g, 0.46 mmol, 1.0 eq) and $K_3PO_4$ (0.252 g, 1.387 mmol, 3.0 eq). After degassing under $N_2$ for 15 min, [(2-Di-cyclohexylphosphino-3,6-dimethoxy-2',4',6'-triisopropyl-1,1'-biphenyl)-2-(2'-amino-1,1'-biphenyl)]palladium (II) methanesulfonate (0.041 g, 0.04 mmol, 0.1 eq) was added. The reaction mixture was stirred at 80° C. for 1.5 h. After completion, the reaction mixture was cooled to RT and diluted with ethyl acetate (50 ml) and water (50 ml). The organic layer was collected, and the aqueous phase was extracted with ethyl acetate (2×20 ml). The combined organic extracts were washed with brine (20 ml), dried over $Na_2SO_4$, filtered, and concentrated under reduced pressure. The residue was purified by column chromatography and the pure product was eluted at 2% Methanol in DCM to afford I-6 (0.040 g, 18.61% yield), MS(ES): m/z 501.5[M+H] 1H NMR (400 MHz, DMSO-d6) δ 9.263 (s, 1H), 9.941 (s, 1H), 8.529-8.496 (t, J=6.4, 13.2 Hz, 2H), 7.928-7.902 (dd, J=4.0, 8.4 Hz, 1H), 7.822 (s, 1H), 7.560-7.529 (dd, J=2.4, 10.0 Hz, 1H), 7.485 (d, J=2.0 Hz, 1H), 7.292 (d, J=8.4 Hz, 1H), 4.416 (s, 2H), 3.952 (d, J=9.6, 2H), 3.466-3.340 (m, 4H), 3.144 (s, 1H), 2.192 (s, 6H), 1.719-1.598 (m, 4H).

Example 6. Method FP

Preparation of 4-((3-((dimethylamino)methyl)-4-morpholinophenyl)amino)-7-(1-methyl-1H-pyrrolo[2,3-b]pyridin-4-yl)-1,2-dihydro-3H-pyrrolo[3,4-c]pyridin-3-one (I-7)

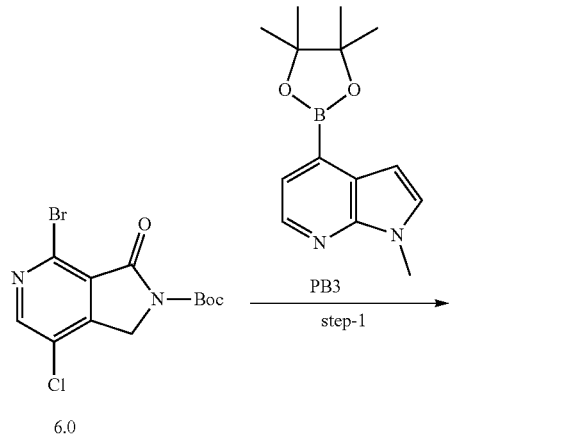

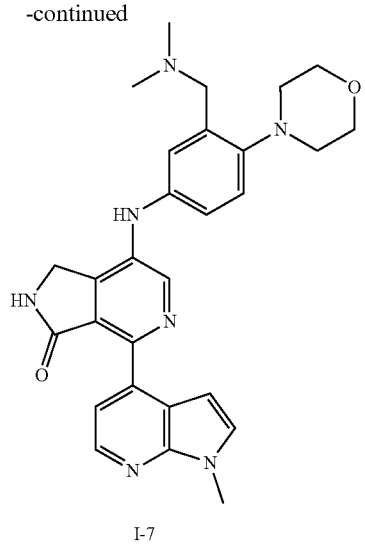

Step-1. tert-butyl 7-chloro-4-(1-methyl-1H-pyrrolo[2,3-b]pyridin-4-yl)-3-oxo-1,3-dihydro-2H-pyrrolo[3,4-c]pyridine-2-carboxylate (6.1)

A solution of tert-butyl 4-bromo-7-chloro-3-oxo-1,3-dihydro-2H-pyrrolo[3,4-c]pyridine-2-carboxylate (6.0) (0.5 g, 1.44 mmol, 1.0 eq), 1-methyl-4-(4,4,5,5-tetramethyl-1,3,2-dioxaborolan-2-yl)-1H-pyrrolo[2,3-b]pyridine (PB3) (0.370 g, 1.44 mmol, 1.0 eq), potassium phosphate tribasic (0.91 g, 4.32 mmol, 3.0 eq) in 1,4-Dioxane:water (8 ml:2 ml) was degassed and purged with $N_2$ for 15 min. [1,1'-Bis(diphenylphosphino)ferrocene]dichloropalladium(II) (0.011 g, 0.14 mmol, 0.1 eq) was added and stirred at 110° C. for 20 min in microwave. After completion, the reaction mixture was cooled to RT, diluted with water (60 ml), extracted with ethyl acetate (3×30 ml), and the combined organic extracts were washed with brine (30 ml), then dried over $Na_2SO_4$, filtered, and concentrated under reduced pressure. The crude residue was purified by column chromatography by 2.0% gradient elution methanol in dichloromethane to afford pure (6.1) (0.425 g, 74.8%), MS(ES): m/z 399[M+H]$^+$ Step-2. tert-butyl 7-((3-((dimethylamino)methyl)-4-morpholinophenyl)amino)-4-(1-methyl-1H-pyrrolo[2,3-b]pyridin-4-yl)-3-oxo-1,3-dihydro-2H-pyrrolo[3,4-c]pyridine-2-carboxylate (6.2)

A solution of tert-butyl 7-chloro-4-(1-methyl-1H-pyrrolo[2,3-b]pyridin-4-yl)-3-oxo-1,3-dihydro-2H-pyrrolo[3,4-c]pyridine-2-carboxylate (6.1) (0.25 g, 0.628 mmol, 1.0 eq), 3-((dimethylamino)methyl)-4-morpholinoaniline (0.150 g, 0.628 mmol, 1.0 eq), $K_2CO_3$ (0.26 g, 1.88 mmol, 3.0 eq) in 1,4-Dioxane (5 ml) was degassed under $N_2$ stream. After 15 min Xantphos (0.072 g, 0.125 mmol, 0.2 eq) and Tris(dibenzylideneacetone)dipalladium(0) (0.06 g, 0.062 mmol, 0.1 eq) were added and the reaction was heated to 110° C. and stirred for 1 h. After completion, the reaction mixture was cooled to RT, then diluted water (50 ml) and with ethyl acetate (3×20 ml) and the combined organic extracts were washed with brine (50 ml), then dried over $Na_2SO_4$, filtered, and concentrated under reduced pressure. The crude residue was purified by column chromatography by 50% gradient elution ethyl acetate in hexane to afford (6.2) (0.2 g, 53.38%) as a brown solid. MS(ES): m/z=598 [M+H]$^+$ Step-3. 7-((3-((dimethylamino)methyl)-4-mor-
pholinophenyl)amino)-4-(1-methyl-1H-pyrrolo[2,3-
b]pyridin-4-yl)-1,2-dihydro-3H-pyrrolo[3,4-c]pyri-
din-3-one (I-7)

To a solution of (6.2) (0.2 g, 0.33 mmol, 1.0 eq) in DCM (5 ml) was added dropwise 4M HCl in Dioxane (0.8 ml, 3.35 mmol, 3.0 eq) at 0° C. The reaction mixture was stirred at RT for 30 min. After completion, the reaction mixture was basified using saturated sodium bicarbonate solution, then extracted with 10% methanol in dichloromethane (3×20 ml). The combined organic layer was concentrated under reduced pressure to obtain crude which was purified by preparative HPLC using column: SUNFIRE C18 (250*19) mm 5 u, mobile phase: 0.1% Formic acid (FA) in water/acetonitrile as buffer, flow 16 ml/min, gradient 0-38 min and the obtained fraction was lyophilized to afford the format salt of I-7. The salt was dissolved into methanol (3 ml) and neutralized with tetralkyl ammonium carbonate polymer-bound (basic resin) to isolate the free base of to provide I-7 (0.04 g, 24.02%) as a solid. MS(ES): m/z=498 [M+H]+ 1H NMR (400 MHz, DMSO-d6) δ 9.285 (s, 1H), 8.940 (s, 1H), 8.519 (s, 1H), 8.329 (d, J=4.8 Hz, 1H), 7.957-7.905 (dd, J=2.0, 8.8, 1H), 7.613 (d, J=7.6 Hz, 1H), 7.572 (d, J=2.8 Hz, 1H), 7.276 (d, J=4.8 Hz, 1H), 7.136 (d, J=8.8 1H), 6.537 (d, J=3.6, 1H), 4.536 (s, 2H), 3.873 (s, 3H), 3.741 (s, 4H), 3.470 (s, 2H). 2.889 (d, J=4.0 2H), 2.216 (s, 6H).

Example 7. Method GP

Preparation of (S)-4-((5-(((dimethylamino)methyl)-6-
(tetrahydrofuran-3-yl)pyridin-3-yl)amino)-7-(7-flu-
oroimidazo[1,2-a]pyridin-3-yl)-1,2-dihydro-3H-pyr-
rolo[3,4-c]pyridin-3-one (I-29) and (R)—4-((5-
((dimethylamino)methyl)-6-(tetrahydrofuran-3-yl)
pyridin-3-yl)amino)-7-(7-fluoroimidazo[1,2-a]
pyridin-3-yl)-1,2-dihydro-3H-pyrrolo[3,4-c]pyridin-
3-one (I-30)

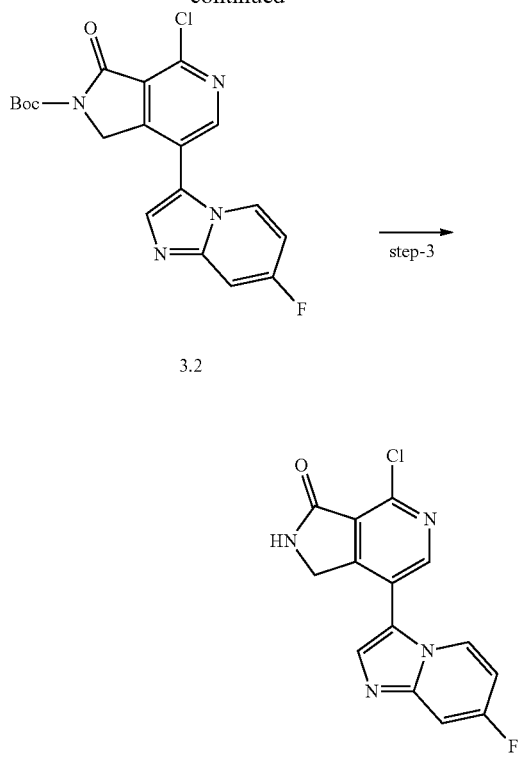

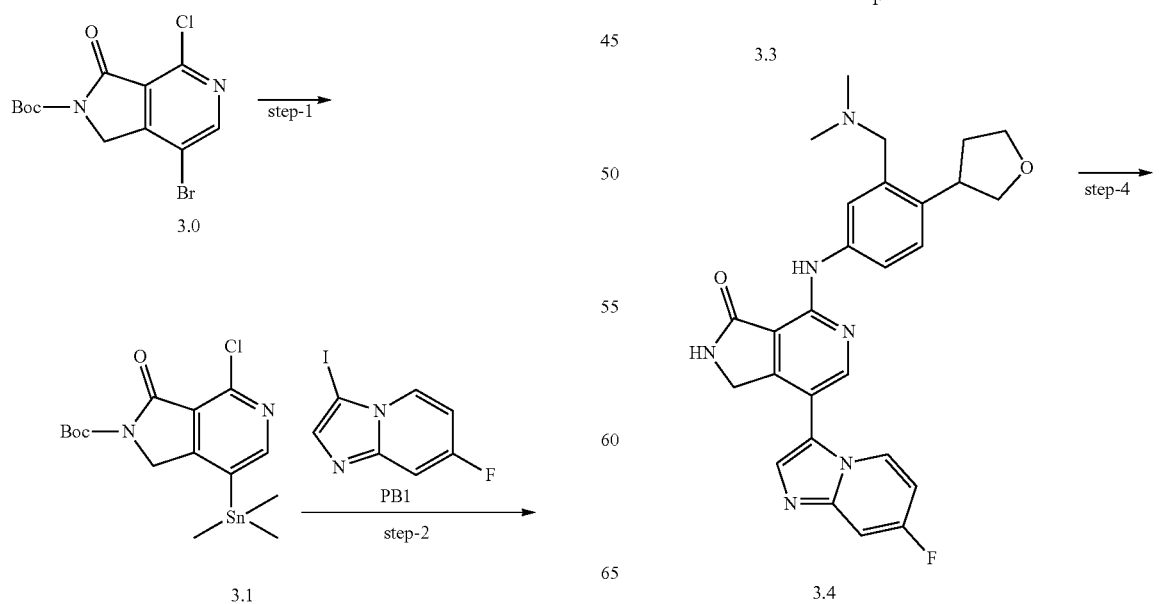

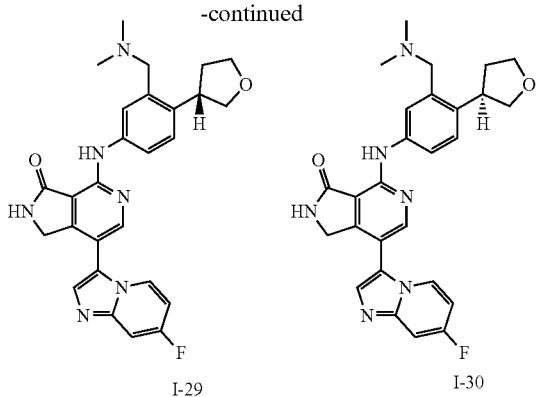

I-29　　　　　　　　　　I-30

Step-1. tert-butyl 4-chloro-3-oxo-7-(trimethylstannyl)-1,3-dihydro-2H-pyrrolo[3,4-c]pyridine-2-carboxylate (7.1)

To a solution of tert-butyl 7-bromo-4-chloro-3-oxo-1,3-dihydro-2H-pyrrolo[3,4-c]pyridine-2-carboxylate (7.0) (0.500 g, 1.44 mmol, 1.0 eq) in toluene (8 ml) was added hexamethylditin (0.712 g, 2.17 mmol, 1.5 eq). After degassing under $N_2$ for 15 min, Bis(triphenylphosphine)palladium (II) dichloride (0.051 g, 0.072 mmol, 0.05 eq) was added. After stirring at 115° C. for 2 h, the reaction was completed. The reaction mixture was cooled to RT and diluted with ethyl acetate (100 ml) and water (50 ml). The organic layer was collected, and the aqueous phase was extracted with ethyl acetate (2×30 ml). The combined organic extracts were washed with brine (20 ml), dried over $Na_2SO_4$, filtered, and concentrated under reduced pressure. The residue was purified by column chromatography eluting with 9% ethyl acetate gradient in hexane to afford (7.1) (0.300 g, 48.3%). MS(ES): m/z=431.5 [M+2]+

Step-2. tert-butyl 4-chloro-7-(7-fluoroimidazo[1,2-a]pyridin-3-yl)-3-oxo-1,3-dihydro-2H-pyrrolo[3,4-c]pyridine-2-carboxylate (7.2)

To a solution of tert-butyl 4-chloro-3-oxo-7-(trimethylstannyl)-1,3-dihydro-2H-pyrrolo[3,4-c]pyridine-2-carboxylate (7.1) (0.500 g, 1.15 mmol, 1.0 eq) in DMF (8 ml) was added 7-fluoro-3-iodoimidazo[1,2-a]pyridine (PB1) (0.303 g, 1.15 mmol, 1.0 eq). After degassing with $N_2$ for 15 min, Tetrakis(triphenylphosphine)palladium(0) (0.066 g, 0.05 mmol, 0.05 eq) and CuI (0.022 g, 0.115 mmol, 0.1 eq) were added. After stirring at 105° C. for 1.5 h, the reaction was completed and then the reaction mixture was cooled to RT and diluted with ethyl acetate (20 ml) and water (15 ml). The organic layer was collected, and the aqueous phase was extracted with ethyl acetate (2×30 ml). The combined organic extracts were washed with brine (10 ml), dried over $Na_2SO_4$, filtered, and concentrated under reduced pressure. The residue was purified by column chromatography eluting with 50% ethyl acetate gradient in hexane to afford (7.2) (0.380 g, 81.4%), MS (ES): m/z 402.8[M+H]+

Step-3. 4-chloro-7-(7-fluoroimidazo[1,2-a]pyridin-3-yl)-1,2-dihydro-3H-pyrrolo[3,4-c]pyridin-3-one (7.3)

To a solution of tert-butyl 4-chloro-7-(7-fluoroimidazo[1,2-a]pyridin-3-yl)-3-oxo-1,3-dihydro-2H-pyrrolo[3,4-c]pyridine-2-carboxylate (7.2) (0.920 g, 2.2 mmol, 1.0 eq) into DCM (15 ml) at 0° C. was added HCl in dioxane (5 ml). The reaction mixture was stirred at RT for 1 h and after the completion of reaction, the reaction mixture was neutralized using saturated sodium bicarbonate solution, and extracted with DCM to afford title compound 7.3 (0.600 g, 84.05%). The compound was further used in the next step without any purification. MS (ES): m/z 302.6 (M+H).

Step-4. 7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (7.4)

To a solution of 4-chloro-7-(7-fluoroimidazo[1,2-a]pyridin-3-yl)-1,2-dihydro-3H-pyrrolo[3,4-c]pyridin-3-one (7.3) (0.100 g, 0.33 mmol, 1.0 eq) in DMF (3 ml) were added 5-((dimethylamino)methyl)-6-(tetrahydrofuran-3-yl)pyridin-3-amine (0.073 g, 0.33 mmol, 1.0 eq) and $K_3PO_4$ (0.210 g, 0.99 mmol, 3.0 eq). After degassing under $N_2$ for 15 min, [(2-Di-cyclohexylphosphino-3,6-dimethoxy-2',4',6'-triisopropyl-1,1'-biphenyl)-2-(2'-amino-1,1'-biphenyl)]palladium (II) methanesulfonate (0.030 g, 0.03 mmol, 0.1 eq) was added. After stirring at 80° C. for 1.5 h, the reaction was completed and then the reaction mixture was cooled to RT and diluted with ethyl acetate (100 ml) and water (50 ml). The organic layer was collected, and the aqueous phase was extracted with ethyl acetate (2×30 ml). The combined organic extracts were washed with brine (20 ml), dried over $Na_2SO_4$, filtered, and concentrated under reduced pressure. The residue was purified by column chromatography and the pure compound was eluted with 3% Methanol in DCM to afford title compound (7.4) (0.060 g, 36.2%), MS(ES): m/z 488.5[M+H]

Step-5. (S)-4-((5-((dimethylamino)methyl)-6-(tetrahydrofuran-3-yl)pyridin-3-yl)amino)-7-(7-fluoroimidazo[1,2-a]pyridin-3-yl)-1,2-dihydro-3H-pyrrolo[3,4-c]pyridin-3-one (I-29) and (R)—4-((5-((dimethylamino)methyl)-6-(tetrahydrofuran-3-yl)pyridin-3-yl)amino)-7-(7-fluoroimidazo[1,2-a]pyridin-3-yl)-1,2-dihydro-3H-pyrrolo[3,4-c]pyridin-3-one (I-30)

60 mg racemic mixture of 7-(7-fluoroimidazo[1,2-a]pyridin-3-yl)-4-((4-(3-(2-hydroxypropan-2-yl)piperidin-1-yl)phenyl)amino)-1,2-dihydro-3H-pyrrolo[3,4-c]pyridin-3-one (7.4) was separated on Shimadzu LC-20AP and UV detector with CHIRALPAK IC (250*21.0) mm, 5 micron, column flow was 20.0 ml/min. Mobile phase were used (A) 0.1% DEA in Methanol. (B) 0.1% DEA in Methanol to afford I-29 (25 mg) and I-30 (24 mg). The stereochemistry was arbitrarily assigned. I-29 MS(ES): m/z 488.5 [M+H]. 1H NMR (400 MHz, DMSO-d6) δ 8.93 (d, J=2.6 Hz, 1H), 8.51 (d, J=13.1 Hz, 4H), 8.07 (d, J=2.7 Hz, 1H), 7.82 (s, 1H), 7.52 (d, J=9.4 Hz, 1H), 6.99 (dt, J=7.5, 4.2 Hz, 1H), 4.42 (s, 2H), 4.05 (t, J=7.7 Hz, 1H), 3.93 (q, J=7.7 Hz, 1H), 3.84 (p, J=7.4 Hz, 2H), 3.66 (t, J=7.7 Hz, 1H), 2.18 (s, 6H), 1.09 (t, J=7.0 Hz, 1H). I-30: MS(ES): m/z 488.5 [M+H]. 1H NMR (400 MHz, DMSO-d6) δ 8.93 (d, J=2.6 Hz, 1H), 8.51 (d, J=13.1 Hz, 4H), 8.07 (d, J=2.7 Hz, 1H), 7.82 (s, 1H), 7.52 (d, J=9.4 Hz, 1H), 6.99 (dt, J=7.5, 4.2 Hz, 1H), 4.42 (s, 2H), 4.05 (t, J=7.7 Hz, 1H), 3.93 (q, J=7.7 Hz, 1H), 3.84 (p, J=7.4 Hz, 2H), 3.66 (t, J=7.7 Hz, 1H), 2.18 (s, 6H), 1.09 (t, J=7.0 Hz, 1H).

Example 8. Additional Compounds

The following compounds in Table 3 were made according to the Methods AP-GP above, using the intermediates described above.

TABLE 3

| | STRUCTURE | NAME | LCMS | HNMR | Method SM |
|---|---|---|---|---|---|
| I-8 | 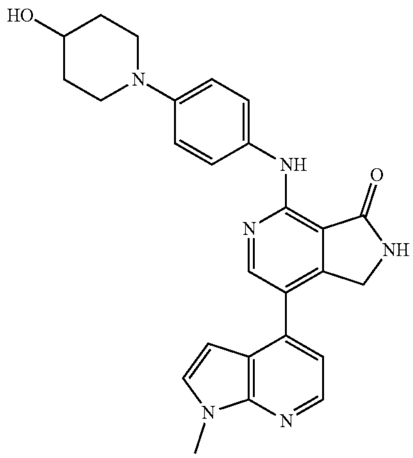 [SMILES: Cn1ccc2c(-c3cnc(Nc4ccc(N5CCC(O)CC5)cc4)c4c3CNC4=O)ccnc21] | 4-((4-(4-hydroxypiperidin-1-yl)phenyl)amino)-7-(1-methyl-1H-pyrrolo[2,3-b]pyridin-4-yl)-1,2-dihydro-3H-pyrrolo[3,4-c]pyridin-3-one | m/z = 455.35 [M + H]+ | 1H NMR (400 M Hz, DMSO-d6) δ 9.145 (s, 1H), 8.885 (s, 1H), 8.497 (s, 1H), 8.317 (d, J = 4.4 Hz, 1H), 7.642 (d, J = 8 8 Hz, 2H), 7.60 (d, J = 3.2 Hz, 1H), 7.632 (d, J = 3.2 Hz 1H), 7.253 (d, J = 4.8 Hz, 1H), 6.953 (d, J = 8.4 Hz 2H), 6.536 (d, J = 3.2 Hz, 1H), 4.692 (s, 1H), 4.523 (s, 2H), 3.865 (s, 3H), 3.603 (s, 1H), 3.454 (s, 1H), 3.350 (s, 2H), 2.809-2.759 (t, J = 6.4, 8.0 Hz 2H), 1.812 (s, 2H), 1.892 (d, J = 4.8, 2H). | AP 1-(4-aminophenyl)piperidin-4-ol PB3 |
| I-9 | 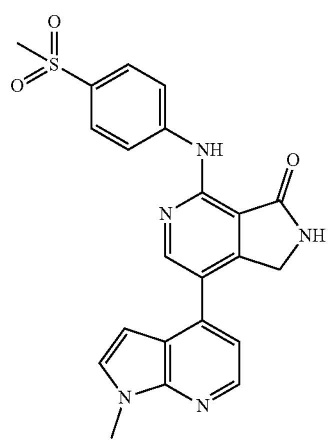 [SMILES: Cn1ccc2c(-c3cnc(Nc4ccc(S(C)(=O)=O)cc4)c4c3CNC4=O)ccnc21] | 7-(1-methyl-1H-pyrrolo[2,3-b]pyridin-4-yl)-4-((4-(methylsulfonyl)phenyl)amino)-1,2-dihydro-3H-pyrrolo[3,4-c]pyridin-3-one | m/z = 434.24 [M + H]+ | 1H NMR (400 MHz, DMSO-d6) δ 9.779 (s, 1H), 9.084 (s, 1H), 8.636 (s, 1H), 8.346 (d, J = 4.8 Hz, 1H), 8.129 (d, J = 8.8 Hz, 2H), 7.888 (d, J = 8.8 Hz, 2H), 7.624 (d, J = 0.8 Hz 1H), 7.305 (d, J = 4.8 Hz, 1H), 6.556 (d, J = 3.2 Hz 1H), 4.575 (s, 2H), 3.874 (s, 3H), 3.192 (s, 3H). | AP 4-(Methylsulfonyl)aniline PB3 |
| I-10 | 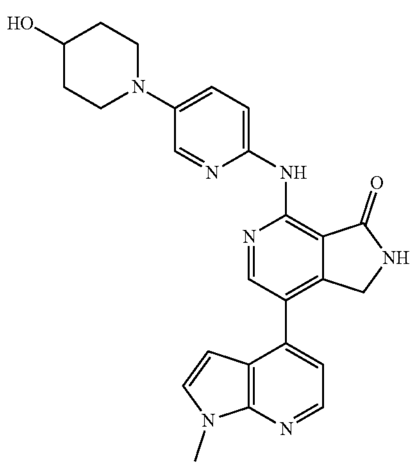 [SMILES: Cn1ccc2c(-c3cnc(Nc4ccc(N5CCC(O)CC5)cn4)c4c3CNC4=O)ccnc21] | 4-((5-(4-hydroxypiperidin-1-yl)pyridin-2-yl)amino) methyl-1H-pyrrolo[2,3-b]pyridin-4-yl)-1,2-dihydro-3H-pyrrolo[3,4-c]pyridin-3-one | m/z = 456.41 [M + H]+ | 1H NMR (400 MHz, DMSO-d6) δ 9.671 (s, 1H), 8.947 (s, 1H), 8.577 (s, 1H), 8.447 (d, J = 9.2 Hz, 1H), 8.330 (d, J = 4.8 Hz, 2H), 8.017 (s, 1H), 7.612 (s, 1H), 7.489 (d, J = 8.0 Hz, 1H), 7.282 (d, J = 4.8 Hz 1H), 6.552 (s, 1H), 4.723 (d, J = 2.0, 1H), 4.542 (s, 2H), 3.869 (s, 3H), 3.623 (s, 1H), 3.502 (s, 1H), 3.472 (s, 1H), 2.855-2.801 (t, J = 6.4, 8.0 Hz 2H), 1.826 (s, 2H), 1.501 (d, J = 4.8, 2H). | AP 1-(6-aminopyridin-3-yl)piperidin-4-ol PB3 |

TABLE 3-continued

| | STRUCTURE | NAME | LCMS | HNMR | Method SM |
|---|---|---|---|---|---|
| I-11 | 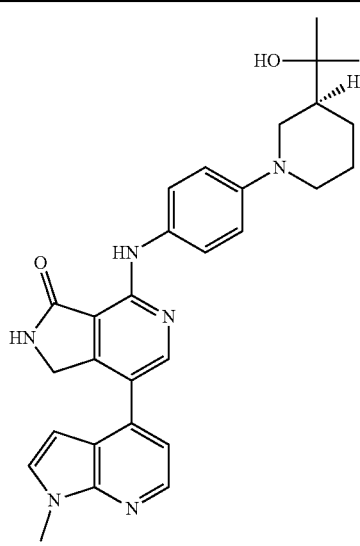 | (S)-4-((4-(3-(2-hydroxypropan-2-yl)piperidin-1-yl)phenyl)amino)-7-(1-methyl-1H-pyrrolo[2,3-b]pyridin-4-yl)-1,2-dihydro-3H-pyrrolo[3,4-c]pyridin-3-one | m/z = 497.54 [M + H]+ Chiral HPLC Method-X2 Ret. time = 4.89 min | 1H NMR (400 MHz, DMSO-d6) δ 9.145 (s, 1H), 8.868 (s, 1H), 8.506 (s, 1H), 8.333 (d, J = 4.8 Hz, 1H), 8.262 (s, 1H), 7.657 (d, J = 8.8 Hz, 2H), 7.608 (d, J = 3.2 Hz 1H), 7.272 (d, J = 4.8 Hz, 1H), 6.953 (d, J = 9.2 Hz 2H), 6.534 (d, J = 3.2 Hz, 1H), 4.535 (s, 1H), 4.263-4.229 (s, 1H), 3.933 (s, 3H), 3.835 (s, 1H), 3.706 (s, 1H), 3.629 (s, 1H), 2.440-2.381 (t, J = 6.4, 8.0 Hz 1H), 1.851 (d, J = 2.8, 1H), 1.754 (d, J = 2.8, 2H), 1.601-1.540 (t, J = 6.4, 8.0 Hz 2H), 1.104 (s, 3H), 1.056 (s, 3H). | PA1 AP PB3 |
| I-12 | 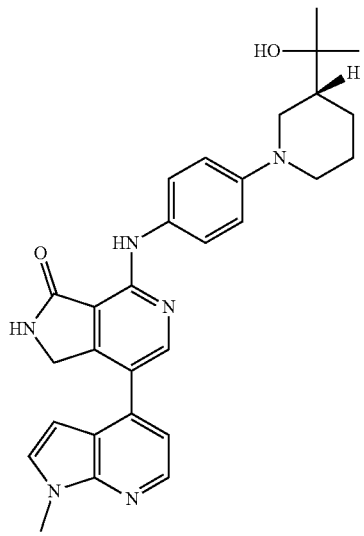 [SMILES: Cn1ccc2c(-c3cnc(Nc4ccc(N5CCC[C@@H](C(C)(C)O)C5)cc4)c4c3CNC4=O)ccnc21] | (R)-4-((4-(3-(2-hydroxypropan-2-yl)piperidin-1-yl)phenyl)amino)-7-(1-methyl-1H-pyrrolo[2,3-b]pyridin-4-yl)-1,2-dihydro-3H-pyrrolo[3,4-c]pyridin-3-one | m/z = 497.54 [M + H]+ Chiral HPLC Method-X2 Ret. time = 5.74 min | 1H NMR (400 MHz, DMSO-d6) δ 9.145 (s, 1H), 8.868 (s, 1H), 8.506 (s, 1H), 8.333 (d, J = 4.8 Hz, 1H), 8.262 (s, 1H), 7.657 (d, J = 8.8 Hz, 2H), 7.608 (d, J = 3.2 Hz 1H), 7.272 (d, J = 4.8 Hz, 1H), 6.953 (d, J = 9.2 Hz 2H), 6.534 (d, J = 3.2 Hz, 1H), 4.535 (s, 1H), 4.263-4.229 (s, 1H), 3.933 (s, 3H), 3.835 (s, 1H), 3.706 (s, 1H), 3.629 (s, 1H), 2.440-2.381 (t, J = 6.4, 8.0 Hz 1H), 1.851 (d, J = 2.8, 1H), 1.754 (d, J = 2.8, 2H), 1.601-1.540 (t, J = 6.4, 8.0 Hz 2H), 1.126 (s, 3H), 1.00 (s, 3H). | PA1 AP PB3 |
| I-13 | 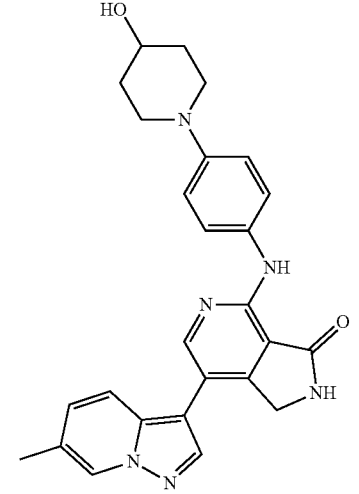 [SMILES: Cc1ccc2c(-c3cnc(Nc4ccc(N5CCC(O)CC5)cc4)c4c3CNC4=O)cnn2c1] | 4-((4-(4-hydroxypiperidin-1-yl)phenyl)amino)-7-(6-methylpyrazolo[1,5-a]pyridin-3-yl)-1,2-dihydro-3H-pyrrolo[3,4-c]pyridin-3-one | m/z = 455.2 [M + H]+ | 1H NMR (400 MHz, DMSO-d6) δ 9.00 (s, 1H), 8.87 (s, 1H), 8.60 (s, 1H), 8.46 (s, 1H), 8.25 (s, 1H), 7.82-7.80 (d, J = 9.2 Hz, 1H), 7.72-7.57 (m, 2H), 7.20-7.18 (d, J = 9.1 Hz, 1H), 7.03-6.90 (m, 2H), 4.70 (d, J = 4.2 Hz, 1H), 4.57 (s, 2H), 3.47 (d, J = 11.6 Hz, 3H), 2.87-2.75 (m, 2H), 2.34 (s, 3H), 1.95-1.75 (m, 2H), 1.61-1.45 (m, 2H). | AP 1-(4-aminophenyl)piperidin-4-ol PB2 |

TABLE 3-continued

| | STRUCTURE | NAME | LCMS | HNMR | Method SM |
|---|---|---|---|---|---|
| I-14 | 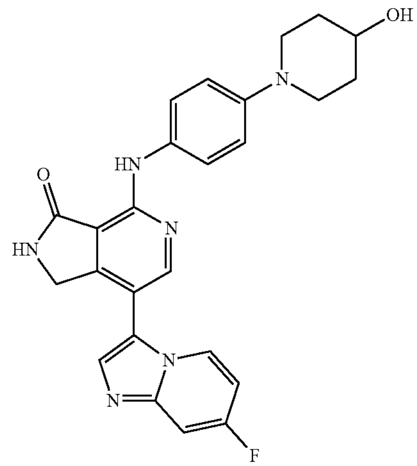 [SMILES: O=C1NCc2c(-c3cnc4cc(F)ccn34)cnc(Nc3ccc(N4CCC(O)CC4)cc3)c21] | 7-(7-fluoroimidazo[1,2-a]pyridin-3-yl)-4-((4-(4-hydroxypiperidin-1-yl)phenyl)amino)-1,2-dihydro-3H-pyrrolo[3,4-c]pyridin-3-one | m/z = 459.8 [M + H]+ | 1H NMR (400 MHz, DMSO-d6) δ 9.09 (s, 1H), 8.88 (s, 1H), 8.54-8.43 (m, 2H), 7.81 (s, 1H), 7.72-7.59 (m, 2H), 7.54 (dd, J = 10.0, 2.7 Hz, 1H), 7.05-6.90 (m, 3H), 4.71 (d, J = 4.2 Hz, 1H), 4.41 (s, 2H), 3.62 (dq, J = 9.0, 4.5 Hz, 2H), 2.80 (ddd, J = 12.8, 10.3, 2.9 Hz, 2H), 1.84 (dd, J = 11.5, 5.1 Hz, 2H), 1.51 (dtd, J = 13.2, 9.5, 3.5 Hz, 2H), 1.25 (s, 1H). | CP 1-(4-aminophenyl)piperidin-4-ol PB1 |
| I-15 | 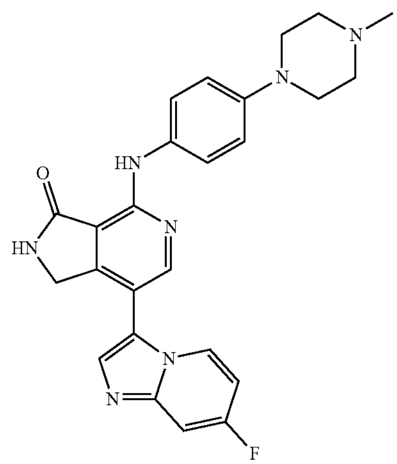 [SMILES: CN1CCN(c2ccc(Nc3ncc(-c4cnc5cc(F)ccn45)c4c3C(=O)NC4)cc2)CC1] | 7-(7-fluoroimidazo[1,2-a]pyridin-3-yl)-4-((4-(4-methylpiperazin-1-yl)phenyl)amino)-1,2-dihydro-3H-pyrrolo[3,4-c]pyridin-3-one | m/z = 458.2 [M + H]+ | 1H NMR (400 MHz, DMSO-d6) δ 9.13 (s, 1H), 8.89 (s, 1H), 8.52-8.50 (m, 1H), 8.47 (s, 1H), 7.81 (s, 1H), 7.71-7.68 (m, 2H), 7.56-7.54 (dd, J = 10.1, 2.6 Hz, 1H), 7.00-6.98 (m, 3H), 4.41 (s, 2H), 3.20 (bs, 4H), 2.77 (bs, 4H), 2.45 (s, 3H). | CP 4-(4-methylpiperazin-1-yl)aniline PB1 |
| I-16 | 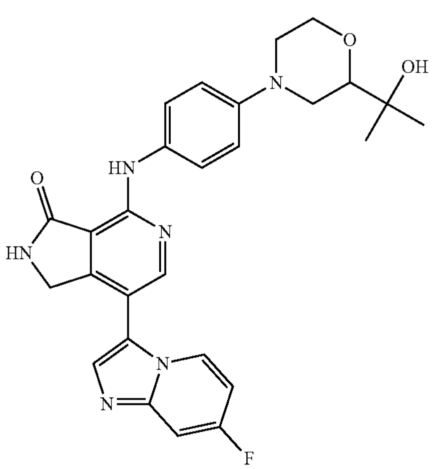 [SMILES: CC(C)(O)C1CN(c2ccc(Nc3ncc(-c4cnc5cc(F)ccn45)c4c3C(=O)NC4)cc2)CCO1] | 7-(7-fluoroimidazo[1,2-a]pyridin-3-yl)-4-((4-(2-(2-hydroxypropan-2-yl)morpholino)phenyl)amino)-1,2-dihydro-3H-pyrrolo[3,4-c]pyridin-3-one | m/z = 503.8 [M + H]+ | 1H NMR (400 MHz, DMSO-d6) δ 9.13 (s, 1H), 8.89 (s, 1H), 8.51 (dd, J = 7.6, 5.7 Hz, 1H), 8.48 (s, 1H), 7.82 (s, 1H), 7.76-7.67 (m, 2H), 7.55 (dd, J = 10.0, 2.6 Hz, 1H), 6.99 (dd, J = 7.9, 4.8 Hz, 3H), 4.51 (s, 1H), 4.41 (s, 2H), 4.02-3.99 (dd, J = 10.6, 3.4 Hz, 1H), 3.65 (td, J = 11.5, 2.5 Hz, 2H), 3.47 (d, J = 11.8 Hz, 1H), 3.31 (dd, J = 10.7, 2.4 Hz, 2H), 2.67-2.60 (m, 1H), 1.18 (s, 3H), 1.12 (s, 3H), | AP PA2 PB1 |

TABLE 3-continued

| | STRUCTURE | NAME | LCMS | HNMR | Method SM |
|---|---|---|---|---|---|
| I-17 | 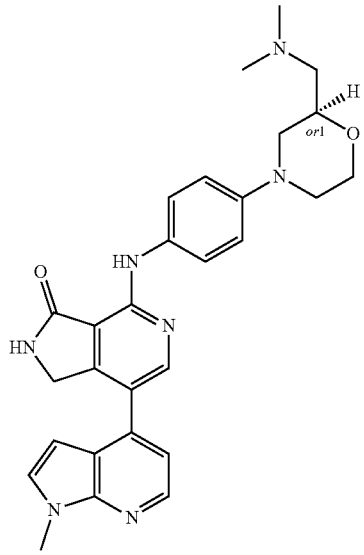 [SMILES: CN(C)C[C@@H]1CN(c2ccc(Nc3ncc(-c4ccnc5c4ccn5C)c4c3C(=O)NC4)cc2)CCO1] | rel-(R)-4-((4-(2-((dimethylamino)methyl)morpholino)phenxl)amino)-7-(1-methyl-1H-pyrrolo[2,3-b]pyridin-4-yl)-1,2-dihydro-3H-pyrrolo[3,4-c]pyridin-3-one | m/z = 498.2 [M + H]+ Chiral HPLC method X3: Ret.time = 9.72 | 1H NMR (400 MHz, DMSO-d6) δ 9.19 (s, 1H), 8.90 (s, 1H), 8.52 (s, 1H), 8.33 (d, J = 4.8 Hz, 1H), 7.70 (d, J = 8.6 Hz, 2H), 7.61 (d, J = 3.5 Hz, 1H), 7.28 (d, J = 4.9 Hz, 1H), 6.98 (d, J = 8.6 Hz, 2H), 6.55 (d, J = 3.5 Hz, 1H), 4.54 (s, 2H), 3.94 (d, J = 11.6 Hz, 1H), 3.88 (s, 3H), 3.75-3.61 (m, 2H), 3.55 (d, J = 11.9 Hz, 1H), 3.46 (d, J = 11.6 Hz, 1H), 2.72-2.61 (m, 1H), 2.37 (td, J = 12.6, 11.0, 4.3 Hz, 1H), 2.21 (s, 6H), 1.24 (s, 2H). | AP PA3 PB3 |
| I-18 | 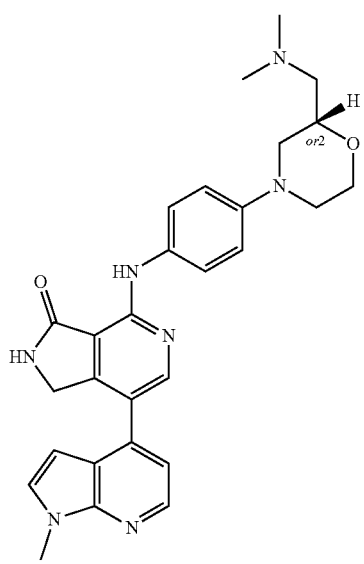 [SMILES: CN(C)C[C@H]1CN(c2ccc(Nc3ncc(-c4ccnc5c4ccn5C)c4c3C(=O)NC4)cc2)CCO1] | rel-(R)-4-((4-(2-((dimethylamino)methyl)morpholino)phenyl)amino)-7-(1-methyl-1H-pyrrolo[2,3-b]pyridin-4-yl)-1,2-dihydro-3H-pyrrolo[3,4-c]pyridin-3-one | m/z = 498.2 [M + H]+ Chiral HPLC method X3: Ret.time = 9.95 | 1H NMR (400 MHz, DMSO-d6) δ 9.19 (s, 1H), 8.90 (s, 1H), 8.52 (d, J = 1.3 Hz, 1H), 8.33 (d, J = 4.8 Hz, 1H), 7.70 (d, J = 8.5 Hz, 2H), 7.61 (d, J = 3.6 Hz, 1H), 7.28 (d, J = 5.0 Hz, 1H), 6.98 (d, J = 8.7 Hz, 2H), 6.61-6.48 (m, 1H), 4.54 (s, 2H), 3.94 (d, J = 11.6 Hz, 1H), 3.88 (s, 3H), 3.75-3.61 (m, 2H), 3.55 (d, J = 11.9 Hz, 1H), 3.46 (d, J = 11.6 Hz, 1H), 2.72-2.61 (m, 1H), 2.37 (td, J = 12.6, 11.0, 4.3 Hz, 1H), 2.21 (s, 6H), 1.24 (s, 2H). | AP PA3 PB3 |
| I-19 | 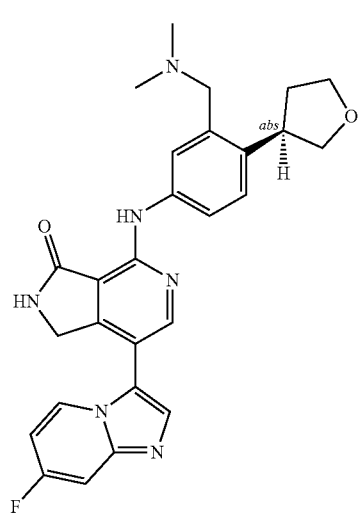 [SMILES: CN(C)Cc1cc(Nc2ncc(-c3cnc4cc(F)ccn34)c3c2C(=O)NC3)ccc1[C@H]1CCOC1] | (R)-((3-((dimethylamino)methyl)-4-(tetrahydrofuran-3-yl)phenyl)amino)-7-(7-fluoroimidazo[1,2-a]pyridin-3-yl)-1,2-dihydro-3H-pyrrolo[3,4-c]pyridin-3-one | m/z = 487.2 [M + H]+ Chiral HPLC method X4: Ret.time = 19.99 | 1H NMR (400 MHz, DMSO-d6) δ 9.28 (s, 1H), 8.95 (s, 1H), 8.52 (d, J = 2.7 Hz, 2H), 7.90 (dd, J = 8.5, 2.4 Hz, 1H), 7.82 (s, 1H), 7.60-7.47 (m, 2H), 7.32 (d, J = 8.5 Hz, 1H), 6.98 (td, J = 7.5, 2.7 Hz, 1H), 4.42 (s, 2H), 3.97 (ddd, J = 13.0, 9.2, 6.3 Hz, 2H), 3.78 (dq, J = 17.7, 7.6 Hz, 2H), 3.53 (t, J = 7.6 Hz, 1H), 3.46 (s, 1H), 2.18 (s, 6H), 1.91 (dd, J = 12.1, 7.7 Hz, 1H), 1.24 (s, 1H). | EP PA9 PB1 |

TABLE 3-continued

| | STRUCTURE | NAME | LCMS | HNMR | Method SM |
|---|---|---|---|---|---|
| I-20 | 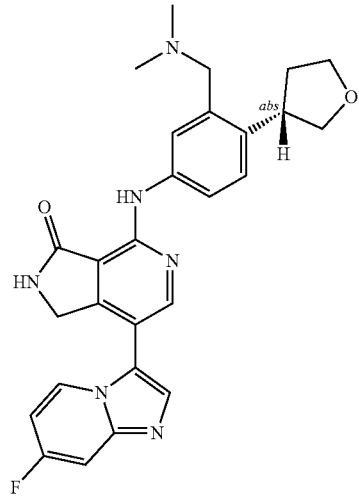 [SMILES: CN(C)Cc1cc(Nc2ncc(-c3cnc4cc(F)ccn34)c3c2C(=O)NC3)ccc1[C@@H]1CCOC1] | (S)-4-((3-((dimethylamino)methyl)-4-(tetrahydrofuran-3-yl)phenyl)amino)-7-(7-fluoroimidazo[1,2-a]pyridin-3-yl)-1,2-dihydro-3H-pyrrolo[3,4-c]pyridin-3-one | m/z = 487.1 [M + H]+ Chiral HPLC method X4: Ret.time = 19.99 | 1H NMR (400 MHz, DMSO-d6) δ 9.28 (s, 1H), 8.94 (s, 1H), 8.52 (d, J = 3.1 Hz, 2H), 7.90 (dd, J = 8.5, 2.4 Hz, 1H), 7.82 (s, 1H), 7.32 (d, J = 8.5 Hz, 1H), 6.98 (td, J = 7.5, 2.7 Hz, 1H), 4.42 (s, 2H), 4.05-3.94 (m, 2H), 3.86-3.76 (m, 2H), 3.54 (t, J = 7.6 Hz, 1H), 3.48 (d, J = 12.8 Hz, 1H), 3.39 (d, J = 2.4 Hz, 1H), 2.31-2.24 (m, 1H), 2.18 (s, 6H), 1.99-1.88 (m, 1H), 1.24 (s, 1H). | EP PA9 PB1 |
| I-21 | 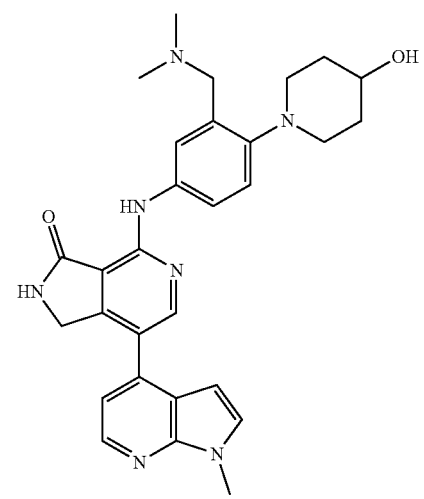 [SMILES: CN(C)Cc1cc(Nc2ncc(-c3ccnc4c3ccn4C)c3c2C(=O)NC3)ccc1N1CCC(O)CC1] | 4-((3-((dimethylamino)methyl)-4-(4-hydroxypiperidin-1-yl)phenyl)amino)-7-(1-methyl-1H-pyrrolo[2,3-b]pyridin-4-yl)-1,2-dihydro-3H-pyrrolo[3,4-c]pyridin-3-one | m/z = 512.2 [M + H]+ | 1H NMR (400 MHz, DMSO-d6) δ 9.273 (s, 1H), 8.930 (s, 1H), 8.522 (s, 1H), 8.325 (d, J = 4.8 Hz, 1H), 7.901-7.873 (dd, J = 2.0, 8.8, 1H), 7.613 (d, J = 7.6 Hz, 1H), 7.557 (d, J = 2.8 Hz, 1H), 7.280 (d, J = 4.8 Hz, 1H), 7.109 (d, J = 8.8 1H), 6.543 (d, J = 3.6. 1H), 4.668 (s, 1H), 4.540 (s, 2H), 3.881 (s, 3H), 3.617-3.596 (m, 1H), 3.453 (s, 2H), 3.031 (d, J = 1.2 2H), 2.684-2.635 (m, 2H), 2.220 (s, 6H), 1.857 (d, J = 2.0 2H), 1.607-1.559 (m, 2H). | FP PA5 PB3 |
| I-22 | 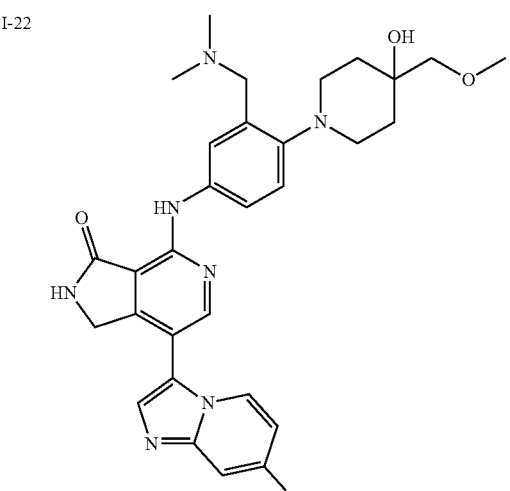 | 4-((3-((dimethylamino)methyl)-4-(4-hydroxy-4-(methoxymethyl)piperidin-1-yl)phenyl)amino)-7-(7-fluoroimidazo[1,2-a]pyridin-3-yl)-1,2-dihydro-3H-pyrrolo[3,4-c]pyridin-3-one | m/z = 560.2 [M + H]+ | 1H NMR (400 MHz, DMSO-d6) δ 9.213 (s, 1H), 8.929 (s, 1H), 8.524-8.590 (m, 2H), 7.887-7.851 (dd, J = 2.0, 8.8, 1H), 7.815 (s, 1H), 7.577-7.527 (m, 2H), 7.117 (d, J = 4.8 Hz, 1H), 7.000-6.957 (m, 1H), 4.409 (s, 2H), 4.350 (s, 1H) 3.439 (s, 2H), 3.315 (s, 3H), 3.208 (s, 2H), 2.954-2.902 (m, 2H) 2.801 (d, J = 10.8 2H), 2.205 (s, 6H), 1.775-1.724 (m, 2H), 1.524-1.493 (m, 2H). | DP PA7 PB1 |

TABLE 3-continued

| | STRUCTURE | NAME | LCMS | HNMR | Method SM |
|---|---|---|---|---|---|
| I-23 | 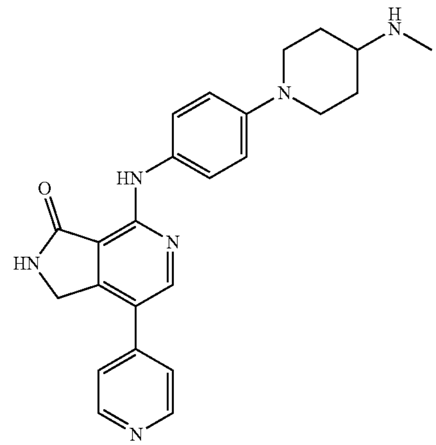 [SMILES: CNC1CCN(c2ccc(Nc3ncc(-c4ccncc4)c4c3C(=O)NC4)cc2)CC1] | 4-((4-(4-(methylamino)piperidin-1-yl)phenyl)amino)-7-(pyridin-4-yl)-1,2-dihydro-3H-pyrrolo[3,4-c]pyridin-3-one | m/z = 415.1 [M + H]+ | 1H NMR (400 MHz, DMSO-d6) δ 9.210 (s, 1H), 8.964 (s, 1H), 8.639 (d, J = 6.0, 2H), 8.557 (s, 1H), 8.312 (s, 1H), 7.764-7.332 (m, 3H), 5.971 (d, J = 8.8 Hz, 2H), 4.717 (s, 2H), 3.631 (d, J = 2.8, 3H), 2.514-2.337 (m, 4H), 1.948 (d, J = 9.6 2H), 1.437 (d, J = 11.2 3H), 1.243 (s, 1H). | DP PA8 pyridin-4-ylboronic acid |
| I-24 | 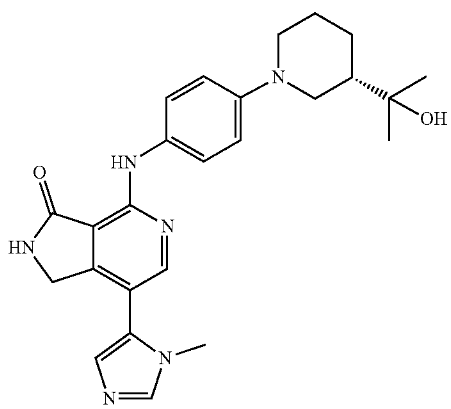 [SMILES: Cn1cncc1-c1cnc(Nc2ccc(N3CCC[C@H](C(C)(C)O)C3)cc2)c2c1CNC2=O] | (S)-4-((4-(3-(2-hydroxypropan-2-yl(piperidin-1-yl)phenyl)amino)-7-(1-methyl-1H-imidazol-5-yl)-1,2-dihydro-3H-pyrrolo[3,4-c]pyridin-3-one | m/z = 447.0 [M + H]+ Chiral HPLC method X5: Ret. time = 6.71 | 1H NMR (400 MHz, DMSO-d6) δ 9.020 (s, 1H), 8.861 (s, 1H), 8.315 (s, 1H), 7.759 (s, 1H), 7.625 (d, J = 5.2 2H), 7.149 (s, 1H), 6.934 (d, J = 8.8 Hz, 2H), 4.430 (s, 2H), 4.274 (s, 1H) 3.774 (d, J = 8.8 1H), 3.645 (s, 4H), 2.422-2.344 (m, 3H), 1.856- 1.823 (m, 1H), 1.764-1.731 (m, 1H), 1.589-1.530 (m, 3H), 1.175-1.143 (m, 6H). | DP PA9 (1-methyl-1H-imidazol-5-yl)boronic acid |
| I-25 | 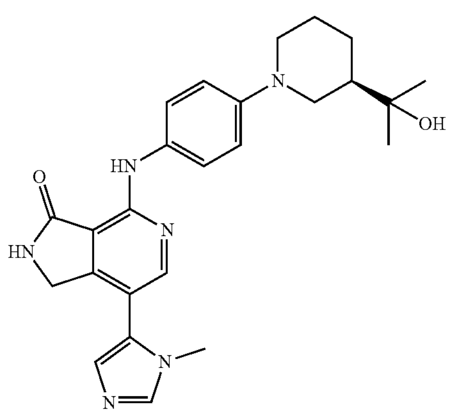 [SMILES: Cn1cncc1-c1cnc(Nc2ccc(N3CCC[C@@H](C(C)(C)O)C3)cc2)c2c1CNC2=O] | (R)-4-((4-(3-(2-hydroxypropan-2-yl)piperidin-1-yl)phenyl)amino)-7-(1-methyl-1H-imidazol-5-yl)-1,2-dihydro-3H-pyrrolo(3,4-c]pyridin-3-one | m/z = 447.2 [M + H]+ Chiral HPLC method X5: Ret. time = 6.68 min | 1H NMR (400 MHz, DMSO-d6) δ 9.020 (s, 1H), 8.860 (s, 1H), 8.314 (s, 1H), 7.757 (s, 1H), 7.645 (d, J = 5.2 2H), 7.147 (s, 1H), 6.932 (d, J = 8.8 Hz, 2H), 4.429 (s, 2H), 4.274 (s, 1H), 3.773 (d, J = 8.8 1H), 3.640 (s, 4H), 1.856-1.823 (m, 1H), 2.422-2.344 (m, 2H), 1.857-1.827 (m, 1H), 1.764-1.731 (m, 1H), 1.589-1.530 (m, 3H), 1.175-1.143 (m, 6H). | DP PA9 (1-methyl-1H-imidazol-5-yl)boronic acid |

TABLE 3-continued

| | STRUCTURE | NAME | LCMS | HNMR | Method SM |
|---|---|---|---|---|---|
| I-26 | 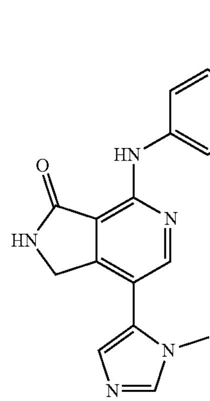 | 7-(1-methyl-1H-imidazol-5-yl)-4-((4-(piperazin-1-yl)phenyl)amino)-1,2-dihydro-3H-pyrrolo[3,4-c]pyridin-3-one | m/z = 390.2 [M + H]+ | 1H NMR (400 MHz, DMSO-d6) δ 9.029 (s, 1H), 8.840 (s, 1H), 8.308 (s, 1H), 7.744 (s, 1H), 7.633 (d, J = 7.6 2H), 7.135 (s, 1H), 6.930 (d, J = 8.0 Hz, 2H), 4.418 (s, 2H), 3.634 (s, 3H) 3.011 (s, 4H), 2.865 (s, 4H), 1.239 (s, 1H). | DP PA10 (1-methyl-1H-imidazol-5-yl)boronic acid |
| I-27 | 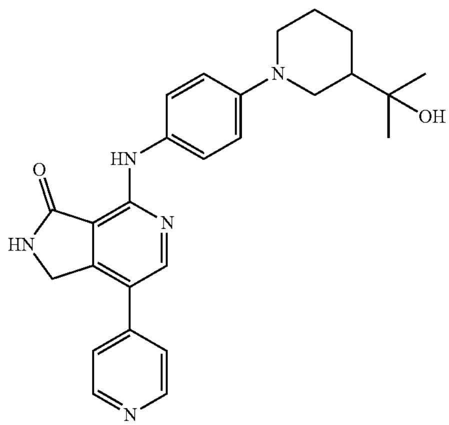 [SMILES: CC(C)(O)C1CCCN(c2ccc(Nc3ncc(-c4ccncc4)c4c3C(=O)NC4)cc2)C1] | 4-((4-(2-(2-hydroxypropan-2-yl)morpholino)phenyl)amino)-7-(pyridin-4-yl)-1,2-dihydro-3H-pyrrolo[3,4-c]pyridin-3-one | m/z = 446.63 [M + H]+ | 1H NMR (400 MHz, DMSO-d6) δ 9.232 (s, 1H), 8.973 (s, 1H), 8.643 (s, 1H), 8.629 (s, 1H), 8.562 (s, 1H), 7.688-7.652 (m, 3H), 6.971 (d, J = 8.8 Hz, 2H), 4.717 (s, 2H), 4.506 (s, 1H), 3.96 (d, J = 8.8, 1H) 3.667-3.613 (m, 2H), 3.460 (d, J = 11.6 1H), 3.338-3.287 (m, 1H), 2.614 (d, J = 3.2 1H), 1.237 (s, 1H), 1.174 (s, 3H), 1.110 (s, 3H). | DP PA2 pyridin-4-ylboronic acid |
| I-28 | 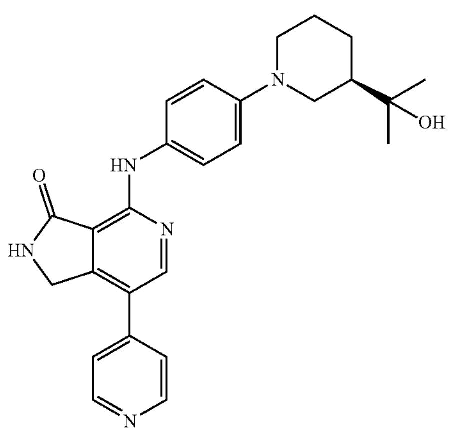 [SMILES: CC(C)(O)[C@@H]1CCCN(c2ccc(Nc3ncc(-c4ccncc4)c4c3C(=O)NC4)cc2)C1] | (R)-4-((4-(2-(2-hydroxypropan-2-yl)morpholino)phenyl)amino)-7-(pyridin-4-yl)-1,2-dihydro-3H-pyrrolo[3,4-c]pyridin-3-one | m/z =446.0 [M + H]+ Chiral HPLC method X1: Ret. time = 12.73 min | 1H NMR (400 MHz, DMSO-d6) δ 9.233 (s, 1H), 8.976 (s, 1H), 8.644 (s, 1H), 8.630 (s, 1H), 8.563 (s, 1H), 7.689-7.652 (m, 4H), 6.970 (d, J = 8.8 Hz, 2H), 4.717 (s, 2H), 4.506 (s, 1H), 3.96 (d, J = 8.8, 1H) 3.643-3.614 (m, 2H), 3.460 (d, J = 11.6 1H), 3.338-3.287 (m, 1H), 2.616 (d, J = 3.2 1H), 1.237 (s, 1H), 1.174 (s, 3H), 1.110 (s, 3H). | DP PA2 pyridin-4-ylboronic acid |

Preparative HPLC Conditions

Certain compounds were purified using reverse phase HPLC using a Waters Fractionlynx preparative HPLC system (2525 pump, 2996/2998 UV/VIS detector, 2767 liquid handler) or Gilson preparative HPLC system (322 pump, 155 UV/VIS detector, GX-281 liquid handler).

The column used for the preparative purification of the compounds was a Waters Sunfire OBD, Phenomenex Luna Phenyl Hexyl or Waters Xbridge Phenyl at 10 um 19×150 mm.

Appropriate focused gradients were selected based on acetonitrile and methanol solvent systems under either acidic or basic conditions. The standard gradient used was 5% ACN to 20% over 1 min, hold 2.5 min, to 80% ACN over 12.5 min, hold 7.5 min. This was followed by 3 min re-equilibration at initial conditions. A flow rate of 20 ml/min was used.

All compounds were screened analytically prior to the purification step. Each sample was run under both acidic and basic conditions (2 ul injection, 5/95 gradient for 2.25 minutes). A decision was then made by the analyst as to what pH and which gradient to use depending on where the desired product elutes and the separation achieved.

The modifiers used under acidic/basic conditions were formic acid (0.1% V/V) and ammonium bicarbonate (10 mM) respectively or TFA (0.1% V/V) if required.

The purification was controlled by Waters FractionLynx software through monitoring at 210-400 nm and triggered a threshold collection value at 260 nm and the presence of target molecular ion as observed under ESI conditions. Collected fractions were analysed by LCMS (Waters Acquity systems with Waters SQD). The fractions that contained the desired product were dried overnight by Genevac lypholisation, and further dried using BioPharma shelf freeze dryers.

Some of the compounds may have gone through a second purification process in order to achieve the required purity due to complex mixtures. More focused gradient or isocratic conditions may have been used for the second separations.

Preparative SFC Conditions

Certain compounds were purified using Supercritical Fluid Chromatography (SFC) using either Waters Thar Prep100 preparative SFC system (P200 CO2 pump, 2545 modifier pump, 2998 UV/VIS detector, 2767 liquid handler with Stacked Injection Module) or Waters Thar Investigator semi preparative system (Waters Fluid Delivery Module, 2998 UV/VIS detector, Waters Fraction Collection Module). Where the Waters 2767 liquid handler was used it acted as both auto-sampler and fraction collector.

Appropriate isocratic methods were selected based on methanol, ethanol or isopropanol solvent systems under un-modified or basic conditions. The standard method used was modifier/CO2, 100 ml/min (or as appropriate), 120 Bar backpressure, 40° C. column temperature were the specific modifier composition was as stated by the method development.

All compounds were screened analytically prior to the purification step. Each sample was run under both un-modified and basic conditions (2.0 ul injection, 5/55 gradient for 2.25 minutes) across ethanol, methanol and isopropanol. If necessary, secondary screen across extended solvents such as acetonitrile, ethyl acetate and THF may also be reviewed. A decision was then made by the analyst as to what pH and which isocratic condition to use depending on where the desired product elutes and the separation achieved.

The modifier used under basic conditions was diethyl amine (0.1% V/V). Alternate modifiers such as formic acid (0.1% V/V), acetic acid (0.1% V/V), etc may be used as an acidic modifier.

The purification was controlled either by Waters FractionLynx or Waters ChromScope software through monitoring at 210-400 nm and triggered a threshold collection value at an appropriate wavelength. Collected fractions were analysed by SFC (Waters/Thar SFC systems with Waters SQD or Waters UPCC with Waters QDa). The fractions that contained the desired product were concentrated by vacuum centrifugation and further dried using Biopharma shelf freeze dryers.

All samples were pre-purified by achiral systems and purity checked before SFC chiral purification.

Some of the compounds went through a second purification process in order to achieve the required % ee or % de purity.

CHIRAL HPLC Analytical Method X1

Chiral compound was analysed on Agilent 1260 Series HPLC and PDA detector. The column used: Chiralpak IB-N (250*4.6 mm), 5 micron, column flow was 1.0 ml/min. Mobile phase: (A) 0.1% DEA in n-Hexane and (B) 0.1% DEA in Proapne 2-ol:Acetonitrile (70:30). The UV spectra were recorded at 306 nm Lambdamax. Gradient ratio was as described in Table 4 below.

TABLE 4

| Time (min) | % A | % B |
|---|---|---|
| 0.01 | 80 | 20 |
| 5.00 | 45 | 55 |
| 10.00 | 30 | 70 |
| 20.00 | 30 | 70 |
| 20.01 | 80 | 20 |
| 25.00 | 80 | 20 |

CHIRAL SFC Analytical Method X2

Chiral compound was analysed on Waters SFC Investigator and PDA detector. The column used: Chiralcel OJ-H (250*4.6 mm), 5 micron, column flow was 4.0 ml/min and ABPR was 100 bar. Mobile phase: (A) Liquid Carbon dioxide (Liq. CO2) and (B) 0.1% DEA in Methanol. The UV spectra were recorded at 298 nm Lambdamax. Gradient ratio was as described in Table 5 below.

TABLE 5

| % B Start | % B End | Time duration |
|---|---|---|
| 5 | 50 | 8 |
| 50 | 50 | 8 |

CHIRAL HPLC Analytical Method X3

Chiral compound was analysed on Agilent 1260 Series HPLC and PDA detector. The column used: Chiralpak IH (250*4.6 mm), 5 micron, column flow was 1.0 ml/min. Mobile phase: (A) 0.1% DEA in n-Hexane and (B) 0.1% DEA in Propan-2-ol:Acetonitrile (70:30). The UV spectra were recorded at 308 nm Lambdamax. Isocratic ratio was as described in Table 6 below.

TABLE 6

| Time (min) | % A | % B |
|---|---|---|
| 0.01 | 65 | 35 |
| 20.0 | 65 | 35 |

CHIRAL HPLC Analytical Method X4

Chiral compound was analysed on Agilent 1100 Series HPLC and PDA detector. The column used: Chiralpak IC (250*4.6) mm, 5 micron, column flow was 1.0 ml/min. Mobile phase: (A) 0.1% Diethylamine in Methanol and (B) 0.1% Diethylamine in Acetonitrile. The UV spectra were recorded at 315 nm Lambda max. Isocratic ratio was as described in Table 7 below.

TABLE 7

| Time (min) | % A | % B |
|---|---|---|
| 0.01 | 50 | 50 |
| 50.0 | 50 | 50 |

CHIRAL SFC Analytical Method X5

Chiral compound was analysed on Waters SFC Investigator and PDA detector. The column used Chiralcel IH (250*4.6 mm), 5 micron, column flow was 4.0 ml/min and ABPR was 100 bar. Mobile phase: (A) Liquid Carbon dioxide (Liq. CO2) and (B) 0.1% DEA in IPA:CAN (50:50). The UV spectra were recorded at 298 nm Lambdamax. Gradient ratio was as described in Table 8 below.

TABLE 8

| % B Start | % B End | Time duration |
|---|---|---|
| 5 | 50 | 0.01 |
| 50 | 50 | 10 |

Example 20. HPK1 Biochemical Enzyme Assay

HPK1 biochemical enzyme assay: HPK1 enzyme inhibition was measured using a microfluidic mobility shift assay. Reactions were performed in a 384-well plate, containing 1.5 nM HPK1 (Invitrogen), in assay buffer (Cana Biosciences; pH 7.4). Test compounds were titrated in ten point curves (top final assay concentration 3 µM), and preincubated with enzyme/substrate mix for 30 min prior to initiation of the reaction by addition of ATP (1 mM final concentration) and substrate (1 µM final concentration; Carma Biosciences) diluted in assay buffer supplemented by $MgCl_2$ (final assay concentration of 5 mM). Following 60 min incubation at RT, the reaction was terminated by addition of 60 µl/well termination buffer (Carma Biosciences) and signal determination using a Caliper EZ Reader (Perkin Elmer, UK).

Table 9 shows the activity of selected compounds of this invention in the HPK1 biochemical enzyme assay. Compounds having an activity designated as "A" provided an $IC_{50} \leq 100$ nM; compounds having an activity designated as "B" provided an $IC_{50} > 100$ nM.

TABLE 9

| Compound | HPK1 1000UM ATP caliper IC50 (nM) A ≤ 100 nM B > 100 nM |
|---|---|
| I-1 | B |
| I-3 | A |
| I-4 | B |
| I-5 | B |
| I-6 | A |
| I-7 | A |
| I-8 | A |
| I-9 | B |
| I-10 | B |
| I-11 | A |
| I-12 | A |
| I-13 | A |
| I-14 | B |
| I-15 | B |
| I-16 | A |
| I-17 | A |
| I-18 | A |
| I-19 | A |
| I-20 | B |
| I-21 | B |
| I-22 | B |
| I-23 | B |
| I-24 | A |
| I-25 | B |
| I-26 | B |
| I-27 | B |
| I-28 | B |

While we have described a number of embodiments of this invention, it is apparent that our examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I:

I or a pharmaceutically acceptable salt, stereoisomer, or tautomer thereof,
wherein:
  X is —NR—;
  $R^1$ is a 3- to 7-membered carbocyclyl, 3- to 7-membered heterocyclyl, 8- to 10-membered heterocyclyl, phenyl, or 5- or 6-membered heteroaryl;
    wherein the 3- to 7-membered carbocyclyl or 3- to 7-membered heterocyclyl is monocyclic and saturated or partially unsaturated;
    wherein the 8- to 10-membered heterocyclyl is bicyclic and saturated or partially unsaturated;
    wherein the 5- or 6-membered heteroaryl is monocyclic;
    wherein the 3- to 7-membered heterocyclyl contains 1 or 2 heteroatoms independently selected from the group consisting of N, O, and S;
    wherein the 8- to 10-membered heterocyclyl or 5- or 6-membered heteroaryl contains 1, 2, 3, or 4 heteroatoms independently selected from the group consisting of N, O, and S; and
    wherein the 3- to 7-membered carbocyclyl, 3- to 7-membered heterocyclyl, 8- to 10-membered heterocyclyl, phenyl, or 5- or 6-membered heteroaryl is substituted with q independently selected $R^C$ substituents;
  $R^2$ is a 3- to 7-membered carbocyclyl, 3- to 7-membered heterocyclyl, 6- to 11-membered cyclyl, phenyl, or 5- or 6-membered heteroaryl;
    wherein the 3- to 7-membered carbocyclyl or 3- to 7-membered heterocyclyl is monocyclic and saturated or partially unsaturated;
    wherein the 6- to 11-membered cyclyl is (a) bicyclic, (b) fused, bridged, or spirocyclic, and (c) saturated, partially unsaturated, or fully unsaturated;
    wherein the 5- or 6-membered heteroaryl is monocyclic;
    wherein the 3- to 7-membered heterocyclyl contains 1 or 2 heteroatoms independently selected from the group consisting of N, O, and S;
    wherein the 6- to 11-membered cyclyl contains 0, 1, 2, or 3 heteroatoms independently selected from the group consisting of N, O, and S;
    wherein the 5- or 6-membered heteroaryl contains 1, 2, 3, or 4 heteroatoms independently selected from the group consisting of N, O, and S; and wherein the 3- to 7-membered carbocyclyl, 3- to 7-membered heterocyclyl, 6- to 11-membered cyclyl, phenyl, or 5- or 6-membered heteroaryl is substituted with q independently selected $R^C$ substituents;

each $R^3$ is independently H or $C_{1-6}$ aliphatic, wherein the $C_{1-6}$ aliphatic is substituted with s independently selected $R^D$ substituents;

each $R^C$ is independently halogen, CN, $NO_2$, $C_{1-6}$ aliphatic, C(O)R, $C(O)NR_2$, C(O)NROR, C(O)OR, $NR_2$, $NRC(NR)NR_2$, NRCN, NRC(O)R, $NRC(O)NR_2$, NRC(O)OR, $NRNR_2$, NRS(O)R, $NRS(O)_2R$, $NRS(O)_2NR_2$, $N=S(O)R_2$, OR, OC(O)R, $OC(O)NR_2$, $=O$, $P(O)R_2$, $P(O)RNR_2$, P(O)ROR, SR, S(O)R, $S(O)NR_2$, S(NR)(O)R, $S(O)_2R$, $S(O)_2NR_2$, 3- to 7-membered carbocyclyl, 3- to 7-membered heterocyclyl, 5- to 8-membered cyclyl, 6- to 11-membered cyclyl, 6- to 11-membered heterocyclyl, phenyl, naphthalenyl, 5- or 6-membered heteroaryl, or 8- to 10-membered heteroaryl;

wherein each 3- to 7-membered carbocyclyl or 3- to 7-membered heterocyclyl is independently monocyclic and saturated or partially unsaturated;

wherein each 5- to 8-membered cyclyl is independently (a) bicyclic, (b) bridged, and (c) saturated or partially unsaturated;

wherein each 6- to 11-membered cyclyl is independently spirocyclic and saturated or partially unsaturated;

wherein each 6- to 11-membered heterocyclyl is independently bicyclic and saturated or partially unsaturated;

wherein each 5- or 6-membered heteroaryl is independently monocyclic;

wherein each 8- to 10-membered heteroaryl is independently bicyclic;

wherein each 3- to 7-membered heterocyclyl independently contains 1 or 2 heteroatoms independently selected from the group consisting of N, O, P, Si, and S;

wherein each 5- to 8-membered cyclyl and 6- to 11-membered cyclyl independently contains 0, 1, 2, or 3 heteroatoms independently selected from the group consisting of N, O, and S;

wherein each 6- to 11-membered heterocyclyl independently contains 1, 2, or 3 heteroatoms independently selected from the group consisting of N, O, and S;

wherein each 5- or 6-membered heteroaryl independently contains 1, 2, 3, or 4 heteroatoms independently selected from the group consisting of N, O, and S;

wherein each 8- to 10-membered heteroaryl independently contains 1, 2, 3, 4, or 5 heteroatoms independently selected from the group consisting of N, O, and S; and wherein each $C_{1-6}$ aliphatic, 3- to 7-membered carbocyclyl, 3- to 7-membered heterocyclyl, 5- to 8-membered cyclyl, 6- to 11-membered cyclyl, 6- to 11-membered heterocyclyl, phenyl, naphthalenyl, 5- or 6-membered heteroaryl, or 8- to 10-membered heteroaryl is independently substituted with r independently selected R substituents and s independently selected $R^D$ substituents;

each R is independently H, halogen, CN, $C_10.6$ aliphatic, 3- to 7-membered carbocyclyl, 3- to 7-membered heterocyclyl, 5- to 8-membered cyclyl, 6- to 10-membered cyclyl, 6- to 11-membered heterocyclyl, 7- to 12-membered heterocyclyl, phenyl, naphthalenyl, 5- or 6-membered heteroaryl, or 8- to 10-membered heteroaryl;

wherein each 3- to 7-membered carbocyclyl or 3- to 7-membered heterocyclyl is independently monocyclic and saturated or partially unsaturated;

wherein each 5- to 8-membered cyclyl is independently (a) bicyclic, (b) bridged, and (c) saturated or partially unsaturated;

wherein each 6- to 10-membered cyclyl is independently spirocyclic and saturated or partially unsaturated;

wherein each 6- to 11-membered heterocyclyl and 7- to 12-membered heterocyclyl is independently bicyclic and saturated or partially unsaturated;

wherein each 5- or 6-membered heteroaryl is independently monocyclic;

wherein each 8- to 10-membered heteroaryl is independently bicyclic;

wherein each 3- to 7-membered heterocyclyl independently contains 1 or 2 heteroatoms independently selected from the group consisting of N, O, and S;

wherein each 5- to 8-membered cyclyl and 6- to 10-membered cyclyl independently contains 0, 1, 2, or 3 heteroatoms independently selected from the group consisting of N, O, and S;

wherein each 6- to 11-membered heterocyclyl independently contains 1 or 2 heteroatoms independently selected from the group consisting of N, O, and S; and wherein each 7- to 12-membered heterocyclyl, 5- or 6-membered heteroaryl, and 8- to 10-membered heteroaryl independently contains 1, 2, 3, or 4 heteroatoms independently selected from the group consisting of N, O, and S; and wherein each $C_{1-6}$ aliphatic, 3- to 7-membered carbocyclyl, 3- to 7-membered heterocyclyl, 5- to 8-membered cyclyl, 6- to 10-membered cyclyl, 6- to 11-membered heterocyclyl, 7- to 12-membered heterocyclyl, phenyl, naphthalenyl, 5- or 6-membered heteroaryl, or 8- to 10-membered heteroaryl is independently substituted with s independently selected $R^D$ substituents; or any two R substituents, together with the nitrogen heteroatom to which they are attached, independently forms a 4- to 7-membered heterocyclyl, 7- to 12-membered heterocyclyl, or 8- to 10-membered heteroaryl;

wherein each 4- to 7-membered heterocyclyl is independently monocyclic and saturated, partially unsaturated, or fully saturated;

wherein each 7- to 12-membered heterocyclyl is independently bicyclic and saturated or partially unsaturated;

wherein each 8- to 10-membered heteroaryl is independently bicyclic;

wherein each 4- to 7-membered heterocyclyl, 7- to 12-membered heterocyclyl, and 8- to 10-membered heteroaryl optionally and independently contains 1, 2, or 3 additional heteroatoms independently selected from the group consisting of N, O, and S; and wherein each 4- to 7-membered heterocyclyl, 7- to 12-membered heterocyclyl, and 8- to 10-membered heteroaryl is independently substituted with s independently selected $R^D$ substituents;

each $R^D$ is independently halogen, CN, NO₂, C(O)R, C(O)NR₂, C(O)NROR, C(O)OR, NR₂, NRC(NR)NR₂, NRCN, NRC(O)R, NRC(O)NR₂, NRC(O)OR, NRNR₂, NRS(O)R, NRS(O)₂R, NRS(O)₂NR₂, N=S(O)R₂, OR, OC(O)R, OC(O)NR₂, =O, P(O)R₂, P(O)RNR₂, P(O)ROR, SR, S(O)R, S(O)NR₂, S(NR)(O)R, S(O)₂R, or S(O)₂NR₂;

each q is independently 0, 1, 2, 3, or 4;

r is 0, 1, 2, 3, or 4; and s is 0, 1, 2, 3, or 4.

2. The compound of claim 1, or a pharmaceutically acceptable salt, stereoisomer, or tautomer thereof, wherein X is —NH—.

3. The compound of claim 1, or a pharmaceutically acceptable salt, stereoisomer, or tautomer thereof, wherein $R^1$ is 3- to 7-membered heterocyclyl, 8- to 10-membered heterocyclyl, phenyl, or 5- or 6-membered heteroaryl;
   wherein the 3- to 7-membered heterocyclyl is monocyclic and saturated or partially unsaturated;
   wherein the 8- to 10-membered heterocyclyl is bicyclic and saturated or partially unsaturated;
   wherein the 5- or 6-membered heteroaryl is monocyclic;
   wherein the 3- to 7-membered heterocyclyl contains 1 or 2 heteroatoms independently selected from the group consisting of N, O, and S;
   wherein the 8- to 10-membered heterocyclyl or 5- or 6-membered heteroaryl contains 1, 2, 3, or 4 heteroatoms independently selected from the group consisting of N, O, and S; and
   wherein the 3- to 7-membered heterocyclyl, 8- to 10-membered heterocyclyl, phenyl, or 5- or 6-membered heteroaryl is substituted with q independently selected $R^C$ substituents.

4. The compound of claim 3, or a pharmaceutically acceptable salt, stereoisomer, or tautomer thereof, wherein $R^1$ is phenyl or 5- or 6-membered heteroaryl;
   wherein the 5- or 6-membered heteroaryl is monocyclic;
   wherein the 5- or 6-membered heteroaryl contains 1, 2, 3, or 4 heteroatoms independently selected from the group consisting of N, O, and S; and
   wherein the phenyl or 5- or 6-membered heteroaryl is substituted with q independently selected $R^C$ substituents.

5. The compound of claim 3, or a pharmaceutically acceptable salt, stereoisomer, or tautomer thereof, wherein $R^1$ is phenyl, pyrazolyl, pyridinyl, pyrimidinyl, or pyrazinyl, wherein the phenyl, pyrazolyl, pyridinyl, pyrimidinyl, or pyrazinyl is substituted with q independently selected $R^C$ substituents.

6. The compound of claim 5, or a pharmaceutically acceptable salt, stereoisomer, or tautomer thereof, wherein $R^1$ is:

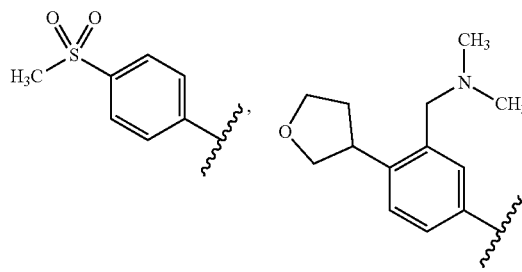

-continued

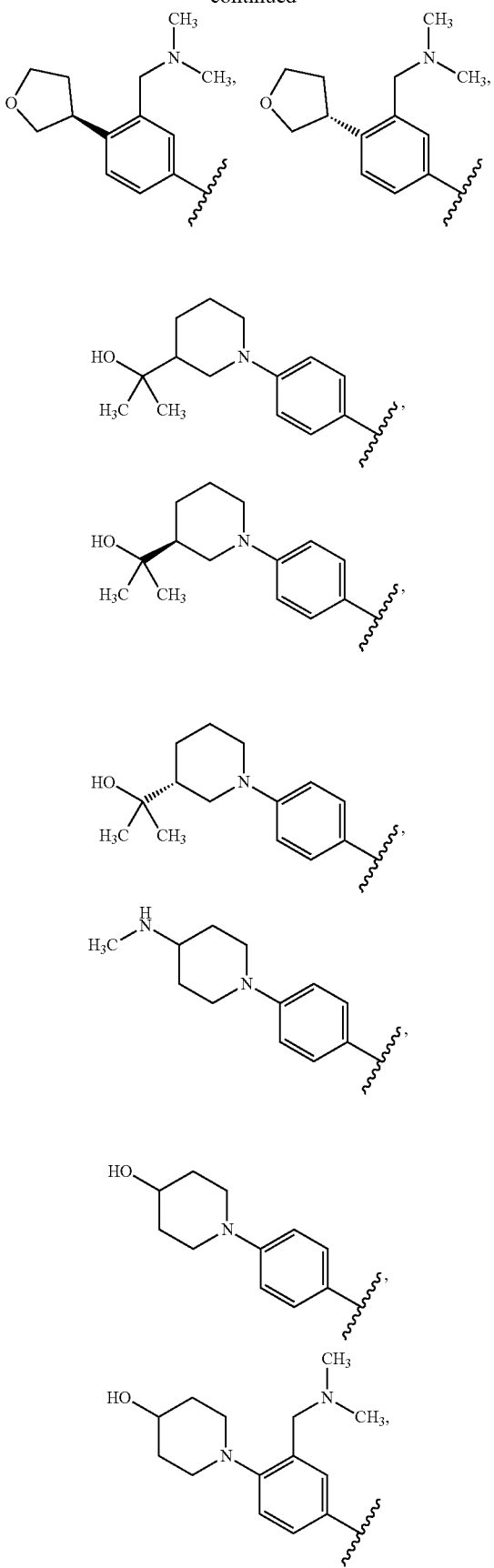

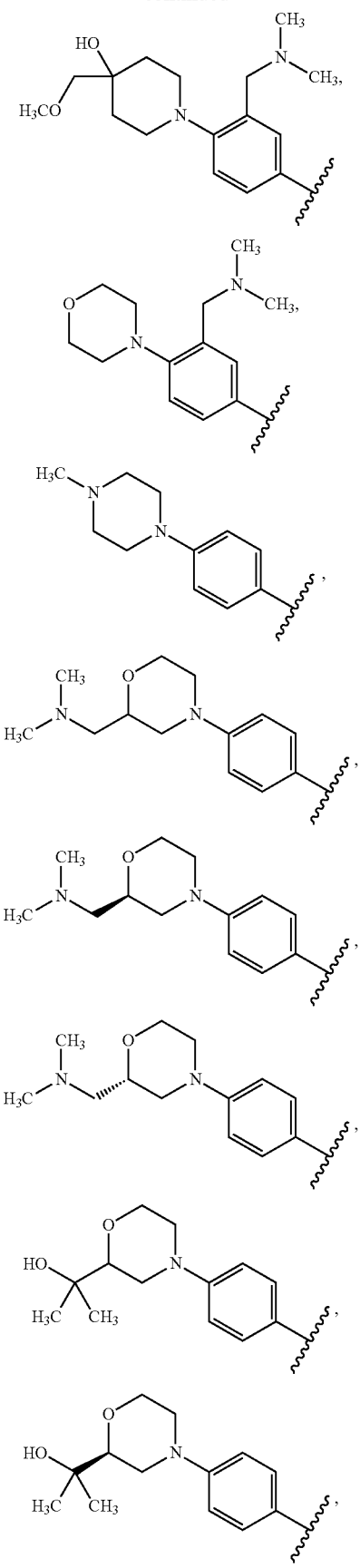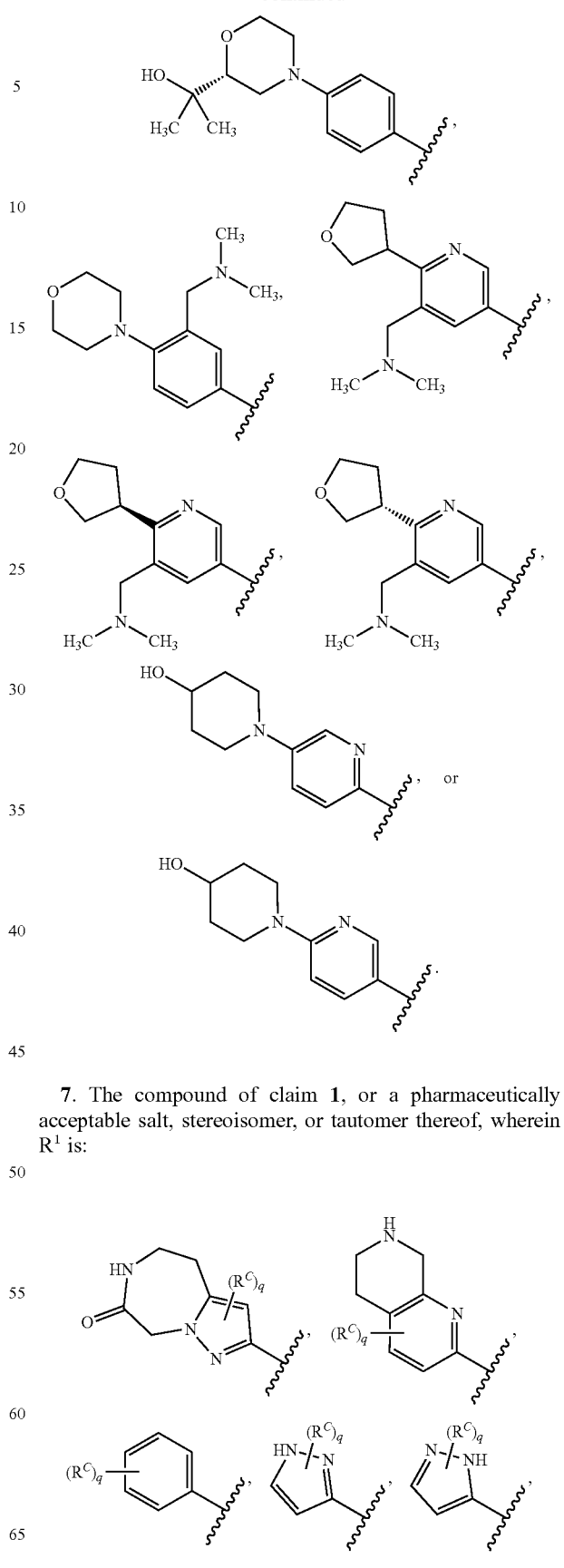
7. The compound of claim 1, or a pharmaceutically acceptable salt, stereoisomer, or tautomer thereof, wherein $R^1$ is:

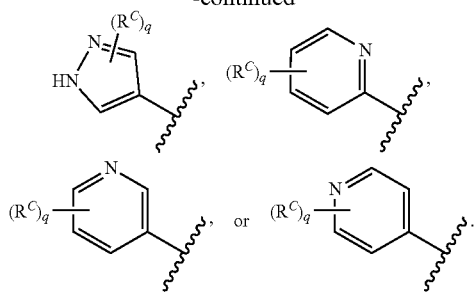

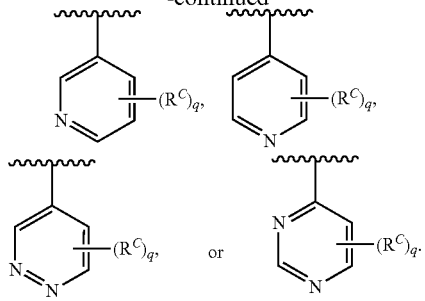

8. The compound of claim 1, or a pharmaceutically acceptable salt, stereoisomer, or tautomer thereof, wherein $R^2$ is 3- to 7-membered carbocyclyl, 3- to 7-membered heterocyclyl, phenyl, or 5- or 6-membered heteroaryl;
wherein the 3- to 7-membered carbocyclyl or 3- to 7-membered heterocyclyl is monocyclic and saturated or partially unsaturated;
wherein the 5- or 6-membered heteroaryl is monocyclic;
wherein the 3- to 7-membered heterocyclyl contains 1 or 2 heteroatoms independently selected from the group consisting of N, O, and S;
wherein the 5- or 6-membered heteroaryl contains 1, 2, 3, or 4 heteroatoms independently selected from the group consisting of N, O, and S; and
wherein the 3- to 7-membered carbocyclyl, 3- to 7-membered heterocyclyl, phenyl, or 5- or 6-membered heteroaryl is substituted with q independently selected $R^C$ substituents.

9. The compound of claim 8, or a pharmaceutically acceptable salt, stereoisomer, or tautomer thereof, wherein $R^2$ is cyclopropyl, tetrahydropyranyl, morpholinyl, phenyl, pyrrolyl, pyrazolyl, imidazolyl, oxazolyl, pyridinyl, pyridazinyl, or pyrimidinyl, wherein the cyclopropyl, tetrahydropyranyl, morpholinyl, phenyl, pyrrolyl, pyrazolyl, imidazolyl, oxazolyl, pyridinyl, pyridazinyl, or pyrimidinyl is substituted with q independently selected $R^C$ substituents.

10. The compound of claim 8, or a pharmaceutically acceptable salt, stereoisomer, or tautomer thereof, wherein $R^2$ is:

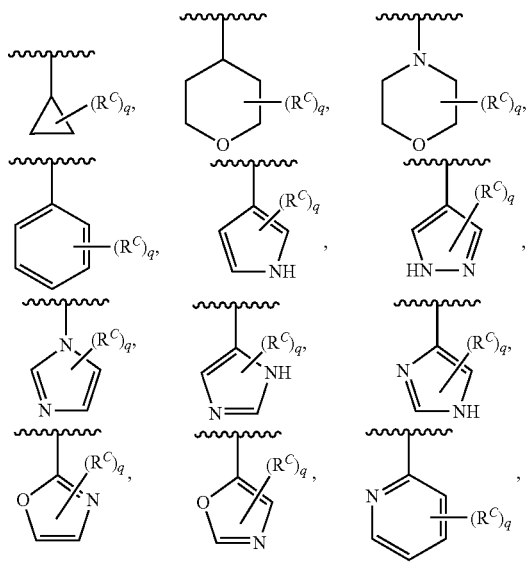

11. The compound of claim 8, or a pharmaceutically acceptable salt, stereoisomer, or tautomer thereof, wherein $R^2$ is:

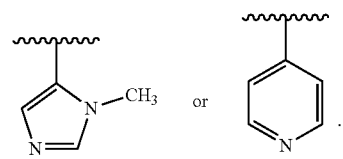

12. The compound of claim 1, or a pharmaceutically acceptable salt, stereoisomer, or tautomer thereof, wherein $R^2$ is a 6- to 11-membered cyclyl;
wherein the 6- to 11-membered cyclyl is (a) bicyclic, (b) fused, bridged, or spirocyclic, and (c) saturated, partially unsaturated, or fully unsaturated;
wherein the 6- to 11-membered cyclyl contains 0, 1, 2, or 3 heteroatoms independently selected from the group consisting of N, O, and S; and
wherein the 6- to 11-membered cyclyl is substituted with q independently selected $R^C$ substituents.

13. The compound of claim 12, or a pharmaceutically acceptable salt, stereoisomer, or tautomer thereof, wherein $R^2$ is a 9-membered heterocyclyl;
wherein the 9-membered heterocyclyl is (a) bicyclic, (b) fused, and (c) saturated, partially unsaturated, or fully unsaturated;
wherein the 9-membered heterocyclyl contains 1, 2, or 3 N heteroatoms; and
wherein the 9-membered heterocyclyl is substituted with q independently selected $R^C$ substituents.

14. The compound of claim 13, or a pharmaceutically acceptable salt, stereoisomer, or tautomer thereof, wherein $R^2$ is:

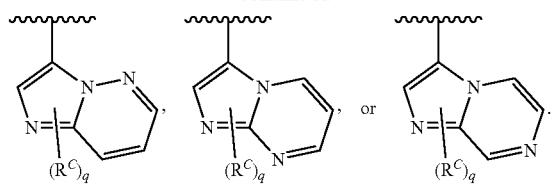

15. The compound of claim 13, or a pharmaceutically acceptable salt, stereoisomer, or tautomer thereof, wherein $R^2$ is:

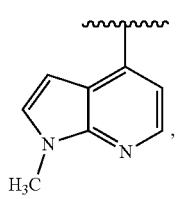

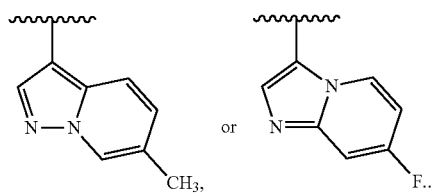

16. The compound of claim 1, or a pharmaceutically acceptable salt, stereoisomer, or tautomer thereof, wherein each $R^3$ is independently H or $C_{1-4}$ aliphatic, wherein the $C_{1-4}$ aliphatic is substituted with s independently selected $R^D$ substituents.

17. The compound of claim 1, or a stereoisomer thereof, wherein the compound, or stereoisomer thereof, is selected from the group consisting of:

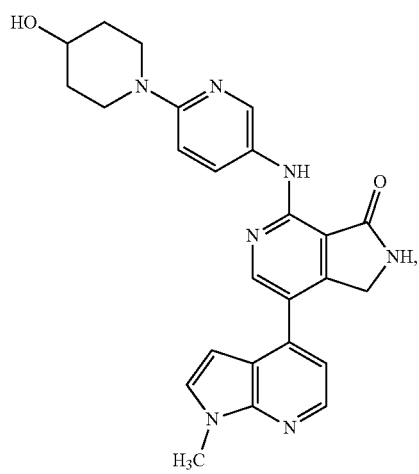

I-1

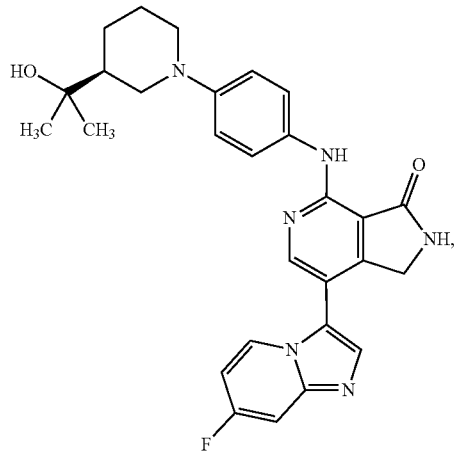

I-3

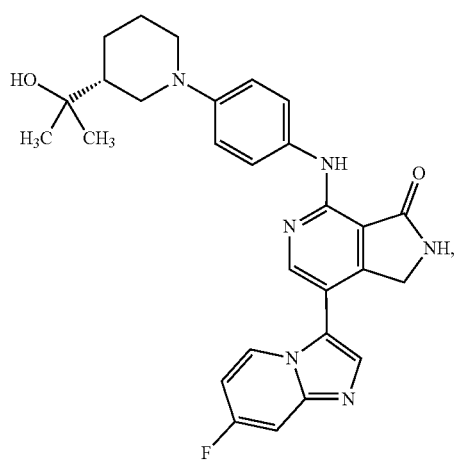

I-4

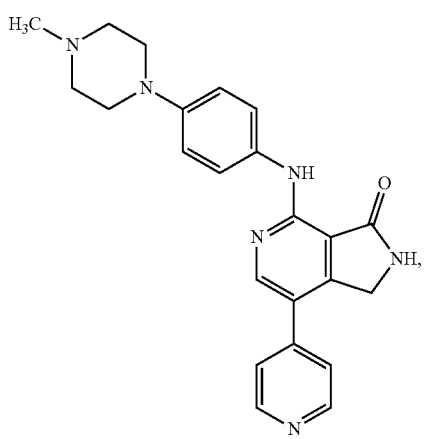

I-5

I-6
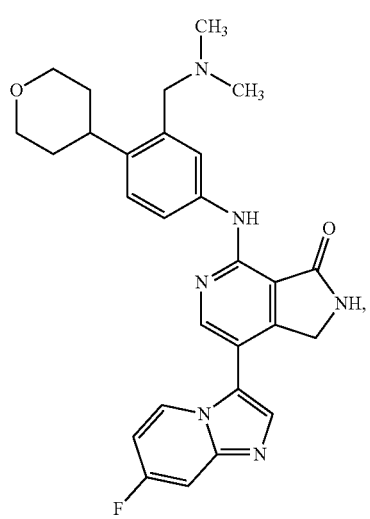
I-7
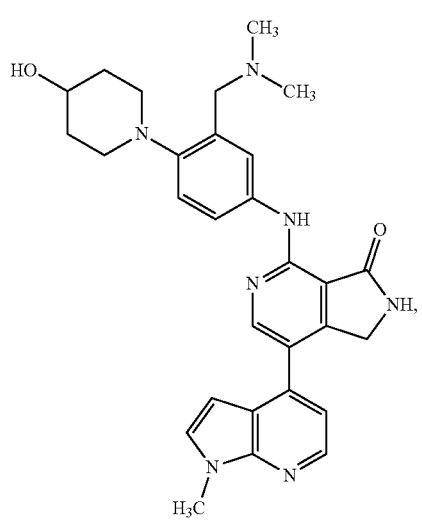
I-8
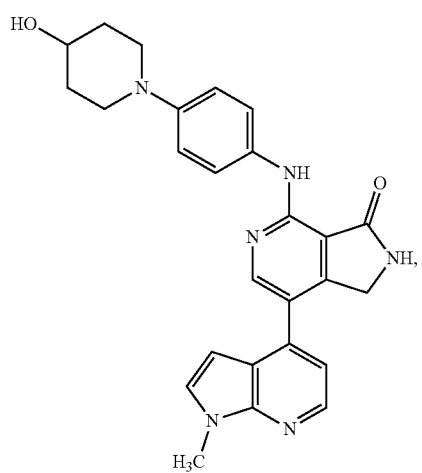
I-9
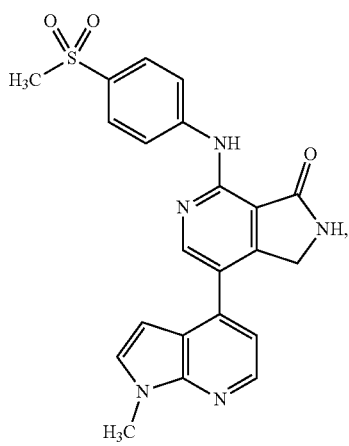
I-10
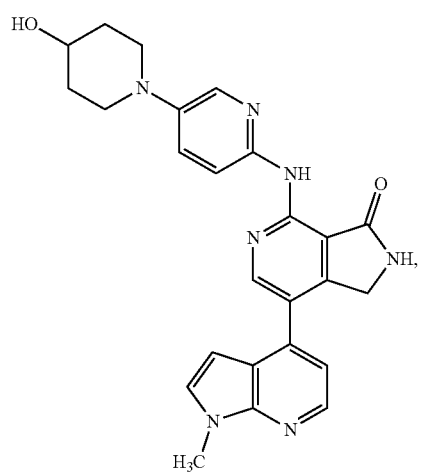
I-11
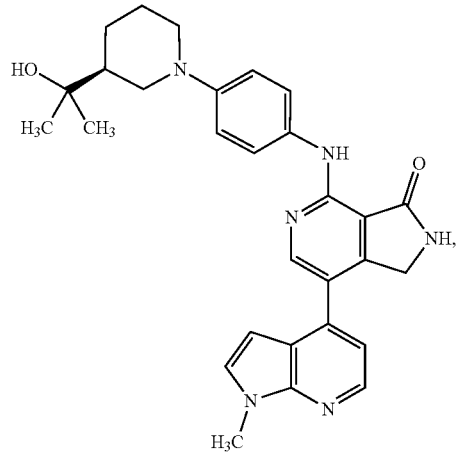

I-12
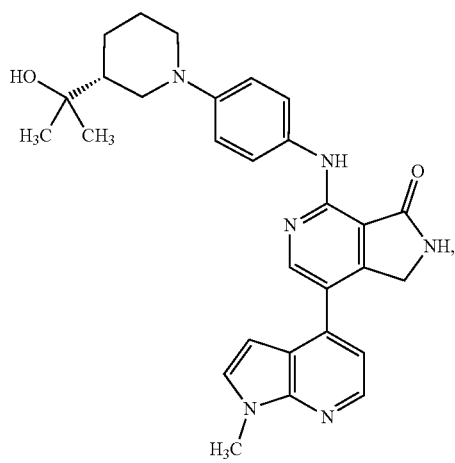
I-13
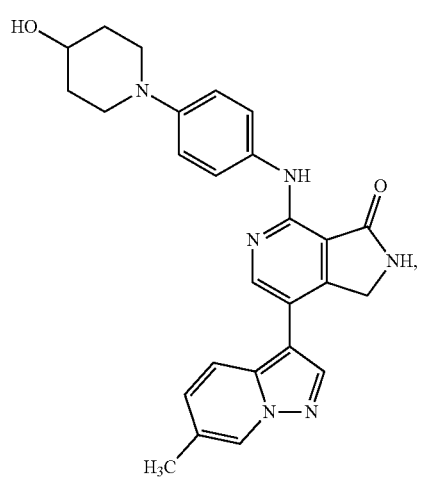
I-14
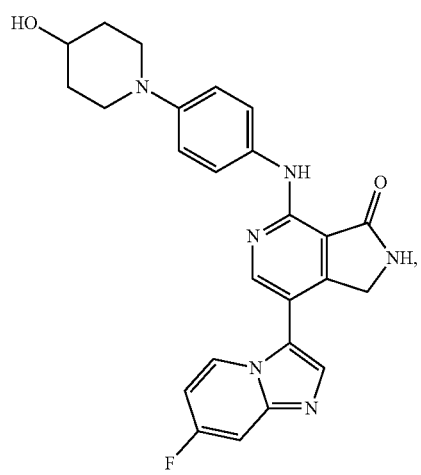
I-15
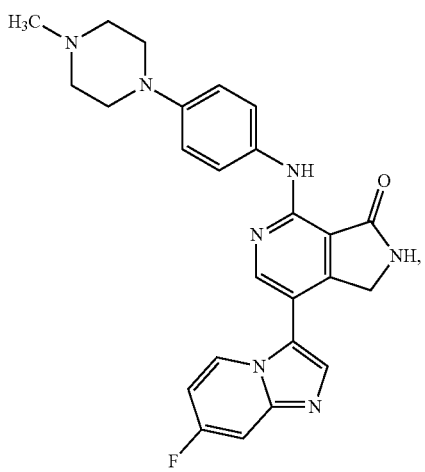
I-16
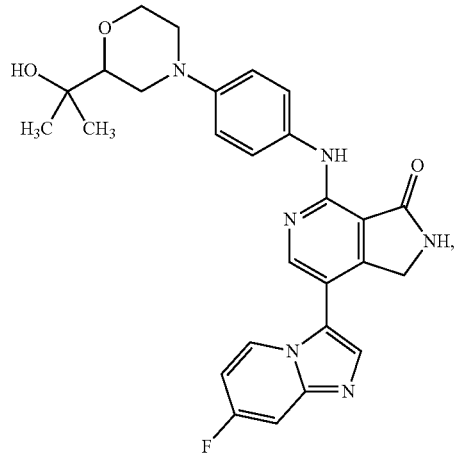
I-17
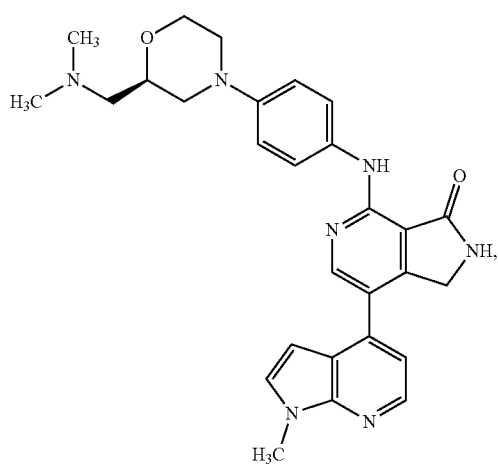

I-18
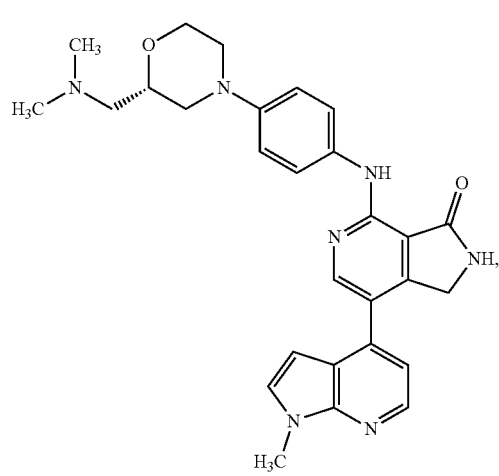
I-19
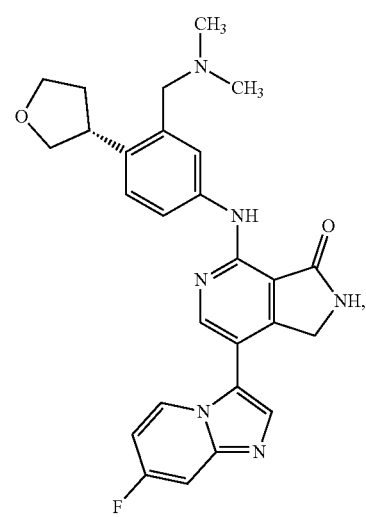
I-20
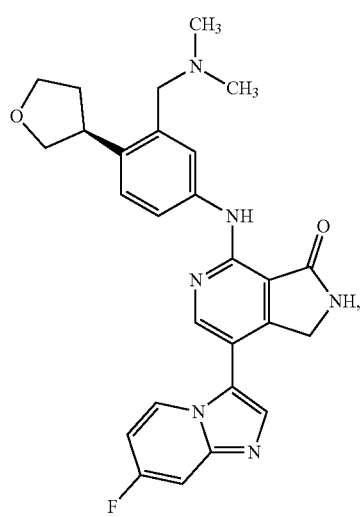
I-21
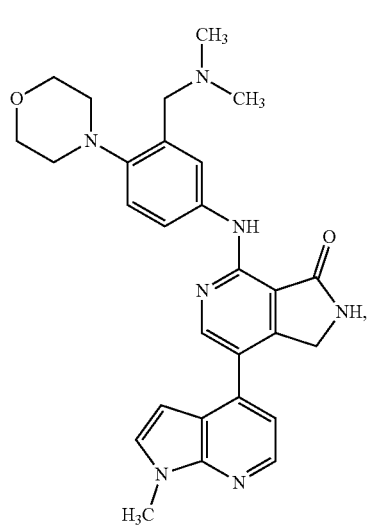
I-22
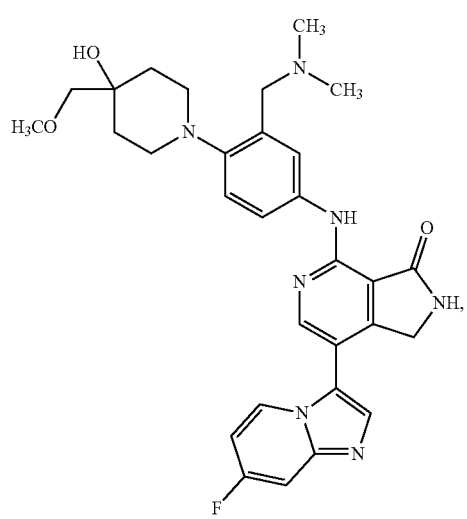
I-23
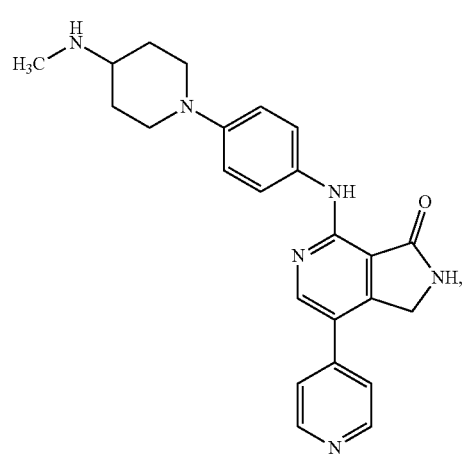

I-24
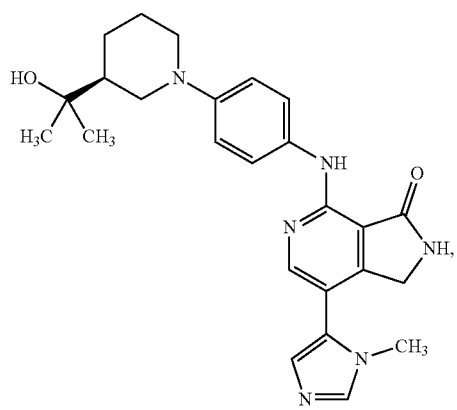
I-25
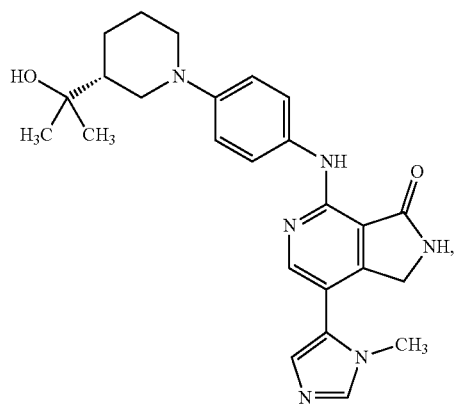
I-26
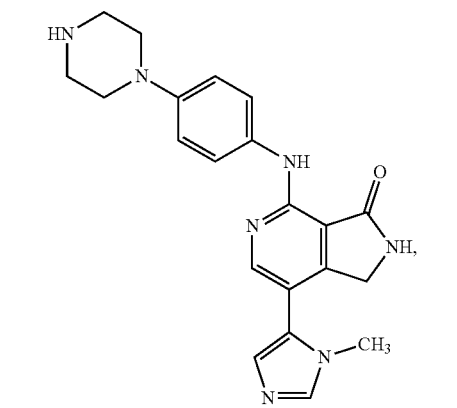
I-27
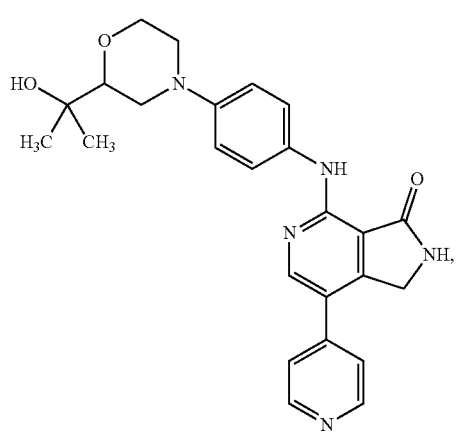
I-28
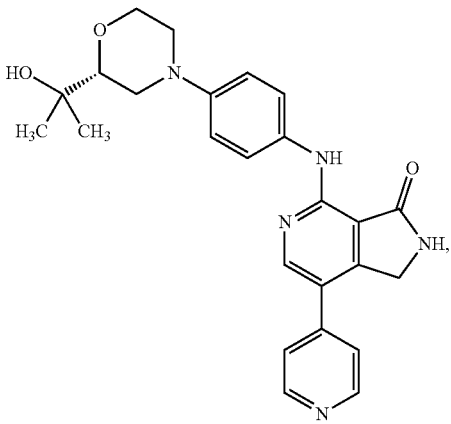
I-29
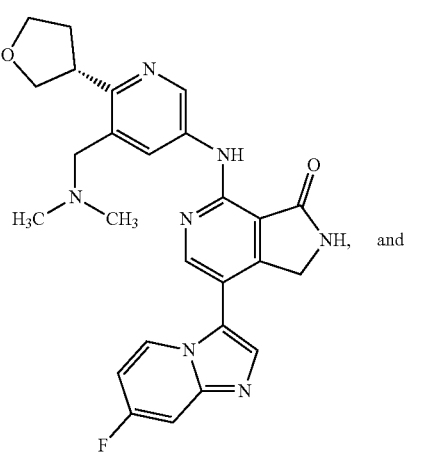
and
I-30
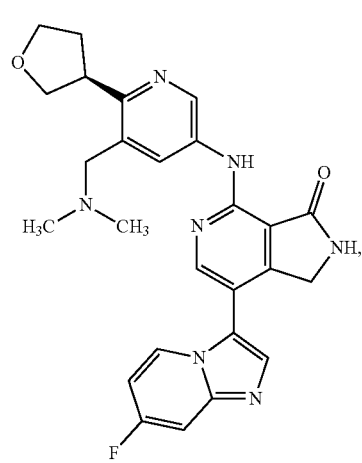
or a pharmaceutically acceptable salt or tautomer thereof.
18. A pharmaceutical composition comprising a pharmaceutically acceptable carrier, adjuvant, or vehicle and a compound of claim 1, or a pharmaceutically acceptable salt, stereoisomer, or tautomer thereof.

19. A compound:
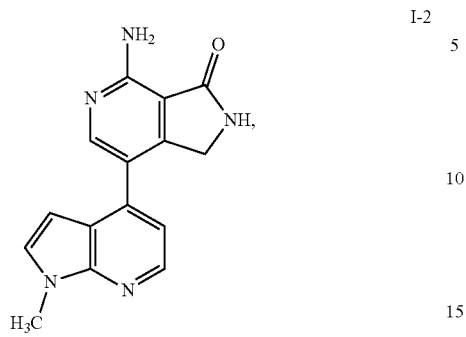
I-2
or a pharmaceutically acceptable salt or tautomer thereof.
* * * * *